US011926658B2

(12) United States Patent
Corti

(10) Patent No.: US 11,926,658 B2
(45) Date of Patent: Mar. 12, 2024

(54) MULTISPECIFIC ANTIBODIES SPECIFICALLY BINDING TO ZIKA VIRUS EPITOPES

(71) Applicant: HUMABS BIOMED SA, Bellinzona (CH)

(72) Inventor: Davide Corti, Bellinzona (CH)

(73) Assignee: HUMABS BIOMED SA, Bellinzona (CH)

( * ) Notice: Subject to any disclaimer, the term of this patent is extended or adjusted under 35 U.S.C. 154(b) by 386 days.

(21) Appl. No.: 16/640,622

(22) PCT Filed: Aug. 31, 2018

(86) PCT No.: PCT/EP2018/073489
§ 371 (c)(1),
(2) Date: Feb. 20, 2020

(87) PCT Pub. No.: WO2019/043166
PCT Pub. Date: Mar. 7, 2019

(65) Prior Publication Data
US 2020/0317755 A1  Oct. 8, 2020

(30) Foreign Application Priority Data

Aug. 31, 2017  (WO) ................. PCT/EP2017/071891

(51) Int. Cl.
| | | |
|---|---|---|
| *C07K 16/10* | (2006.01) | |
| *A61K 39/00* | (2006.01) | |
| *A61P 31/14* | (2006.01) | |
| *C12N 15/85* | (2006.01) | |
| *G01N 33/569* | (2006.01) | |
| *A61K 48/00* | (2006.01) | |

(52) U.S. Cl.
CPC .......... *C07K 16/1081* (2013.01); *A61P 31/14* (2018.01); *C12N 15/85* (2013.01); *G01N 33/56983* (2013.01); *A61K 2039/505* (2013.01); *A61K 2039/54* (2013.01); *A61K 2039/545* (2013.01); *A61K 48/00* (2013.01); *C07K 2317/31* (2013.01); *C07K 2317/35* (2013.01); *C07K 2317/52* (2013.01); *C07K 2317/55* (2013.01); *C07K 2317/565* (2013.01); *G01N 2333/185* (2013.01); *G01N 2800/26* (2013.01); *G01N 2800/52* (2013.01)

(58) Field of Classification Search
CPC ............ C07K 16/1081; C07K 2317/31; C07K 2317/35; C07K 2317/52; C07K 2317/55; C07K 2317/565; A61P 31/14; C12N 15/85; G01N 33/56983; G01N 2333/185; G01N 2800/26; G01N 2800/52; A61K 48/00; A61K 2039/505; A61K 2039/54; A61K 2039/545
See application file for complete search history.

(56) References Cited

U.S. PATENT DOCUMENTS

| | | |
|---|---|---|
| 3,766,162 A | 10/1973 | Spector |
| 3,791,932 A | 2/1974 | Schuurs et al. |
| 3,817,837 A | 6/1974 | Rubenstein et al. |
| 4,179,337 A | 12/1979 | Davis et al. |
| 4,233,402 A | 11/1980 | Maggio et al. |
| 4,495,285 A | 1/1985 | Shimizu et al. |
| 4,609,546 A | 9/1986 | Hiratani |
| 4,676,980 A | 6/1987 | Segal et al. |
| 4,766,106 A | 8/1988 | Katre et al. |
| 4,831,175 A | 5/1989 | Gansow et al. |
| 5,595,721 A | 1/1997 | Kaminski et al. |
| 10,421,804 B2 | 9/2019 | Kyratsous et al. |
| 10,588,956 B2 | 3/2020 | Sumathy et al. |
| 11,021,533 B2* | 6/2021 | Crowe, Jr. ............... A61P 31/14 |
| 11,117,954 B2 | 9/2021 | Corti |
| 2005/0163783 A1 | 7/2005 | Braslawsky et al. |
| 2017/0014502 A1 | 1/2017 | Sumathy et al. |
| 2019/0194260 A1 | 6/2019 | Whitehead et al. |
| 2019/0324040 A1* | 10/2019 | Watkins ........... G01N 33/56983 |
| 2020/0062831 A1* | 2/2020 | Kyratsous ............... A61P 21/00 |
| 2021/0347864 A1* | 11/2021 | Crowe, Jr. .......... C07K 16/1081 |

FOREIGN PATENT DOCUMENTS

| | | |
|---|---|---|
| CN | 105954512 A | 9/2016 |
| CN | 106279409 A | 1/2017 |
| CN | 106841601 A | 6/2017 |
| CN | 106885903 A | 6/2017 |
| WO | WO 0052031 A2 | 9/2000 |
| WO | WO 0052473 A2 | 9/2000 |
| WO | WO 2008143954 A2 | 11/2008 |

(Continued)

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Anonymous, "C01864M Data Sheet," May 3, 2016, retrieved from the internet on Mar. 7, 2017: <<http://www.amsbio.com/datasheets/C01864M-1.pdf>>, 1 page.
Anonymous, "C01865M Data Sheet," Jun. 23, 2016, retrieved from the internet on Mar. 7, 2016: <<http://www.amsbio.com/datasheets/C01865M-1.pdf>>, 1 page.
Anonymous, "C01866M Data Sheet," Apr. 26, 2016, retrieved from the internet on Mar. 7, 2016: <<http://www.amsbio.com/datasheets/C01866M-1.pdf>>, 1 page.

(Continued)

*Primary Examiner* — Robert S Landsman
(74) *Attorney, Agent, or Firm* — Seed IP Law Group LLP

(57) ABSTRACT

The invention relates to multispecific antibodies, and antigen binding fragments thereof, that specifically bind to distinct Zika virus epitopes and potently neutralize infection of ZIKV. The invention also relates to nucleic acids that encode such antibodies and antibody fragments. In addition, the invention relates to the use of the antibodies and antibody fragments of the invention in prophylaxis and treatment of ZIKV infection.

21 Claims, 32 Drawing Sheets

Specification includes a Sequence Listing.

(56) References Cited

FOREIGN PATENT DOCUMENTS

| WO | WO 2015103072 A1 | 7/2015 |
|----|------------------|--------|
| WO | WO 2018017497 A1 | 1/2018 |

OTHER PUBLICATIONS

Anonymous, "Choose the Best ZIKA Virus Antibodies", retrieved from the internet on Mar. 7, 2017: <<http://www.arigobio.com/news/view/Zika_Virus>>, 4 pages.
Anonymous, "Zika virus antigens and antibodies," retrieved from the internet on Mar. 7, 2017: <<http://www.amsbio.com/zika-virus-antigens-antibodies.aspx>>, 4 pages.
Armour et al., "Recombinant human IgG molecules lacking Fcγ receptor I binding and monocyte triggering activities," *Eur. J. Immunol.* 29:2613-2624, 1999. (12 pages).
Arnon et al., "Monoclonal Antibodies for Immunotargeting of Drugs in Cancer Therapy," in *Monoclonal Antibodies and Cancer Therapy*, ed. Reisfeld et al., pp. 243-256, 1985. (16 pages).
Baldwin et al., "Analysis, Results, and Future Prospective of the Therapeutic Use of Radiolabeled Antibody in Cancer Therapy," in Monoclonal Antibodies for Cancer Detection and Therapy, ed. Academic Press, New York, 1985, pp. 303-316.
Barba-Spaeth et al., "Structural basis of potent Zika-dengue virus antibody cross-neutralization," *Nature* 536:48-53, Aug. 2016. (20 pages).
Bardelli et al., "Epitope mapping by solution NMR spectroscopy," *J. Mol. Recognit*.28(6): 393-400, 2015. (8 pages).
Beltramello et al., "The Human Immune Response to Dengue Virus is Dominated by Highly Cross-Reactive Antibodies Endowed with Neutralizing and Enhancing Activity," *Cell Host Microbe* 8(3):271-283, Sep. 2010, NIH Public Access Author Manuscript (25 pages).
Boerner et al., "Production of Antigen-Specific Human Monoclonal Antibodies From In Vitro-Primed Human Splenocytes," *J. Immunol.* 147(1):86-95, Jul. 1, 1991. (11 pages).
Bressanelli et al., "Structure of a flavivirus envelope glycoprotein in its low-pH-induced membrane fusion conformation," *Embo J* 23(4):728-738, 2004. (11 pages).
Brüggemann et al., "Designer Mice: The Production of Human Antibody Repertoires in Transgenic Animals," *Year Immunol*. 7:1993; 3340 (8 pages).
Burton, "Immunoglobulin G: Functional Sites," *Mol. Immunol.* 22(3):161-206, 1985 (48 pages).
Byrne et al., "A tale of two specificities: bispecific antibodies for therapeutic and diagnostic applications," *Trends in Biotechnology* 31(11):621-632, Nov. 2013 (12 pages).
Calvet et al., "Detection and sequencing of Zika virus from amniotic fluid of fetuses with microcephaly in Brazil: a case study," *The Lancet* 16:653-660, Jun. 2016 (8 pages).
Cao-Lormeau et al., "Emerging arboviruses in the Pacific," *Lancet* 384:1571-1572, Nov. 2014 (2 pages).
Cao-Lormeau et al., "Guillain-Barré Syndrome outbreak associated with Zika virus infection in French Polynesia: a case-control study," *Lancet* 287:1531-1539, Apr. 2016 (9 pages).
Capel et al., "Heterogeneity of Human IgG Fc Receptors," *Immunomethods* 4:25-34, 1994 (10 pages).
Chan et al., "Therapeutic antibodies for autoimmunity and inflammation," *Nat Rev Immu* 10:301-316, 2010 (16 pages).
Chu et al., "Inhibition of B cell receptor-mediated activation of primary human B cells by coengagement of CD19 and FcγRIIb with Fc-engineered antibodies," *Molecular Immunology* 45:3926-3933, 2008 (8 pages).
Cole et al., "The EBV-Hybridoma Technique and its Application to Human Lung Cancer," *Monoclonal Antibodies and Cancer Therapy*: 77-96, 1985 (22 pages).
Corti et al., "Cross-neutralization of four paramyxoviruses by a human monoclonal antibody," *Nature* 501:439-443, Sep. 2013 (7 pages).
D'Ortenzio et al., "Evidence of Sexual Transmission of Zika Virus," *N Engl J Med* 374(22):2195-2198, Jun. 2016 (4 pages).

Dai et al., "Structures of the Zika Virus Envelope Protein and Its Complex with a Flavivirus Broadly Protective Antibody," *Cell Host Microbe* 19:696-704, May 2016 (10 pages).
De Haas et al., "Fcγ receptors of phagocytes," *J. Lab. Clin. Med.* 126(4):330-341, 1995 (3 pages).
Dejnirattisai et al., "Cross-Reacting Antibodies Enhance Dengue Virus Infection in Humans," *Science* 328(5979):745-748, May 7, 2010 (5 pages).
Dejnirattisai et al., "Dengue virus sero-cross-reactivity drives antibody-dependent enhancement of infection with zika virus," *Nat Immunol.* 17(9):1102-1109, Jun. 23, 2016 (8 pages).
Dick et al., "Zika Virus (I). Isolations and Serological Specificity," *Transactions of the Royal Society of Tropical Medicine and Hygiene* 46(5):509-520, Sep. 1952 (12 pages).
DiGiammarino et al., "Design and Generation of DVD-Ig™ Molecules for Dual-Specific Targeting," *Methods Mol. Biol.* 899:145-156, 2012.
Dowall et al., "A Susceptible Mouse Model for Zika Virus Infection," *PLoS Negl Trop Dis* 10:1-13, May 2016 (13 pages).
Duffy et al., "Zika Virus Outbreak on Yap Island, Federated States of Micronesia," *N Engl J Med.* 360(24):2536-2543, Jun. 2009 (8 pages).
Duncan et al., "The binding cite for Clq on IgG," *Nature* 332(21):738-740, Apr. 1988 (3 pages).
Fauci et al., "Zika Virus in the Americas—Yet Another Arbovirus Threat," *N Engl J Med* 374(4):601-604, Feb. 2016 (4 pages).
Freire et al, "Mapping Putative B-Cell Zika Virus NS1 Epitopes Provides Molecular Basis for Anti-NS1 Antibody Discrimination between Zika and Dengue Viruses," *ACS Omega* 2:3913-3920, Jul. 25, 2017.
Ganesan et al., "FcγRIIb on liver sinusoidal endothelium clears small immune complexes," *Journal of Immunology* 189(10):4981-4988, Nov. 2012, HHS Public Access Author Manuscript (23 pages).
Gessner et al., "The IgG Fc receptor family," *Ann Hematol* 76:231-248, 1998 (6 pages).
Goebel et. al., "A sensitive virus yield assay for evaluation of antivirals against Zika Virus," *J. Virol. Methods* 238:13-20, 2016 (8 pages).
Gong et al., "Fabs-in-tandem immunoglobulin is a novel and versatile bispecific design for engaging multiple therapeutic targets," *MABS* 9(7):1118-1128, 2017 (11 pages).
Grevys et al., "Fc Engineering of Human IgGI for Altered Binding to the Neonatal Fc Receptor Affects Fc Effector Functions," *The Journal of Immunology* 194:5497-5508, 2015 (12 pages).
Halstead et al., "Dengue Hemorrhagic Fever in Infants: Research Opportunities Ignored," *Emerging Infect Dis.* 8(12):1474-1479, Dec. 2002 (6 pages).
Halstead, "Dengue Antibody-Dependent Enhancement: Knowns and Unknowns," *Microbiol Spectr*.: 249-271, Dec. 2014 (18 pages).
Halstead, "Neutralization and Antibody-Dependent Enhancement of Dengue Viruses," *Adv Virus Res.* 60:421-467, 2003 (47 pages).
Hellström et al., "Antibodies for Drug Delivery," in Controlled Drug Delivery, ed. Robinson et al. (2d ed; Marcel Dekker, nc.), 1987, pp. 623-653 (33 pages).
Hessell et al., "Fc receptor but not complement binding is important in antibody protection against HIV," *Nature* 449:101-104, Sep. 2007 (5 pages).
Heymann et al., "Zika virus and microcephaly: why is this situation a PHEIC?" *Lancet* 387:719-721, Feb. 2016 (3 pages).
Hoogenboom et al., "By-passing Immunisation: Human Antibodies from Synthetic Repertoires of Germline VH Gene Segments Rearranged in Vitro," *J. Mol. Biol.* 227:381-388, 1992 (8 pages).
Hung et al., "Dengue Hemorrhagic Fever in Infants: A Study of Clinical and Cytokine Profiles," *J Infect Dis.* 189:221-232, Jan. 2004 (12 pages).
Jakobovits et al., "Analysis of homozygous mutant chimeric mice: Deletion of the immunoglobulin heavy-chain joining region blocks B-cell development and antibody production," *Proc. Natl. Acad. Sci. USA* 90:2551-2555, Mar. 1993 (5 pages).
Jakobovits et al., "Germ-line transmission and expression of a human-derived yeast artificial chromosome," *Letters to Nature* 362:255-258, Mar. 1993 (4 pages).

(56) References Cited

OTHER PUBLICATIONS

Julander et al., "Efficacy of the broad-spectrum antiviral compound BCX4430 against Zika virus in cell culture and in a mouse model," *Antiviral Res* 137:14-22, Jan. 2017, HHS Public Acces Author Manuscript (21 pages).

Kostyuchenko et al., "Structure of the thermally stable Zika virus," *Nature* 533:425-428, May 2016 (12 pages).

Li et al., "Enzyme-Linked Immunosorbent Assay-Format Tissue Culture Infectious Dose-50 Test for Titrating Dengue Virus," *PLoS ONE* 6(7):Jul. 2011 (4 pages).

MacNamara, "Zika Virus: A Report on Three Cases of Human Infection During an Epidemic of Jaundice in Nigeria," *Transactions of the Royal Society of Tropical Medicine and Hygiene* 48(2):139-145, Mar. 1954 (7 pages).

Magnani et al., "A human inferred germline antibody binds to an immunodominant epitope and neutralizes Zika virus," *PLOS Neglected Tropical Diseases* 11:6, Jun. 12, 2017, pp. 1-17.

Marchetto et al., "A Model for Neural Development and Treatment of Rett Syndrome Using Human Induced Pluripotent Stem Cells," *Cell* 143:527-539, Nov. 2010 (13 pages).

Marks et al., "By-passing Immunization: Human Antibodies from V-Gene Libraries Displayed on Page," *J. Mol. Biol.* 222:581-597, 1991 (17 pages).

Mlakar et al., "Zika Virus Associated with Microcephaly," *The New England Journal of Medicine*, p. 1-8, Feb. 10, 2016.

Modis et al., "Structure of the dengue virus envelope protein after membrane fusion," *Nature* 427:313-319, Jan. 2004 (7 pages).

Moore et al., "Accelerated Clearance of IgE in Chimpanzees is Mediated by Xmab7195, An Fc-Engineered Antibody With Enhanced Affinity for Inhibitory Receptor FcγRIIb," *Am. J. Respir. Crit.* 189:A4261, 2014 (Abstract Only).

Muller et al., "The flavivirus NS1 protein: Molecular and structural biology, immunology, role in pathogenesis and application as a diagnostic biomarker," *Antiviral Research* 98(2):192-208, May 2013 (17 pages).

Musso et al., "Potential Sexual Transmission of Zika Virus," *Emerg Infect Dis.* 21(2):359-361 Feb. 2015 (3 pages).

Musso et al., "Rapid spread of emerging Zika virus in the Pacific area," *Clin. Microbiol. Infect.* 20:O595-O596, 2014 (2 pages).

Musso et al., "Zika virus: following the path of dengue and chikungunya?" *The Lancet* 386:243-244, Jul. 2015 (2 pages).

Nigro et al., "Passive Immunization during Pregnancy for Congenital Cytomegalovirus Infection," *N Engl J Med* 353: 1350-1362, Sep. 2005 (13 pages).

Perez et al., "Utilization of Immunoglobulin G Fc Receptors by Human Immunodeficiency Virus Type 1: a Specific Role for Antibodies against the Membrane-Proximal External Region of gp41," *J Virol* 83(15):7397-7410, Aug. 2009 (14 pages).

Petersen et al., "Zika Virus," *The New England Journal of Medicine* 374(16):1552-1563, Apr. 2016 (12 pages).

Piccoli et al., "Neutralization and clearance of GM-CSF by autoantibodies in pulmonary alveolar proteinosis," *Nat. Commun.* 6(7375):1-9, Jun. 16, 2015.

Quick et al., "Multiplex PCR method for MinION and Illumina sequencing of Zika and other virus genomes directly from clinical samples," *Nat Protoc* 12(6):1261-1276, Jun. 2017, HHS Public Access Author Manuscript (28 pages).

Ravetch et al., "Fc Receptors," *Annu. Rev. Immunol.* 9:457-492, 1991 (36 pages).

Rothman, "Dengue: defining protective versus pathologic immunity," *J Clin Invest.* 113(7):946-951, Apr. 2004 (6 pages).

Rubin et al., "Zika Virus and Microcephaly," *N Engl J Med* 374(10):984-985, Mar. 2016 (2 pages).

Sapparapu et al., "Neutralizing human antibodies prevent Zika virus replication and fetal disease in mice," *Nature* 540:Nov. 7, 2016. (15 pages).

Screaton et al., "New insights into the immunopathology and control of dengue virus infection," *Nat Rev Immunol.* 15:745-759, Dec. 2015 (15 pages).

Shields et al., "High Resolution Mapping of the Binding Site on Human IgGI for FcγRI, FcγRII, FcγRIII, and FcRn and Design of IgG1 Variants with Improved Binding to the FcγR," *J. Biol. Chem.* 276(9):6591-6604, Mar. 2, 2001 (published, JBC Papers in Press, Nov. 28, 2000) (15 pages).

Simonelli et al., "Rapid Structural Characterization of Human Antibody-Antigen Complexes through Experimentally Validated Computational Docking," *J. Mol. Biol.* 396:1491-1507, 2010 (published online Jan. 4, 2010) (17 pages).

Simonelli et al., "Rational Engineering of a Human Anti-Dengue Antibody through Experimentally Validated Computational Docking," *PLoS ONE* 8(2):e55561, Feb. 6, 2013 (11 pages).

Sirohi et al., "The 3.8 Å resolution cryo-EM structure of Zika virus," *Science* 352(6284):467-470, Apr. 22, 2016 (published online Mar. 31, 2016) (8 pages).

Song et al., "Zika virus NS1 structure reveals diversity of electrostatic surfaces among flaviviruses," *Nature Structural & Molecular Biology* 23(5):456-459, May 2016 (published online Apr. 18, 2016) (4 pages).

Spiess et al., "Alternative molecular formats and therapeutic applications for bispecific antibodies," *Molecular Immunology* 67:95-106, Jan. 27, 2015 (12 pages).

Stettler et al., "Specificity, cross-reactivity, and function of antibodies elicited by Zika virus infection," *Science* 353(6301):823-826, Aug. 19, 2016 (published online Jul. 14, 2016) (44 pages).

Swanstrom et al., "Dengue Virus Envelope Dimer Epitope Monoclonal Antibodies Isolated from Dengue Patients are Protective against Zika Virus," *MBIO* 7(4):e01123-16, Jul. 19, 2016 (8 pages).

Tang et al., "Zika Virus Infects Human Cortical Neural Precursors and Attenuates Their Growth," *Cell Stem Cell* 18(5):587-590, May 5, 2016 (HHS Public Access, Author Manuscript, available in PMC May 5, 2017) (8 pages).

Thorpe, "Antibody Carriers of Cytotoxic Agents in Cancer Therapy: A Review," Monoclonal Antibodies '84: Biological and Clinical Applications, ed. Pinchera et al. pp. 475-506 (Editrice Kurtis, Milano, Italy, 1985) (33 pages).

Thorpe et al., "The Preparation and Cytotoxic Properties of Antibody-Toxin Conjugates," *Immunol. Rev.* 62:119-158, 1982 (41 pages).

Tiller et al., "Efficient generation of monoclonal antibodies from single human B cells by single cell RT-PCR and expression vector cloning," *J Immunol Methods* 329(1-2):112-124, Jan. 1, 2008 (NIH Public Access, Author Manuscript, available in PMC Jul. 1, 2008) (19 pages).

Traggiai et al., "An efficient method to make human monoclonal antibodies from memory B cells: potent neutralization of SARS coronavirus," *Nat. Med.* 10(8):871-875, Aug. 2004 (published online Jul. 11, 2004) (5 pages).

Van de Winkel et al., "Biology of Human Immunoglobulin G Fc Receptors," *Journal of Leukocyte Biology* 49:511-524, 1991 (14 pages).

Van Dijk et al., "Human antibodies as next generation therapeutics," *Curr. Opin. Chem. Biol.* 5:368-374, 2001 (7 pages).

Wang et al., "A human bi-specific antibody against Zika virus with high therapeutic potential," *Cell* 171(1):229-241, Sep. 21, 2017. (HHS Public Access, Author Manuscript, available in PMC Sep. 21, 2018) (47 pages).

Ward et al., "The effector functions of immunoglobulins: implications for therapy," *Ther. Immunol.* 2:77-94, 1995 (18 pages).

Weidle et al., "The Intriguing Options of Multispecific Antibody Formats for Treatment of Cancer," *Cancer Genomics and Proteomics* 10:1-18, 2013 (18 pages).

Willis et al., "Characterization of Zika virus binding and enhancement potential of a large panel of flavivirus murine monoclonal antibodies," *Virology* 508:1-6, May 2, 2017 (6 pages).

Wines et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A," *J. Immunol.* 164:5313-5318, 2000 (6 pages).

Wu et al., "Simultaneous targeting of multiple disease mediators by a dual-variable-domain immunoglobulin," *Nat Biotechnol.* 25(11):1290-1297, Nov. 2007 (published online Oct. 14, 2007) (8 pages).

Yang et al., "Immunization of Zika virus envelop protein domain III induces specific and neutralizing immune responses against Zika

(56) References Cited

OTHER PUBLICATIONS virus," *Vaccine* 35(33):4287-4294, Jul. 24, 2017 (HHS Public Access, Author Manuscript, available in PMC Jul. 24, 2018) (18 pages).

Yu et al., "Delineating antibody recognition against Zika virus during natural infection," *JCI Insight* 2(12):e93042, Jun. 15, 2017 (17 pages).

Zhao et al., "Structural Basis of Zika Virus-Specific Antibody Protection," *Cell* 166(4):1016-1027, Aug. 11, 2016 (13 pages).

\* cited by examiner

|  | Binding (EC50, ng/ml) | | | | | | | | | | Neut. (IC50, ng/ml) | | |
|---|---|---|---|---|---|---|---|---|---|---|---|---|---|
|  | ZIKV E | DENV1 E | DENV2 E | DENV3 E | DENV4 E | DENV1 VLP | DENV2 VLP | DENV3 VLP | DENV4 VLP | DIII ZKA | ZIKV neut | DENV1 neut | |
| ZKA3 | 172 | 510 | 108 | 17 | 134 | 12 | 28 | 10 | 7 | - | 411 | 346 | |
| ZKA4 | 172 | 135 | 23 | 9 | 22 | 9 | 11 | 10 | 8 | - | 961 | 592 | |
| ZKA5 | 243 | 877 | 133 | 22 | 123 | 37 | 32 | 25 | 31 | - | 1978 | - | |
| ZKA6 | 79 | 355 | 28 | 13 | 58 | 13 | 14 | 9 | 10 | - | 1661 | - | |
| ZKA7 | 112 | 329 | 74 | 11 | 95 | 9 | 18 | 8 | 7 | - | 646 | 513 | |
| ZKA8 | 70 | 136 | 31 | 8 | 28 | 8 | 11 | 7 | 11 | - | 1336 | 102 | |
| ZKA76 | 408 | - | - | - | - | - | - | - | - | 3756 | 62 | nd | |
| ZKA78 | 2759 | 1407 | 982 | 33 | 385 | 158 | 83 | 131 | 136 | - | 2863 | 266 | |
| ZKA117 | 376 | 1780 | 341 | 49 | 391 | 142 | 86 | 36 | 158 | - | 1945 | 83 | |
| ZKB27 | 225 | - | - | - | - | nd | nd | nd | nd | - | 257 | nd | |
| ZKB29 | 285 | - | - | - | - | nd | nd | nd | nd | - | - | nd | |
| ZKB30 | 1560 | 2011 | 2320 | 344 | 459 | nd | nd | nd | nd | - | - | nd | |
| ZKB32 | 1668 | - | - | - | - | nd | nd | nd | nd | - | 545 | nd | |
| ZKB34 | 122 | - | - | - | - | nd | nd | nd | nd | - | - | nd | |
| ZKB39 | 136 | - | - | - | - | nd | nd | nd | nd | - | 667 | nd | |
| ZKB41 | 241 | - | - | - | - | nd | nd | nd | nd | - | - | nd | |
| ZKB45 | 125 | - | - | - | - | nd | nd | nd | nd | - | 1461 | nd | |
| ZKB46 | 3238 | - | - | - | - | nd | nd | nd | nd | - | - | nd | |
| ZKB51 | 645 | 220 | 115 | 66 | 62 | nd | nd | nd | nd | - | - | nd | EDI/II |
| ZKB52 | 3398 | - | - | - | - | nd | nd | nd | nd | - | - | nd | |
| ZKB53 | 59 | - | - | - | - | nd | nd | nd | nd | - | - | nd | |
| ZKB84 | 4373 | - | - | - | - | nd | nd | nd | nd | - | - | nd | |
| ZKC21 | 2069 | 4201 | 3659 | 877 | 1252 | nd | nd | nd | nd | - | - | nd | |
| ZKC22 | 161 | 347 | 133 | 330 | 75 | nd | nd | nd | nd | - | - | nd | |
| ZKC23 | 87 | 2162 | 97 | 37 | 21 | nd | nd | nd | nd | - | - | nd | |
| ZKC24 | 92 | 177 | 71 | 240 | 55 | nd | nd | nd | nd | - | - | nd | |
| ZKC26 | 52 | 150 | 61 | 21 | 28 | nd | nd | nd | nd | - | 420 | nd | |
| ZKD4 | 20 | 80 | 24 | 8 | 11 | nd | nd | nd | nd | - | - | nd | |
| ZKD5 | 42 | 254 | 103 | 17 | 41 | nd | nd | nd | nd | - | - | nd | |
| ZKD6 | 115 | 585 | 600 | 31 | 96 | nd | nd | nd | nd | - | - | nd | |
| ZKD7 | 33 | 474 | 147 | 12 | 44 | nd | nd | nd | nd | - | - | nd | |
| ZKD8 | 24 | 169 | 62 | 12 | 25 | nd | nd | nd | nd | - | - | nd | |
| ZKD15 | 581 | - | - | - | - | nd | nd | nd | nd | - | - | nd | |
| ZKD16 | 62 | 692 | 475 | 10 | 27 | nd | nd | nd | nd | - | - | nd | |
| ZKD17 | 14 | 93 | 32 | 7 | 12 | nd | nd | nd | nd | - | - | nd | |
| ZKD20 | 565 | - | - | 50 | - | nd | nd | nd | nd | - | - | nd | |
| ZKD21 | 53 | 63 | 189 | 13 | 17 | nd | nd | nd | nd | - | - | nd | |
| ZKA64 | 65 | - | - | - | - | - | - | - | - | 161 | 155 | - | |
| ZKA134 | 168 | - | - | - | - | - | - | - | - | 626 | 432 | nd | |
| ZKA190 | 113 | - | - | - | - | - | - | - | - | 444 | 12 | nd | |
| ZKA246 | 473 | - | - | - | - | - | - | - | - | 5974 | 243 | nd | |
| ZKA256 | 115 | - | - | - | - | - | - | - | - | 214 | 224 | nd | |
| ZKB31 | 73 | - | - | - | - | nd | nd | nd | nd | 18 | - | nd | |
| ZKB42 | 5561 | 7073 | 6485 | 12065 | 6884 | nd | nd | nd | nd | 5158 | - | nd | EDIII |
| ZKB50 | 653 | 10000 | - | - | - | nd | nd | nd | nd | - | - | nd | |
| ZKB85 | 953 | - | - | - | - | nd | nd | nd | nd | 2400 | 2387 | nd | |
| ZKB47 | 13 | - | - | - | - | nd | nd | nd | nd | 574 | - | nd | |
| ZKC6 | 8575 | - | - | - | - | nd | nd | nd | nd | 5533 | 32 | nd | |
| ZKC25 | 162 | 144 | 147 | 150 | 158 | nd | nd | nd | nd | 200 | - | nd | |
| ZKD18 | 17 | - | - | - | - | nd | nd | nd | nd | 12 | - | nd | |
| ZKA81 | - | - | - | - | - | nd | nd | nd | nd | - | 243 | nd | |
| ZKA144 | - | - | - | - | - | nd | nd | nd | nd | - | 48 | nd | |
| ZKA146 | - | - | - | - | - | nd | nd | nd | nd | - | 45 | nd | |
| ZKA155 | - | - | - | - | - | nd | nd | nd | nd | - | 99 | nd | |
| ZKA160 | - | - | - | - | - | nd | nd | nd | nd | - | 38 | 26 | |
| ZKA167 | - | - | - | - | - | nd | nd | nd | nd | - | 121 | nd | |
| ZKA169 | - | - | - | - | - | nd | nd | nd | nd | - | 321 | nd | |
| ZKA171 | - | - | - | - | - | nd | nd | nd | nd | - | 47 | nd | |
| ZKA172 | - | - | - | - | - | nd | nd | nd | nd | - | 9 | nd | |
| ZKA174 | - | - | - | - | - | nd | nd | nd | nd | - | 55 | - | |
| ZKA183 | - | - | - | - | - | nd | nd | nd | nd | - | 34 | nd | |
| ZKA185 | - | - | - | - | - | nd | nd | nd | nd | - | 13 | - | |
| ZKA189 | - | - | - | - | - | nd | nd | nd | nd | - | 273 | nd | |
| ZKA191 | - | - | - | - | - | nd | nd | nd | nd | - | 52 | nd | |
| ZKA195 | - | - | - | - | - | nd | nd | nd | nd | - | 33 | - | NNB |
| ZKA207 | - | - | - | - | - | nd | nd | nd | nd | - | 43 | nd | |
| ZKA215 | - | - | - | - | - | nd | nd | nd | nd | - | 26 | nd | |
| ZKA218 | - | - | - | - | - | nd | nd | nd | nd | - | 14 | nd | |
| ZKA228 | - | - | - | - | - | nd | nd | nd | nd | - | 36 | nd | |
| ZKA230 | - | - | - | - | - | nd | nd | nd | nd | - | 10 | nd | |
| ZKB75 | - | - | - | - | - | nd | nd | nd | nd | - | 190 | nd | |
| ZKB79 | - | - | - | - | - | nd | nd | nd | nd | - | 391 | nd | |
| ZKB83 | - | - | - | - | - | nd | nd | nd | nd | - | 59 | nd | |
| ZKC3 | - | - | - | - | - | nd | nd | nd | nd | - | 170 | nd | |
| ZKC8 | - | - | - | - | - | nd | nd | nd | nd | - | 762 | nd | |
| ZKC15 | - | - | - | - | - | nd | nd | nd | nd | - | 15 | nd | |
| ZKC18 | - | - | - | - | - | nd | nd | nd | nd | - | 662 | nd | |
| ZKD1 | - | - | - | - | - | nd | nd | nd | nd | - | 1141 | nd | |

Figure 1

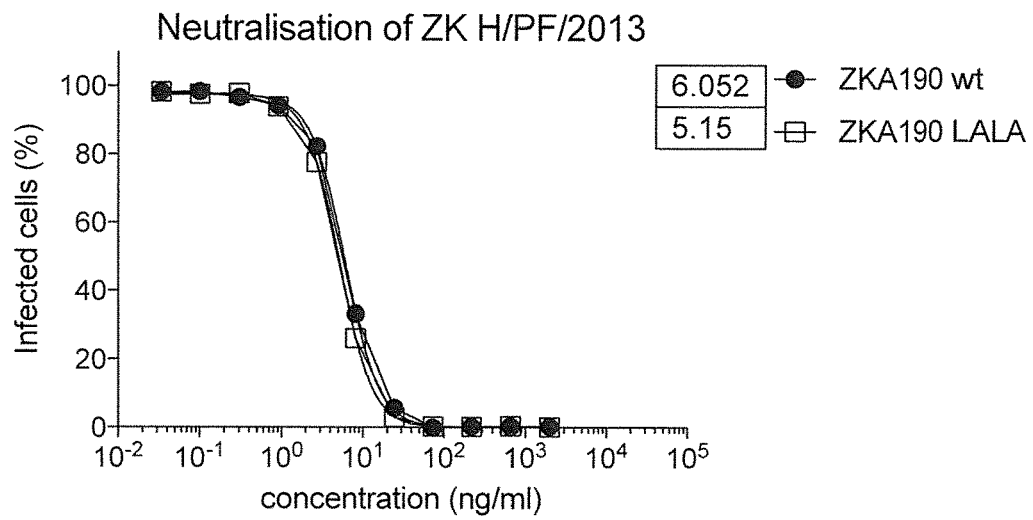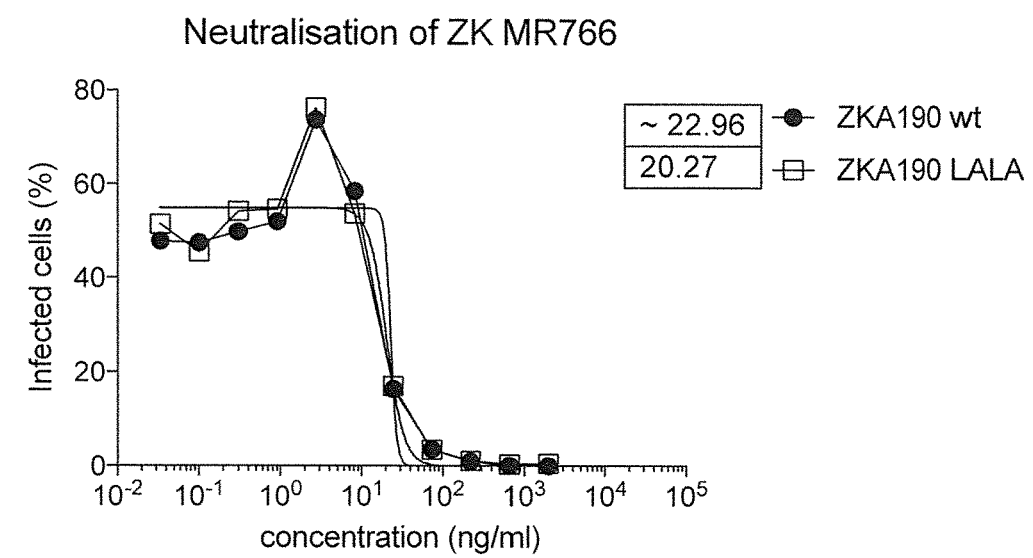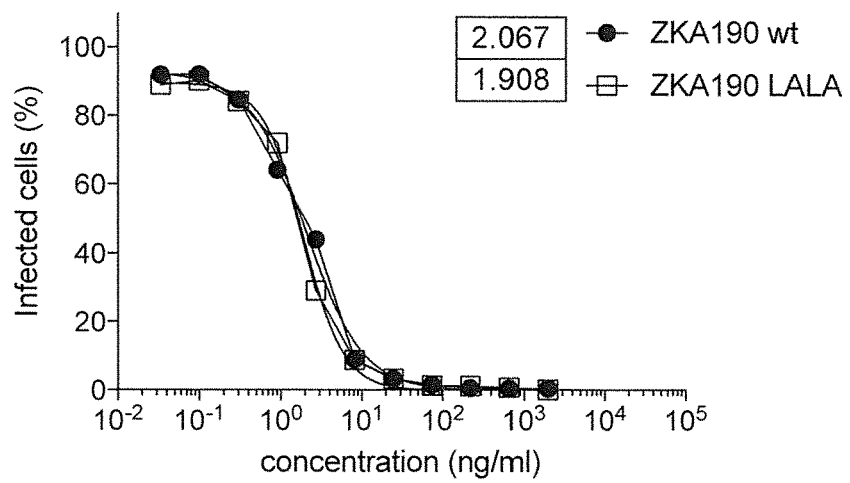
Figure 9

A

B

| ZIKV strain | IC50 (ng/ml) | |
|---|---|---|
| | ZKA190 | C8 |
| H/PF/2013 | 4,09 | 115,80 |
| MR766 | 8,37 | 1,67 |
| MRS-OPY | 0,65 | 23,48 |
| PV10552 | 1,09 | 34,60 |

C

| | ZKA190 | C8 |
|---|---|---|
| Number of values | 4 | 4 |
| | | |
| Minimum | 0,6484 | 1,665 |
| 25% Percentile | 0,7581 | 7,119 |
| Median | 2,586 | 29,04 |
| 75% Percentile | 7,302 | 95,5 |
| Maximum | 8,374 | 115,8 |
| | | |
| Mean | 3,549 | 43,89 |
| Std. Deviation | 3,561 | 49,86 |
| Std. Error of Mean | 1,781 | 24,93 |
| | | |
| Lower 95% CI of mean | -2,118 | -35,45 |
| Upper 95% CI of mean | 9,215 | 123,2 |
| | | |
| Coefficient of variation | 100,35% | 113,60% |
| | | |
| Geometric mean | 2,216 | 19,89 |
| Geometric SD factor | 3,246 | 5,977 |
| | | |
| Sum | 14,19 | 175,5 |

MULTISPECIFIC ANTIBODIES SPECIFICALLY BINDING TO ZIKA VIRUS EPITOPES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 470082_409USPC_SEQUENCE_LISTING.txt. The text file is 118 KB, was created on Feb. 20, 2020, and is being submitted electronically via EFS-Web.

The present invention relates to multispecific antibodies, and antigen binding fragments thereof, that bind specifically to distinct Zika virus (ZIKV) epitopes. Such antibodies potently neutralize infection of Zika virus (ZIKV) and minimize or abolish the generation of Zika virus escape mutants. The invention also relates to nucleic acids that encode such antibodies and antibody fragments. In addition, the invention relates to the use of the antibodies and antibody fragments of the invention in prevention and treatment of ZIKV infection.

Zika virus (ZIKV), a mosquito-borne flavivirus, is a public health emergency. ZIKV was first isolated from macaques in 1947 in the Zika forest in Uganda (G. W. A. Dick, S. F. Kitchen, A. J. Haddow, Zika virus. I. Isolations and serological specificity. *Trans. R. Soc. Trop. Med. Hyg.* 46, 509-520 (1952)) and the first human infection was reported in Nigeria in 1954 F. N. Macnamara, Zika virus: a report on three cases of human infection during an epidemic of jaundice in Nigeria. *Trans. R. Soc. Trop. Med. Hyg.* 48, 139-145 (1954)). Since then, ZIKV infections were sporadically reported in Africa and southeast Asia (D. Musso, Van Mai Cao-Lormeau, D. J. Gubler, Zika virus: following the path of dengue and chikungunya? *The Lancet.* 386, 243-244 (2015)), but epidemics were reported in Micronesia in 2007 (M. R. Duffy et al., Zika virus outbreak on Yap Island, Federated States of Micronesia. *N Engl J Med.* 360, 2536-2543 (2009)) and in French Polynesia in 2013-14, with the virus subsequently spreading to other countries in the Oceanian continent (V.-M. Cao-Lormeau, D. Musso, Emerging arboviruses in the Pacific. *Lancet.* 384, 1571-1572 (2014); D. Musso, E. J. Nilles, V.-M. Cao-Lormeau, Rapid spread of emerging Zika virus in the Pacific area. *Clin. Microbiol. Infect.* 20, 0595-6 (2014)). After its introduction into Brazil in 2015, ZIKV has spread rapidly and in February 2016 the World Health Organization (WHO) declared it a Public Health Emergency of International Concern (L. R. Baden, L. R. Petersen, D. J. Jamieson, A. M. Powers, M. A. Honein, Zika Virus. *N. Engl. J. Med.* 374, 1552-1563 (2016); A. S. Fauci, D. M. Morens, Zika Virus in the Americas—Yet Another Arbovirus Threat. *N Engl J Med,* 160113142101009 (2016); D. L. Heymann et al., Zika virus and microcephaly: why is this situation a PHEIC? *Lancet.* 387, 719-721 (2016)). The main route of ZIKV infection is through bites by *Aedes* mosquitos, but the virus may also be sexually (D. Musso et al., Potential sexual transmission of Zika virus. *Emerg Infect Dis.* 21, 359-361 (2015)) and vertically transmitted (J. Mlakar et al., Zika Virus Associated with Microcephaly. *N Engl J Med.* 374, 951-958 (2016)). While most of the ZIKV infections are asymptomatic or cause only mild symptoms, there is evidence that ZIKV infection can lead to neurological complications, such as Guillain-Barré Syndrome in adults (V.-M. Cao-Lormeau et al., Guillain-Barré Syndrome outbreak associated with Zika virus infection in French Polynesia: a case-control study. *Lancet.* 0 (2016), doi:10.1016/50140-6736(16)00562-6) and congenital birth defects including microcephaly in the developing fetus (G. Calvet, R. S. Aguiar, A. Melo, S. A. Sampaio, Detection and sequencing of Zika virus from amniotic fluid of fetuses with microcephaly in Brazil: a case study. *Lancet Infect Dis* (2016), doi:10.1016/s1473-3099(16)00095-5; J. Mlakar et al., Zika Virus Associated with Microcephaly. *N Engl J Med.* 374, 951-958 (2016); E. J. Rubin, M. F. Greene, L. R. Baden, Zika Virus and Microcephaly. *N Engl J Med* (2016), doi:10.1056/NEJMe1601862), likely through its ability to infect human neural progenitor cells (H. Tang et al., Zika Virus Infects Human Cortical Neural Progenitors and Attenuates Their Growth. *Stem Cell,* 1-5 (2016)).

ZIKV belongs to the genus flavivirus, which also includes the West Nile virus, dengue virus, tick-borne encephalitis virus, yellow fever virus, and several other viruses which may cause encephalitis. Flaviviruses are enveloped, with icosahedral and spherical geometries. The diameter is around 50 nm. Genomes are linear positive-sense RNA and non-segmented, around 10-11 kb in length. The genome of flaviviruses encodes 3 structural proteins (Capsid, prM, and Envelope) and 8 non-structural proteins (NS1, NS2A, NS2B, NS3, NS4A, NS4B, NS5 and NS5B).

While flavivirus envelope (E) proteins mediate fusion and are the main target of neutralizing antibodies, the non-structural protein 1 (NS1) is secreted by infected cells and is involved in immune evasion and pathogenesis (D. A. Muller, P. R. Young, The flavivirus NS1 protein: molecular and structural biology, immunology, role in pathogenesis and application as a diagnostic biomarker. *Antiviral Res.* 98, 192-208 (2013)). Two recent structural studies showed a high level of structural similarity between the E protein of ZIKV and that of other flaviviruses, such as dengue virus (DENV), yellow fever virus (YFV) and West Nile virus (WNV) but also revealed unique features that may be related to the ZIKV neurotropism (L. Dai et al., Structures of the Zika Virus Envelope Protein and Its Complex with a Flavivirus Broadly Protective Antibody. *Cell Host Microbe* (2016), doi:10.1016/j.chom.2016.04.013; D. Sirohi et al., The 3.8 Å resolution cryo-EM structure of Zika virus. *Science,* aaf5316 (2016)). Similarly, the structural analysis of ZIKV NS1 revealed conserved features with NS1 of other flaviviruses although with different electrostatic characteristics (J. Kim et al., Zika virus NS1 structure reveals diversity of electrostatic surfaces among flaviviruses, 1-6 (2016)).

A phenomenon that is characteristic of certain flaviviruses is the disease-enhancing activity of cross-reactive antibodies elicited by previous infection by heterologous viruses. In the case of Dengue virus (DENV), for which 4 serotypes are known, there is epidemiological evidence that a primary infection protects from reinfection with the same serotype, but represents a risk factor for the development of severe disease upon reinfection with a different serotype (S. B. Halstead, Dengue Antibody-Dependent Enhancement: Knowns and Unknowns. *Microbiol Spectr.* 2, 249-271 (2014)). The exacerbated disease is triggered by E and prM-specific antibodies that fail to neutralize the incoming virus but instead enhance its capture by Fc receptor-expressing (FcR$^+$) cells, leading to enhanced viral replication and activation of cross-reactive memory T cells. The resulting cytokine storm is thought to be the basis of the most severe form of disease known as dengue hemorragic fever/dengue shock syndrome (S. B. Halstead, Neutralization and antibody-dependent enhancement of dengue viruses. *Adv Virus Res.* 60, 421-467 (2003); G. Screaton, J. Mongkolsapaya, S.

Yacoub, C. Roberts, New insights into the immunopathology and control of dengue virus infection. *Nat Rev Immunol.* 15, 745-759 (2015). The role of antibodies in severe dengue is supported by studies showing that waning levels of maternal antibodies in infants represent a higher risk for development of severe dengue disease (S. B. Halstead, Neutralization and antibody-dependent enhancement of dengue viruses. *Adv Virus Res.* 60, 421-467 (2003); S. B. Halstead et al., Dengue hemorrhagic fever in infants: research opportunities ignored. *Emerging Infect Di s.* 8, 1474-1479 (2002); T. H. Nguyen et al., Dengue hemorrhagic fever in infants: a study of clinical and cytokine profiles. *J Infect Dis.* 189, 221-232 (2004); A. L. Rothman, Dengue: defining protective versus pathologic immunity. *J Clin Invest.* 113, 946-951 (2004)).

Recently, it was shown that most antibodies that reacted to DENV envelope protein also bound to ZIKV, but those that recognize the major linear fusion-loop epitope (FLE) did not neutralize ZIKV and instead promoted antibody-dependent enhancement (ADE) of ZIKV infection (Dejnirattisai W, Supasa P, Wongwiwat W, Rouvinski A, Barba-Spaeth G, Duangchinda T, Sakuntabhai A, Cao-Lormeau V M, Malasit P, Rey F A, Mongkolsapaya J, Screaton G R: Dengue virus sero-cross-reactivity drives antibody-dependent enhancement of infection with zika virus. Nat Immunol. 2016 Jun. 23. doi: 10.1038/ni.3515. [Epub ahead of print]).

Moreover, organisms with high rates of mutations, such as various viruses, for example Zika virus, often rely on so-called "mutational escape" as a mechanism to avoid destruction by host cells. Namely, a virus can defend itself from host immune responses by making mutations in its genotype and phenotype (referred to as "escape mutations"). Accordingly, the generation of escape mutants (i.e., viruses carrying escape mutations) can reduce the efficacy of antibody medications.

In view of the above, it is an object of the present invention to provide multispecific antibodies, which potently neutralize Zika virus (ZIKV). Such antibodies do preferably not contribute to antibody-dependent enhancement (ADE) of Zika virus infection. It is also an object of the present invention to provide highly specific anti-ZIKV antibodies eliminating or minimizing generation of ZIKV escape mutants.

The object underlying the present invention is solved by the claimed subject matter.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Further, the term "antibody" as used herein includes both antibodies and antigen binding fragments thereof.

As used herein, the term "antibody" encompasses various forms of antibodies including, without being limited to, whole antibodies, antibody fragments, in particular antigen binding fragments, human antibodies, chimeric antibodies, humanized antibodies, recombinant antibodies and genetically engineered antibodies (variant or mutant antibodies) as long as the characteristic properties according to the invention are retained. Monoclonal antibodies are preferred and especially preferred are monoclonal antibodies with human CDRs or human variable regions. In particular, antibodies, or antigen binding fragments thereof, according to the present invention are preferably derived from human antibodies (i.e., they comprise CDRs and/or variable regions of human antibodies). More preferably, antibodies, or antigen binding fragments thereof, according to the present invention, also comprise constant regions of human antibodies. Most preferably, all constant and variable regions of the antibodies, or antigen binding fragments thereof, according to the present invention are of human origin, i.e. human constant and human variable regions, such as constant and variable regions of a human antibody.

Human antibodies are well-known in the state of the art (van Dijk, M. A., and van de Winkel, J. G., *Curr. Opin. Chem. Biol.* 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., *Proc. Natl. Acad. Sci. USA* 90 (1993) 2551-2555; Jakobovits, A., et al., *Nature* 362 (1993) 255-258; Bruggemann, M., et al., *Year Immunol.* 7 (1993) 3340). Human antibodies can also be produced in phage display libraries (Hoogenboom, H. R., and Winter, G., *J. Mol. Biol.* 227 (1992) 381-388; Marks, J. D., et al., *J. Mol. Biol.* 222 (1991) 581-597). The techniques of Cole et al. and Boerner et al. are also available for the preparation of human monoclonal antibodies (Cole et al., *Monoclonal Antibodies and Cancer Therapy*, Alan R. Liss, p. 77 (1985); and Boerner, P., et al., *J. Immunol.* 147 (1991) 86-95). Preferably, human monoclonal antibodies are prepared by using improved EBV-B cell immortalization as described in Traggiai E, Becker S, Subbarao K, Kolesnikova L, Uematsu Y, Gismondo M R, Murphy B R, Rappuoli R, Lanzavecchia A. (2004): An efficient method to make human monoclonal antibodies from memory B cells: potent neutralization of SARS coronavirus. Nat Med. 10(8):871-5. The term "human antibody" as used herein also comprises such antibodies which are modified, e.g. in a variable region or in a constant region, to generate the properties according to the invention as described herein.

Antibodies of the invention can be of any isotype (e.g., IgA, IgG, IgM i.e. an α, γ or μ heavy chain), but will preferably be IgG. Within the IgG isotype, antibodies may be IgG1, IgG2, IgG3 or IgG4 subclass, whereby IgG1 is preferred. Antibodies of the invention may have a κ or a λ light chain.

The antibody according to the present invention, or the antigen binding fragment thereof, may be a purified antibody or a single chain antibody, such as a bispecific single-chain Fv fragment (scFv).

The invention also provides fragments of the antibodies of the invention, particularly fragments that retain the antigen-binding activity of the antibodies. Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies. Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. For example, the invention includes a bispecific scFv comprising the CDRs from an antibody of the invention. Antibody fragments of the invention may impart monovalent or multivalent interactions and be contained in a variety of structures. For instance, scFv molecules may be synthesized to create a trivalent "triabody" or a tetravalent "tetrabody." The scFv molecules may include a domain of the Fc region resulting in bivalent minibodies.

Antibodies according to the present invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies according to the present invention may be immunogenic in human and/or in non-human (or heterologous) hosts e.g., in mice. For example, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

Doses are often expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned.

The term "specifically binding" and similar reference does not encompass non-specific sticking.

The term "vaccine" as used herein is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response. In particular, an "antigen" or an "immunogen" refers typically to a substance which may be recognized by the immune system, preferably by the adaptive immune system, and which is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

As used herein, "sequence variant" (also referred to as "variant") refers to any alteration in a reference sequence, whereby a reference sequence is any of the sequences listed in the "Tables of Sequences and SEQ ID Numbers" (sequence listing), i.e. SEQ ID NO: 1 to SEQ ID NO: 273. Thus, the term "sequence variant" includes nucleotide sequence variants and amino acid sequence variants. Of note, the sequence variants referred to herein are in particular functional sequence variants, i.e. sequence variants maintaining the biological function of, for example, the antibody. In the context of the present invention such a maintained biological function is preferably the neutralization of ZIKV infection and/or the binding of the antibody to the ZIKV E protein. Preferred sequence variants are thus functional sequence variants having at least 70%, at least 75%, at least 80%, at least 85%, at least 88%, at least 90%, at least 92%, at least 95%, at least 96%, at least 97%, at least 98% or at least 99% sequence identity to a reference sequence. The phrase "functional sequence variant thereof having at least 70%, at least 75%, at least 80%, at least 85%, at least 88%, at least 90%, at least 92%, at least 95%, at least 96%, at least 97%, at least 98% or at least 99% sequence identity", as used herein, means (i) that the sequence variant is functional as described herein and (ii) the higher the % sequence identity, the more preferred the sequence variant. In other words, the phrase "functional sequence variant thereof having at least 70%, at least 75%, at least 80%, at least 85%, at least 88%, at least 90%, at least 92%, at least 95%, at least 96%, at least 97%, at least 98% or at least 99% sequence identity", means in particular that the functional sequence variant has at least 70% sequence identity, preferably at least 75% sequence identity, preferably at least 80% sequence identity, more preferably at least 85% sequence identity, more preferably at least 88% sequence identity, even more preferably at least 90% sequence identity, even more preferably at least 92% sequence identity, still more preferably at least 95% sequence identity, still more preferably at least 96% sequence identity, particularly preferably at least 97% sequence identity, particularly preferably at least 98% sequence identity and most preferably at least 99% sequence identity to the respective reference sequence.

The term "sequence variant" includes in particular such variants that comprise mutations and/or substitutions in comparison to the reference sequence. Exemplary variants of an Fc moiety sequence include, but are not limited to, those that have an L to A substitution at position CH2 4, CH2 5, or both.

Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information; http://www.ncbi.nlm.nih.gov/) [Blosum 62 matrix; gap open penalty=11 and gap extension penalty=1].

As used herein, a "nucleotide sequence variant" has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "nucleotide sequence variant" can either result in a change in the respective reference amino acid sequence, i.e. in an "amino acid sequence variant" or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 80%, preferably at least 90%, more preferably at least 95% sequence identical to the reference sequence.

An "amino acid sequence variant" has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 80% identical to the reference sequence, preferably, at least 90% identical, more preferably at least 95% identical, most preferably at least 99% identical to the reference sequence. Variant sequences which are at least 90% identical have no more than 10 alterations, i.e. any combination of deletions, insertions or substitutions, per 100 amino acids of the reference sequence.

While it is possible to have non-conservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydoxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Importantly, the alterations in the sequence variants do not abolish the functionality of the respective reference sequence, in the present case, e.g., the functionality of a sequence of an antibody, or antigen binding fragment thereof, to bind to the same epitope and/or to sufficiently neutralize infection of ZIKV. Guidance in determining which nucleotides and amino acid residues, respectively, may be substituted, inserted or deleted without abolishing such functionality are found by using computer programs well known in the art.

As used herein, a nucleic acid sequence or an amino acid sequence "derived from" a designated nucleic acid, peptide, polypeptide or protein refers to the origin of the nucleic acid, peptide, polypeptide or protein. Preferably, the nucleic acid sequence or amino acid sequence which is derived from a particular sequence has an amino acid sequence that is essentially identical to that sequence or a portion thereof, from which it is derived, whereby "essentially identical" includes sequence variants as defined above. Preferably, the nucleic acid sequence or amino acid sequence which is derived from a particular peptide or protein, is derived from the corresponding domain in the particular peptide or protein. Thereby, "corresponding" refers in particular to the same functionality. For example, an "extracellular domain" corresponds to another "extracellular domain" (of another protein), or a "transmembrane domain" corresponds to another "transmembrane domain" (of another protein). "Corresponding" parts of peptides, proteins and nucleic acids are thus easily identifiable to one of ordinary skill in the art. Likewise, sequences "derived from" other sequence are usually easily identifiable to one of ordinary skill in the art as having its origin in the sequence.

Preferably, a nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein one or more amino acid residues may be substituted with other amino acid residues or one or more amino acid residue insertions or deletions may occur.

As used herein, the term "mutation" relates to a change in the nucleic acid sequence and/or in the amino acid sequence in comparison to a reference sequence, e.g. a corresponding genomic sequence. A mutation, e.g. in comparison to a genomic sequence, may be, for example, a (naturally occurring) somatic mutation, a spontaneous mutation, an induced mutation, e.g. induced by enzymes, chemicals or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making a mutation, e.g. in a nucleic acid sequence or in an amino acid sequence. A mutation includes substitution, deletion and insertion of one or more nucleotides or amino acids as well as inversion of several successive nucleotides or amino acids. To achieve a mutation in an amino acid sequence, preferably a mutation may be introduced into the nucleotide sequence encoding said amino acid sequence in order to express a (recombinant) mutated polypeptide. A mutation may be achieved e.g., by altering, e.g., by site-directed mutagenesis, a codon of a nucleic acid molecule encoding one amino acid to result in a codon encoding a different amino acid, or by synthesizing a sequence variant, e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Multispecific Antibodies Binding to Distinct Zika Virus Epitopes

The present invention is based, amongst other findings, on the discovery that multispecific antibodies, and antigen-binding fragments thereof, that bind specifically to distinct Zika virus epitopes. Such antibodies minimize or eliminate the generation of Zika virus escape mutants. In particular, there is currently no prevention/treatment available for Zika virus infection. The antibodies according to the present invention are highly effective in preventing as well as treating or attenuating Zika virus infection. Moreover, due to the specificity of the antibodies for Zika virus, they do not elicit ADE, but rather block ADE.

In a first aspect the present invention provides an isolated multispecific antibody, or an antigen binding fragment thereof, that specifically binds to distinct Zika virus epitopes. In other words, the present invention provides an isolated multispecific antibody, or an antigen binding fragment thereof, that comprises at least two epitope binding sites, which specifically bind to distinct Zika virus epitopes.

Importantly, in contrast to conventional ("ordinary") antibodies exhibiting just one single specificity, multispecific antibodies are able to bind to at least two different epitopes. In the present case, the multispecific antibodies specifically bind to (at least two) distinct Zika virus epitopes.

Accordingly, as used herein, the term "multispecific" refers to the ability to bind to at least two different epitopes, e.g. on different antigens, such as different Zika virus (ZIKV) proteins or on the same antigen, e.g. the same ZIKV protein. Preferably, the multispecific antibodies, or the antigen binding fragments thereof, according to the present invention bind to at least two different epitopes on the same ZIKV protein, most preferably to at least two different epitopes on Zika virus envelope (E) protein.

Preferably, the antibody, or antigen binding fragment thereof, according to the present invention is bispecific, trispecific, tetraspecific or pentaspecific, more preferably the antibody, or the antigen binding fragment thereof, is bispecific, trispecific or tetraspecific, even more preferably the antibody, or the antigen binding fragment thereof, is bispecific or trispecific, and most preferably the antibody, or the antigen binding fragment thereof, is bispecific.

As used herein, terms like "bispecific", "trispecific", "tetraspecific" etc. refer to the number of different epitopes to which the antibody, or the antigen binding fragment thereof, can bind to. For example, conventional monospecific IgG-type antibodies have two identical epitope binding sites (paratopes) and can, thus, only bind to identical epitopes (but not to different epitopes). A multispecific antibody, in contrast, has at least two different types of epitope binding sites (paratopes) and can, thus, bind to at least two different epitopes. As used herein, the term "paratope" refers to an epitope-binding site of the antibody. Accordingly, the terms "paratope" and "epitope binding site" are used herein interchangeably. Moreover, a single "specificity" may refer to one, two, three or more identical paratopes in a single antibody. The actual number of paratopes in one single antibody molecule is referred to as "valency". Preferably, the antibody, or antigen binding fragment thereof, according to the present invention is bivalent, trivalent, tetravalent, hexavalent or octavalent, more preferably, the antibody, or the antigen binding fragment thereof, is bivalent or tetravalent, most preferably, the antibody, or the antigen binding fragment thereof, is tetravalent.

Most preferably, the antibody, or antigen binding fragment thereof, according to the present invention is bispecific and tetravalent.

It is also preferred that the antibody, or antigen binding fragment thereof, according to the present invention comprises exactly two (identical) copies of each of the distinct epitope binding sites specifically binding to at least two distinct, Zika virus epitopes.

For example, a single native IgG antibody is monospecific and bivalent, since it has two identical paratopes (two identical copies). However, a multispecific antibody comprises at least two (different) paratopes. Thus, the term "multispecific" refers to antibodies, and antigen binding fragments, having more than one paratope and the ability to bind to two or more different epitopes. The term "multispecific antibodies/antigen binding fragments" comprises in particular bispecific antibodies as defined above, but typically also protein, e.g. antibody, scaffolds, which bind in particular to three or more different epitopes, i.e. antibodies having three or more paratopes.

In particular, the multispecific antibody, or the antigen binding fragment thereof, may comprise two or more paratopes, wherein some paratopes may be identical so that all paratopes of the antibody belong to at least two different types of paratopes and, hence, the antibody has at least two specificities. For example, the multispecific antibody or antigen binding fragment thereof according to the present invention may comprise four paratopes, wherein each two paratopes are identical (i.e. have the same specificity) and, thus, the antibody or fragment thereof is bispecific and tetravalent (two identical paratopes for each of the two specificities). Thus, "one specificity" refers in particular to one or more paratopes exhibiting the same specificity (which typically means that such one or more paratopes are identical) and, thus, "two specificities" may be realized by two, three, four five, six or more paratopes as long as they refer to only two specificities. For example, a multispecific antibody may comprise one single paratope for each (of the at least two) specificity, i.e. the multispecific antibody comprises in total at least two paratopes. For example, a bispecific antibody comprises one single paratope for each of the two specificities, i.e. the antibody comprises in total two paratopes. Most preferably, the antibody comprises exactly two (identical) paratopes for each of the two specificities, i.e. the antibody comprises in total four paratopes. Alternatively, the antibody may comprise three (identical) paratopes for each of the two specificities, i.e. the antibody comprises in total six paratopes.

As used herein, the term "antigen" refers to any structural substance which serves as a target for the receptors of an adaptive immune response, in particular as a target for antibodies, T cell receptors, and/or B cell receptors. An "epitope", also known as "antigenic determinant", is the part (or fragment) of an antigen that is recognized by the immune system, in particular by antibodies, T cell receptors, and/or B cell receptors. Thus, one antigen has at least one epitope, i.e. a single antigen has one or more epitopes. An antigen may be (i) a peptide, a polypeptide, or a protein, (ii) a polysaccharide, (iii) a lipid, (iv) a lipoprotein or a lipopeptide, (v) a glycolipid, (vi) a nucleic acid, or (vii) a small molecule drug or a toxin. Thus, an antigen may be a peptide, a protein, a polysaccharide, a lipid, a combination thereof including lipoproteins and glycolipids, a nucleic acid (e.g. DNA, siRNA, shRNA, antisense oligonucleotides, decoy DNA, plasmid), or a small molecule drug (e.g. cyclosporine A, paclitaxel, doxorubicin, methotrexate, 5-aminolevulinic acid), or any combination thereof. Preferably, the antigen is selected from (i) a peptide, a polypeptide, or a protein, (ii) a polysaccharide, (iii) a lipid, (iv) a lipoprotein or a lipopeptide and (v) a glycolipid; more preferably, the antigen is a peptide, a polypeptide, or a protein.

The antibody, or the antigen binding fragment thereof, according to the present invention, binds to at least two different Zika virus epitopes. The at least to different Zika virus epitopes may be located on different Zika virus antigens, such as different Zika virus (ZIKV) proteins, or on the same Zika virus antigen, e.g. on the same ZIKV protein. Preferred examples of ZIKV antigens/proteins include capsid, prM, envelope and the non-structural proteins NS1, NS2A, NS2B, NS3, NS4A, NS4B, NS5 and NS5B. Most preferably, the antibody, or the antigen binding fragment thereof, according to the present invention, binds to (at least two) distinct epitopes on Zika virus envelope protein (ZIKV E protein). In other words, most preferably the antibody, or the antigen binding fragment thereof, according to the present invention comprises at least two epitope binding sites, which specifically bind to distinct epitopes on Zika virus envelope protein (ZIKV E protein). ZIKV includes a nucleocapsid core, which comprising single-stranded RNA wrapped by core proteins. The nucleocapsid core is encapsulated by a lipid bilayer membrane with "membrane proteins" and "envelope proteins". ZIKV envelope protein (E protein) is the dominant antigen. The structure and domains of ZIKV E protein is described, for example, in Dai L, Song J, Lu X, Deng Y Q, Musyoki A M, Cheng H, Zhang Y, Yuan Y, Song H, Haywood J, Xiao H, Yan J, Shi Y, Qin C F, Qi J, Gao G F. Structures of the Zika Virus Envelope Protein and Its Complex with a Flavivirus Broadly Protective Antibody. Cell Host Microbe. 2016 May 11; 19(5):696-704.

Preferably, the (at least two) distinct Zika virus epitopes, to which the antibody, or the antigen binding fragment thereof, according to the present invention, binds to, are non-overlapping epitopes. In particular, the amino acids forming the first Zika virus epitope, to which the antibody, or the antigen binding fragment thereof, according to the present invention, binds to, are distinct from the amino acids forming the second Zika virus epitope, to which the antibody, or the antigen binding fragment thereof, according to the present invention, binds to.

The antibody, or the antigen binding fragment thereof, according to the present invention may be of any antibody format. In particular, multispecific antibodies preferably encompass "whole" antibodies, such as whole IgG- or IgG-like molecules, while antigen binding fragments in the context of the present invention preferably refer to small recombinant formats, such as a format based on bispecific T-cell engagers (BiTE®s; except that in the context of the present invention both specificities target Zika virus, accordingly, the T-cell specificity of BiTE®s may be replaced by a (second) ZIKV specificity), tandem single chain variable fragment molecules (taFvs), diabodies (Dbs), single chain diabodies (scDbs) and various other derivatives of these (cf bispecific antibody formats as described by Byrne H. et al. (2013) Trends Biotech, 31 (11): 621-632 with FIG. 2 showing various bispecific antibody formats; Weidle U. H. et al. (2013) Cancer Genomics and Proteomics 10: 1-18, in particular FIG. 1 showing various bispecific antibody formats; and Chan, A. C. and Carter, P. J. (2010) Nat Rev Immu 10: 301-316 with FIG. 3 showing various bispecific antibody formats). Examples of bispecific antibody formats include, but are not limited to, Fabs-in-tandem-Ig, DVD-Ig, quadroma, chemically coupled Fab (fragment antigen binding), and BiTE® (bispecific T cell engager). In one embodiment of the present invention the antibody is preferably a Fabs-in-tandem-Ig (FIT-Ig) or a DVD-Ig.

Thus, the antibody, or the antigen binding fragment thereof, according to the present invention may be selected from the group comprising Fabs-in-tandem-Ig (FIT-Ig); DVD-Ig; hybrid hybridoma (quadroma); Multispecific anticalin platform (Pieris); Diabodies; Single chain diabodies; Tandem single chain Fv fragments; TandAbs, Trispecific Abs (Affimed) (105-110 kDa); Darts (dual affinity retargeting; Macrogenics); Bispecific Xmabs (Xencor); Bispecific T cell engagers (Bites; Amgen; 55 kDa); Triplebodies; Tribody=Fab-scFv Fusion Protein (CreativeBiolabs) multifunctional recombinant antibody derivates (110 kDa); Duobody platform (Genmab); Dock and lock platform; Knob into hole (KIH) platform; Humanized bispecific IgG antibody (REGN1979) (Regeneron); Mab$^2$ bispecific antibodies (F-Star); DVD-Ig=dual variable domain immunoglobulin (Abbott); kappa-lambda bodies; TBTI=tetravalent bispecific tandem Ig; and CrossMab.

The antibody, or the antigen binding fragment thereof, according to the present invention may be selected from bispecific IgG-like antibodies (BsIgG) comprising CrossMab; DAF (two-in-one); DAF (four-in-one); Duta-Mab; DT-IgG; Knobs-in-holes common LC; Knobs-in-holes assembly; Charge pair; Fab-arm exchange; SEEDbody; Triomab; LUZ-Y; Fcab; κλ-body; and Orthogonal Fab. These bispecific antibody formats are shown and described for example in Spiess C., Zhai Q. and Carter P. J. (2015) Molecular Immunology 67: 95-106, in particular FIG. 1 and corresponding description, e.g. p. 95-101.

Preferably, the antibody, or the antigen binding fragment thereof, according to the present invention may be selected from bispecific antibody fragments comprising Nanobody; Nanobody-HAS; BiTE; Diabody; DART; TandAb; scDiabody; sc-Diabody-CH3; Diabody-CH3; Triple Body; Miniantibody; Minibody; TriBi minibody; scFv-CH3 KIH; Fab-scFv; scFv-CH-CL-scFv; F(ab')2; F(ab')2-scFv2; scFv-KIH; Fab-scFv-Fc; Tetravalent HCAb; scDiabody-Fc; Diabody-Fc; Tandem scFv-Fc; and Intrabody. These bispecific antibody formats are shown and described for example in Spiess C., Zhai Q. and Carter P. J. (2015) Molecular Immunology 67: 95-106, in particular FIG. 1 and corresponding description, e.g. p. 95-101.

More preferably, the antibody, or the antigen binding fragment thereof, according to the present invention may be selected from IgG-appended antibodies with an additional antigen-binding moiety comprising DVD-IgG; IgG(H)-scFv; scFv-(H)IgG; IgG(L)-scFv; scFV-(L)IgG; IgG(L,H)-Fv; IgG(H)-V; V(H)-IgG; IgG(L)-V; V(L)-IgG; KIH IgG-scFab; 2scFv-IgG; IgG-2scFv; scFv4-Ig; scFv4-Ig; Zybody; and DVI-IgG (four-in-one). These bispecific antibody formats are shown and described for example in Spiess C., Zhai Q. and Carter P. J. (2015) Molecular Immunology 67: 95-106, in particular FIG. 1 and corresponding description, e.g. p. 95-101. Of those antibody formats DVD-Ig (dual variable domain immunoglobulin (Abbott)) is even more preferred. This antibody format is described in detail, for example, in Wu C, Ying H, Grinnell C, Bryant S, Miller R, Clabbers A, Bose S, McCarthy D, Zhu R R, Santora L, Davis-Taber R, Kunes Y, Fung E, Schwartz A, Sakorafas P, Gu J, Tarcsa E, Murtaza A, Ghayur T. Simultaneous targeting of multiple disease mediators by a dual-variable-domain immunoglobulin. Nat Biotechnol. 2007 November; 25(11): 1290-7; or in DiGiammarino E, Ghayur T, Liu J. Design and generation of DVD-Ig™ molecules for dual-specific targeting. Methods Mol Biol. 2012; 899:145-56.

Most preferably, the antibody, or the antigen binding fragment thereof, according to the present invention is an IgG-appended antibody of the Fabs-in-tandem-Ig (FIT-Ig) format. In others words, the antibody, or the antigen binding fragment thereof, according to the present invention is most preferably of the Fabs-in-tandem-Ig (FIT-Ig) format. The Fabs-in-tandem-Ig (FIT-Ig) format is described in detail, for example, in WO 2015/103072 A1, which is incorporated by reference herein in its entirety, or in Gong S, Ren F, Wu D, Wu X, Wu C: Fabs-in-tandem immunoglobulin is a novel and versatile bispecific design for engaging multiple therapeutic targets. MAbs 2017. Similar to DVD-Ig, also FIT-Ig is a bispecific tetravalent symmetric format. FIT-Ig may be produced using three polypeptides: Polypeptide 1 usually comprises the light chain of the outer Fab fused, preferably without linkers, to the N-terminal region of the inner Fab heavy chain. Polypeptide 2 usually comprises the heavy chain variable and CH1 regions of the outer Fab, and polypeptide 3 usually comprises by the light chain of the inner Fab. Accordingly, an antibody of the FIT-Ig format usually comprises an "inner Fab" and an "outer Fab".

Preferably, the antibody according to the present invention, or the antigen-binding fragment thereof, neutralizes Zika virus infection. In other words, the antibody, or the antigen binding fragment thereof, according to the present invention, reduces preferably viral infectivity of Zika virus.

To study and quantitate virus infectivity (or "neutralization") in the laboratory the person skilled in the art knows various standard "neutralization assays". For a neutralization assay animal viruses are typically propagated in cells and/or cell lines. In the context of the present invention a neutralization assay is preferred, wherein cultured cells are incubated with a fixed amount of Zika virus (ZIKV) in the presence (or absence) of the antibody to be tested. As a readout for example flow cytometry may be used. Alternatively, also other readouts are conceivable, such as determining the amount of ZIKV non-structural proteins (such as ZIKV NS1) secreted into culture supernatant. For example, a ZIKV nonstructural protein 1 (NS1) antigen capture enzyme-linked immunosorbent assay (ELISA)-based tissue culture infectious dose-50 (TCID50) test (TCID50-ELISA) may be used as an alternative to the standard plaque assay for titrating Zika virus—in a similar manner as described for dengue virus (DENV) by Li J, Hu D-M, Ding X-X, Chen Y, Pan Y-X, Qiu L-W, Che X-Y: Enzyme-linked immunosorbent assay-format tissue culture infectious dose-50 test for titrating dengue virus. PLoS ONE 2011, 6:e22553. In such an assay for example the ZIKV NS1-binding antibodies as described in the present application may be advantageously used.

In a preferred embodiment of a ZIKV neutralization assay, cultured cells, for example Vero cells, are incubated with a fixed amount of ZIKV in the presence or absence of the antibody to be tested, for example for about four days. After incubation, cells may be washed and further cultivated. To measure virus infectivity, flow cytometry may be used. To this end, cells may be fixed, e.g. with 2% formaldehyde, permeabilizes, e.g. in PBS (phosphate buffered saline) 1% FCS (fetal calf serum) 0.5% saponin, and stained, e.g. with mouse antibody 4G2. Cells may then be incubated with a goat anti-mouse IgG conjugated to a dye, such as Alexa Fluor488 and analyzed by flow cytometry. Alternatively, viable cells may be detected by flow cytometry using for example the WST-1 reagent (Roche). A preferred ZIKV strain to be used in such a neutralization assay is ZIKV H/PF/2013.

The antibody and antigen binding fragment of the invention have high neutralizing potency. The concentration of the antibody required for 50% neutralization of Zika virus ($IC_{50}$) as compared to no-antibody controls, is, for example, up to about 3 µg/ml or up to about 1 µg/ml. Preferably, the concentration of the antibody of the invention required for 50% neutralization of ZIKV ($IC_{50}$) is up to about 500 ng/ml, more preferably the concentration of the antibody of the invention required for 50% neutralization of ZIKV ($IC_{50}$) is up to about 250 ng/ml, even more preferably the concentration of the antibody of the invention required for 50% neutralization of ZIKV ($IC_{50}$) is up to about 150 ng/ml. Most preferably, the concentration of the antibody of the invention required for 50% neutralization of ZIKV ($IC_{50}$) is about 100 ng/ml or less, e.g. about 90 ng/ml or less, about 80 ng/ml or less, about 70 ng/ml or less, about 60 ng/ml or less, about 50 ng/ml or less, about 45 ng/ml or less, about 40 ng/ml or less, about 35 ng/ml or less, about 30 ng/ml or less, about 25 ng/ml or less, about 20 ng/ml or less or, particularly preferably, about 15 ng/ml or less. In particular, the concentration of the antibody of the invention required for 50% neutralization of ZIKV ($IC_{50}$) is preferably about 50 ng/ml or less. This means that only low concentrations of the antibody are required for 50% neutralization of ZIKV. The concentration of the antibody of the invention required for 50% neutralization of ZIKV ($IC_{50}$) can be measured using standard neutralization assays as known to one of skill in the art or, in particular, as described above.

In general, binding of an antibody may be assessed by use of a standard ELISA (enzyme-linked immunosorbent assay), which is well-known to the skilled person. An exemplary standard ELISA may be performed as follows: ELISA plates may be coated (e.g., overnight at 4° C.) with a sufficient amount (e.g., 1 □g/ml) of the protein/complex/particle to which binding of the antibody is to be tested (for example, for DENV binding as outlined below, DENV E proteins and/or DENV VLPs are used), e.g. in PBS. Plates may then be blocked, e.g. with a 1% w/v solution of Bovine Serum Albumin (BSA) in PBS, and incubated with the antibody to be tested (e.g. for about 1.5 hours at room temperature). After washing, antibody binding can be revealed, e.g. using goat anti-human IgG coupled to alkaline phosphatase. Plates may then be washed, the required substrate (e.g., p-NPP) may be added and plates may be read, e.g. at 405 nm. The relative affinities of antibody binding may be determined by measuring the concentration of mAb ($EC_{50}$) required to achieve 50% maximal binding at saturation. The $EC_{50}$ values may be calculated by interpolation of binding curves fitted with a four-parameter nonlinear regression with a variable slope.

Preferably, the antibody, or an antigen binding fragment thereof, according to the present invention does essentially not bind to Dengue virus-like particles and/or to Dengue envelope protein. More preferably, the antibody, or an antigen binding fragment thereof, according to the present invention does essentially not bind to Dengue virus-like particles and/or to Dengue envelope protein of any of the four DENV serotypes DENV1, DENV2, DENV3 and DENV4. Thereby "essentially not binding" means that for the antibody, or an antigen binding fragment thereof, no $EC_{50}$-value up to $10^2$ ng/ml, preferably up to $10^3$ ng/ml, more preferably up to $5*10^3$ ng/ml, even more preferably up to $8*10^3$ ng/ml, and most preferably up to $10^4$ ng/ml can be determined in a standard ELISA to Dengue virus-like particles (DENV VLP) and/or to Dengue envelope protein (DENV E protein). In other words, the concentration of the antibody, or an antigen binding fragment thereof, required to achieve 50% maximal binding at saturation ($EC_{50}$) to Dengue virus-like particles (DENV VLP) and/or to Dengue envelope protein (DENV E protein) in a standard ELISA is typically more than $10^2$ ng/ml, preferably more than $10^3$ ng/ml, more preferably more than $5*10^3$ ng/ml, even more preferably more than $8*10^3$ ng/ml, and most preferably more than $10^4$ ng/ml.

Preferably, the antibody, or an antigen binding fragment thereof, according to the present invention does not contribute to antibody-dependent enhancement (ADE) of Zika virus infection. More preferably, the antibody, or an antigen binding fragment thereof, according to the present invention blocks antibody-dependent enhancement (ADE) of Zika virus infection.

ADE may be assessed by a flow-cytometry based assay using, for example cultured cells or cell lines, such as K562 cells. For example, the antibodies to be tested and ZIKV may be mixed for 1 hour at 37° C. and added to 5000 K562 cells/well. After four days, cells may be fixed, permeabilized, and stained with m4G2, e.g. as described above for neutralization assays. The number of infected cells was determined by flow cytometry, as described above for neutralization assays.

Preferably, the antibody according to the present invention, or the antigen-binding fragment thereof, eliminates generation of ZIKV escape mutants. Elimination of generation of escape mutants can easily be assessed by the person skilled in the art. For example, to identify the propensity of an antibody or antibody fragment to generate escape mutants, ZIKV is repeatedly passaged in the presence of sub-neutralizing concentrations of the antibody or antigen binding fragment thereof of interest. As shown in examples 10 and 11 of the present application, ZIKV escape mutants ("MARMs") typically appear after the third or fourth passage of ZIKV. Accordingly, an antibody can be considered to eliminate the generation of ZIKV escape mutants, if even after five passages of the virus (ZIKV) in presence of sub-neutralizing concentrations of that antibody or antigen binding fragment thereof, no ZIKV escape mutants can be identified. More preferably, no ZIKV escape mutants can be identified after six passages of the virus (ZIKV) in presence of sub-neutralizing concentrations of the antibody, or antigen binding fragment thereof, according to the present invention. Even more preferably, no ZIKV escape mutants can be identified after seven passages of the virus (ZIKV) in presence of sub-neutralizing concentrations of the antibody, or antigen binding fragment thereof, according to the present invention. Most preferably, no ZIKV escape mutants can be identified after eight passages of the virus (ZIKV) in presence of sub-neutralizing concentrations of the antibody, or antigen binding fragment thereof, according to the present invention.

For example, to assess the propensity of an antibody or antibody fragment to generate escape mutants, ZIKV, for example strain H/PF/2013, is incubated with various sub-neutralizing concentrations of the antibody/antigen binding fragment of interest, e.g., for at least 30 min, for example, at about 37° C. (body temperature). Thereafter, (living) cells, for example Vero cells, are added, followed by incubation, e.g. for at least one day, preferably 3-4 days, for example, at about 37° C. (body temperature) to allow virus propagation to occur. Then, supernatants from three conditions may be selected: the lowest concentration of the antibody/antigen binding fragment of interest at which full protection of the monolayer was observed, one concentration at which a partial CPE effect on the cell monolayer was observed and one concentration at which 100% of the cell monolayer was destroyed by the ZIKV CPE. One part of the selected supernatant can be used for micro-neutralization assays and subsequent sequencing of the virus (to identify escape mutants), while another part of the (same) selected supernatant can be used for the next selection step (passage). Namely, for the next passage, (a part of the) selected supernatant can be mixed with the various sub-neutralizing concentrations of the antibody/antigen binding fragment of interest and incubated, as described above, followed by an addition of (living) cells and incubation as described above, to finally again select supernatants. This selection and propagation process is repeated to arrive at least at five passages, preferably at least six passages, more preferably at least seven passages, and most preferably at least eight passages.

Preferably, each CDR or each variable region of at least one epitope binding site of the antibody, or an antigen binding fragment thereof, according to the present invention is a human CDR or a human variable region, respectively. More preferably, each CDR or each variable region comprised in the antibody, or an antigen binding fragment thereof, according to the present invention is a human CDR or a human variable region, respectively. Most preferably, all constant regions and variable regions comprised in the antibody, or an antigen binding fragment thereof, according to the present invention are a human constant regions and human variable regions.

It is also preferred that the antibody, or an antigen binding fragment thereof, according to the present invention is a monoclonal antibody, preferably a monoclonal antibody wherein each CDR or each variable region comprised in the antibody, or an antigen binding fragment thereof, according to the present invention is a human CDR or a human variable region, respectively.

Preferably, the antibody, or the antigen binding fragment thereof, according to the present invention is of the IgG type, such as IgG1 type, IgG2 type, IgG3 type, or IgG4 type, more preferably of the IgG1 type. More preferably, the antibody, or the antigen binding fragment thereof, according to the present invention comprises (i) a heavy chain constant region of the IgG1 CH1-CH2-CH3 type, wherein "CH1" refers to the constant domain 1 of the heavy chain, "CH2" refers to the constant domain 2 of the heavy chain, and "CH3" refers to the constant domain 3 of the heavy chain; and (ii) a light chain constant region of the IgG CL type, wherein "CL" refers to the constant domain of the light chain. Even more preferably, the antibody, or the antigen binding fragment thereof, according to the present invention comprises a heavy chain constant region of the IgG1 CH1-CH2-CH3 type comprising or consisting of an amino acid sequence according to SEQ ID NO: 91 or 92, or a functional sequence variant thereof, and a light chain constant region of the IgG CL type comprising or consisting of an amino acid sequence according to SEQ ID NO: 93 or 94, or a functional sequence variant thereof.

Accordingly, it is preferred that the antibody according to the present invention, or an antigen binding fragment thereof, comprises an Fc moiety. More preferably, the Fc moiety is derived from human origin, e.g. from human IgG1, IgG2, IgG3, and/or IgG4, whereby human IgG1 is particularly preferred. Various multispecific antibody formats comprising an Fc moiety are known in the art. Preferred antibody formats comprising an Fc moiety are the IgG-appended antibody formats described above. Typically, an antibody comprising an Fc moiety is more effective and displays a longer half-life than antibodies or antibody fragments without Fc moiety.

As used herein, the term "Fc moiety" refers to a sequence derived from the portion of an immunoglobulin heavy chain beginning in the hinge region just upstream of the papain cleavage site (e.g., residue 216 in native IgG, taking the first residue of heavy chain constant region to be 114) and ending at the C-terminus of the immunoglobulin heavy chain. Accordingly, an Fc moiety may be a complete Fc moiety or a portion (e.g., a domain) thereof. A complete Fc moiety comprises at least a hinge domain, a CH2 domain, and a CH3 domain (e.g., EU amino acid positions 216-446). An additional lysine residue (K) is sometimes present at the extreme C-terminus of the Fc moiety, but is often cleaved from a mature antibody. Each of the amino acid positions within an Fc moiety have been numbered according to the art-recognized EU numbering system of Kabat, see e.g., by Kabat et al., in "Sequences of Proteins of Immunological Interest", U.S. Dept. Health and Human Services, 1983 and 1987.

Preferably, in the context of the present invention an Fc moiety comprises at least one of: a hinge (e.g., upper, middle, and/or lower hinge region) domain, a CH2 domain, a CH3 domain, or a variant, portion, or fragment thereof. In preferred embodiments, an Fc moiety comprises at least a hinge domain, a CH2 domain or a CH3 domain. More preferably, the Fc moiety is a complete Fc moiety. The Fc moiety may also comprises one or more amino acid insertions, deletions, or substitutions relative to a naturally-occurring Fc moiety. For example, at least one of a hinge domain, CH2 domain or CH3 domain (or portion thereof) may be deleted. For example, an Fc moiety may comprise or consist of: (i) hinge domain (or portion thereof) fused to a CH2 domain (or portion thereof), (ii) a hinge domain (or portion thereof) fused to a CH3 domain (or portion thereof), (iii) a CH2 domain (or portion thereof) fused to a CH3 domain (or portion thereof), (iv) a hinge domain (or portion thereof), (v) a CH2 domain (or portion thereof), or (vi) a CH3 domain or portion thereof.

It will be understood by one of ordinary skill in the art that the Fc moiety may be modified such that it varies in amino acid sequence from the complete Fc moiety of a naturally occurring immunoglobulin molecule, while retaining at least one desirable function conferred by the naturally-occurring Fc moiety. Such functions include Fc receptor (FcR) binding, antibody half-life modulation, ADCC function, protein A binding, protein G binding, and complement binding. The portions of naturally occurring Fc moieties, which are responsible and/or essential for such functions are well known by those skilled in the art.

For example, to activate the complement cascade C1q binds to at least two molecules of IgG1 or one molecule of IgM, attached to the antigenic target (Ward, E. S., and Ghetie, V., *Ther. Immunol.* 2 (1995) 77-94). Burton, D. R., described (*Mol. Immunol.* 22 (1985) 161-206) that the heavy chain region comprising amino acid residues 318 to 337 is involved in complement fixation. Duncan, A. R., and Winter, G. (*Nature* 332 (1988) 738-740), using site directed mutagenesis, reported that Glu318, Lys320 and Lys322 form the binding site to C1q. The role of Glu318, Lys320 and Lys 322 residues in the binding of C1q was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on hematopoietic cells. Fc receptors belong to the immunoglobulin superfamily, and were shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC; Van de Winkel, J. G., and Anderson, C. L., *J. Leukoc. Biol.* 49 (1991) 511-524). FcRs are defined by their specificity for immunoglobulin classes; Fc receptors for IgG antibodies are referred to as FcγR, for IgE as FcεR, for IgA as FcαR and so on and neonatal Fc receptors are referred to as FcRn. Fc receptor binding is described for example in Ravetch, J. V., and Kinet, J. P., *Annu. Rev. Immunol.* 9 (1991) 457-492; Capel, P. J., et al., *Immunomethods* 4 (1994) 25-34; de Haas, M., et al., *J Lab. Clin. Med.* 126 (1995) 330-341; and Gessner, J. E., et al., *Ann. Hematol.* 76 (1998) 231-248.

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. Therefore, Fc moieties providing cross-linking of receptors (FcγR) are preferred. In humans, three classes of FcγR have been characterized, which are: (i) FcγRI (CD64), which binds monomeric IgG with high affinity and is expressed on macrophages, monocytes, neutrophils and eosinophils; (ii) FcγRII (CD32), which binds complexed IgG with medium to low affinity, is widely expressed, in particular on leukocytes, is known to be a central player in antibody-mediated immunity, and which can be divided into FcγRIIA, FcγRIIB and FcγRIIC, which perform different functions in the immune system, but bind with similar low affinity to the IgG-Fc, and the ectodomains of these receptors are highly homologous; and (iii) FcγRIII (CD16), which binds IgG with medium to low affinity and exists as two types: FcγRIIIA found on NK cells, macrophages, eosinophils and some monocytes and T cells and mediating ADCC and FcγRIIIB, which is highly expressed on neutrophils. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. Importantly, 75% of all FcγRIIB is found in the liver (Ganesan, L. P. et al., 2012: FcγRIIb on liver sinusoidal endothelium clears small immune complexes. Journal of Immunology 189: 4981-4988). FcγRIIB is abundantly expressed on Liver Sinusoidal Endothelium, called LSEC, and in Kupffer cells in the liver and LSEC are the major site of small immune complexes clearance (Ganesan, L. P. et al., 2012: FcγRIIb on liver sinusoidal endothelium clears small immune complexes. Journal of Immunology 189: 4981-4988).

Accordingly, in the present invention such antibodies, and antigen binding fragments thereof, are preferred, which are able to bind to FcγRIIb, for example antibodies comprising an Fc moiety for binding to FcγRIIb, in particular an Fc region, such as, for example IgG-type antibodies. Moreover, it is possible to engineer the Fc moiety to enhance FcγRIIB binding by introducing the mutations S267E and L328F as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933. Thereby, the clearance of immune complexes can be enhanced (Chu, S., et al., 2014: Accelerated Clearance of IgE In Chimpanzees Is Mediated By Xmab7195, An Fc-Engineered Antibody With Enhanced Affinity For Inhibitory Receptor FcγRIIb. Am J Respir Crit, American Thoracic Society International Conference Abstracts). Accordingly, in the context of the present invention such antibodies, or antigen binding fragments thereof, are preferred, which comprise an engineered Fc moiety with the mutations S267E and L328F, in particular as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933.

On B-cells it seems to function to suppress further immunoglobulin production and isotype switching to say for example the IgE class. On macrophages, FcγRIIB acts to inhibit phagocytosis as mediated through FcγRIIA. On eosinophils and mast cells the b form may help to suppress activation of these cells through IgE binding to its separate receptor.

Regarding FcγRI binding, modification in native IgG of at least one of E233-G236, P238, D265, N297, A327 and P329 reduces binding to FcγRI. IgG2 residues at positions 233-236, substituted into IgG1 and IgG4, reduces binding to FcγRI by $10^3$-fold and eliminated the human monocyte response to antibody-sensitized red blood cells (Armour, K. L., et al. *Eur. J. Immunol.* 29 (1999) 2613-2624). Regarding FcγRII binding, reduced binding for FcγRIIA is found e.g. for IgG mutation of at least one of E233-G236, P238, D265, N297, A327, P329, D270, Q295, A327, R292 and K414. Regarding FcγRIII binding, reduced binding to FcγRIIIA is found e.g. for mutation of at least one of E233-G236, P238, D265, N297, A327, P329, D270, Q295, A327, S239, E269, E293, Y296, V303, A327, K338 and D376. Mapping of the binding sites on human IgG1 for Fc receptors, the above mentioned mutation sites and methods for measuring binding to FcγRI and FcγRIIA are described in Shields, R. L., et al., *J. Biol. Chem.* 276 (2001) 6591-6604.

Regarding binding to the crucial FcγRII, two regions of native IgG Fc appear to be critical for interactions of FcγRIIs and IgGs, namely (i) the lower hinge site of IgG Fc, in particular amino acid residues L, L, G, G (234-237, EU numbering), and (ii) the adjacent region of the CH2 domain of IgG Fc, in particular a loop and strands in the upper CH2 domain adjacent to the lower hinge region, e.g. in a region of P331 (Wines, B. D., et al., J. Immunol. 2000; 164: 5313-5318). Moreover, FcγRI appears to bind to the same site on IgG Fc, whereas FcRn and Protein A bind to a different site on IgG Fc, which appears to be at the CH2-CH3 interface (Wines, B. D., et al., J. Immunol. 2000; 164: 5313-5318).

For example, the Fc moiety may comprise or consist of at least the portion of an Fc moiety that is known in the art to be required for FcRn binding or extended half-life. Alternatively or additionally, the Fc moiety of the antibody of the invention comprises at least the portion of known in the art to be required for Protein A binding and/or the Fc moiety of the antibody of the invention comprises at least the portion of an Fc molecule known in the art to be required for protein G binding. Preferably, the retained function is the neutralization of Zika virus infection, which is assumed to be mediated by FcγR binding. Accordingly, a preferred Fc moiety comprises at least the portion known in the art to be required for FγR binding. As outlined above, a preferred Fc moiety may thus at least comprise (i) the lower hinge site of native IgG Fc, in particular amino acid residues L, L, G, G (234-237, EU numbering), and (ii) the adjacent region of the CH2 domain of native IgG Fc, in particular a loop and strands in the upper CH2 domain adjacent to the lower hinge region, e.g. in a region of P331, for example a region of at least 3, 4, 5, 6, 7, 8, 9, or 10 consecutive amino acids in the upper CH2 domain of native IgG Fc around P331, e.g. between amino acids 320 and 340 (EU numbering) of native IgG Fc.

Preferably, the antibody, or antigen binding fragment thereof, according to the present invention comprises an Fc region. As used herein, the term "Fc region" refers to the portion of an immunoglobulin formed by two or more Fc moieties of antibody heavy chains. For example, the Fc region may be monomeric or "single-chain" Fc region (i.e., a scFc region). Single chain Fc regions are comprised of Fc moieties linked within a single polypeptide chain (e.g., encoded in a single contiguous nucleic acid sequence). Exemplary scFc regions are disclosed in WO 2008/143954 A2. Preferably, the Fc region is a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties.

The Fc moieties of the Fc region may be of the same or different class and/or subclass. For example, the Fc moieties may be derived from an immunoglobulin (e.g., a human immunoglobulin) of an IgG1, IgG2, IgG3 or IgG4 subclass. Preferably, the Fc moieties of Fc region are of the same class and subclass. However, the Fc region (or one or more Fc moieties of an Fc region) may also be chimeric, whereby a chimeric Fc region may comprise Fc moieties derived from different immunoglobulin classes and/or subclasses. For example, at least two of the Fc moieties of a dimeric or single-chain Fc region may be from different immunoglobulin classes and/or subclasses. Additionally or alternatively, the chimeric Fc regions may comprise one or more chimeric Fc moieties. For example, the chimeric Fc region or moiety may comprise one or more portions derived from an immunoglobulin of a first subclass (e.g., an IgG1, IgG2, or IgG3 subclass) while the remainder of the Fc region or moiety is of a different subclass. For example, an Fc region or moiety of an Fc polypeptide may comprise a CH2 and/or CH3 domain derived from an immunoglobulin of a first subclass (e.g., an IgG1, IgG2 or IgG4 subclass) and a hinge region from an immunoglobulin of a second subclass (e.g., an IgG3 subclass). For example, the Fc region or moiety may comprise a hinge and/or CH2 domain derived from an immunoglobulin of a first subclass (e.g., an IgG4 subclass) and a CH3 domain from an immunoglobulin of a second subclass (e.g., an IgG1, IgG2, or IgG3 subclass). For example, the chimeric Fc region may comprise an Fc moiety (e.g., a complete Fc moiety) from an immunoglobulin for a first subclass (e.g., an IgG4 subclass) and an Fc moiety from an immunoglobulin of a second subclass (e.g., an IgG1, IgG2 or IgG3 subclass). For example, the Fc region or moiety may comprise a CH2 domain from an IgG4 immunoglobulin and a CH3 domain from an IgG1 immunoglobulin. For example, the Fc region or moiety may comprise a CH1 domain and a CH2 domain from an IgG4 molecule and a CH3 domain from an IgG1 molecule. For example, the Fc region or moiety may comprise a portion of a CH2 domain from a particular subclass of antibody, e.g., EU positions 292-340 of a CH2 domain. For example, an Fc region or moiety may comprise amino acids a positions 292-340 of CH2 derived from an IgG4 moiety and the remainder of CH2 derived from an IgG1 moiety (alternatively, 292-340 of CH2 may be derived from an IgG1 moiety and the remainder of CH2 derived from an IgG4 moiety).

Moreover, an Fc region or Fc moiety may (additionally or alternatively) for example comprise a chimeric hinge region. For example, the chimeric hinge may be derived, e.g. in part, from an IgG1, IgG2, or IgG4 molecule (e.g., an upper and lower middle hinge sequence) and, in part, from an IgG3 molecule (e.g., an middle hinge sequence). In another example, an Fc region or moiety may comprise a chimeric hinge derived, in part, from an IgG1 molecule and, in part, from an IgG4 molecule. In another example, the chimeric hinge may comprise upper and lower hinge domains from an IgG4 molecule and a middle hinge domain from an IgG1 molecule. Such a chimeric hinge may be made, for example, by introducing a proline substitution (Ser228Pro) at EU position 228 in the middle hinge domain of an IgG4 hinge region. In another embodiment, the chimeric hinge can comprise amino acids at EU positions 233-236 are from an IgG2 antibody and/or the Ser228Pro mutation, wherein the remaining amino acids of the hinge are from an IgG4 antibody (e.g., a chimeric hinge of the sequence ESKY-GPPCPPCPAPPVAGP). Further chimeric hinges, which may be used in the Fc moiety of the antibody according to the present invention are described in US 2005/0163783 A1.

In the present invention it is preferred that the Fc moiety, or the Fc region, comprises or consists of an amino acid sequence derived from a human immunoglobulin sequence (e.g., from an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc moiety or in the Fc region.

Preferably, the antibody according to the present invention comprises, in particular in addition to an Fc moiety as described above, other parts derived from a constant region, in particular from a constant region of IgG, preferably from a constant region of IgG1, more preferably from a constant region of human IgG1. More preferably, the antibody according to the present invention comprises, in particular in addition to an Fc moiety as described above, all other parts of the constant regions, in particular all other parts of the constant regions of IgG, preferably all other parts of the constant regions of IgG1, more preferably all other parts of the constant regions of human IgG1.

Particularly preferred sequences of constant regions are the amino acid sequences according to SEQ ID NOs: 91-94 (encoded, for example, by nucleic acid sequences according to SEQ ID NOs: 95-98, respectively). Preferably, the amino acid sequence of IgG1 CH1-CH2-CH3 is according to SEQ ID NO: 91 or a functional sequence variant thereof, as described herein. Even more preferably, the amino acid sequence of IgG1 CH1-CH2-CH3 is according to SEQ ID NO: 92 or a functional sequence variant thereof, as described herein, wherein the "LALA" mutation is maintained.

As outlined above, a particularly preferred antibody according to the present invention comprises a (complete) Fc region derived from human IgG1. More preferably, the antibody according to the present invention comprises, in particular in addition to a (complete) Fc region derived from human IgG1 also all other parts of the constant regions of IgG, preferably all other parts of the constant regions of IgG1, more preferably all other parts of the constant regions of human IgG1.

Without being bound to any theory, it is believed that antibody-dependent enhancement (ADE) of Zika virus infection is brought about by the binding of the Fc moiety of the antibody, in particular, the Fc moiety of the heavy chain of an IgG molecule, to an Fc receptor, e.g., an Fcγ receptor on a host cell. It is thus preferred that the antibody according to the present invention, or an antigen binding fragment thereof, comprises one or more mutations in the Fc moiety. The mutation(s) may be any mutation that reduces binding of the antibody to an Fc receptor (FcR), in particular reduces binding of the antibody to an Fcγ receptor (FcγR). On the other hand, it is preferred that the antibody according to the present invention comprises a (complete) Fc moiety/Fc region, wherein the interaction/binding with FcRn is not compromised. Accordingly, it is particularly preferred that the antibody according to the present invention, or an antigen binding fragment thereof, comprises one or more mutations in the Fc moiety, which (i) reduce(s) binding of the antibody to an Fcγ receptor, but do(es) not compromise interaction with FcRn. One example of such a mutation is the "LALA" mutation described below.

In general, binding of the antibody to an Fc receptor may be assessed by various methods known to the skilled person, such as ELISA (Hessell A J, Hangartner L, Hunter M, Havenith C E G, Beurskens F J, Bakker J M, Lanigan C M S, Landucci G, Forthal D N, Parren P W H I, et al.: Fc receptor but not complement binding is important in antibody protection against HIV. Nature 2007, 449:101-104; Grevys A, Bern M, Foss S, Bratlie D B, Moen A, Gunnarsen K S, Aase A, Michaelsen T E, Sandlie I, Andersen J T: Fc Engineering of Human IgG1 for Altered Binding to the Neonatal Fc Receptor Affects Fc Effector Functions. 2015, 194:5497-5508) or flow-cytometry (Perez L G, Costa M R, Todd C A, Haynes B F, Montefiori D C: Utilization of immunoglobulin G Fc receptors by human immunodeficiency virus type 1: a specific role for antibodies against the membrane-proximal external region of gp41. J Virol 2009, 83:7397-7410; Piccoli L, Campo I, Fregni C S, Rodriguez B M F, Minola A, Sallusto F, Luisetti M, Corti D, Lanzavecchia A: Neutralization and clearance of GM-CSF by autoantibodies in pulmonary alveolar proteinosis. Nat Commun 2015, 6:1-9).

In general, the antibody according to the present invention may be glycosylated. N-linked glycans attached to the CH2 domain of a heavy chain, for instance, can influence C1q and FcR binding, with aglycosylated antibodies having lower affinity for these receptors. Accordingly, the CH2 domain of the Fc moiety of the antibody according to the present invention may comprise one or more mutations, in which a glycosylated residue is substituted by a non-glycosylated residue. The glycan structure can also affect activity e.g. differences in complement-mediated cell death may be seen depending on the number of galactose sugars (0, 1 or 2) at the terminus of a glycan's biantennary chain. Preferably, the antibody's glycans do not lead to a human immunogenic response after administration.

Furthermore, the antibody according to the present invention can be modified by introducing random amino acid mutations into particular region of the CH2 or CH3 domain of the heavy chain in order to alter their binding affinity for FcR and/or their serum half-life in comparison to unmodified antibodies. Examples of such modifications include, but are not limited to, substitutions of at least one amino acid from the heavy chain constant region selected from the group consisting of amino acid residues 250, 314, and 428.

Particularly preferably, the Fc moiety of an antibody of the invention comprises a substitution at positions CH2 4, CH2 5, or both. In general, the amino acid at positions 4 and 5 of CH2 of the wild-type IgG1 and IgG3 is a leucine ("L"). Preferably, the antibody according to the present invention comprises an amino acid at position CH2 4, CH2 5, or both, that is not an L. More preferably, antibody according to the present invention comprises an alanine ("A") at position CH2 4, or CH2 5, or both. Most preferably, the antibody according to the present invention comprises both, a CH2 L4A and a CH2 L5A substitution. Such antibodies are referred to herein as a "LALA" variant. Interestingly, such a "LALA" mutation in the Fc moiety does not only result in a lack of contribution of the respective antibody in antibody-dependent enhancement (ADE) of Zika virus infection, but also blocks antibody-dependent enhancement (ADE) of Zika virus infection. An exemplary amino acid sequence of IgG1 CH1-CH2-CH3 comprising the "LALA" mutation is according to SEQ ID NO: 92. Accordingly, the amino acid sequence of IgG1 CH1-CH2-CH3 is preferably according to SEQ ID NO: 92 or a functional sequence variant thereof, as described herein, wherein the "LALA" mutation is maintained. Most preferably, the antibody is of the FIT-Ig format described above comprising a "LALA" mutation in the Fc moiety as described herein.

Preferably, the antibody, or antigen binding fragment thereof, according to the present invention does not comprise a binding site for an Fc receptor. More preferably, the antibody, or antigen binding fragment thereof, does not comprise an Fc region, even more preferably, the antibody, or antigen binding fragment thereof, does not comprise an Fc moiety. Various multispecific antibody formats without Fc moiety are known in the art and described above.

As described above, the antibody, or the antigen binding fragment thereof, according to the present invention preferably binds specifically to (at least two) distinct epitopes on Zika virus envelope protein (ZIKV E protein). More preferably, the antibody, or antigen binding fragment thereof, binds to domain III of Zika virus envelope protein (EDIII, also referred to as "DIII"). In other words, it is preferred that the antibody, or antigen binding fragment thereof, according to the present invention binds to an epitope of Zika virus envelope protein, which includes one or more amino acid residues of domain III of Zika virus envelope protein (EDIII). ZIKV includes a nucleocapsid core, which comprising single-stranded RNA wrapped by core proteins. The nucleocapsid core is encapsulated by a lipid bilayer membrane with "membrane proteins" and "envelope proteins". ZIKV envelope protein (E protein) is the dominant antigen. The ectodomain of the envelope protein comprises three distinct domains: E protein domain I (EDI), E protein domain II (EDII), and E protein domain III (EDIII). EDIII is highly conserved among different ZIKV strains (see FIG. 8 for an alignment of amino acid sequences of EDIII of different ZIKV strains). Antibodies binding to domain III of Zika virus envelope protein (EDIII) show (i) increased neutralization of ZIKV and (ii) decreased cross-reactivity with DENV (in particular essentially no cross-reactivity with DENV) as compared to antibodies binding to domain I/II of Zika virus envelope protein (EDI/II).

Accordingly, the antibody, or antigen binding fragment thereof, more preferably binds to domain III of Zika virus envelope protein (EDIII) with EDIII having the following amino acid sequence (SEQ ID NO: 263):

```
TAAFTFTKXPAEXXHGTVTVEXQYXGXDGPCKXPXQMAVDXQTLTPVGRL
ITANPVITEXTENSKMMLELDPPFGDSYIVIGXGXKKITHHWHRS
``` wherein X may be any (naturally occurring) amino acid. In other words, it is preferred that the, the antibody, or antigen binding fragment thereof, according to the present invention binds to an epitope of Zika virus envelope protein, which includes one or more amino acid residues of SEQ ID NO: 263.

It is also preferred that the antibody, or antigen binding fragment thereof, according to the present invention binds to domain III of Zika virus envelope protein (EDIII) with EDIII having the following amino acid sequence (SEQ ID NO: 265):

```
X1GX2X3YSLCTAAFTFTKX4PAEX5X6HGTVTVEX7QYX8GX9DGPCKX10
PX11QMAVDX12QTLTPVGRLITANPVITEX13TX14NSKMMLELDPPFGD
SYIVIGX15GX16X17KITHHWHRSG
``` wherein
  X1 may be any (naturally occurring) amino acid, preferably K, A, or E;
  X2 may be any (naturally occurring) amino acid, preferably V, F, or L;
  X3 may be any (naturally occurring) amino acid, preferably S or F;
  X4 may be any (naturally occurring) amino acid, preferably I or V;
  X5 may be any (naturally occurring) amino acid, preferably T or V;
  X6 may be any (naturally occurring) amino acid, preferably L or D;
  X7 may be any (naturally occurring) amino acid, preferably V or G;
  X8 may be any (naturally occurring) amino acid, preferably A or G;
  X9 may be any (naturally occurring) amino acid except R, preferably T or A;
  X10 may be any (naturally occurring) amino acid, preferably V or I;
  X11 may be any (naturally occurring) amino acid, preferably A or V;
  X12 may be any (naturally occurring) amino acid, preferably M or T;
  X13 may be any (naturally occurring) amino acid, preferably S or G;
  X14 may be any (naturally occurring) amino acid, preferably E or K;
  X15 may be any (naturally occurring) amino acid, preferably V or I;
  X16 may be any (naturally occurring) amino acid, preferably E, A, K, or D; and
  X17 may be any (naturally occurring) amino acid, preferably E, A, or K, more preferably K or A.

In other words, it is preferred that the, the antibody, or antigen binding fragment thereof, according to the present invention binds to an epitope of Zika virus envelope protein, which includes one or more amino acid residues of SEQ ID NO: 265.

For example, EDIII stretches from amino acid 309 to amino acid 403 of ZIKV E protein of the ZIKV H/PF/2013 strain (Genbank accession number KJ776791). Accordingly, the antibody, or antigen binding fragment thereof, most preferably binds to domain III of Zika virus envelope protein (EDIII) with EDIII having the following amino acid sequence (SEQ ID NO: 264):

```
TAAFTFTKIPAETLHGTVTVEVQYAGTDGPCKVPAQMAVDMQTLTPVGRL
ITANPVITESTENSKMMLELDPPFGDSYIVIGVGEKKITHHWHRS.
```

In other words, it is preferred that the antibody, or antigen binding fragment thereof, according to the present invention binds to an epitope of Zika virus envelope protein, which includes one or more amino acid residues of SEQ ID NO: 264.

More preferably, the antibody, or antigen binding fragment thereof, according to the present invention binds to an epitope of Zika virus envelope protein, which includes one or more amino acid residues of the lateral ridge (LR) of EDIII and/or one or more amino acid residues of the EDI-EDIII hinge region. The EDIII lateral ridge and EDI-EDIII hinge region are known to the skilled person and described, for example, in Zhao, H., Fernandez, E., Dowd, K. A., Speer, S. D., Platt, D. J., Gorman, M. J., Govero, J., Nelson, C. A., Pierson, T. C., Diamond, M. S., et al. (2016). Structural Basis of Zika Virus-Specific Antibody Protection. Cell 166(4):1016-27 and in Kostyuchenko V A, Lim E X, Zhang S, Fibriansah G, Ng T S, Ooi J S, Shi J, Lok S M. Structure of the thermally stable Zika virus. Nature. 2016 May 19; 533(7603):425-8. Without being bound to any theory, it is assumed that (i) binding to the LR may inhibit fusion by trapping a fusion transitional state of the virus and (ii) binding to the EDI-EDIII hinge and EDIII may hinder the movement of EDIII to form the trimeric post-fusion structure, thereby halting membrane fusion.

Accordingly, it is preferred that the antibody, or antigen binding fragment thereof, according to the present invention (is able to) inhibit(s) a post-attachment step of ZIKV. "Post-attachment" typically refers to any step of ZIKV infection after attachment of ZIKV to the cell membrane (of the cell targeted by ZIKV). For example, the antibody, or antigen binding fragment thereof, according to the present invention preferably (is able to) prevent(s) membrane fusion. Furthermore, it is also preferred that the antibody, or antigen binding fragment thereof, according to the present invention (is able to) cause(s) aggregation of ZIKV (particles). Most preferably, the antibody, or antigen binding fragment thereof, according to the present invention (is able to) (i) inhibit(s) a post-attachment step of ZIKV and (ii) cause(s) aggregation of ZIKV (particles).

Particularly preferably, the antibody, or antigen binding fragment thereof, according to the present invention comprises at least one CDR, preferably all six CDRs, more preferably a variable region, even more preferably both variable regions (i.e., an epitope binding site), in particular a specificity, of the exemplified human antibody ZKA190, which binds to ZIKV EDIII (cf Example 1, FIG. 1). Amino acid sequences of CDRs and variable regions of ZKA190, which are preferably comprised in the antibody, or antigen binding fragment thereof, according to the present invention, are described in Tables 1 and 2 below.

It is also preferred that the antibody, or antigen binding fragment thereof, binds to a quaternary epitope displayed on a ZIKV infectious virion. Despite considerable neutralizing activity, such antibodies show typically no detectable binding to recombinant ZIKV E protein or to ZIKV EDIII in a standard ELISA (as described above), i.e. if tested in vitro, in particular in purified form (i.e. ZIKV E protein "outside/without" a virion, a virus-like particle or the like). Thereby, "no detectable binding" typically means that no $EC_{50}$ up to 10000 ng/ml was detected in a standard ELISA. In other words, if the $EC_{50}$ detectable in a standard ELISA is above 10000 ng/ml, it is referred to as "no detectable binding".

Therefore, such antibodies are also referred to herein as "neutralizing-non-E-binding" (NNB) antibodies. The quaternary epitope displayed on a ZIKV infectious virion is typically a conformational epitope. For example, the quaternary epitope displayed on a ZIKV infectious virion may be formed at the interface of two envelope protein monomers making up a dimer ("envelope dimer epitope"; EDE) or it may be formed across neighbouring dimers ("herringbone epitope").

Particularly preferably, the antibody, or antigen binding fragment thereof, according to the present invention comprises at least one CDR, preferably all six CDRs, more preferably a variable region, even more preferably both variable regions (i.e., an epitope binding site), in particular a specificity, of the exemplified human antibody ZKA230, which binds to a quaternary epitope displayed on a ZIKV infectious virion (cf Example 1, FIG. 1) Amino acid sequences of CDRs and variable regions of ZKA230, which are preferably comprised in the antibody, or antigen binding fragment thereof, according to the present invention, are described in Tables 1 and 2 below.

It is also preferred that the antibody, or antigen binding fragment thereof, binds to domain II of Zika virus envelope protein (EDII). EDII is an elongated finger-like domain containing a conserved fusion loop that interacts with the host cell endosomal membrane extending approx. from amino acid position 52 to amino acid position 132 and approx. from amino acid position 193 to amino acid position 280 of ZIKV E protein (Dai L, Song J, Lu X, Deng Y Q, Musyoki A M, Cheng H, Zhang Y, Yuan Y, Song H, Haywood J, Xiao H, Yan J, Shi Y, Qin C F, Qi J, Gao G F. Structures of the Zika Virus Envelope Protein and Its Complex with a Flavivirus Broadly Protective Antibody. Cell Host Microbe. 2016 May 11; 19(5):696-704).

Particularly preferably, the antibody, or antigen binding fragment thereof, according to the present invention comprises at least one CDR, preferably all six CDRs, more preferably a variable region, even more preferably both variable regions (i.e., an epitope binding site), in particular a specificity, of the exemplified human antibody ZKA185, which binds to ZIKV EDII. Amino acid sequences of CDRs and variable regions of ZKA185, which are preferably comprised in the antibody, or antigen binding fragment thereof, according to the present invention, are described in Tables 1 and 2 below.

Preferably, the antibody, or antigen binding fragment thereof, according to the present invention (i) binds to domain III of Zika virus envelope protein (EDIII) and (ii) binds to domain II of Zika virus envelope protein (EDII). In other words, it is preferred that antibody, or antigen binding fragment thereof, according to the present invention comprises (i) an epitope binding site, which specifically binds to domain III of Zika virus envelope protein (EDIII), and (ii) an epitope binding site, which specifically binds to domain II of Zika virus envelope protein (EDII). As described above, it is preferred that domain III of Zika virus envelope protein comprises or consists of an amino acid sequence as set forth in SEQ ID NO: 263 or 265, in particular as set forth in SEQ ID NO: 264. Moreover, as described above, it is also preferred that the antibody, or antigen binding fragment thereof, binds to an epitope of Zika virus envelope protein, which includes one or more amino acid residues of the lateral ridge (LR) of EDIII and/or one or more amino acid residues of the EDI-EDIII hinge region. In other words, the epitope binding site targeting EDIII preferably binds to one or more amino acid residues of the lateral ridge (LR) of EDIII and/or one or more amino acid residues of the EDI-EDIII hinge region.

It is also preferred that the antibody, or antigen binding fragment thereof, according to the present invention (i) binds to domain III of Zika virus envelope protein (EDIII) and (ii) binds to a quaternary epitope displayed on a ZIKV infectious virion. In other words, it is preferred that antibody, or antigen binding fragment thereof, according to the present invention comprises (i) an epitope binding site, which specifically binds to domain III of Zika virus envelope protein (EDIII), and (ii) an epitope binding site, which specifically binds to a quaternary epitope displayed on a ZIKV infectious virion. As described above, it is preferred that domain III of Zika virus envelope protein comprises or consists of an amino acid sequence as set forth in SEQ ID NO: 263 or 265, in particular as set forth in SEQ ID NO: 264. Moreover, as described above, it is also preferred that the antibody, or antigen binding fragment thereof, binds to an epitope of Zika virus envelope protein, which includes one or more amino acid residues of the lateral ridge (LR) of EDIII and/or one or more amino acid residues of the EDI-EDIII hinge region. In other words, the epitope binding site targeting EDIII preferably binds to one or more amino acid residues of the lateral ridge (LR) of EDIII and/or one or more amino acid residues of the EDI-EDIII hinge region.

In general, a single epitope binding site (also referred to as "paratope" or "antigen receptor") of the antibody according to the present invention, or the antigen binding fragment thereof, preferably comprises three complementarity determining regions (CDRs) on a heavy chain and (at least) three CDRs on a light chain. In general, complementarity determining regions (CDRs) are the hypervariable regions present in heavy chain variable domains and light chain variable domains. Typically, the CDRs of a heavy chain and the connected light chain of an antibody together form the antigen receptor (epitope binding site). Usually, the three CDRs (CDR1, CDR2, and CDR3) are arranged non-consecutively in the variable domain. Since epitope binding sites are typically composed of two variable domains (for example, on two different polypeptide chains, i.e. heavy and light chain), there are six CDRs for each epitope binding site (heavy chain: CDRH1, CDRH2, and CDRH3; light chain: CDRL1, CDRL2, and CDRL3). The CDRs on the heavy and/or light chain may be separated by framework regions, whereby a framework region (FR) is a region in the variable domain which is less "variable" than the CDR. For example, a chain (or each chain, respectively) may be composed of four framework regions, separated by three CDR's.

The sequences of the heavy chains and light chains of various exemplified human anti ZIKV E protein antibodies, comprising three different CDRs on the heavy chain and three different CDRs on the light chain were determined (cf Tables 1 and 2 below). The position of the CDR amino acids are defined according to the IMGT numbering system (IMGT: http://www.imgt.org/; cf. Lefranc, M.-P. et al. (2009) Nucleic Acids Res. 37, D1006-D1012). Preferably, the antibody, or antigen binding fragment thereof, according to the present invention comprises at least one CDR of the following exemplified antibodies. More preferably, the antibody, or antigen binding fragment thereof, according to the present invention comprises all six CDRs (of an epitope binding site) of the following exemplified antibodies. Even more preferably, the antibody, or antigen binding fragment thereof, according to the present invention comprises the heavy chain variable region (VH) and the light chain variable region (VL) of the following exemplified antibodies.

Table 1 shows the SEQ ID NO's of the amino acid sequences of the heavy chain CDR's (CDRH1, CDRH2, and CDRH3) and of the heavy chain variable region (referred to as "VH") of exemplary antibodies:

| Antibody name | CDRH1 | CDRH2 | CDRH3 | VH |
|---|---|---|---|---|
| ZKA190 | 1 | 2 | 3 | 8 |
| ZKA185 | 19 | 20 | 21 | 26 |
| ZKA230 | 37 | 38 | 39 | 44 |
| ZKA78 | 55 | 56 | 57 | 62 |
| ZKA64 | 73 | 74 | 75 | 80 |
| ZKA3 | 99 | 100 | 101 | 102 |

-continued

| Antibody name | CDRH1 | CDRH2 | CDRH3 | VH |
|---|---|---|---|---|
| ZKA4 | 103 | 104 | 105 | 106 |
| ZKA5 | 107 | 108 | 109 | 110 |
| ZKA6 | 111 | 112 | 113 | 114 |
| ZKA7 | 115 | 116 | 117 | 118 |
| ZKA8 | 119 | 120 | 121 | 122 |
| ZKA76 | 123 | 124 | 125 | 126 |
| ZKA117 | 127 | 128 | 129 | 130 |
| ZKB27 | 131 | 132 | 133 | 134 |
| ZKB29 | 135 | 136 | 137 | 138 |
| ZKB34 | 139 | 140 | 141 | 142 |
| ZKB39 | 143 | 144 | 145 | 146 |
| ZKB46 | 147 | 148 | 149 | 150 |
| ZKB53 | 151 | 152 | 153 | 154 |
| ZKC26 | 155 | 156 | 157 | 158 |
| ZKD5 | 159 | 160 | 161 | 162 |
| ZKD7 | 163 | 164 | 165 | 166 |
| ZKD8 | 167 | 168 | 169 | 170 |
| ZKD15 | 171 | 172 | 173 | 174 |
| ZKD16 | 175 | 176 | 177 | 178 |
| ZKD17 | 179 | 180 | 181 | 182 |
| ZKD20 | 183 | 184 | 185 | 186 |
| ZKA134 | 187 | 188 | 189 | 190 |
| ZKA246 | 191 | 192 | 193 | 194 |
| ZKA256 | 195 | 196 | 197 | 198 |
| ZKB42 | 199 | 200 | 201 | 202 |
| ZKB85 | 203 | 204 | 205 | 206 |
| ZKB47 | 207 | 208 | 209 | 210 |
| ZKC6 | 211 | 212 | 213 | 214 |
| ZKA160 | 215 | 216 | 217 | 218 |
| ZKA172 | 219 | 220 | 221 | 222 |
| ZKA174 | 223 | 224 | 225 | 226 |
| ZKA189 | 227 | 228 | 229 | 230 |
| ZKA195 | 231 | 232 | 233 | 234 |
| ZKA215 | 235 | 236 | 237 | 238 |
| ZKA218 | 239 | 240 | 241 | 242 |
| ZKB75 | 243 | 244 | 245 | 246 |
| ZKB83 | 247 | 248 | 249 | 250 |
| ZKC3 | 251 | 252 | 253 | 254 |
| ZKC18 | 255 | 256 | 257 | 258 |
| ZKD1 | 259 | 260 | 261 | 262 |

Table 2 below shows the SEQ ID NO's of the amino acid sequences of the light chain CDR's (CDRL1, CDRL2, and CDRL3) and of the light chain variable region (referred to as "VL") of exemplary antibodies:

| Antibody name | CDRL1 | CDRL2 | CDRL2 long | CDRL3 | VL |
|---|---|---|---|---|---|
| ZKA190 | 4 | 5 | 6 | 7 | 9 |
| ZKA185 | 22 | 23 | 24 | 25 | 27 |
| ZKA230 | 40 | 41 | 42 | 43 | 45 |
| ZKA78 | 58 | 59 | 60 | 61 | 63 |
| ZKA64 | 76 | 77 | 78 | 79 | 81 |

It is thus preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 1 and/or in Table 2.

It is preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 3, 75, 39, 21, 57, 101, 105, 109, 113, 117, 121, 125, 129, 133, 137, 141, 145, 149, 153, 157, 161, 165, 169, 173, 177, 181, 185, 189, 193, 197, 201, 205, 209, 213, 217, 221, 225, 229, 233, 237, 241, 245, 249, 253, 257, and 261, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 3, 21, and 39, 57 and 75 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 3, 21, and 39 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 21 or according to SEQ ID NO: 39; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 3 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein (i) the at least one heavy chain CDRH1 comprises an amino acid sequence according to any of SEQ ID NOs: 1, 19, 37, 55, 73, 99, 103, 107, 111, 115, 119, 123, 127, 131, 135, 139, 143, 147, 151, 155, 159, 163, 167, 171, 175, 179, 183, 187, 191, 195, 199, 203, 207, 211, 215, 219, 223, 227, 231, 235, 239, 243, 247, 251, 255, and 259, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to any of SEQ ID NOs: 2, 20, 38, 56, 74, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244, 248, 252, 256, and 260, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to any of SEQ ID NOs: 3, 21, 39, 57, 75, 101, 105, 109, 113, 117, 121, 125, 129, 133, 137, 141, 145, 149, 153, 157, 161, 165, 169, 173, 177, 181, 185, 189, 193, 197, 201, 205, 209, 213, 217, 221, 225, 229, 233, 237, 241, 245, 249, 253, 257, and 261, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to any of SEQ ID NOs: 1, 19, 37, 55 and 73 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to any of SEQ ID NOs: 2, 20, 38, 56 and 74 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to any of SEQ ID NOs: 3, 21, 39, 57 and 75 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to any of SEQ ID NOs: 1, 19, and 37 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to any of SEQ ID NOs: 2, 20, and 38 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to any of SEQ ID NOs: 3, 21, and 39 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to SEQ ID NO: 1 or according to SEQ ID NO: 73; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to SEQ ID NO: 2 or according to SEQ ID NO: 74; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to SEQ ID NO: 3 or according to SEQ ID NO: 75; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to SEQ ID NO: 19 or according to SEQ ID NO: 37; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to SEQ ID NO: 20 or according to SEQ ID NO: 38; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to SEQ ID NO: 21 or according to SEQ ID NO: 39; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to SEQ ID NO: 1 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to SEQ ID NO: 2 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to SEQ ID NO: 3 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to any of SEQ ID NOs: 4, 22, 40, 58 and 76 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 5, 6, 23, 24, 41, 42, 59, 60, 77 and 78 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to any of SEQ ID NOs: 7, 25, 43, 61 and 79 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to any of SEQ ID NOs: 4, 22, and 40 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 5, 6, 23, 24, 41, and 42, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to any of SEQ ID NOs: 7, 25, and 43 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 4 or according to SEQ ID NO: 76; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 5, 6, 77 and 78 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 7 or according to SEQ ID NO: 79; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 22 or according to SEQ ID NO: 40; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 23, 24, 41 and 42 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 25 or according to SEQ ID NO: 43; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 4 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to SEQ ID NO: 5 or 6, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 7 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention comprises CDRH1, CDRH2, and CDRH3 amino acid sequences (i) according to SEQ ID NOs: 1-3; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 19-21; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 37-39; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 55-57; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 73-75; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 99-101; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 103-105; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 107-109; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 111-113; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (x) according to SEQ ID NOs: 115-117; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xi) according to SEQ ID NOs: 119-121; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xii) according to SEQ ID NOs: 123-125; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xiii) according to SEQ ID NOs: 127-129; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xiv) according to SEQ ID NOs: 131-133; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xv) according to SEQ ID NOs: 135-137; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xvi) according to SEQ ID NOs: 139-141; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xvii) according to SEQ ID NOs: 143-145; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xviii) according to SEQ ID NOs: 147-149; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xix) according to SEQ ID NOs: 151-153; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xx) according to SEQ ID NOs: 155-157; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxi) according to SEQ ID NOs: 159-161; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxii) according to SEQ ID NOs: 163-165; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxiii) according to SEQ ID NOs: 167-169; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxiv) according to SEQ ID NOs: 171-173; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxv) according to SEQ ID NOs: 175-177; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxvi) according to SEQ ID NOs: 179-181; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxvii) according to SEQ ID NOs: 183-185; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxviii) according to SEQ ID NOs: 187-189; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxix) according to SEQ ID NOs: 191-193; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxx) according to SEQ ID NOs: 195-197; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxi) according to SEQ ID NOs: 199-201; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxii) according to SEQ ID NOs: 203-205; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxiii) according to SEQ ID NOs: 207-209; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxiv) according to SEQ ID NOs: 211-213; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxv) according to SEQ ID NOs: 215-217; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxvi) according to SEQ ID NOs: 219-221; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxvii) according to SEQ ID NOs: 223-225; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxviii) according to SEQ ID NOs: 227-229; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxix) according to SEQ ID NOs: 231-233; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xl) according to SEQ ID NOs: 235-237; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xli) according to SEQ ID NOs: 239-241; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xlii) according to SEQ ID NOs: 243-245; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xliii) according to SEQ ID NOs: 247-249; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xliv) according to SEQ ID NOs: 251-253; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xlv) according to SEQ ID NOs: 255-257; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xlvi) according to SEQ ID NOs: 259-261; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Accordingly, it is also preferred that the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 37-41 and 43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 37-40 and 42-43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 55-59 and 61; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 55-58 and 60-61; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 73-77 and 79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (x) according to SEQ ID NOs: 73-76 and 78-79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 37-41 and 43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 37-40 and 42-43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 73-77 and 79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (viii) according to SEQ ID NOs: 73-76 and 78-79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 73-77 and 79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (iv) according to SEQ ID NOs: 73-76 and 78-79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

It is also preferred that preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 37-41 and 43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (vi) according to SEQ ID NOs: 37-40 and 42-43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention as described above comprises CDRH1, CDRH2, and CDRH3 amino acid sequences and CDRL1, CDRL2, and CDRL3 amino acid sequences (i) according to SEQ ID NOs:

19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises (a) a first epitope binding site comprising CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; and (b) a second epitope binding site comprising CDRH1, CDRH2, and CDRH3 amino acid sequences and CDRL1, CDRL2, and CDRL3 amino acid sequences (i) according to SEQ ID NOs: 19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention as described above comprises CDRH1, CDRH2, and CDRH3 amino acid sequences and CDRL1, CDRL2, and CDRL3 amino acid sequences (i) according to SEQ ID NOs: 37-41 and 43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 37-40 and 42-43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises (a) a first epitope binding site comprising CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; and (b) a second epitope binding site comprising CDRH1, CDRH2, and CDRH3 amino acid sequences and CDRL1, CDRL2, and CDRL3 amino acid sequences (i) according to SEQ ID NOs: 37-41 and 43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 37-40 and 42-43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

In addition, it is also preferred that the antibody, or the antigen binding fragment thereof, according to the present invention comprises a heavy chain variable region (VH) and, optionally, a light chain variable region (VL), wherein the heavy chain variable region (VH) comprises or consists of an amino acid sequence according to any of SEQ ID NOs: 8, 26, 44, 62, 80, 102, 106, 110, 114, 118, 122, 126, 130, 134, 138, 142, 146, 150, 154, 158, 162, 166, 170, 174, 178, 182, 186, 190, 194, 198, 202, 206, 210, 214, 218, 222, 226, 230, 234, 238, 242, 246, 250, 254, 258, and 262; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Moreover, it is also preferred that the antibody, or the antigen binding fragment thereof, according to the present invention comprises (i) a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (ii) a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iii) a heavy chain variable region (VH) amino acid sequence according to SEQ ID NO: 44 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 45 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iv) a heavy chain variable region (VH) amino acid sequence according to SEQ ID NO: 62 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 63 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (v) a heavy chain variable region (VH) amino acid sequence according to SEQ ID NO: 80 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 81 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises (i) a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (ii) a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iii) a heavy chain variable region (VH) amino acid sequence according to SEQ ID NO: 44 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 45 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (iv) a heavy chain variable region (VH) amino acid sequence according to SEQ ID NO: 80 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 81 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises (i) a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (ii) a heavy chain variable region (VH) amino acid sequence according to SEQ ID NO: 80 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 81 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises (i) a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (ii) a heavy chain variable region (VH) amino acid sequence according to SEQ ID NO: 44 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 45 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention as described above comprises a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention as described above comprises
(a) a first epitope binding site comprising a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and
(b) a second epitope binding site comprising a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention as described above comprises a heavy chain variable region (VH) amino acid sequence according to SEQ ID NO: 44 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 45 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention as described above comprises
(a) a first epitope binding site comprising a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and
(b) a second epitope binding site comprising a heavy chain variable region (VH) amino acid sequence according to SEQ ID NO: 44 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 45 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Particularly preferably, the antibody, or the antigen binding fragment thereof, according to the present invention is in the Fabs-in-tandem-Ig (FIT-Ig) format and the outer Fab of the FIT-Ig format comprises an epitope binding site comprising CDRH 1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity. More preferably, the outer Fab of the FIT-Ig format comprises an epitope binding site comprising a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. Even more preferably, the inner Fab of the FIT-Ig format comprises an epitope binding site comprising CDRH1, CDRH2, and CDRH3 amino acid sequences and CDRL1, CDRL2, and CDRL3 amino acid sequences (i) according to SEQ ID NOs: 19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity. Still more preferably, the inner Fab of the FIT-Ig format comprises an epitope binding site comprising a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or an antigen binding fragment thereof, according to the present invention is for use as a medicament. In other words, the antibody, or an antigen binding fragment thereof, according to the present invention may be used in the preparation of a medicament. More preferably, the antibody, or an antigen binding fragment thereof, according to the present invention is for use in the prevention and/or treatment of Zika virus infection. In other words, the antibody, or an antigen binding fragment thereof, according to the present invention may be used in the preparation of a medicament or use in the prevention and/or treatment of Zika virus infection. This aspect is described in more detail below.

Nucleic Acid Molecules

In another aspect, the invention also provides a nucleic acid molecule comprising at least one polynucleotide encoding the antibody, or the antigen binding fragment thereof, according to the present invention as described above or a fragment thereof, wherein the fragment comprises at least one CDR of the antibody, or the antigen binding fragment thereof.

A nucleic acid molecule is a molecule comprising, preferably consisting of nucleic acid components. The term nucleic acid molecule preferably refers to DNA or RNA molecules. In particular, it is used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

In the nucleic acid molecule according to the present invention, the encoded fragment of the antibody or antigen binding fragment thereof according to the present invention comprises at least one CDR of the antibody, or the antigen binding fragment thereof. Tables 1 and 2 provide the SEQ ID numbers for the amino acid sequences of the CDRs and VH and VL of exemplary antibodies according to the present invention. Accordingly, the nucleic acid molecule according to the present invention preferably comprises a polynucleotide encoding one or more of the amino acid sequences shown in Tables 1 and 2. Preferably, the encoded fragment of the antibody or antigen binding fragment thereof according to the present invention comprises three CDRs, more preferably all three heavy chain CDRs of an epitope binding site (CDRH1, CDRH2, CDRH3) and/or all three light chain CDRs of an epitope binding site (CDRL1, CDRL2, CDRL3). Accordingly, it is preferred that the encoded fragment of the antibody or antigen binding fragment thereof comprises (exactly) three or six CDRs. Accordingly, the nucleic acid molecule according to the present invention preferably comprises a polynucleotide encoding three or six of the CDR amino acid sequences shown in Tables 1 and 2, in particular corresponding CDRH1, CDRH2, and CDRH3 sequences, and/or CDRL1, CDRL2, and CDRL3 sequences. More preferably, the encoded fragment of the antibody or antigen binding fragment thereof comprises a variable region, for example a heavy chain variable region (VH) and/or a light chain variable region (VL). Accordingly, it is preferred that the encoded fragment of the antibody or antigen binding fragment thereof comprises (exactly) one or two variable regions. Accordingly, the nucleic acid molecule according to the present invention preferably comprises a polynucleotide encoding one or two of the variable region amino acid sequences shown in Tables 1 and 2. Most preferably, the encoded fragment of the antibody or antigen binding fragment thereof comprises a (complete) polypeptide chain of the antibody or antigen binding fragment thereof according to the present invention. Such a (complete) polypeptide chain may be, for example, a (complete) heavy chain or a (complete) light chain. However, such a (complete) polypeptide chain may also comprise both, heavy and light chain elements, which is known in the art for many multispecific antibody formats (e.g., polypeptide chains comprising heavy chain constant regions, but also, e.g. in addition to one or more heavy chain variable region(s), a light chain variable region).

The nucleic acid molecule may be mono-, bi-, or multicistronic, such as tricistronic. A bicistronic or multicistronic nucleic acid molecule is typically a nucleic acid molecule that typically may have two (bicistronic) or more (multicistronic) open reading frames (ORFs). An open reading frame in this context is a sequence of codons that is translatable into a peptide or protein. More generally, the nucleic acid molecule of the present invention contains at least one polynucleotide coding for at least one antibody, or antigen binding fragment thereof, according to the present invention. If more the nucleic acid molecule according to the present invention comprises more than one coding polynucleotide, the second, third etc. coding polynucleotide may code for other peptides/proteins and/or may code for antibodies, e.g. according to the present invention, or fragments thereof as well, which may be the same or distinct from the first antibody coding region. In a preferred embodiment, the inventive nucleic acid molecule contains at least two coding polynucleotides, for example (exactly) two or three coding polynucleotides, all of them coding for identical or distinct antibodies or fragments or variants thereof. For example, distinct fragments of an antibody, or an antigen binding fragment thereof, according to the present invention may be encoded by different polynucleotides on the same nucleic acid molecule. In still another embodiment of the present invention, an inventive nucleic acid molecule may code for more than one antibody or a fragment of an antibody within the same coding region. In summary, the inventive nucleic acid molecule may be mono-, bi- or multicistronic.

For example, in one preferred embodiment, the antibody, or the antigen binding fragment thereof, according to the present invention may be a single chain antibody. In this case, it is preferred that the complete single chain of the antibody or the antigen binding fragment thereof is encoded by one single polynucleotide. Accordingly, it is preferred that the nucleic acid molecule according to the present invention is monocistronic, in particular it may comprise one (single) polynucleotide encoding the antibody, or the antigen binding fragment thereof, according to the present invention.

It is also preferred that the antibody, or the antigen binding fragment thereof, according to the present invention comprises (exactly) two distinct polypeptide chains, such as, for example, a heavy chain and a light chain. This may be illustrated by a classical native IgG molecule, which comprises two identical heavy chains and two identical light chains and, thus, two distinct polypeptide chains (even though the antibody finally comprises four polypeptide chains, they may be encoded by two (distinct) polynucleotides). Preferably, such two distinct polypeptide chains (e.g., a heavy chain and a light chain) of the antibody, or the antigen binding fragment thereof, according to the present invention may be encoded by two distinct polynucleotides, which may be located on the same nucleic acid molecule, e.g. in a bicistronic nucleic acid molecule, or on (exactly two) distinct nucleic acid molecules (e.g., each nucleic acid molecule may be monocistronic). Accordingly, it is preferred that the nucleic acid molecule according to the present invention is bicistronic, in particular it may comprise (exactly) two polynucleotides encoding (together) the antibody, or the antigen binding fragment thereof, according to the present invention. It is also preferred that the nucleic acid molecule according to the present invention comprises (at least or exactly) one polynucleotide encoding a fragment of the antibody, or the antigen binding fragment thereof, according to the present invention, as described above (e.g., a (complete) polypeptide chain). Accordingly, it is preferred that the nucleic acid molecule according to the present invention is monocistronic. Moreover, the antibody, or the antigen binding fragment thereof, according to the present invention may be encoded by a plurality of (e.g., monocistronic) nucleic acid molecules. For example, an antibody comprising two distinct polypeptide chains may be encoded by two polynucleotides located on two distinct nucleic acid molecules.

It is also preferred that the antibody, or the antigen binding fragment thereof, according to the present invention comprises (exactly) three distinct polypeptide chains. Accordingly, it is preferred that the nucleic acid molecule is tricistronic (e.g., encoding all three polypeptide chains comprised in such an antibody, or the antigen binding fragment thereof, according to the present invention). However, it is also preferred that the nucleic acid molecule is mono- or bicistronic, for example encoding one single or two polypeptide chains comprised in such an antibody, or the antigen binding fragment thereof, according to the present invention. For example, a plurality of nucleic acid molecules, such as two or three nucleic acid molecules, may encode (together) the antibody, or the antigen binding fragment thereof, according to the present invention.

For example, the antibody, or the antigen binding fragment thereof, according to the present invention is particularly preferably in the Fabs-in-tandem-Ig (FIT-Ig) format, which usually comprises the following three polypeptide chains:

Polypeptide 1 comprising or consisting of the light chain of the outer Fab and the heavy chain of the inner Fab including the constant domains CH1-CH2-CH3, preferably with the "LALA" mutation as described above, wherein preferably the light chain of the outer Fab is fused, preferably without linkers, to the N-terminus of the heavy chain of the inner Fab;

Polypeptide 2 comprising or consisting of the heavy chain of the outer Fab (VH and CH1 of the outer Fab); and Polypeptide 3 comprising or consisting of the light chain of the inner Fab.

Accordingly, such a FIT-Ig may preferably be encoded by one (e.g., tricistronic) nucleic acid molecule, by three (e.g., monocistronic) nucleic acid molecule, or by two (e.g., one monocistronic, one bicistronic) nucleic acid molecules.

Accordingly, it is preferred that the nucleic acid molecule according to the present invention comprises a polynucleotide encoding polypeptide 1 of a FIT-Ig antibody according to the present invention. More preferably, the nucleic acid molecule does not comprise polynucleotides encoding polypeptide 2 or polypeptide 3 of the FIT-Ig antibody according to the present invention. Such a nucleic acid molecule is preferably monocistronic.

It is also preferred that the nucleic acid molecule according to the present invention comprises a polynucleotide encoding polypeptide 2 of a FIT-Ig antibody according to the present invention. More preferably, the nucleic acid molecule does not comprise polynucleotides encoding polypeptide 1 or polypeptide 3 of the FIT-Ig antibody according to the present invention. Such a nucleic acid molecule is preferably monocistronic.

It is also preferred that the nucleic acid molecule according to the present invention comprises a polynucleotide encoding polypeptide 3 of a FIT-Ig antibody according to the present invention. More preferably, the nucleic acid molecule does not comprise polynucleotides encoding polypeptide 1 or polypeptide 2 of the FIT-Ig antibody according to the present invention. Such a nucleic acid molecule is preferably monocistronic.

It is also preferred that the nucleic acid molecule according to the present invention comprises a polynucleotide encoding polypeptide 1 and a polynucleotide encoding polypeptide 2 of a FIT-Ig antibody according to the present invention. More preferably, the nucleic acid molecule does not comprise a polynucleotide encoding polypeptide 3 of the FIT-Ig antibody according to the present invention. Such a nucleic acid molecule is preferably bicistronic.

It is also preferred that the nucleic acid molecule according to the present invention comprises a polynucleotide encoding polypeptide 1 and a polynucleotide encoding polypeptide 3 of a FIT-Ig antibody according to the present invention. More preferably, the nucleic acid molecule does not comprise a polynucleotide encoding polypeptide 2 of the FIT-Ig antibody according to the present invention. Such a nucleic acid molecule is preferably bicistronic.

It is also preferred that the nucleic acid molecule according to the present invention comprises a polynucleotide encoding polypeptide 2 and a polynucleotide encoding polypeptide 3 of a FIT-Ig antibody according to the present invention. More preferably, the nucleic acid molecule does not comprise a polynucleotide encoding polypeptide 1 of the FIT-Ig antibody according to the present invention. Such a nucleic acid molecule is preferably bicistronic.

Particularly preferably, the nucleic acid molecule according to the present invention comprises a polynucleotide encoding polypeptide 1, a polynucleotide encoding polypeptide 2 and a polynucleotide encoding polypeptide 3 of a FIT-Ig antibody according to the present invention. Such a nucleic acid molecule is preferably tricistronic.

In general, the nucleic acid molecule may be a DNA molecule or an RNA molecule. Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA. Preferably, the nucleic acid molecule is a DNA plasmid or an mRNA molecule. A DNA plasmid is a circular, preferably double-stranded, DNA molecule.

Table 3 below provides the SEQ ID numbers for exemplary nucleic acid sequences encoding the CDRs and VH and VL of exemplary antibodies according to the present invention. Due to the redundancy of the genetic code, the present invention also comprises sequence variants of these nucleic acid sequences and in particular such sequence variants, which encode the same amino acid sequences.

TABLE 3 shows exemplary nucleic acid sequences of the CDR's and the heavy chain variable region (VH) and the light chain variable region (VL) of five exemplary antibodies ("ZKA190", "ZKA64", "ZKA230", "ZKA185", "ZKA78"):

| ZKA190 | SEQ ID NO. | Nucleic acid sequence |
|---|---|---|
| CDRH1 | 10 | ggattcaccttcagtaaatatggc |
| CDRH2 | 11 | atatcatatgagggaagtaataaa |
| CDRH3 | 12 | gcgaaatcggggacccaatactatgatactactggttatg agtataggggtttggaatactttggctac |
| CDRL1 | 13 | cagagtgttagtagcagttac |
| CDRL2 | 14 | gatgcatcc |
| CDRL2 long | 15 | ctcatctatgatgcatccagcagggcc |
| CDRL3 | 16 | cagcagtatggtaggtcaaggtggaca |
| VH | 17 | caggtgcagctggtggagtctgggggaggcgtggtccagc ctgggaggtccctgagactctcctgtgcagcctctggatt caccttcagtaaatatggcatgcactgggtccgccaggct ccaggcaaggggctggagtgggtggcagttatatcatatg agggaagtaataaaattatgcagactccgtgaagggccg attcaccatctccagagacaattccaagaacacgctgtat ctgcaaatgaacagcctgagagctgaggacacggcagtgt attactgtgcgaaatcggggacccaatactatgatactac tggttatgagtataggggtttggaatactttggctactgg ggccagggaaccctggtcaccgtctcctcag |
| VL | 18 | gaaattgtgttgacgcagtctccaggcaccctgtctttgt ctccaggggaaagagccaccctctcctgcagggccagtca gagtgttagtagcagttacttagcctggtaccagcagaaa cgtggccaggctcccaggctcctcatctatgatgcatcca gcagggccactggcatcccagacaggttcagtggcagtgg gtctgggacagacttcactctcaccatcagcagactggag cctgaagattttgcagtgtattactgtcagcagtatggta ggtcaaggtggacattcggccaagggaccaaggtggaaat caaac |

| ZKA185 | SEQ ID NO. | Nucleic acid sequence |
|---|---|---|
| CDRH1 | 28 | ggatatagttttaccagttactgg |
| CDRH2 | 29 | tttgatcctagtgactctcaaacc |
| CDRH3 | 30 | gcgagaagatattgtagtagtagttgttatgtggacaat |
| CDRL1 | 31 | gcattgccaaataaattt |
| CDRL2 | 32 | gaggacaac |
| CDRL2 long | 33 | gtcatctatgaggacaacaaacgaccc |
| CDRL3 | 34 | tactcaacagacagcagttctaatcccctgggagta |
| VH | 35 | gaagtgcagctggtgcagtccggagcagaggtgaaaaagc ccggggagtctctgaggatctcctgtaagggttctggata tagttttaccagttactggatcacctgggtgcgccagatg cccgggaaaggcctggagtggatggcgaagtttgatccta gtgactctcaaaccaactacagcccgtccttccaaggcca cgtcaccatctcagttgacaagtccatcagcactgcctac ttgcagtggagcagcctgaaggcctcggacaccgccatgt attactgtgcgagaagatattgtagtagtagttgtta tgtggacaattggggccagggaaccctggtcaccatcttc tcag |
| VL | 36 | tcctatgagctgacacagccaccctcggtgtcagtgtccc caggacaaacggccaggatcacctgctctggagatgcatt gccaaataaatttgcttattggtaccggcagaagtcaggc caggcccctgttctggtcatctatgaggacaacaaacgac cctccgggatccctgagagattctctggctccagctcagg gacaatggcacctgactatcagtggggccaggtggag gatgaagctgactaccactgttactcaacagacagcagtt |

TABLE 3-continued shows exemplary nucleic acid sequences of the CDR's and the heavy chain variable region (VH) and the light chain variable region (VL) of five exemplary antibodies ("ZKA190", "ZKA64", "ZKA230", "ZKA185", "ZKA78"):

| | | |
|---|---|---|
| | | ctaatccctgggagta ttcggcggagggaccaagctgac cgtcctag |

| ZKA230 | SEQ ID NO. | Nucleic acid sequence |
|---|---|---|
| CDRH1 | 46 | ggtggctccatcagtagtgactac |
| CDRH2 | 47 | atctattacagtgggagcacc |
| CDRH3 | 48 | gcgaggaggaggaagtatgattccctttgggggagttttg cttttgatatc |
| CDRL1 | 49 | agctccaacatcggaggtaattat |
| CDRL2 | 50 | attaatgat |
| CDRL2 long | 51 | ctcatctgtattaatgatcaccggccc |
| CDRL3 | 52 | gcaacatgggatgacagcctgggtggccttgta |
| VH | 53 | caggtgcagctgcaggagtcgggcccaggcctggtgaagc cttcggagaccctgtccctcacctgcgcagtctctggtgg ctccatcagtagtgactacggagctggatccggcagccc ccagggaagggactggagtggattgggtatctattaca gtgggagcaccaactacaacccctccctcaagagtcgagt caccatatcagtagacacgtccaagaaccacttctccctg aagctgaactctgtgaccgctgcggacacggccgtgtatt actgtgcgaggaggaggaagtatgattccctttgggggag ttttgcttttgatatctggggccaagggacaatggtcacc gtctcttcag |
| VL | 54 | cagtctgtgctgactcagccaccctcagcgtctgggaccc ccgggcagagggtcaccatctcttgttctggaagcagctc caacatcggaggtaattatgtatactggtaccagcagctc ccaggaacggcccccaaactcctcatctgtattaatgatc accggccctcaggggtccctgaccgattctctggctccaa gtctggcacctcagcctccctggccatcagtgggctccag tccgaggatgaggctgattattactgtgcaacatgggatg acagcctgggtggccttgtattcggcgagggaccaagct gaccgtcctag |

| ZKA78 | SEQ ID NO. | Nucleic acid sequence |
|---|---|---|
| CDRH1 | 64 | ggcttcacttttagtaactatgca |
| CDRH2 | 65 | atcgggcgcaacggggactctatc |
| CDRH3 | 66 | gtgaaagatctggccatccccgagtcctacagaattgaag ctgattat |
| CDRL1 | 67 | cagtccgtgctgtaccgctctaacaacaagaattac |
| CDRL2 | 68 | tgggcttca |
| CDRL2 long | 69 | ctgatctattgggcttcaacccgggaa |
| CDRL3 | 70 | cagcagtactattctagtcctcgaact |
| VH | 71 | gaggtgcagctggcagaatcaggcggggactggtccagc ctggcggcagcctgacactgtcttgcagtggatcaggctt cacttttagtaactatgcaatggtgtgggcaaggcaggct cctgggaagggactggagtatgtctctggcatcgggcgca acggggactctatctactatactgatagtgtgaagggccg gttcaccatcagcagagacaatagcaaatccatggtgtac ctgcagatgagctccctgcgaaccgaagacacagcagtgt actattgcgtgaaagatctggccatccccgagtcctacag aattgaagctgattattggggacagggcaccctggtcatc gtgagcgccg |
| VL | 72 | gacatcgtgatgacacagtctccagatagtctggcagtca gtctggggagagggccactattaactgcaagagctcccagtccgtgctgtaccgctctaacaacaagaattacctgtct tggtatcagcagaagcccggacagccccctaaactgctga |

TABLE 3-continued shows exemplary nucleic acid sequences of the CDR's and the heavy
chain variable region (VH) and the light chain variable region (VL)
of five exemplary antibodies ("ZKA190", "ZKA64", "ZKA230", "ZKA185",
"ZKA78"):

|  |  | tctattgggcttcaacccgggaaagcggcgtcccagacag<br>attctcaggcagcgggtccggaacagacttcaccctgaca<br>attagcccctgcaggcagaggacgtggctgtctactatt<br>gtcagcagtactattctagtcctcgaactttcggccaggg<br>gaccaaggtggaaatcaaac |
|---|---|---|
| ZKA64 | SEQ ID NO. | Nucleic acid sequence |
| CDRH1 | 82 | ggctacaccttcacagggtatcac |
| CDRH2 | 83 | attaaccctaattctggcgggacc |
| CDRH3 | 84 | gctcggatgagctcctctatttggggcttcgatcat |
| CDRL1 | 85 | cagtctgtgctgattaac |
| CDRL2 | 86 | ggagcatcc |
| CDRL2 long | 87 | ctgatctatggagcatcctccagggct |
| CDRL3 | 88 | cagcagtacaatgattggcccctatcaca |
| VH | 89 | caggtgcagctggtccagagcggagcagaggtgaagaaac<br>ccggcgcctcagtgaaggtcagctgcaaagcttccggcta<br>caccttcacagggtatcacatcgactgggtgaggcaggca<br>agaggacagggactggaatggatgggacggattaaccta<br>attctggcgggaccaactacgcccagaagtttcagggccg<br>agtgactatgaccagagacaccagcatctccacagcttat<br>atgcagctgtcccggctgagatctgacgatagtgccgtct<br>actattgtgctcggatgagctcctctatttggggcttcga<br>tcattggggcagggaacactggtgactgtcagttcag |
| VL | 90 | gagatcgtgatgactcagtctccagccaccctgtcagtca<br>gcccaggagaacgggcaaccctgtcttgcagagcctccca<br>gtctgtgctgattaacctggcttggtaccagcagaagcca<br>ggccaggcaccccgactgctgatctatggagcatcctcca<br>gggctaccggcattcctgcacgcttcagtggatcaggaag<br>cggaacagagtttaccctgacaatctctagtctgcagtcc<br>gaagacttcgctgtctactattgtcagcagtacaatgatt<br>ggcccctatcacatttggccaggggactagactggagat<br>caagc |

Preferably, the sequence of the nucleic acid molecule according to the present invention comprises or consists of a nucleic acid sequence according to any one of SEQ ID NOs: 10-18, 28-36, 46-54, 64-72, and 82-90; or a functional sequence variant thereof.

It is also preferred that nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a CDR, a VH sequence and/or a VL sequence shown in Tables 1 and 2, for example to the sequences shown in Table 3.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, a VH sequence and/or a VL sequence of an (exemplary) antibody of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

In a further aspect, the present invention also provides a plurality of nucleic acid molecules as described above, wherein each nucleic acid molecule comprises at least one polynucleotide encoding a fragment of the antibody, or of the antigen binding fragment thereof, according to the present invention, as described above. Preferably, the plurality of fragments encoded by the plurality of nucleic acid molecules forms an antibody, or an antigen binding fragment thereof, according to the present invention. In other words, it is preferred that the plurality of nucleic acid molecules according to the present invention encodes the (complete) antibody, or the (complete) antigen binding fragment thereof, according to the present invention. This means that, in particular, no further nucleic acid molecules (in addition to the plurality of nucleic acid molecules according to the present invention) are required to encode/produce the (complete) antibody, or the (complete) antigen binding fragment thereof, according to the present invention. For example, the plurality of nucleic acid molecules according to the present invention, encodes all polypeptide chains of an antibody, or of an antigen binding fragment thereof, according to the present invention.

A preferred example of the plurality of nucleic acid molecules according to the present invention are (exactly) two nucleic acid molecules, wherein each of the nucleic acid molecules comprises one single or more than one (e.g., two or three) polynucleotides, each polynucleotide encoding a (distinct) polypeptide chain of the antibody, or of the antigen binding fragment thereof, according to the present invention. Accordingly, the nucleic acid molecules of such a plurality of nucleic acid molecules are preferably mono- or bicistronic. An example thereof are two nucleic acid molecules encoding together a FIT-Ig antibody according to the present invention as described above (e.g., one bicistronic nucleic acid molecule combined with the corresponding monocistronic nucleic acid molecule, such that polypeptides 1, 2 and 3 of the FIT-Ig are encoded by the two nucleic acid molecules; as described above).

In another preferred example, the present invention provides (exactly) three nucleic acid molecules, wherein each of the nucleic acid molecules comprises one (single) polynucleotide encoding a (distinct) polypeptide chain of the antibody, or of the antigen binding fragment thereof, according to the present invention. Accordingly, the nucleic acid molecules of such a plurality of nucleic acid molecules are preferably monocistronic. An examples thereof are three nucleic acid molecules encoding together a FIT-Ig antibody according to the present invention as described above (e.g., three (e.g., monocistronic) nucleic acid molecules, one encoding polypeptide 1 of the FIT-Ig, another encoding polypeptide 2 of the FIT-Ig, and the third encoding polypeptide 3 of the FIT-Ig; as described above).

Vector

Further included within the scope of the invention are vectors, for example, expression vectors, comprising a nucleic acid molecule according to the present invention. Preferably, a vector comprises a nucleic acid molecule as described above.

The term "vector" refers to a nucleic acid molecule, preferably to a recombinant nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule, such as a DNA plasmid. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

In a further aspect, the present invention also provides a plurality of vectors according to the present invention, preferably encoding the antibody, or the antigen binding fragment thereof, according to the present invention. Accordingly, preferred embodiments and examples of the plurality of nucleic acid molecules according to the present invention as described above also apply for the plurality of vectors according to the present invention.

Cells

In a further aspect, the present invention also provides cell expressing the antibody, or the antigen binding fragment thereof, according to the present invention; and/or comprising the vector according the present invention or the plurality of vectors according the present invention.

Examples of such cells include but are not limited to, eukaryotic cells, e.g., yeast cells, animal cells or plant cells. Preferably, the cells are mammalian cells, more preferably a mammalian cell line. Preferred examples include human cells, CHO cells, HEK293T cells, PER.C6 cells, NS0 cells, human liver cells, myeloma cells or hybridoma cells.

In particular, the cell may be transfected with the vector according to the present invention or with the plurality of vectors according to the present invention, preferably with an expression vector or a plurality thereof. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Moreover, the cells of the present invention may be transfected stably or transiently with the vector according to the present invention or with the plurality of vectors according to the present invention, e.g. for expressing the antibody, or the antigen binding fragment thereof, according to the present invention. Preferably, the cells are stably transfected with the vector according to the present invention or with the plurality of vectors according to the present invention encoding the antibody, or the antigen binding fragment thereof, according to the present invention. Alternatively, it is also preferred that the cells are transiently transfected with the vector according to the present invention or with the plurality of vectors according to the present invention encoding the antibody, or the antigen binding fragment thereof, according to the present invention.

Optional Additional Features of the Antibodies

Antibodies of the invention may be coupled, for example, to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. Labeled antibodies according to the present invention may be thus be used in such assays for example as described in U.S. Pat. Nos. 3,766,162; 3,791,932; 3,817,837; and 4,233,402.

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heterconjugate as described in U.S. Pat. No. 4,676,980. In addition, linkers may be used between the labels and the antibodies of the invention, e.g., as described in U.S. Pat. No. 4,831,175. Antibodies or, antigen-binding fragments thereof may be directly labeled with radioactive iodine, indium, yttrium, or other radioactive particle known in the art, e.g., as described in U.S. Pat. No. 5,595,721. Treatment may consist of a combination of treatment with conjugated and non-conjugated antibodies administered simultaneously or subsequently e.g., as described in WO00/52031; WO00/52473.

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. Nos. 4,766,106; 4,179,337; 4,495,285 and 4,609,546. In some embodiments the polymers may be selected from polyoxyethylated polyols and polyethylene glycol (PEG). PEG is soluble in water at room temperature and has the general formula: $R(O-CH_2-CH_2)_nO-R$, wherein R can be hydrogen, or a protective group such as an alkyl or alkanol group. Preferably, the protective group may have between 1 and 8 carbons. For example, the protective group is methyl. The symbol n is a positive integer. In one embodiment n is between 1 and 1,000. In another embodiment n is between 2 and 500. Preferably, the PEG has an average molecular weight between 1,000 and 40,000, more preferably the PEG has a molecular weight between 2,000 and 20,000, even more preferably the PEG has a molecular weight between 3,000 and 12,000. Furthermore, PEG may have at least one hydroxy group, for example the PEG may have a terminal hydroxy group. For example, it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans inmono-, di-, triglycerides, this branching would not necessarily be seen as a foreign agent in the body. POG may have a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies of the invention may be immunogenic in non-human (or heterologous) hosts e.g., in mice. In particular, the antibodies may have an idiotope that is immunogenic in non-human hosts, but not in a human host. In particular, antibodies of the invention for human use include those that cannot be easily isolated from hosts such as mice, goats, rabbits, rats, non-primate mammals, etc. and cannot generally be obtained by humanization or from xeno-mice.

Pharmaceutical Composition

The present invention also provides a pharmaceutical composition comprising one or more of:
(i) the antibody, or the antibody fragment thereof, according to the present invention;
(ii) the nucleic acid molecule or the plurality of nucleic acid molecules according to the present invention;
(iii) the vector or the plurality of vectors according to the present invention; and/or
(iv) the cell according to the present invention.

In other words, the present invention also provides a pharmaceutical composition comprising the antibody, or the antigen binding fragment thereof, according to the present invention, the nucleic acid molecule according to the present invention, the plurality of nucleic acid molecules according to the present invention, the vector according to the present invention, the plurality of vectors according to the present invention and/or the cell according to the present invention.

The pharmaceutical composition may preferably also contain a pharmaceutically acceptable carrier, diluent and/or excipient. Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. In general, pharmaceutically acceptable carriers in a pharmaceutical composition according to the present invention may be active components or inactive components. Preferably, the pharmaceutically acceptable carrier in a pharmaceutical composition according to the present invention is not an active component in respect to Zika virus infection.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in a pharmaceutical composition may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, similar to Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody may be provided in kit form with sterile water or a sterile buffer.

It is preferred that the active ingredient in the composition is an antibody molecule, an antibody fragment or variants and derivatives thereof, in particular the active ingredient in the composition is an antibody, an antibody fragment or variants and derivatives thereof, according to the present invention. As such, it may be susceptible to degradation in the gastrointestinal tract. Thus, if the composition is to be administered by a route using the gastrointestinal tract, the composition may contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid. A vehicle is typically understood to be a material that is suitable for storing, transporting, and/or administering a compound, such as a pharmaceutically active compound, in particular the antibodies according to the present invention. For example, the vehicle may be a physiologically acceptable liquid, which is suitable for storing, transporting, and/or administering a pharmaceutically active compound, in particular the antibodies according to the present invention. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Preferably, the pharmaceutical composition may be prepared for oral administration, e.g. as tablets, capsules and the like, for topical administration, or as injectable, e.g. as liquid solutions or suspensions, whereby it is particularly preferred that the pharmaceutical composition is an injectable. Solid forms suitable for solution in, or suspension in, liquid vehicles prior to injection are also be preferred, e.g. that the pharmaceutical composition is in lyophilized form.

For injection, e.g. intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated. For injection, the pharmaceutical composition according to the present invention may be provided for example in a pre-filled syringe.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive pharmaceutical composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Dosage treatment may be a single dose schedule or a multiple dose schedule. In particular, the pharmaceutical composition may be provided as single-dose product. Preferably, the amount of the antibody in the pharmaceutical composition—in particular if provided as single-dose product—does not exceed 200 mg, more preferably does not exceed 100 mg, and even more preferably does not exceed 50 mg.

For example, the pharmaceutical composition according to the present invention may be administered daily, e.g. once or several times per day, e.g. once, twice, three times or four times per day, preferably once or twice per day, more preferable once per day, for 1, 2, 3, 4, 5, 6, 7, 8, 9, 10, 11, 12, 13, 14, 15, 16, 17, 18, 19, 20 or 21 or more days, e.g. daily for 1, 2, 3, 4, 5, 6 months. Preferably, the pharmaceutical composition according to the present invention may be administered weekly, e.g. once or twice per week, for 1, 2, 3, 4, 5, 6, 7, 8, 9, 10, 11, 12, 13, 14, 15, 16, 17, 18, 19, 20 or 21 or more weeks, e.g. weekly for 1, 2, 3, 4, 5, 6, 7, 8, 9, 10, 11, or 12 months or weekly for 2, 3, 4, or 5 years. Moreover, the pharmaceutical composition according to the present invention may be preferably administered monthly, e.g. once per month or, more preferably, every second month for 1, 2, 3, 4, or 5 or more years. It is also preferred that the administration continues for the lifetime. In addition, also one single administration only is also envisaged, in particular in respect to certain indications, e.g. for prevention of Zika virus infection in case of accidental exposure, e.g. in non-immunised subjects. However, the most preferred treatment schedule is post-exposure prophylaxis (PEP), wherein one or more single doses are administered as soon as possible after Zika infection. A prophylactic setting, wherein one or more single doses are administered to prevent Zika infection (i.e. before Zika infection, in particular in non-Zika-immunised subjects) is also preferred.

In particular, it is preferred that for a single dose, e.g. a daily, weekly or monthly dose, preferably for a weekly dose, the amount of the antibody, or the antigen binding fragment thereof, in the pharmaceutical composition according to the present invention, does not exceed 1 g, preferably does not exceed 500 mg, more preferably does not exceed 200 mg, even more preferably does not exceed 100 mg, and particularly preferably does not exceed 50 mg.

Pharmaceutical compositions typically include an "effective" amount of one or more antibodies of the invention, i.e. an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.005 to about 100 mg/kg, preferably from about 0.0075 to about 50 mg/kg, more preferably from about 0.01 to about 10 mg/kg, and even more preferably from about 0.02 to about 5 mg/kg, of the antibody of the present invention (e.g. amount of the antibody in the pharmaceutical composition) in relation to the bodyweight (e.g., in kg) of the individual to which it is administered.

Moreover, the pharmaceutical composition according to the present invention may also comprise an additional active component, which may be a further antibody or a component, which is not an antibody. The additional active component is preferably a checkpoint inhibitor. It is also preferred that a ZIKV neutralizing antibody, or an antigen binding fragment thereof, as described herein is combined with a ZIKV NS1-binding antibody, or an antigen binding fragment thereof, as described herein as additional active component (co-agent). Thereby, the pathogenic role of NS1 may be blocked in addition to neutralization of ZIKV. The pharmaceutical composition according to the present invention may comprise one or more of the additional active components, e.g. as described as co-agents below in the context of a combination therapy.

The antibody, or the antigen binding fragment, according to the present invention can be present either in the same pharmaceutical composition as the additional active component or, preferably, the antibody, or the antigen binding fragment, according to the present invention is comprised by a first pharmaceutical composition and the additional active component is comprised by a second pharmaceutical composition different from the first pharmaceutical composition. Accordingly, if more than one additional active component is envisaged, each additional active component and the antibody, or the antigen binding fragment, according to the present invention is preferably comprised by a different pharmaceutical composition. Such different pharmaceutical compositions may be administered either combined/simultaneously or at separate times or at separate locations (e.g. separate parts of the body).

Preferably, antibody, or the antigen binding fragment, according to the present invention and the additional active component provide an additive therapeutic effect or, preferably, a synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

A pharmaceutical composition comprising the antibody according to gZKA190, gZKA64, gZKA230, gZKA185, gZKA78 or an antigen binding fragment thereof, and a pharmaceutically acceptable carrier is preferred.

In one embodiment, a composition of the invention may include antibodies of the invention, wherein the antibodies may make up at least 50% by weight (e.g., 60%, 70%, 75%, 80%, 85%, 90%, 95%, 96%, 97%, 98%, 99% or more) of the total protein in the composition. In such a composition, the antibodies are preferably in purified form.

The present invention also provides a method of preparing a pharmaceutical composition comprising the steps of (i) preparing an antibody of the invention; and (ii) admixing the purified antibody with one or more pharmaceutically-acceptable carriers.

In another embodiment, a method of preparing a pharmaceutical composition comprises the step of: admixing an antibody with one or more pharmaceutically-acceptable carriers, wherein the antibody is a monoclonal antibody that was obtained from a transformed B cell or a cultured plasma cell of the invention.

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cells to a subject, such that the nucleic acid can be expressed in the subject in situ to provide a desired therapeutic effect. Suitable gene therapy and nucleic acid delivery vectors are known in the art.

Pharmaceutical compositions may include an antimicrobial particularly if packaged in a multiple dose format. They may comprise detergent e.g., a Tween (polysorbate), such as Tween 80.

Detergents are generally present at low levels e.g., less than 0.01%. Compositions may also include sodium salts (e.g., sodium chloride) to give tonicity. For example, a concentration of 10±2 mg/ml NaCl is typical.

Further, pharmaceutical compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilization may be adjusted to between 5 and 8, or between 5.5 and 7, or around 6.1 prior to lyophilization.

The compositions of the invention may also comprise one or more immunoregulatory agents. In one embodiment, one or more of the immunoregulatory agents include(s) an adjuvant.

Medical Treatments, Kits and Uses
Medical Treatments

In a further aspect, the present invention provides the use of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention in (i) prevention and/or treatment of Zika virus infection; or in (ii) diagnosis of Zika virus infection. Thereby, use of the antibody, or an antigen binding fragment thereof, according to the present invention (and in particular its preferred embodiments as described above) or of the (plurality of) nucleic acid molecule(s) according to the present invention encoding the antibody, or an antigen binding fragment thereof, according to the present invention is preferred in (i) prevention and/or treatment of Zika virus infection as described herein; or in (ii) diagnosis of Zika virus infection as described herein.

Methods of diagnosis may include contacting an antibody or an antibody fragment with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably plasma or serum. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods are well-known to the person skilled in the art and include, e.g., ELISA (enzyme-linked immunosorbent assay).

Prevention of Zika virus infection refers in particular to prophylactic settings, wherein the subject was not diagnosed with Zika virus infection (either no diagnosis was performed or diagnosis results were negative) and/or the subject does not show symptoms of Zika virus infection. Accordingly, prevention of Zika virus infection includes "post-exposure prophylaxis" (PEP), i.e. preventive treatment after a possible Zika virus infection, for example after a mosquito bite in a Zika virus affected area. Prevention of Zika virus infection is in particular useful in high-risk subjects, such as in pregnant subjects and/or in subjects staying in Zika virus affected areas (such as subjects living in Zika virus affected areas or travelling to Zika virus affected areas).

In therapeutic settings, in contrast, the subject is typically infected by Zika virus, diagnosed with Zika virus infection and/or showing symptoms of Zika virus infection. Of note, the terms "treatment" and "therapy"/"therapeutic" of ZIKV infection include (complete) cure as well as attenuation of ZIKV infection.

Accordingly, the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is preferably used for treatment of Zika virus infection in subjects diagnosed with Zika virus infection or in subjects showing symptoms of Zika infection.

It is also preferred that the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is used for prevention and/or treatment of Zika virus infection in asymptomatic subjects. Those subjects may be diagnosed or not diagnosed with Zika virus infection.

Preferably, the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is used for prevention and/or treatment of Zika virus infection in pregnant subjects, in particular to prevent congenital infection. For example, this may be performed in a similar manner as for the prevention of HCMV congenital infection as described in Nigro G, Adler S P, La Torre R, Best A M, Congenital Cytomegalovirus Collaborating Group: Passive immunization during pregnancy for congenital cytomegalovirus infection; N Engl J Med 2005, 353:1350-1362.

Without being bound to any theory, it is assumed that the antibody, or the antigen-binding fragment thereof, according to the present invention can pass the placenta through the interaction with FcRn, for example if administered to a pregnant subject, e.g. by (i.v.) injection or any other route of administration as described herein. Importantly, the interaction of "LALA" variants of antibodies as described herein with FcRn is not compromised. It is believed that FcRn is already expressed in the first trimester in the placenta.

Alternatively, the antibody, or the antigen-binding fragment thereof, or the (plurality of) nucleic acid molecule(s) according to the present invention may also be administered to the extra-amniotic space.

Preferably, the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is used for prevention and/or treatment of Zika virus infection, wherein the antibody, or the antigen binding fragment thereof, the nucleic acid, the vector, the plurality of nucleic acids, the plurality of vectors, the cell, or the pharmaceutical composition is administered up to seven days after (a possible) Zika virus infection, preferably up to five days after (a possible) Zika virus infection, more preferably up to four days after (a possible) Zika virus infection, even more preferably up to three days after (a possible) Zika virus infection, and most preferably up to one day or two days after (a possible) Zika virus infection. Such a treatment schedule may be useful in therapeutic settings as well as in prophylactic settings, in particular in post-exposure prophylaxis (PEP).

In PEP typically the first administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is as soon as possible after a possible ZIKV infection, e.g. after a mosquito bite in a ZIKV affected area. Accordingly, in PEP the first administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is typically up to one or more days after (a possible) ZIKV infection, as described above.

It is also preferred that the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is used for prevention and/or treatment of Zika virus infection, wherein the antibody, or the antigen binding fragment thereof, the nucleic acid, the vector, the plurality of nucleic acids, the plurality of vectors, the cell, or the pharmaceutical composition is administered up to three months before (a possible) Zika virus infection, preferably up to one month before (a possible) Zika virus infection, more preferably up to two weeks before (a possible) Zika virus infection, even more preferably up to one week before (a possible) Zika virus infection, and most preferably up to one day before (a possible) Zika virus infection. Such a treatment schedule refers in particular to a prophylactic setting.

In general—and in particular in PEP—after the first administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention, one or more subsequent administrations may follow, preferably a single dose per day or per every second day for 1, 2, 3, 4, 5, 6, 7, 8, 9, 10, 11, 12, 13, 1, 15, 16, 17, 18, 19, 20, or 21 days. It is also preferred that after the first administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention, one or more subsequent administrations may follow, preferably a single dose once or twice per week for 1, 2, 3, 4, 5, 6, 7, 8, 9, 10, 11, 12, 13, 1, 15, 16, 17, 18, 19, 20, or 21 weeks. It is also preferred that after the first administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention, one or more subsequent administrations may follow, preferably a single dose every 2 or 4 weeks for 1, 2, 3, 4, 5, 6, 7, 8, 9, 10, 11, 12, 13, 1, 15, 16, 17, 18, 19, 20, or 21 weeks. It is also preferred that after the first administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention, one or more subsequent administrations may follow, preferably a single dose every two or four months for 1, 2, 3, 4, 5, 6, 7, 8, 9, 10, 11, 12, 13, 1, 15, 16, 17, 18, 19, 20, or 21 months. It is also preferred that after the first administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention, one or more subsequent administrations may follow, preferably a single dose once or twice per year for 1, 2, 3, 4, 5, 6, 7, 8, 9, or 10 years.

Preferably, the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is administered at a (single) dose of 0.005 to 100 mg/kg bodyweight, preferably at a (single) dose of 0.0075 to 50 mg/kg bodyweight, more preferably at a (single) dose of 0.01 to 10 mg/kg bodyweight, even more preferably at a (single) dose of 0.05 to 5 mg/kg bodyweight, and particularly preferably at a (single) dose of 0.1 to 1 mg/kg bodyweight.

The antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention may be administered by any number of routes such as oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Intravenous administration, or subcutaneous administration or intramuscular administration are preferred and intravenous administration or subcutaneous administration are more preferred.

In pregnant subjects the antibody, or an antigen binding fragment thereof, or the (plurality of) nucleic acid molecule(s) according to the present invention may also be administered intra- or extra-amniotic, e.g. by injection.

Accordingly, the present invention also provides a method of preventing and/or treating Zika virus infection in a subject, wherein the method comprises administering to a subject in need thereof the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention. Preferred embodiments of this method correspond to preferred embodiments of the medical use as described above (and below, regarding combination therapy). For example, a preferred subject in this method is a subject diagnosed with Zika virus infection or showing symptoms of Zika virus infection. Another preferred subject in this method is a pregnant subject.

Combination Therapy

The administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention in the methods and uses according to the invention can be carried out alone or in combination with a co-agent (also referred to as "additional active component" herein), which is in particular useful for preventing and/or treating ZIKV infection.

The invention encompasses the administration of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention, wherein it is administered to a subject prior to, simultaneously or sequentially with other therapeutic regimens or co-agents useful for treating and/or preventing ZIKV infection. Said antibody, nucleic acid, vector, cell or pharmaceutical composition, that is administered simultaneously with said co-agents can be administered in the same or different composition(s) and by the same or different route(s) of administration.

Said other therapeutic regimens or co-agents may be, for example, a checkpoint inhibitor.

Thus, in another aspect of the present invention the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention is administered in combination with a checkpoint inhibitor for the (medical) uses as described herein.

Preferred checkpoint inhibitors are directed to a blockade of PD-1/PD-L1 and/or of CTLA4 and, thus, include anti- PD-1 antibodies, anti-PD-L1 antibodies and anti-CTLA4 antibodies. Thus, the pharmaceutical composition according to the present invention may comprise one or more of the additional active components.

It is also preferred that a ZIKV neutralizing antibody, or an antigen binding fragment thereof, as described herein is combined with a ZIKV NS1-binding antibody, or an antigen binding fragment thereof, as additional active component (co-agent). Thereby, the pathogenic role of NS1 may be blocked in addition to neutralization of ZIKV. Accordingly, a ZIKV NS1-binding antibody, or an antigen binding fragment thereof, for example as described in PCT/EP2017/067581, which is incorporated herein in its entirety, is a preferred additional active component (co-agent).

The antibody, or an antigen binding fragment thereof, according to the present invention, the nucleic acid molecule according to the present invention, the vector according to the present invention, the plurality of nucleic acid molecules according to the present invention, the plurality of vectors according to the present invention, or the cell according to the present invention can be present either in the same pharmaceutical composition as the additional active component (co-agent) or, preferably, the antibody, or an antigen binding fragment thereof, according to the present invention, the nucleic acid molecule according to the present invention, the vector according to the present invention, the plurality of nucleic acid molecules according to the present invention, the plurality of vectors according to the present invention, or the cell according to the present invention is comprised by a first pharmaceutical composition and the additional active component (co-agent) is comprised by a second pharmaceutical composition different from the first pharmaceutical composition. Accordingly, if more than one additional active component (co-agent) is envisaged, each additional active component (co-agent) is preferably comprised by a different pharmaceutical composition. Such different pharmaceutical compositions may be administered either combined/simultaneously ed/simultaneously or at separate times or at separate locations (e.g. separate parts of the body).

Preferably, the antibody, or the antigen binding fragment, according to the present invention and the additional active component (co-agent) provide an additive therapeutic effect or, preferably, a synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Further Use and Kits

In a further aspect, the present invention also provides the use of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention for monitoring the quality of an anti-Zika vaccine by checking that the antigen of said vaccine contains the specific epitope in the correct conformation. Preferred antigens comprised by such an anti-Zika vaccine to be checked include ZIKV envelope protein or any other molecule/complex comprising or consisting of (i) domain III of ZIKV E protein (EDIII) as described above or (ii) a quaternary ZIKV epitope as described above.

Moreover, the present invention also provides the use of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention in (in vitro) diagnosis of Zika virus infection.

In addition also the use of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention in determining whether an isolated blood sample (e.g., whole blood, serum and/or plasma) is infected with Zika virus is provided.

As described above, methods of diagnosis may include contacting an antibody or an antibody fragment with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably serum or plasma. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods are well-known to the person skilled in the art and include, e.g., ELISA (enzyme-linked immunosorbent assay).

In a further aspect, the present invention also provides a kit of parts comprising at least one antibody, or antigen binding fragment thereof, according to the present invention, at least one nucleic acid according to the present invention, the plurality of nucleic acids according to the present invention, at least one vector according to the present invention, the plurality of vectors according to the present invention, at least one cell according to the present invention, and/or at least one pharmaceutical composition according to the present invention. In addition, the kit may comprise means for administration of of the antibody, or an antigen binding fragment thereof, according to the present invention, the nucleic acid molecule according to the present invention, the vector according to the present invention, the plurality of nucleic acid molecules according to the present invention, the plurality of vectors according to the present invention, the cell according to the present invention or the pharmaceutical composition according to the present invention, such as a syringe or a vessel, a leaflet, and/or a co-agent to be administered as described above.

DESCRIPTION OF FIGURES

FIG. 1 shows the reactivity (ELISA) and ZIKV and DENV1 neutralizing activity of antibodies derived from four ZIKV immune donors (ZKA, ZKB, ZKC and ZKD) to E protein of ZIKV and DENV1-4 and to EDIII-domain of ZIKV E protein; NNB-neutralizing, non-E-protein binding antibodies.

FIG. 9 shows for Example 3 the neutralizing activity of ZKA190 and ZKA190-LALA antibody against three strains of ZIKV (H/PF/2013, MR766 and MRS_OPY_Martinique_PaRi_2015) on Vero cells as measured by flow-cytometry (% of infected cells).

Figure 10:
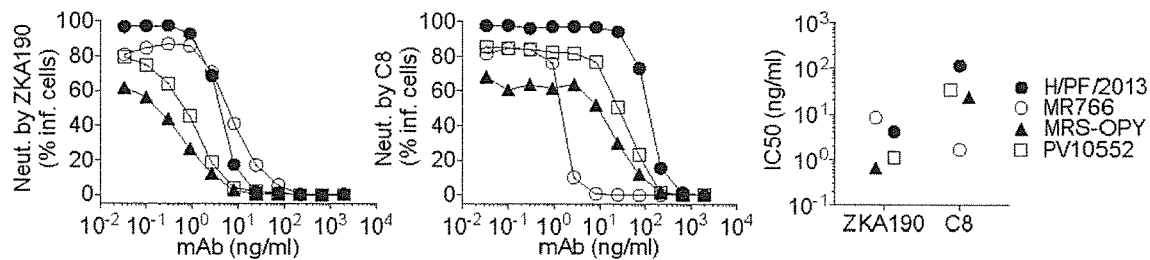

FIG. 10 shows for Example 5 neutralization of ZKA190 and CS mAbs tested against a panel of four strains of ZIKV, as determined by the percentage of infected Vero cells in the presence of increasing amounts of the mAbs (A). Shown are also the IC50 values (B) and statistics (C). Data are representative of at least two independent experiments.

Figure 11:
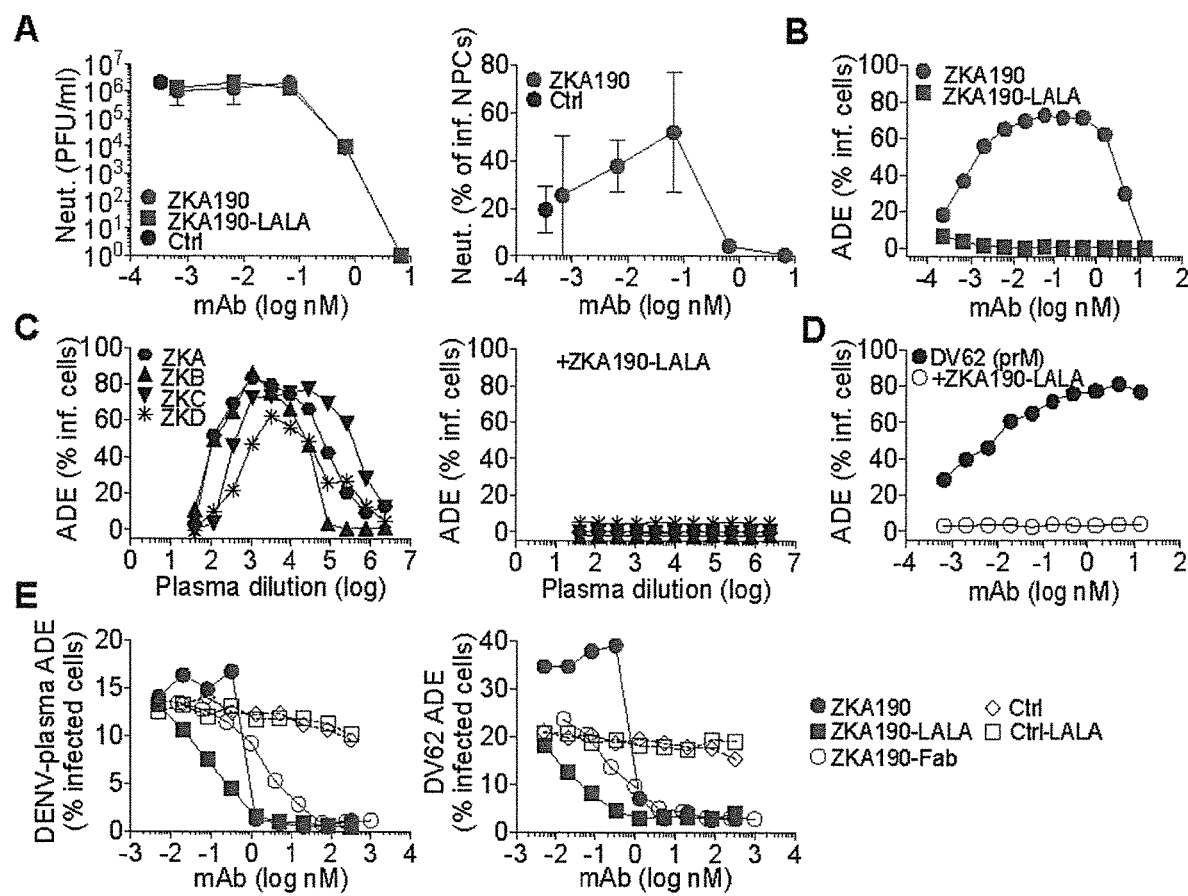

FIG. 11 shows for Example 6 the neutralization and enhancement of ZIKV infection by antibody ZKA190. (A) Neutralization of ZIKV PRVABC59 strain infection of hNPCs by ZKA190, ZKA190-LALA and a control mAb as determined by plaque assay on Vero cells (left panel) and indirect immunofluorescence of infected hNPCs using fluorophore-labelled anti-E antibody (right panel). (B) ADE of ZIKV infection of non-permissive K562 cells by ZKA190 and ZKA190-LALA. (C) ADE induced in K562 cells when ZIKV is pre-incubated with serial dilutions of plasma serum from different ZIKV-positive patients (left panel). When ZKA190 LALA is added to the ZIKV-serum complexes, ADE is inhibited (right panel). (D) ADE induced in K562 cells when ZIKV is pre-incubated with serial dilutions of a prM cross-reactive mAb (DV62) derived from a DENV-immune donor. ZKA190-LALA inhibits ADE of ZIKV when complexed with prM-reactive antibody DV62. (E) Effect on ADE induced by peak enhancing dilution of a DENV2 plasma (left panel) or anti-prM DV62 mAb (right panel) by serial dilutions of indicated mAbs.

Figure 12:
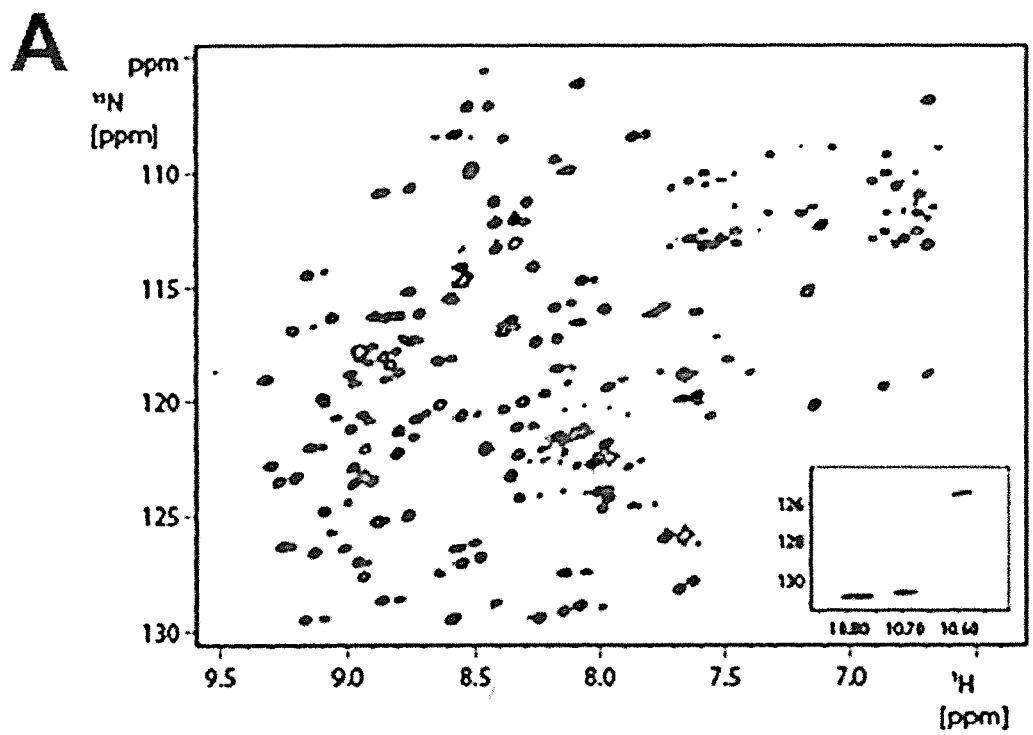
Figure 12:
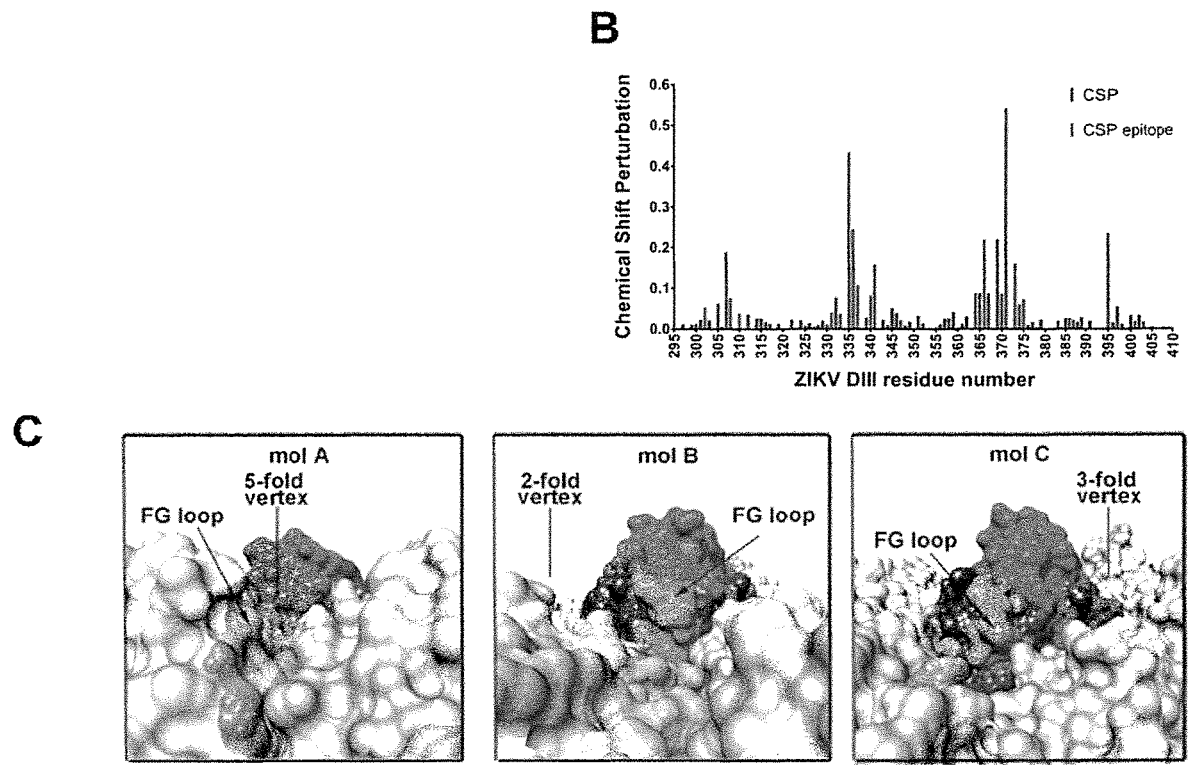
Figure 12:
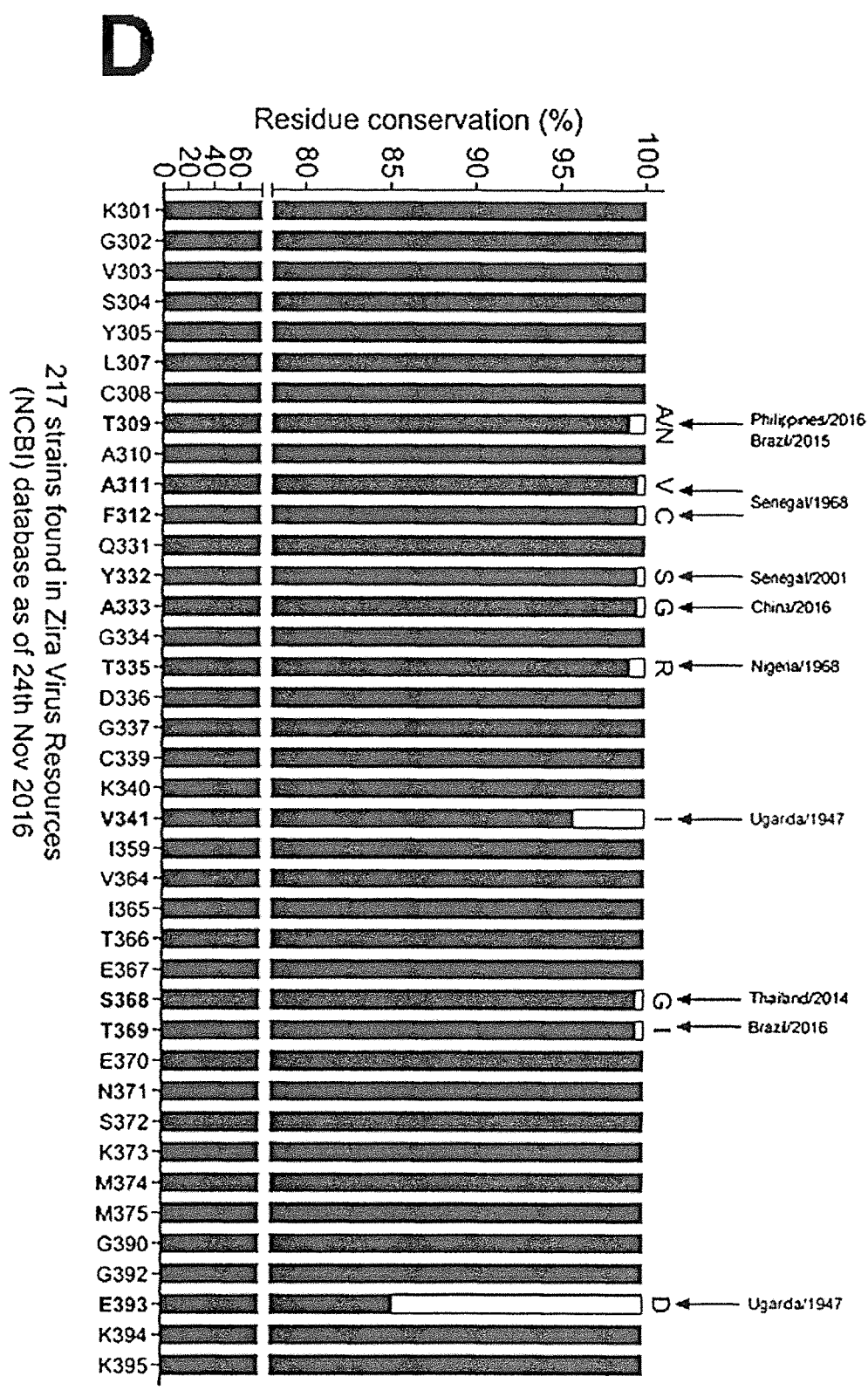
Figure 12:
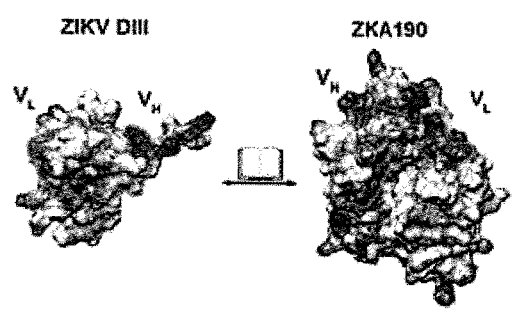

FIG. 12 shows for Example 7 the identification of ZKA190 epitope and analysis of its conservation in ZIKV strains. (A) Overlay of [$^{15}$N,$^{1}$H]-HSQC spectra of $^{15}$N-labeled ZIKV EDIII in absence (black) or presence (red) of unlabelled ZKA190 Fab. Differences identify EDIII residues affected by antibody binding. (B) NMR epitope mapping of ZKA190 Fab in complex with ZKV EDIII. The chemical shift perturbation (CSP, y-axis) is plotted against the EDIII residue number. Residues affected by antibody binding are in red. (C) Residues in FG loop identified by NMR epitope mapping is partially hidden in E protein mol A but largely exposed in mols B and C. EDIII of E protein was coloured in blue. Residues identified by NMR epitope mapping are coloured in magenta except those in the FG loop are coloured in green. Adjacent E proteins are shown as grey surface. (D) Level of amino acid residue conservation in ZKA190 epitope as calculated by the analysis of sequences from 217 ZIKV strains found in ZIKV Resources (NCBI) databases as of Nov. 24, 2016. (E) Open-book representation showing charge complementarity between the epitope and paratope of the docking result. Boundaries of the epitope and paratope are circled in green. The borders between heavy and light chains of Fab and its corresponding footprint on EDIII are shown as yellow dashed lines.

Figure 13:
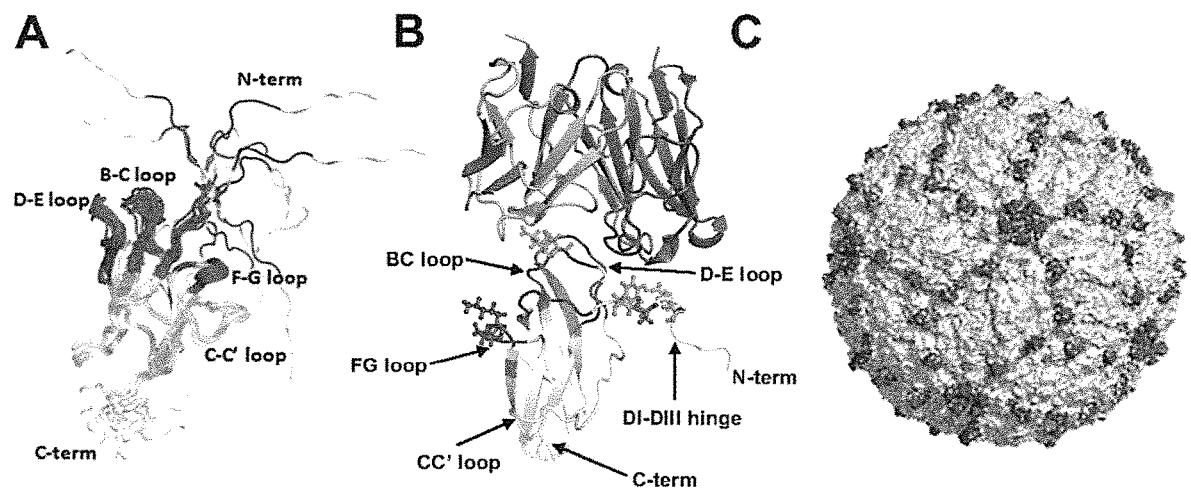

FIG. 13 shows for Example 7 the ZKA190 epitope identified by NMR and Docking. (A) Cartoon representation of the 12 lowest energy NMR structures of ZIKV EDIII, with residues affected by ZKA190 binding in red. Flexibility in the N-terminus of the construct is apparent. (B) Model of the ZKA190:EDIII complex derived by computational docking and molecular simulation validated by NMR results. The NMR identified epitope on EDIII (grey) is in red. The ZKA190 heavy and light chain are colored in dark and light green, respectively. EDIII residues that affect or not antibody binding when mutated are shown as orange and blue sticks, respectively. (C) NMR identified ZKA190 epitope (red) is accessible on the virus surface (white).

Figure 14:
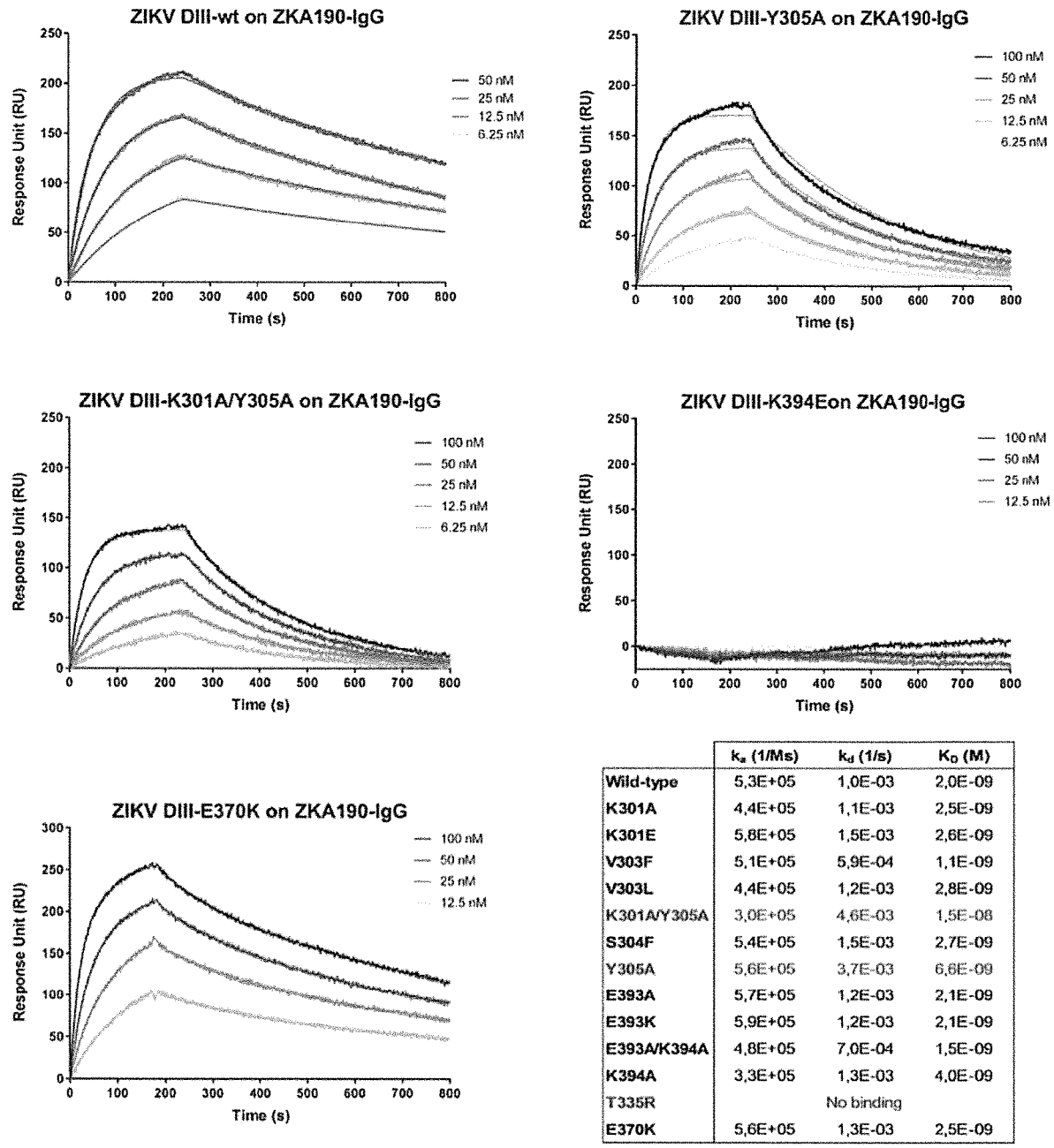

FIG. 14 shows for Examples 7 and 10 the binding of wt or mutated EDIII to ZKA190 IgG. SPR data and binding kinetics are shown. EDIII mutants that affect (red highlights) or do not affect binding are shown as indicated in the figure.

Figure 15:
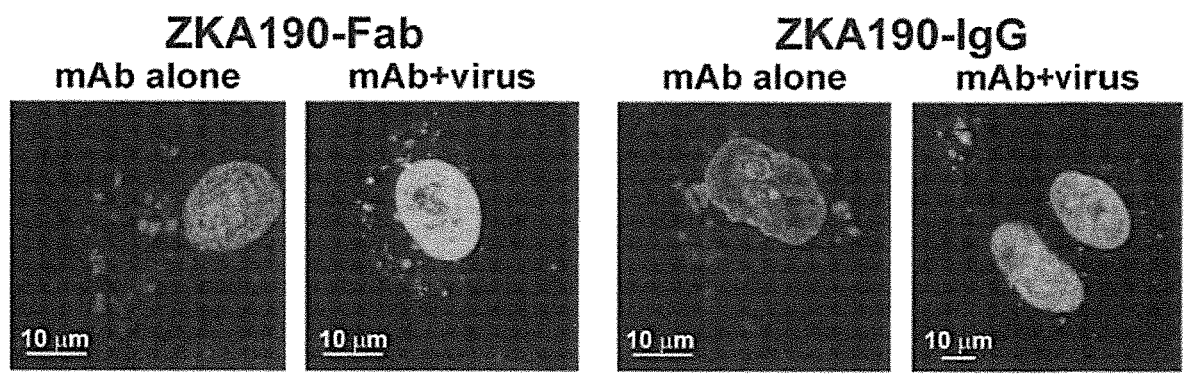

FIG. 15 shows for Example 8 the results of the confocal microscopy experiments. ZIKV incubated with a concentration exceeding 10,000-fold the 1050 value of either ZKA190 Fab or full IgG were added to Vero cells. The ZIKV:antibody complex is detected inside the cells (green) and co-localizes with endosomes (red, yellow overlay). Endosomes and acidic organelles are marked by Lysotracker red; Alexa-488 conjugated ZKA190 is in green. Nuclei are stained with DAPI (blue).

Figure 16:
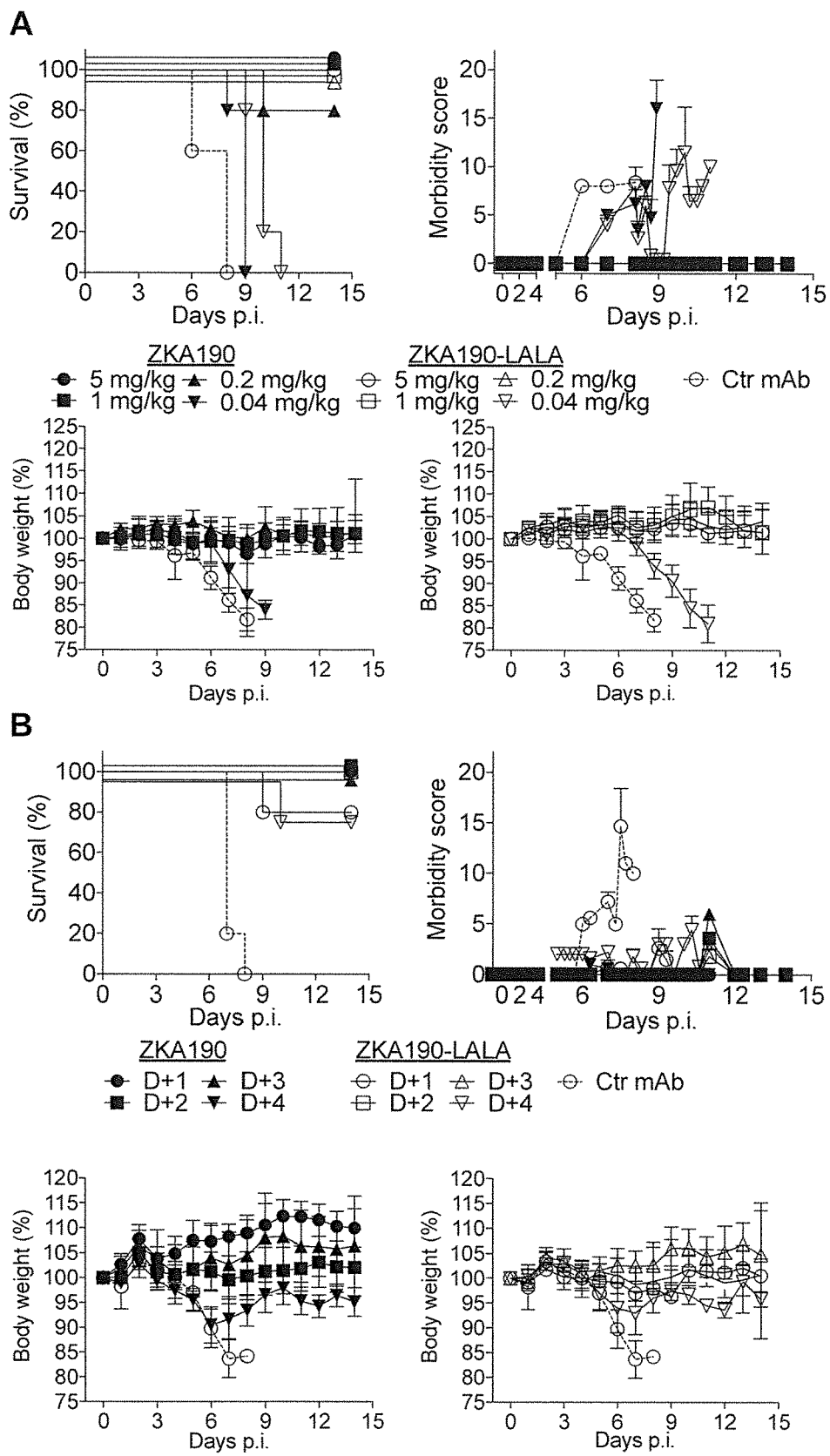

FIG. 16 shows for Example 9 prophylactic and therapeutic efficacy of ZKA190. (A) ZKA190 is strongly protective against ZIKV infection when administered prophylactically to mice (A129 in (A) and AG129 in (B)) challenged with a lethal dose of ZIKV strain MP17451. Experiments used N=4-8 mice per group. Kaplan-Meier survival curves are shown (A). Significance was determined by using the Mantel-Cox log-rank test. Panel A, top left: ZKA190 at 5, 1 and 0.2 mg/kg versus Ctr mAb, P=0.0031; ZKA190 at 0.04 mg/kg versus Ctr mAb, P=0.0116; ZKA190-LALA at 5, 1, 0.2 and 0.04 mg/kg versus Ctr mAb, P=0.0031. Panel A, top right: Morbidity score of mice monitored over a 14-15 day period (two different scoring methods were used; see (Dowall, S. D., Graham, V. A., Rayner, E., Atkinson, B., Hall, G., Watson, R. J., Bosworth, A., Bonney, L. C., Kitchen, S., and Hewson, R. (2016). A Susceptible Mouse Model for Zika Virus Infection. PLoS Negl Trop Dis 10, e0004658-13).

Panel A, lower panels: body weight of mice. Panels B: ZKA190 or ZKA190-LALA were administered at 15 mg/kg at different time-points after ZIKV infection. Panel B, top left: A Kaplan-Meier survival curve is shown. Experiments used N=5 mice per group. Significance was determined by using the Mantel-Cox log-rank test. ZKA190 and ZKA190-LALA given either on day 1, 2, 3 or 4 versus Ctr., P=0.0016. Panel B, top right: Morbidity score of mice monitored over a 14-day according to (Dowall et al., 2016). Mice were monitored over a 14 day period for body weight loss (Panel B, lower panels). Control antibody is MPEG specific for RSV F protein (Corti, D., et al. Cross-neutralization of four paramyxoviruses by a human monoclonal antibody. Nature 501, 439-443 (2013)).

Figure 17:
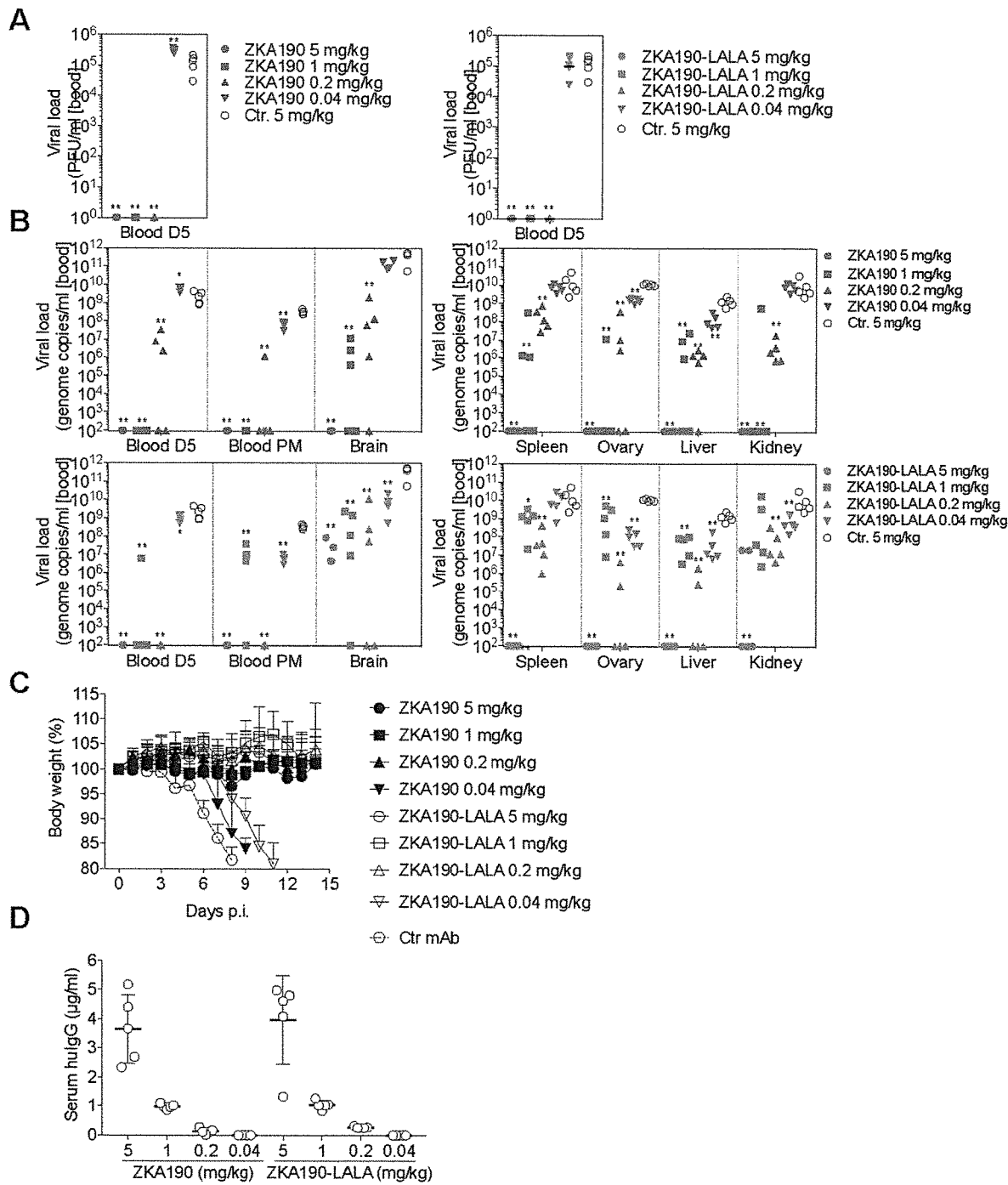

FIG. 17 shows for Example 9 the prophylactic efficacy of the anti-ZIKV EDIII-specific mAb ZKA190 against ZIKV strains MP1741. (A) Shown is the viremia measured as PFU/ml on day 5 in blood of all animals. (B) Viral load was measured as genomic copies/ml by qPCR on day 5 in blood of all animals and in blood and indicated tissues when animals were culled at the end of the study or when the humane end points were met. (C) Mice were monitored over a 14 day period for body weight loss (D) Human serum IgG concentration in day 5 blood samples. Significance was determined compared to control antibody treatment by nonparametric unpaired Mann-Whitney U test. *p<0.05; p<0.01; *p<0.001.

Figure 18:
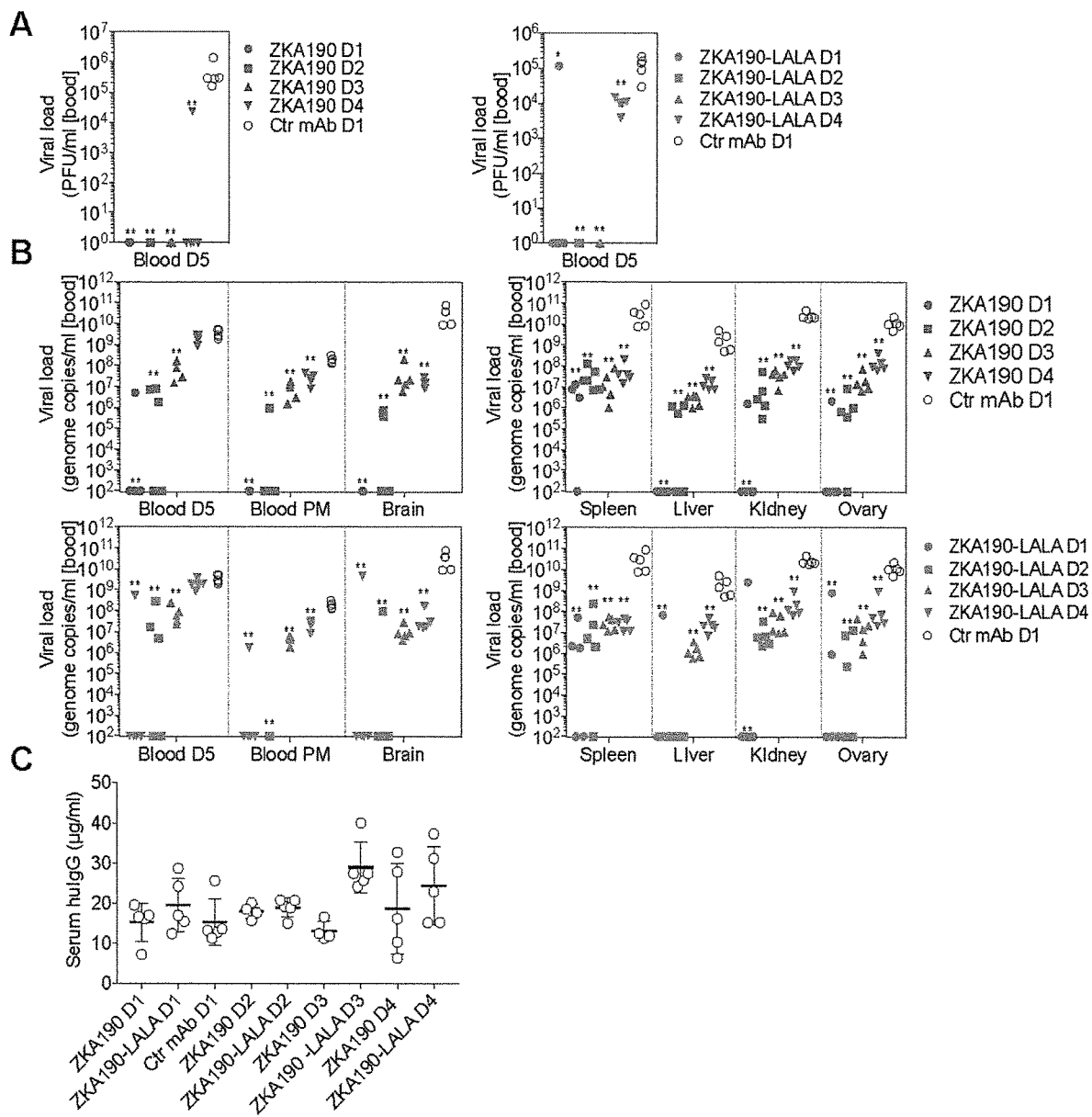

FIG. 18 shows for Example 9 the therapeutic efficacy of the anti-ZIKV EDIII-specific mAb ZKA190. (A) Viral loads were measured as PFUs on day 5 in blood of all animals. (B) Viral loads were measured as genomic copies by qPCR on day 5 in blood of all animals and in blood and indicated tissues when animals were culled at the end of the study or when the human end points were met. Significance was determined compared to control antibody treatment by nonparametric unpaired Mann-Whitney U test. *p<0.05; **p<0.01. (C) Human serum IgG concentration in day 5 blood samples.

Figure 3:
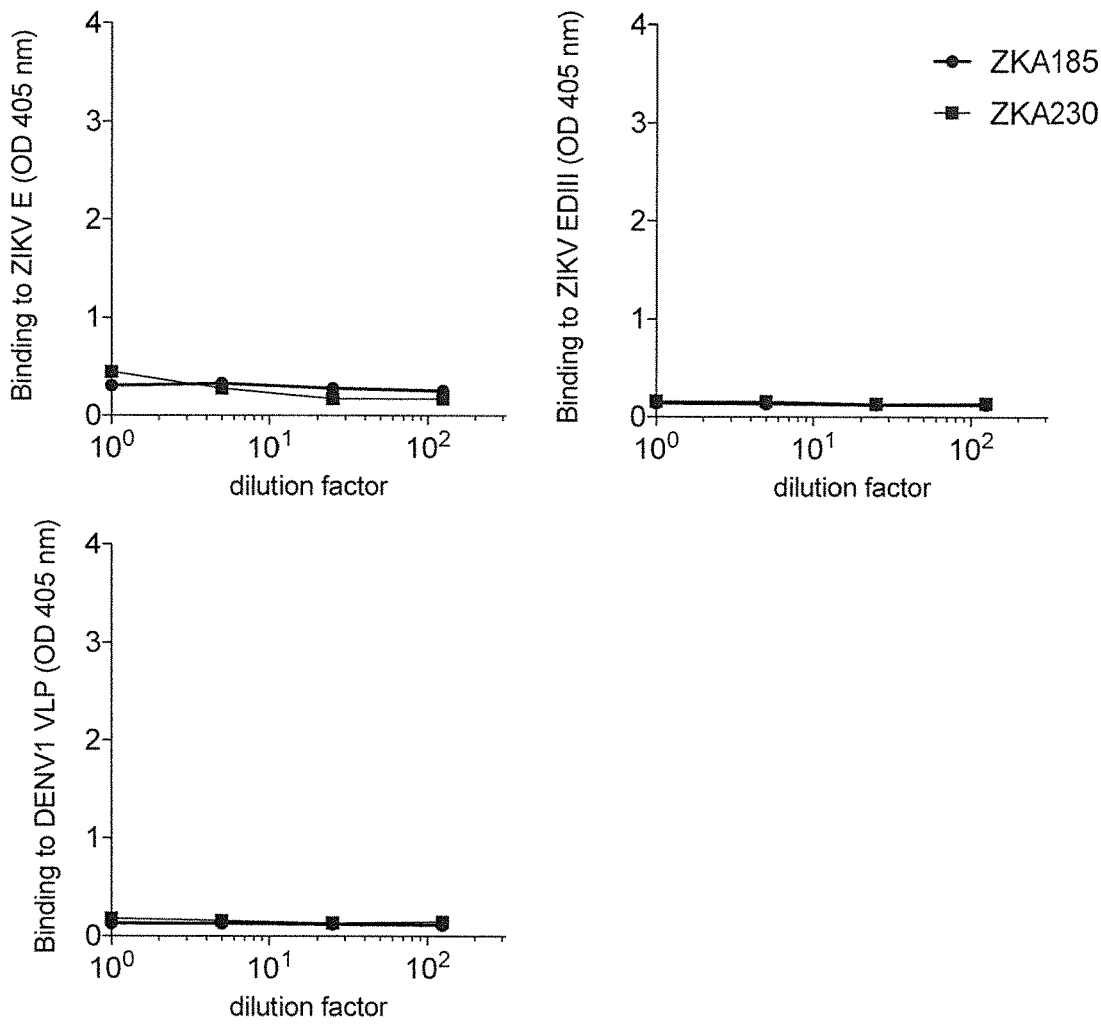
FIG. 3 shows the binding of ZKA185 and ZKA190 antibodies to ZIKV E, DENV1 VLP and to ZIKV EDIII proteins as measured by ELISA.
Figure 19:
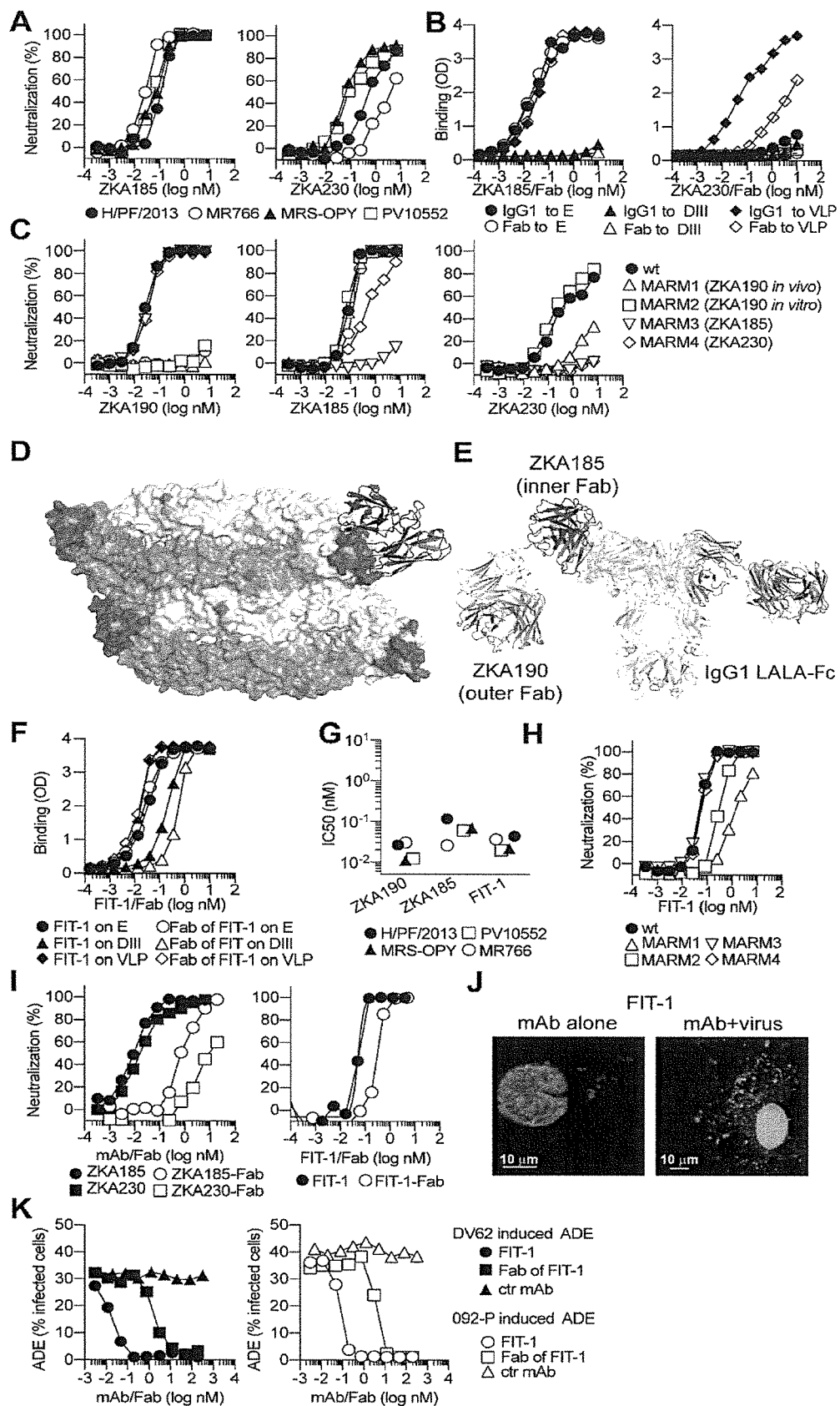

FIG. 19 shows for Example 11 and 12 the engineering of ZKA190 into the bispecific FIT-1 mAb and its in vitro characterization. (A) ZKA185 and ZKA230 mAbs were tested for neutralization of four strains of ZIKV, as determined by the percentage of infected Vero cells in the presence of increasing amounts of mAbs. Data are representative of at least two independent experiments. (B) Binding of ZKA185 and ZKA230 IgG and Fab to recombinant ZIKV VLP, E and DIII antigens as assessed by ELISA. (C) ZKA190, ZKA185 and ZKA230 were tested for neutralization of H/PF/2013 (wt) and MARMs 1-4. (D) Surface representation of two E protein dimers bound by ZKA190 (green); the ZKA190 NMR derived epitope is in red; positions mutated in MARMs are indicated in yellow (E370), blue (T335), orange (D67) and magenta (K84). (E) Model of FIT-1. The natural linkers between inner and outer Fabs allow a flexible movement of Fabs in the FIT-1 antibody. The variable regions of ZKA185 and ZKA190 are highlighted in blue and green, respectively. (F) Binding of FIT-1 IgG and Fab to recombinant ZIKV VLP, E and DIII antigens as assessed by ELISA. (G) ZKA190, ZKA185 and FIT-1 mAbs were tested for neutralization of four strains (IC50 values, G) and four MARMs (H) of ZIKV. (I) Neutralization of ZIKV H/PF/2013 strain by ZKA185, ZKA230 and FIT-1 IgG and Fab determined as in (A). (J) Confocal microscopy experiments as shown in FIG. 3G. (K) Effect on ADE induced by peak enhancing dilution of anti-prM DV62 mAb or DENV2 plasma by serial dilutions of FIT-1 IgG and Fab.

Figure 20:
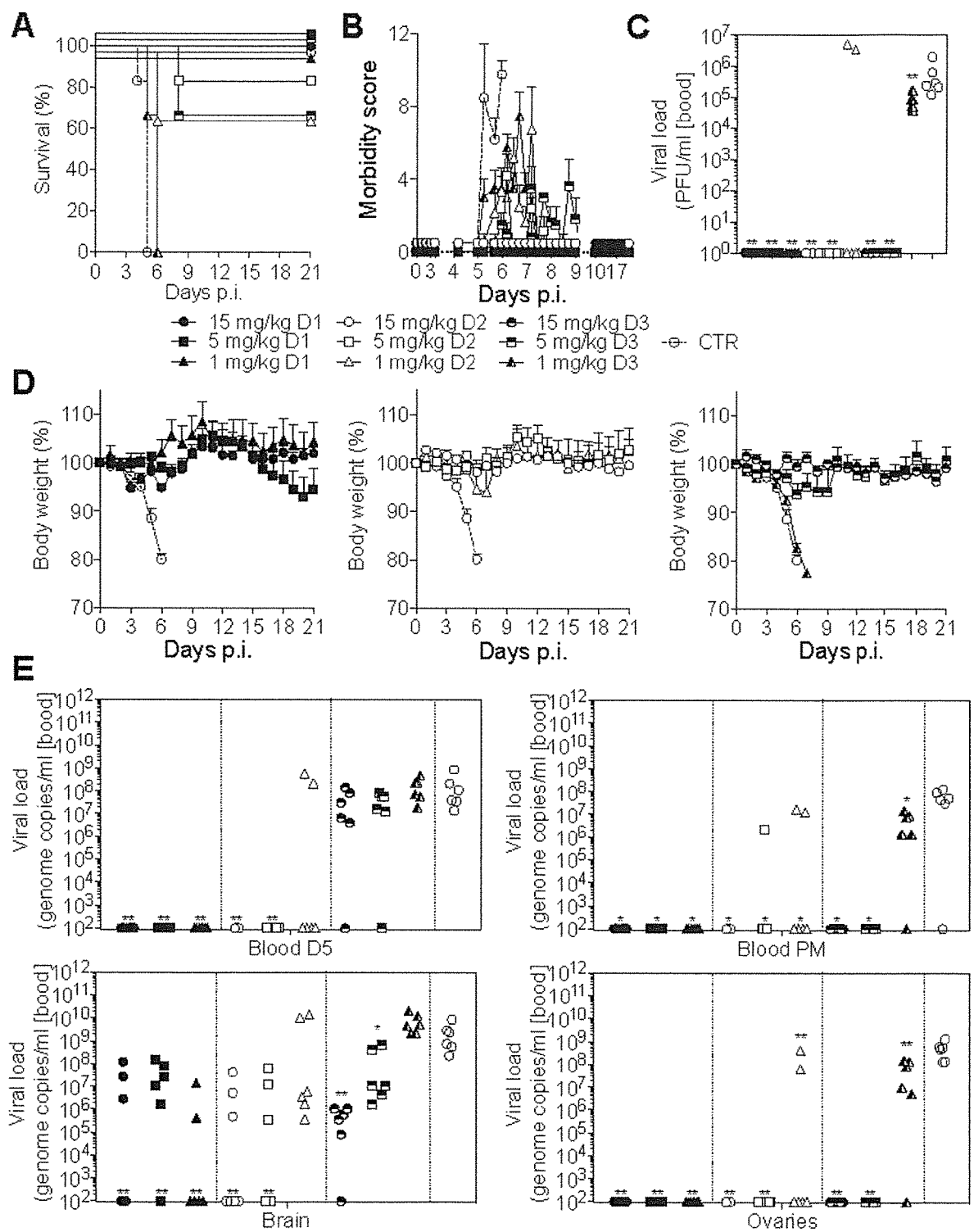

FIG. 20 shows the therapeutic efficacy of FIT-1. FIT-1 is strongly effective against ZIKV infection when administered therapeutically at different time-points to mice (A129) challenged with a lethal dose of ZIKV strain MP17451. Experiments used N=5-6 mice per group. (A) Kaplan-Meier survival curves are shown. Significance was determined by using the Mantel-Cox log-rank test. FIT-1 at 15, 5 and 1 mg/kg given either on day 1, 2 versus Ctr mAb, P=0.0012; ZKA190 at 15 and 5 mg/kg given on day 3 versus Ctr mAb, P=0.0012; ZKA190 at 1 mg/kg given on day 3 versus Ctr mAb, P=0.0170. (B) Morbidity score of mice monitored over a 21 day period (Dowall et al., 2016). (C) Viral loads were measured as PFUs on day 5 in blood of all animals. (D) Mice were monitored over a 21 day period for body weight loss. Control mAb in panel A is MPEG mAb (specific for RSV F protein (Corti, D., et al. Cross-neutralization of four paramyxoviruses by a human monoclonal antibody. Nature 501, 439-443 (2013)). (E) Viral loads were measured as genomic copies by qPCR on day 5 in blood of all animals and in blood and indicated tissues when animals were culled at the end of the study or when the human end points were met. Significance was determined compared to control antibody treatment by nonparametric unpaired Mann-Whitney U test. *p<0.05; **p<0.01.

Figure 21:
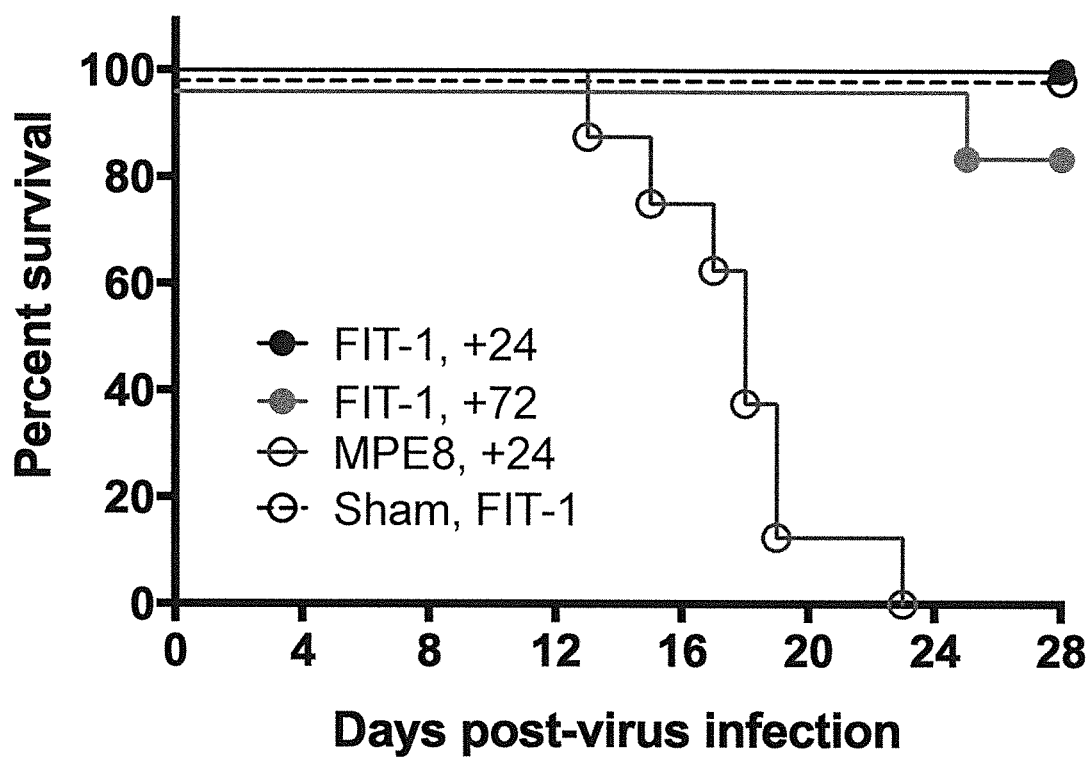

FIG. 21 shows for Example 14 that female AG129 mice treated with FIT-1 after challenge with Malaysian ZIKV were protected from mortality as compared with placebo-treated mice.

Figure 22:
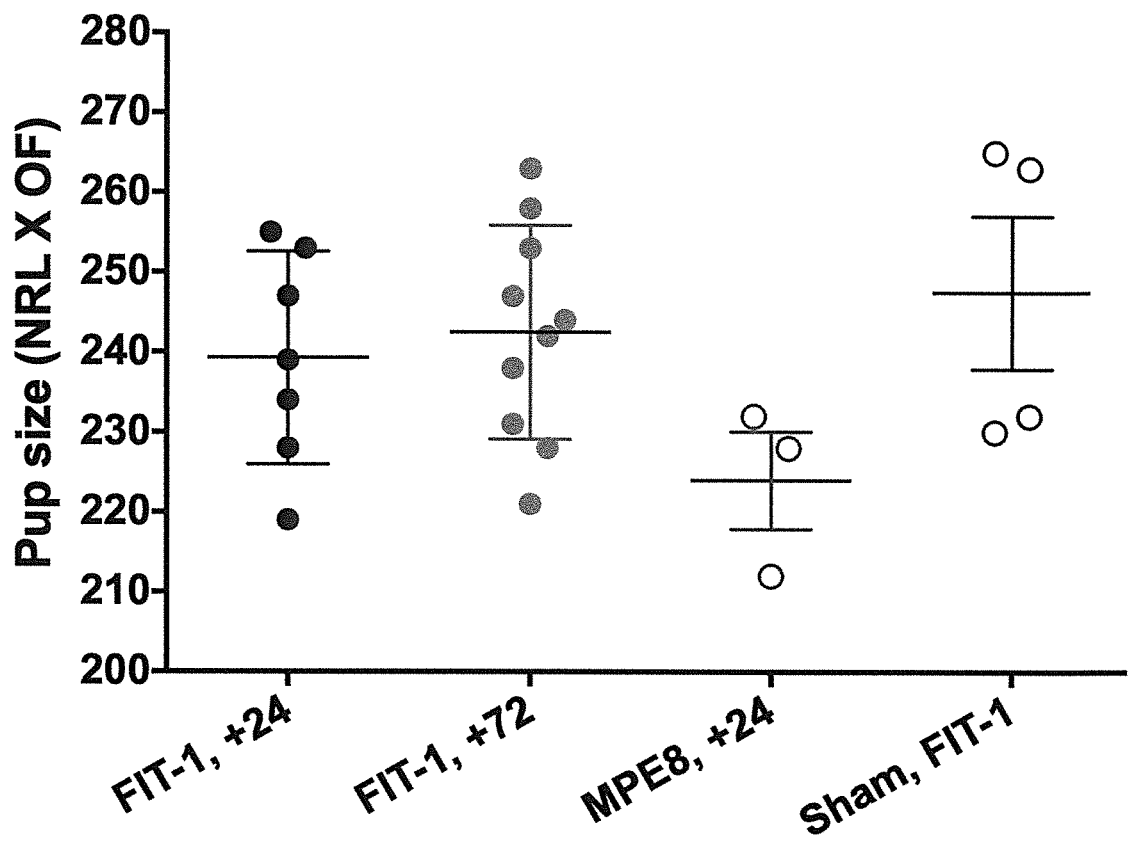

FIG. 22 shows for Example 14 intrauterine growth restriction (IUGR) in pups born to females treated with FIT-1 and challenged with ZIKV.

Figure 23:
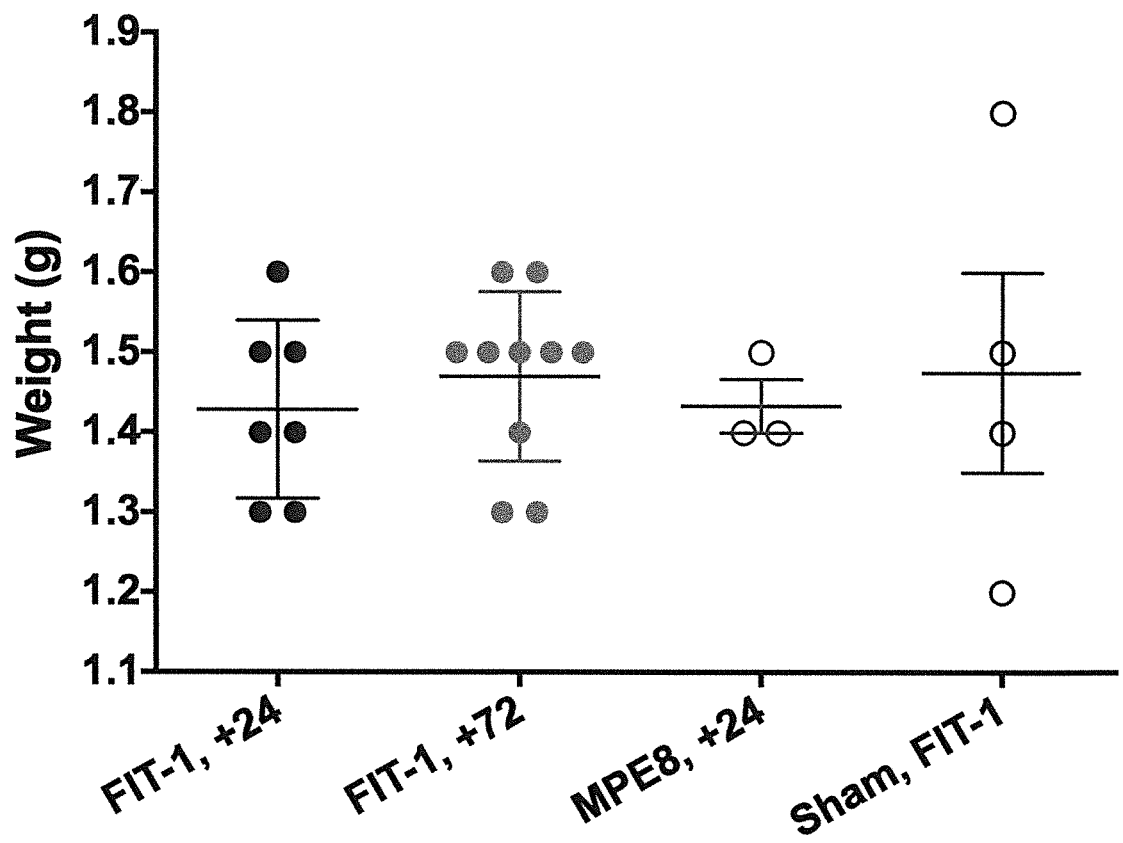

FIG. 23 shows for Example 14 average weight of pups on the date of birth born to females treated with FIT-1 and infected with ZIKV.

Figure 24:
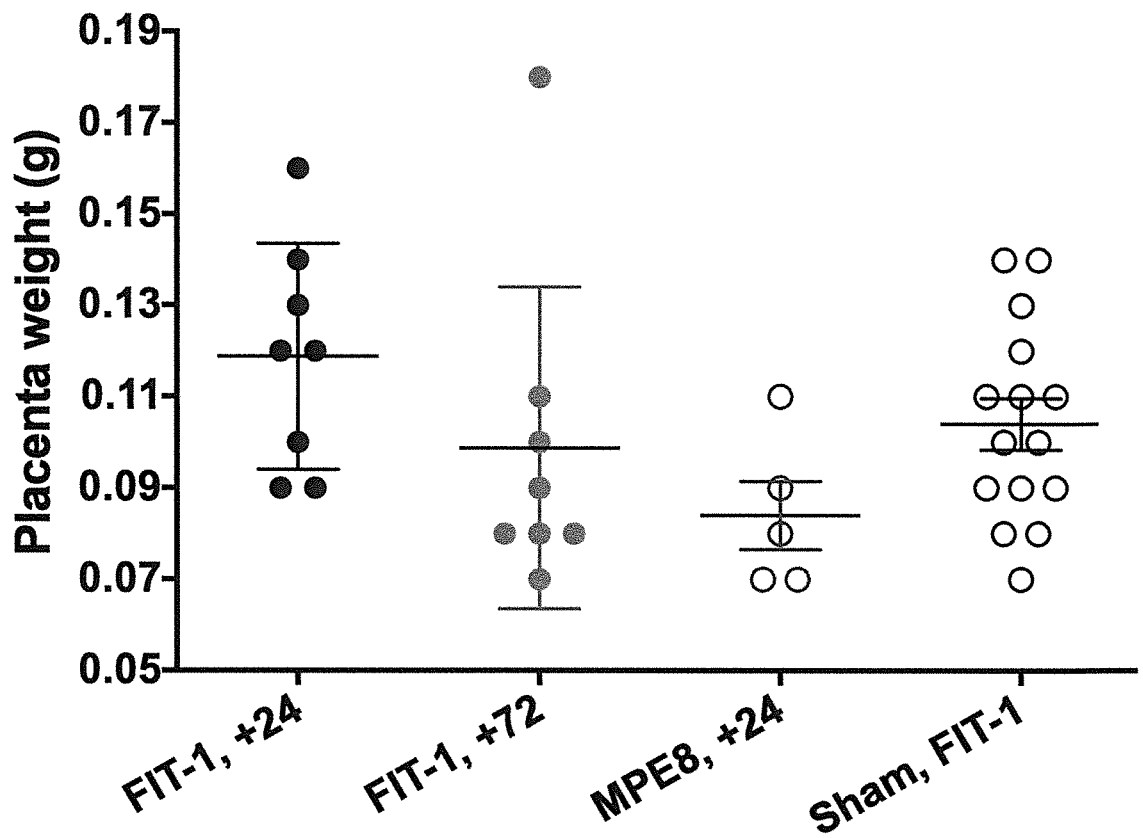

FIG. 24 shows for Example 14 the weight of placenta collected 11 dpi from females treated with FIT-1.

Figure 25:
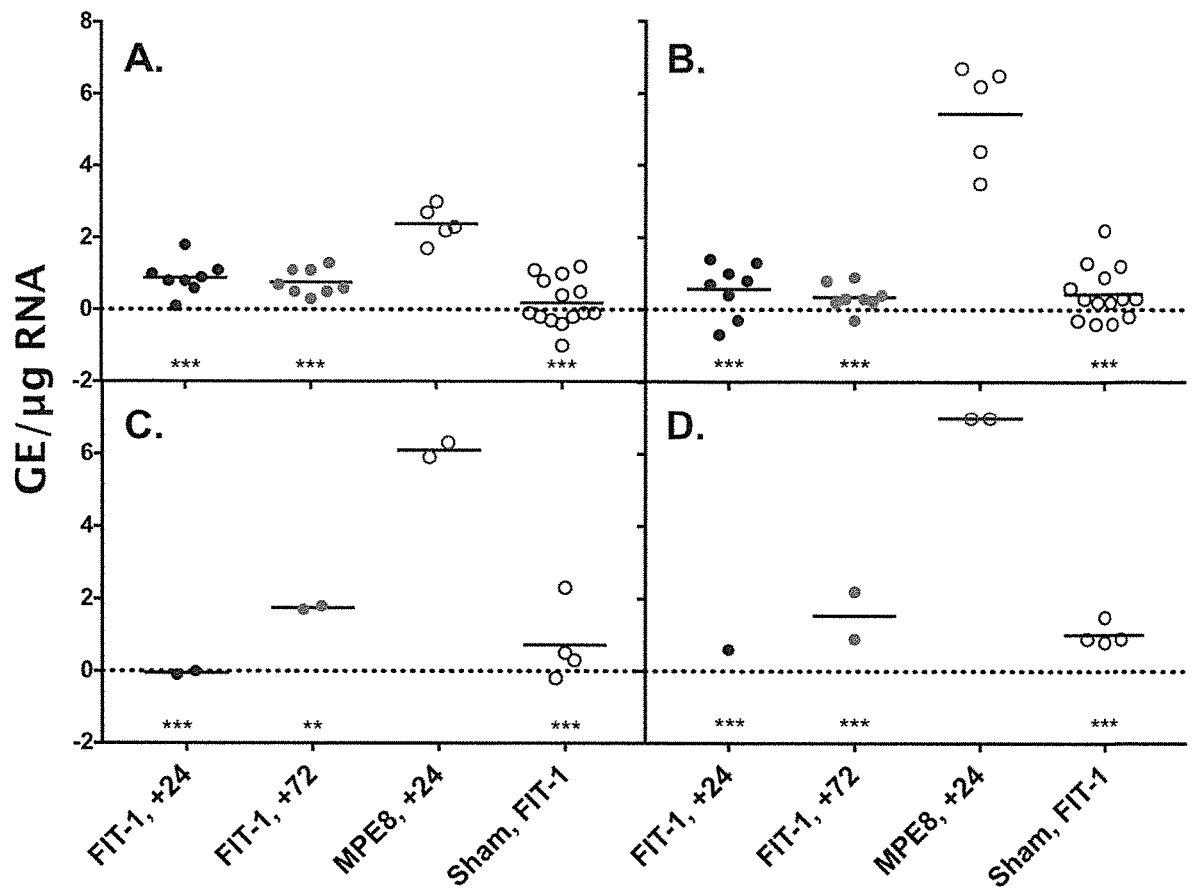

FIG. 25 shows for Example 14 quantification of viral RNA in (A) fetus, (B) placenta, (C) maternal spleen and (D) maternal brain (*P<0.001, P<0.01, as compared with MPE8 treatment).

Figure 26:
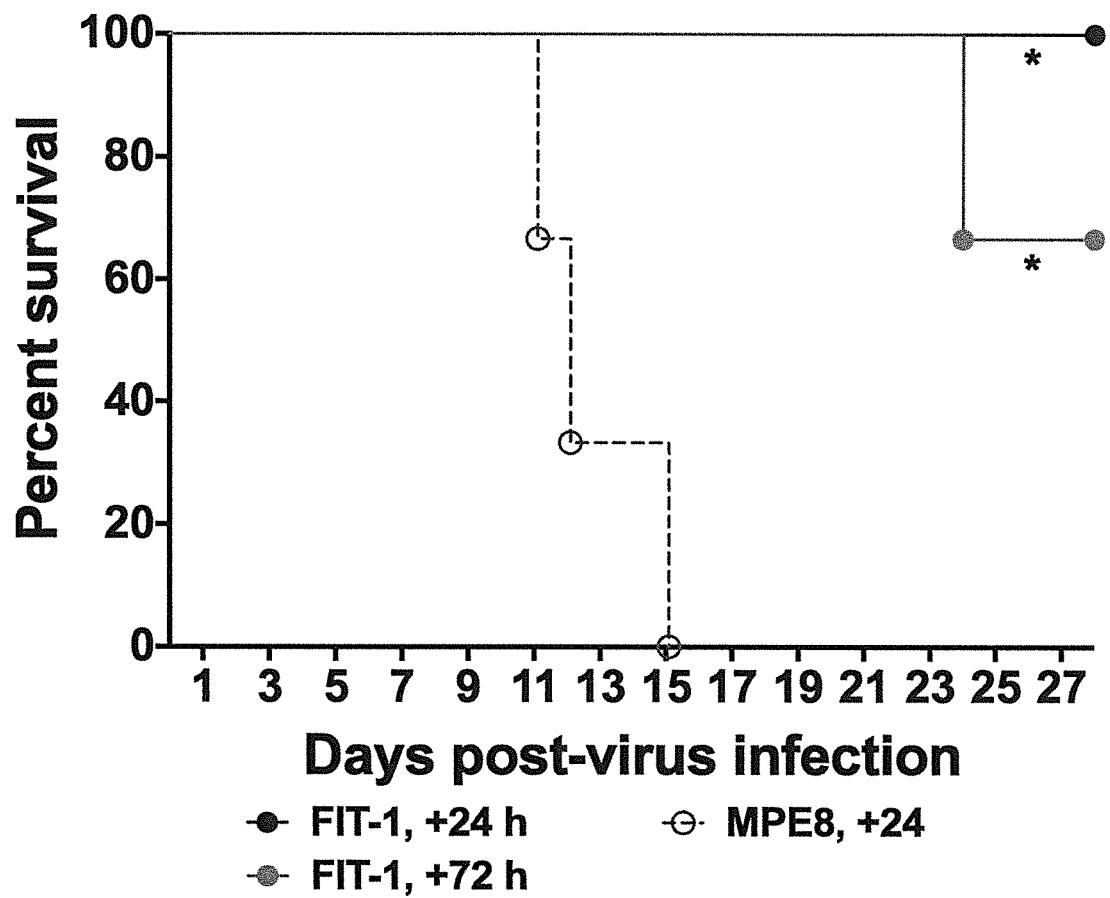

FIG. 26 shows for Example 15 the survival of male AG129 mice infected with ZIKV and treated with FIT-1 24 or 72 h after virus challenge (*P<0.05, as compared with MPE8 negative control treatment).

Figure 27:
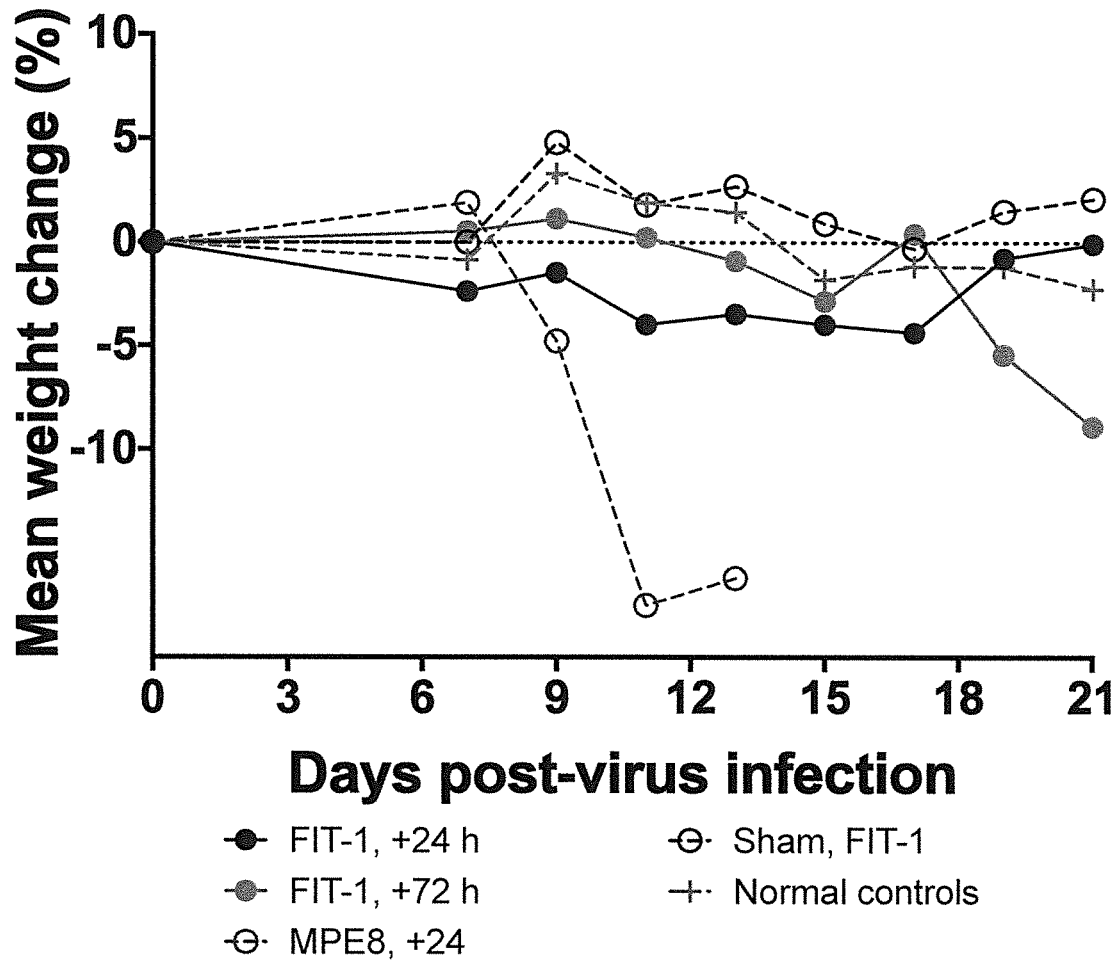

FIG. 27 shows for Example 15 mean percent weight change of AG129 mice treated with FIT-1 at various times after challenge with ZIKV.

Figure 28:
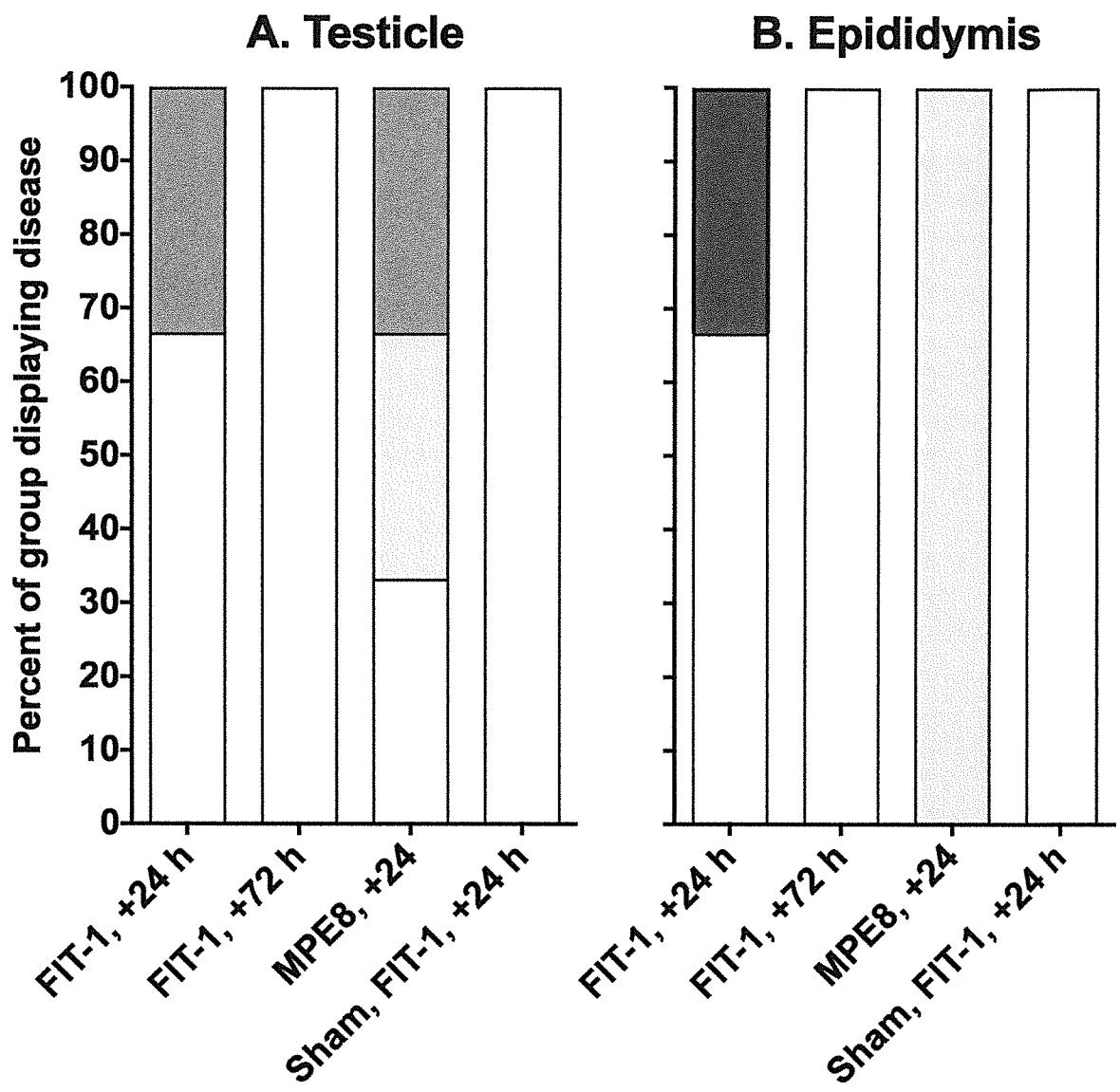

FIG. 28 shows for Example 15 the disease score of the A) testicle or B) epididymis of male AG129 mice treated with FIT-1 24 or 72 h after challenge with ZIKV. Treatment with reactive Ab results in reduction in disease of the testicle and the epididymis.

Figure 29:
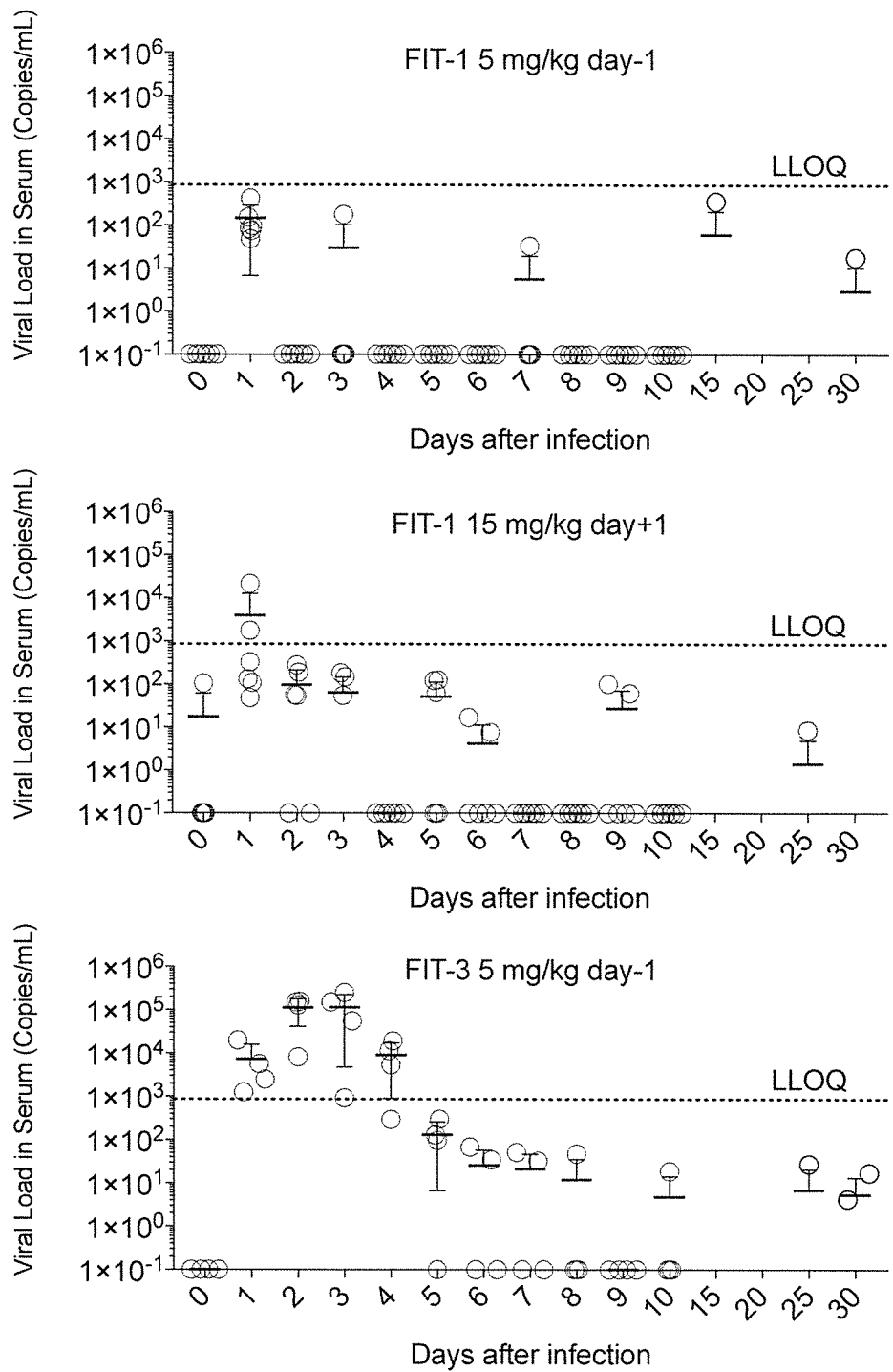

FIG. 29 shows for Example 16 the viral load in serum of the 3 groups tested. The horizontal line indicates the LLOQ of 860 GC/mL.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1: Isolation of ZIKV-Specific Antibodies and Production of Monoclonal Antibodies IgG+ memory B cells were isolated from cryopreserved peripheral blood mononuclear cells (PBMCs) of four ZIKV-infected donors (ZKA, ZKB, ZKC and ZKD) using CD22 microbeads (Miltenyi Biotec), followed by depletion of cells carrying IgM, IgD and IgA by cell sorting. Memory B cells from the ZIKV-infected donors were then immortalized with EBV (Epstein Barr Virus) and CpG (CpG oligodeoxynucleotide 2006) in multiple replicate wells as previously described (Traggiai, E. et al., Nat. Med. 10, 871-875, 2004) and culture supernatants were then tested in a primary screening using in parallel a 384-well based micro-neutralization assay and a binding assay (ELISA) to test their binding to ZIKV NS1 protein or to ZIKV E protein. Results of the binding assay (binding to ZIKV E protein) are shown in FIG. 1.

Neutralization assays were undertaken on Vero cells. In a 384-well plate, ZIKV H/PF/2013 that resulted in an infection rate (m.o.i, multiplicity of infection) of 0.35 was incubated with superntanants for 1 h at 37% (5% CO2) before the addition to pre-seeded 5,000 Vero cells. These were incubated for a further 5 days, after which supernatant was removed and WST-1 reagent (Roche) was added. Positive cultures were collected and expanded. From positive cultures the VH and VL sequences were retrieved by RT-PCR. Antibodies were cloned into human IgG1 and Ig kappa or Ig lambda expression vectors (kindly provided by Michel Nussenzweig, Rockefeller University, New York, US) essentially as described (Tiller T, Meffre E, Yurasov S, Tsuiji M, Nussenzweig M C, Wardemann H (2008) Efficient generation of monoclonal antibodies from single human B cells by single cell RT-PCR and expression vector cloning. J Immunol Methods 329: 112-124). Monoclonal antibodies were produced from EBV-immortalized B cells or by transient transfection of 293 Freestyle cells (Invitrogen). Supernatants from B cells or transfected cells were collected and IgG were affinity purified by Protein A or Protein G chromatography (GE Healthcare) and desalted against PBS.

FIG. 1 provides an overview over selected ZIKV neutralizing antibodies (cf Tables 1 and 2 for the amino acid sequences of their CDRs and heavy/light chain variable regions). The last two columns of FIG. 1 provide the neutralization activities ($IC_{50}$) of ZIKV and DENV1 (if tested). The other columns provide binding activities ($EC_{50}$) of the antibodies to ZIKV E protein (ZIKV E), DENV1 E protein (DENV1 E), DENV2 E protein (DENV2 E), DENV3 E protein (DENV3 E), DENV4 E protein (DENV4 E), DENV1 virus-like particle (DENV1 VLP), DENV2 virus-like particle (DENV2 VLP), DENV3 virus-like particle (DENV3 VLP), DENV4 virus-like particle (DENV4 VLP), and to EDIII-domain of ZIKV E protein (DIII ZKA).

Example 2: Characterization of Antibodies ZKA190, ZKA185, ZKA230, ZKA64 and ZKA78

Figure 4:
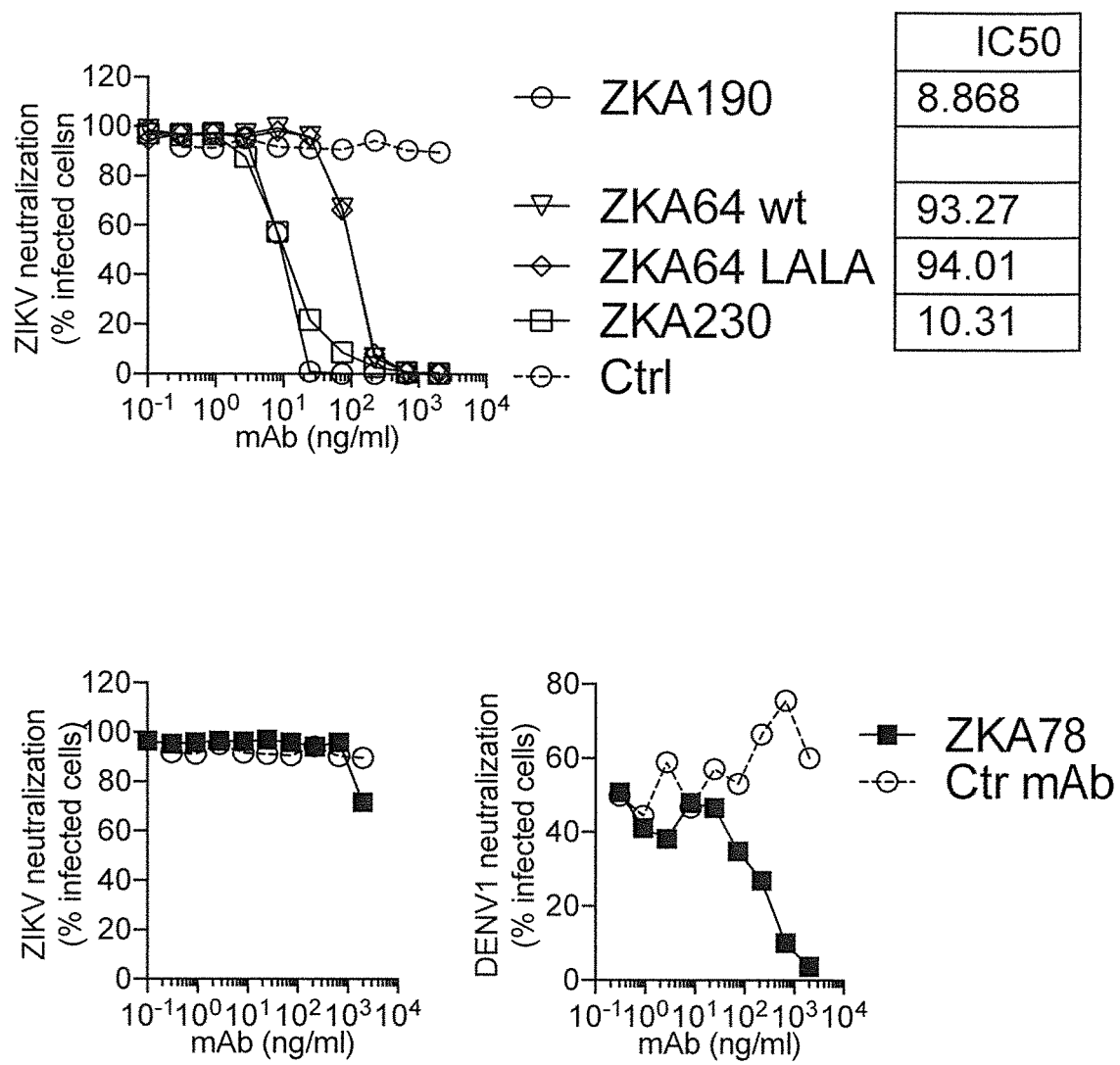
FIG. 4 shows for Example 3 the neutralizing activity of ZKA190, ZKA64, ZKA64-LALA, ZKA230 and ZKA78 antibodies against ZIKV (H/PF/2013 strain) and DENV1 on Vero cells as measured by flow-cytometry (% of infected cells).
Figure 5:
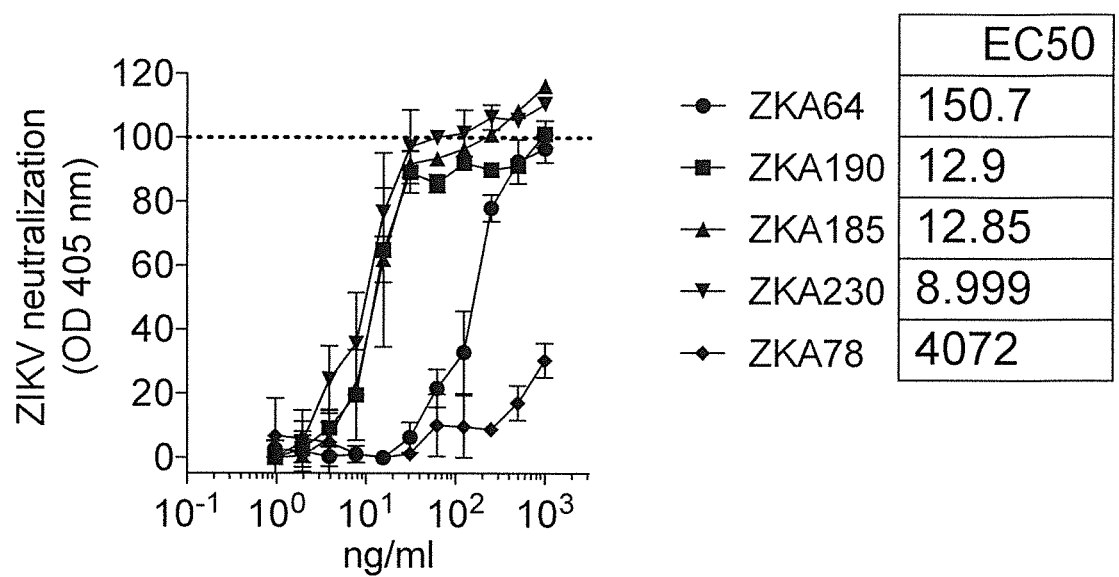
FIG. 5 shows for Example 3 the neutralizing activity of ZKA190, ZKA64, ZKA185, ZKA230 and ZKA78 antibodies against ZIKV (H/PF/2013 strain) on Vero cells as measured with a cell viability readout (wst-1, Roche).

In Example 1, a large number of ZIKV-neutralizing antibodies were identified and characterized for their specificity to ZIKV, in particular ZIKV E protein and ZIKV EDIII as well as for their cross-reactivity towards DENY. Antibodies ZKA190 (SEQ ID NOs: 1-18), ZKA185 (SEQ ID NOs: 19-36), ZKA230 (SEQ ID NOs: 37-54), ZKA64 (SEQ ID NOs: 73-90) and ZKA 78 (SEQ ID NOs: 55-72) described in Example 1 were then selected and further tested against ZIKV E protein ("ZIKV"), ZIKV EDIII ("DIIIZI") and also tested against the E protein of dengue virus (DENY, serotype number 1) by ELISA. To this end, a standard ELISA was used. Briefly, ELISA plates were coated with ZIKV E protein at 1 or 3 μg/ml, blocked with 10% FCS in PBS, incubated with sera or human antibodies and washed. Bound antibodies were detected by incubation with AP-conjugated goat anti-human IgG (Southern Biotech). Plates were then washed, substrate (p-NPP, Sigma) was added and plates were read at 405 nm. The relative affinities of monoclonal antibody binding were determined by measuring the concentration of antibody (EC50) required to achieve 50% maximal binding at saturation.

Results are shown in FIGS. 3 and 4. Of note, ZKA64 and ZKA190 bound to ZIKV E and ZIKV EDIII ("DIII ZI") with low EC50 values, thereby indicating that ZKA64 and ZKA190 are binding to domain III of ZIKV E protein (EDIII). ZKA78 bound to ZIKV E, but not to ZIKV EDIII, indicating that ZKA78 is binding to ZIKV E, but not targeting the EDIII region. Despite their considerable ZIKV neutralizing activity (cf FIG. 1), antibodies ZKA185 and ZKA230 did not show any detectable binding to ZIKV E and ZIKV EDIII (FIG. 3). Accordingly, ZKA185 and ZKA230 were referred to as "neutralizing-non-E-binding" (NNB) antibodies. Those NNB antibodies are assumed to recognize quaternary epitopes that are displayed on the ZIKV infectious virions but not on soluble proteins.

Moreover, none of ZKA190, ZKA185, ZKA230, and ZKA64 showed any detectable binding to DENV E proteins (FIG. 1, DENV1-4 serotypes, and FIGS. 3 and 4), indicating that ZKA190, ZKA185, ZKA230, and ZKA64 are specific for ZIKV and not cross-reactive to dengue virus. ZKA78, in contrast, which is assumed to bind to ZIKV EDI/II, but not to ZIKV EDIII (cf FIG. 2), bound to DENV E proteins (FIGS. 1 and 3), indicating that ZKA78 is a cross-reactive antibody binding to both, ZIKV and DENV.

To further confirm those results, the ZIKV E protein binding antibodies ZKA190, ZKA64 and ZKA78 were additionally tested against E protein of dengue virus (DENV, serotypes number 1-4). ZKA64 and ZKA190 did not bind to DENV1-4 E protein, thereby confirming that ZKA64 and ZKA190 are specific for ZIKV. ZKA78, in contrast, bound to DENV1-4 E, confirming that ZKA78 is a cross-reactive antibody binding to the E protein of both ZIKV and DENV (cf. FIG. 1).

Example 3: The Isolated Antibodies Potently Neutralize ZIKV Infection

The isolated antibodies ZKA190, ZKA185, ZKA230, ZKA64 and ZKA78 were tested for their ability to neutralize ZIKV and DENV1 infection in vitro.

Neutralization of DENV and ZIKV infection by antibodies was measured using a micro-neutralization flow cytometry-based assay. Different dilutions of antibodies were mixed with ZIKV (MOI of 0.35) or attenuated DENV1 (all at MOI of 0.04) for 1 hour at 37° C. and added to 5000 Vero cells/well in 96-well flat-bottom plates. After four days for ZIKV and five days for DENV, the cells were fixed with 2% formaldehyde, permeabilized in PBS 1% FCS 0.5% saponin, and stained with the mouse mAb 4G2. The cells were incubated with a goat anti-mouse IgG conjugated to Alexa Fluor488 (Jackson Immuno-Research, 115485164) and analyzed by flow cytometry. In other cases the ZIKV neutralization data are also determined measuring cell viability using the WST-1 reagent (Roche). The neutralization titer (50% inhibitory concentration [IC50]) was expressed as the antibody concentration that reduced the infection by 50% compared to cell-only control wells.

Results are shown in FIGS. 4, 5 and 9. The EDIII-specific mAbs ZKA64 and ZKA190 and the NNB mAb ZKA230 were highly potent in ZIKV neutralization (strain H/PF/2013), with IC50 values of 93, 9 and 10 ng/ml, respectively (FIG. 4, upper panel). In contrast, the cross-reactive antibody ZKA78 only partially neutralized ZIKV infectivity and cross-neutralized DENV1 infectivity (FIG. 4, lower panels). Similar data were obtained by measuring the ZIKV-induced cytopathic effect as measured with the WST-1 reagent (FIG. 5). In this second assay, NNB antibody ZKA185 was also included in the panel of tested antibodies and showed an IC50 similar to the most potent antibodies ZKA190 (EDIII-specific) and ZKA230 (NNB).

Figure 2:
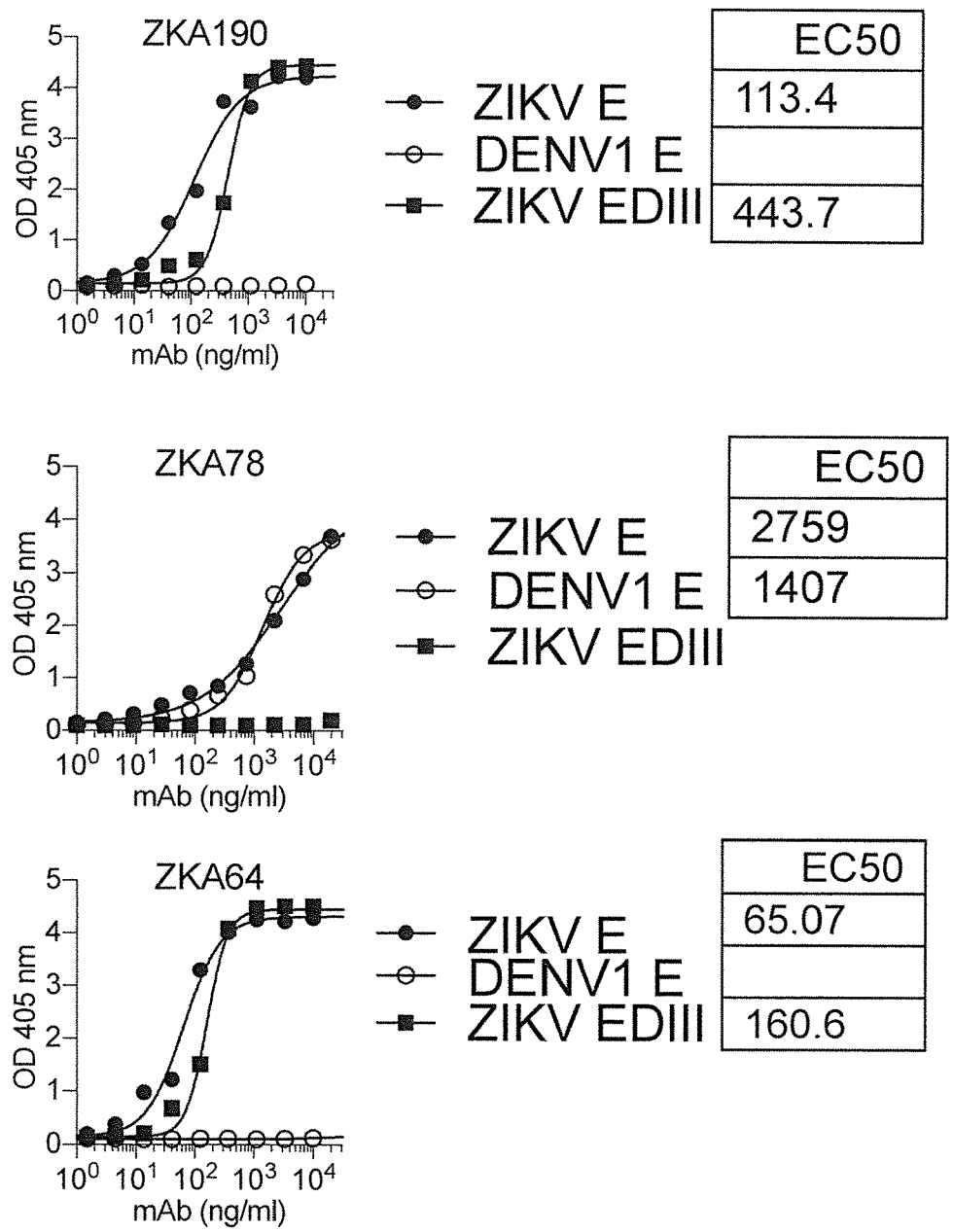
FIG. 2 shows the binding of ZKA190, ZKA78 and ZKA64 antibodies to ZIKV and DENV1 E and to ZIKV EDIII proteins as measured by ELISA.

It is important to note that the ultra-potent ZKA64 and ZKA190 antibodies in addition to their ability to neutralize the ZIKV H/PH/2013 strain (present example), also bound to the E protein and EDIII derived from the ZIKV strains MR766 and SPH2015, respectively (FIG. 1 and FIG. 2). ZKA190 and ZKA190-LALA was also confirmed to effectively neutralize two additional ZIKV strains (MR766 and MRS_OPY_Martinique_PaRi_2015) (FIG. 9). Taken together the results indicate that the ultra-potent ZKA64 and ZKA190 antibodies cross-react with multiple strains of ZIKV belonging to different genotypes and origins (East African and Asian from Uganda, French Polynesia, Martinique and Brazil).

Example 4: The "LALA" Mutation Inhibits Antibody-Dependent Enhancement of ZIKV Infection by Serum Antibodies Neutralizing antibodies were also tested for their ability to enhance the infection of ZIKV in the non-permissive K562 cells (antibody-dependent enhancement assay, ADE assay). ADE was measured by a flow based assay using K562 cells. Antibodies and ZIKV H/PF/2013 (MOI 0.175) were mixed for 1 hour at 37° C. and added to 5000 K562 cells/well. After four days, cells were fixed, permeabilized, and stained with m4G2. The number of infected cells was determined by flow cytometry.

Figure 6:
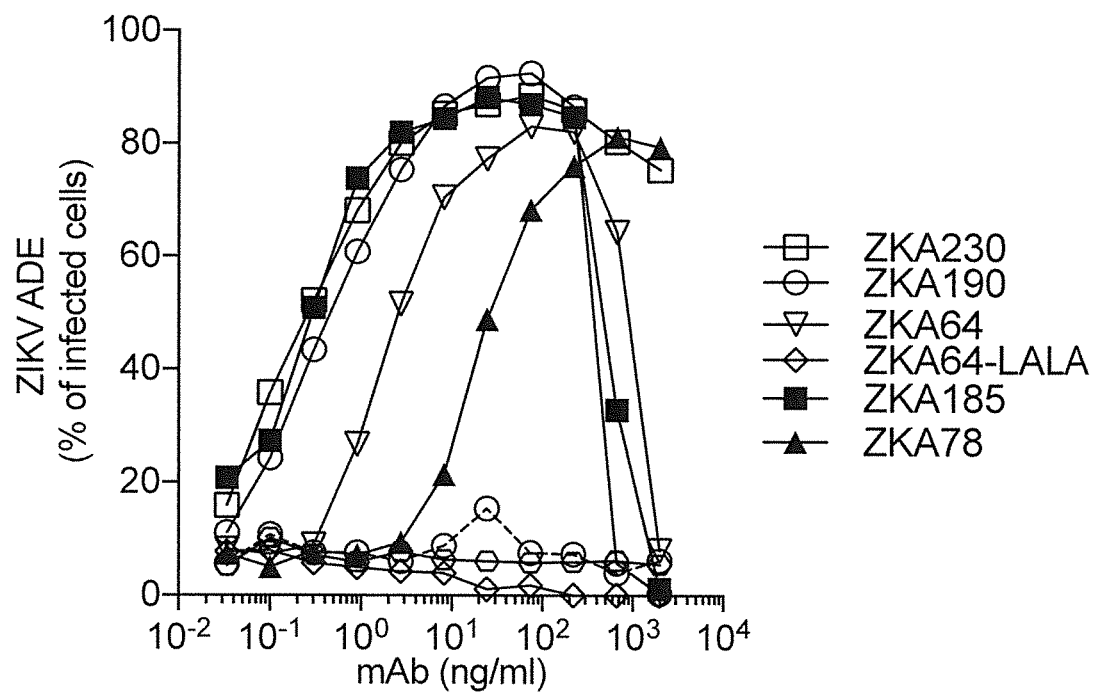
FIG. 6 shows for Example 4 the infection enhancing activity (ADE, antibody-dependent enhancement) of ZKA190, ZKA64, ZKA64-LALA, ZKA185, ZKA230 and ZKA78 antibodies for ZIKV (H/PF/2013 strain) on non-permissive K562 cells as measured by flow-cytometry (% of infected cells).

Results are shown in FIG. 6. All antibodies enhanced infection of ZIKV in the non-permissive K562 cells at a broad range of concentrations, including those that fully neutralized ZIKV infection on Vero cells (FIG. 6). Of note, while EDIII-specific antibodies ZKA64 and ZKA190 fully neutralized ZIKV infections of K562 cells above 1 µg/ml, the NNB antibody ZKA230 failed to do so, a result that might be due to the different mechanisms of neutralization of free viruses versus Fc-gamma-receptor-internalized viruses. In contrast, the cross-reactive ZKA78 that only partially neutralized ZIKV infectivity, effectively enhanced ZIKV infection of K562 cells. These results show that cross-reactive antibodies elicited by either ZIKV or DENV infection can mediate heterologous ADE.

In view thereof it was investigated whether ADE could be also induced by immune sera and whether this could be blocked by neutralizing antibodies delivered as a "LALA variant". To obtain the LALA variant, each of the heavy chains was mutated at amino acids 4 and 5 of CH2 domain by substituting an alanine in place of the natural leucine using site-directed mutagenesis. As described above, LALA variants (of human IgG1 antibodies) do not bind to Fc-gamma-receptors and complement.

To investigate the effect of ZKA64-LALA antibody in ZIKV ADE, an inhibition of ADE assay was used. Since ADE of ZIKV is observed using ZIKV- or DENV-immune plasma, ZIKV (MOI 0.175) was mixed with plasma from primary ZIKV- or DENV-infected donors for 30 minutes at 37° C. ZKA64-LALA antibody was added at 50 µg/ml, mixed with 5000 K562 cells/well and incubated for three days. Cells were then stained with 4G2 and analyzed by flow cytometry.

Figure 7:
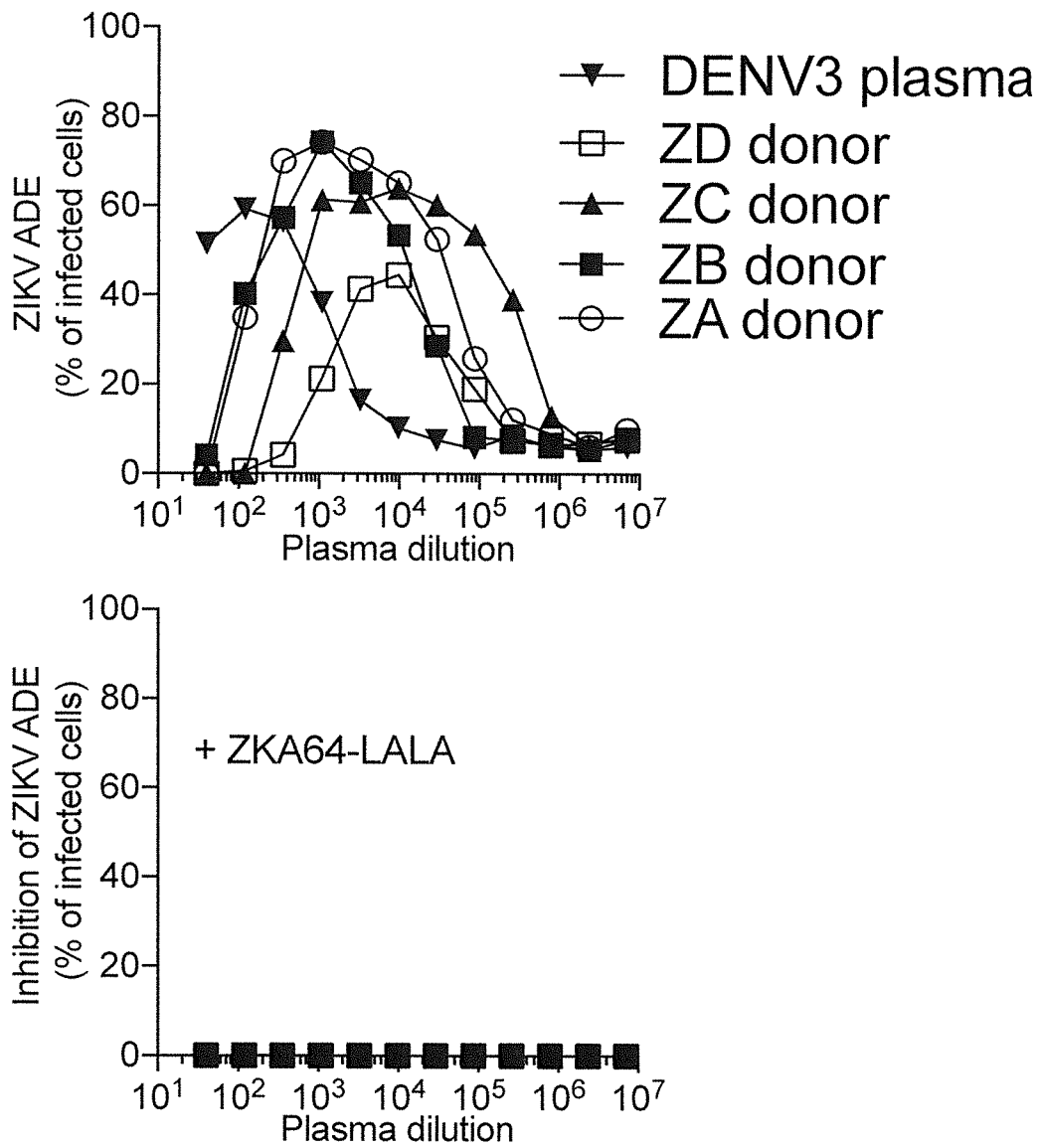
FIG. 7 shows for Example 4 that four ZIKV-immune plasma and one DENV-immune plasma showed similar capacity to enhance ZIKV infection of K562 cells (upper panel). This ADE effect was completely blocked in all five immune plasma by the EDIII-specific ZKA64-LALA antibody (lower panel).
Figure 8:
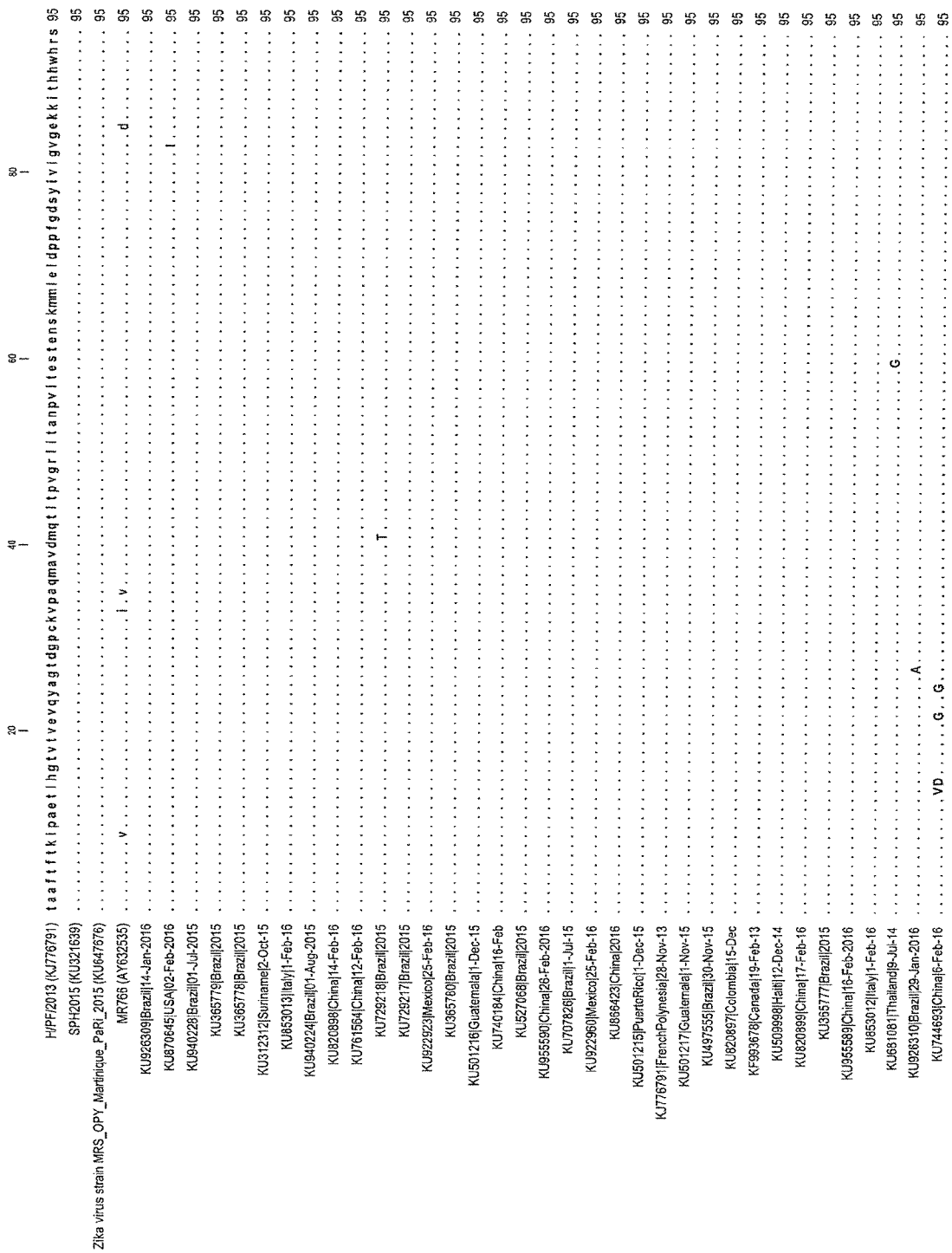
FIG. 8 shows the amino acid alignment of the EDIII region of 39 ZIKV strains from the Asian lineage since 2013 (including the prototypic strain MR766 of the African lineage isolated in 1947).

Results are shown in FIG. 7. In a homologous setting, four ZIKV-immune plasma collected from convalescent patients and one DENV-immune plasma showed similar capacity to enhance ZIKV infection of K562 cells (FIG. 7, upper panel), and this ADE effect was completely blocked by the EDIII-specific ZKA64-LALA antibody (FIG. 7, lower panel).

Of note, the ADE effect of ZIKV- and DENV-immune plasma was completely blocked by the EDIII-specific ZKA64-LALA antibody. The ADE blocking ability of a single EDIII-specific LALA antibody could be related not only to its capacity to out-compete serum enhancing antibodies but also to neutralize virus once internalized into endosomes.

These results indicate that a potently neutralizing antibody, such as ZKA190, ZKA230, ZKA185 or ZKA64, developed in the "LALA" form, have a strong potential to be used in prophylactic or therapeutic settings to prevent congenital ZIKV infection, e.g. in pregnant women and/or in people living in high risk areas. The use of the LALA form avoids the risk of ZIKV ADE and, as shown above, could also block ADE of pre-existing cross-reactive antibodies, such as in the case of patients already immune to DENY.

Example 5: ZKA190 Neutralizes ZIKV More Potently than Prior Art Antibody EDE1 mAb C8

To compare the isolated neutralizing antibodies with highly neutralizing anti-ZIKV antibodies of the prior art, neutralization performance of ZKA190 was compared to that of prior art highly neutralizing mAb EDE1 CS (Barba-Spaeth G, Dejnirattisai W, Rouvinski A, Vaney M C, Medits I, Sharma A, Simon-Loriere E, Sakuntabhai A, Cao-Lormeau V M, Haouz A, England P, Stiasny K, Mongkolsapaya J, Heinz F X, Screaton G R, Rey F A. Structural basis of potent Zika-dengue virus antibody cross-neutralization. Nature. 2016 Aug. 4; 536(7614):48-53). Neutralization of both antibodies was tested against a panel of four distinct ZIKV strains (H/PF/2013; MR766, MRS-OPY and PV 10552).

Briefly, neutralization of ZIKV infection by mAbs was measured using a micro-neutralization flow cytometry-based assay. Different dilutions of mAbs were mixed with ZIKV (MOI of 0.35) for 1 hour at 37° C. and added to 5000 Vero cells/well in 96-well flat-bottom plates. After four days for ZIKV, the cells were fixed with 2% formaldehyde, permeabilized in PBS containing 1% fetal calf serum (Hyclone) and 0.5% saponin, and stained with the mouse mAb 4G2. The cells were incubated with a goat anti-mouse IgG conjugated to Alexa Fluor488 (Jackson Immuno-Research, 115485164) and analyzed by flow cytometry. The neutralization titer (50% inhibitory concentration [IC50]) is expressed as the antibody concentration that reduced the infection by 50% compared to virus-only control wells.

Results are shown in FIG. 10. ZKA190 mAb potently neutralized African, Asian and American strains with an IC50 ranging from 0.6 to 8 ng/ml. In comparison, prior art antibody C8 was about 24-fold less potent.

Example 6: Further Characterization of Antibody ZKA190

The potency of antibody ZKA190 was further investigated in vitro and in vivo. To this end, the mAb was synthesized in IgG1 wild-type (wt) format and in an IgG1 Fc-LALA format. Briefly, the VH and VL sequences were cloned into human Igγ1, Igκ and Igλ expression vectors (kindly provided by Michel Nussenzweig, Rockefeller University, New York, NY, USA), essentially as described (Tiller T, Meffre E, Yurasov S, Tsuiji M, Nussenzweig M C, Wardemann H: Efficient generation of monoclonal antibodies from single human B cells by single cell RT-PCR and expression vector cloning. J Immunol Methods 2008, 329: 112-124). Recombinant mAbs were produced by transient transfection of EXPI293 cells (Invitrogen), purified by Protein A chromatography (GE Healthcare) and desalted against PBS. To obtain the LALA variant, each of the heavy chains was mutated at amino acids 4 and 5 of CH2 domain by substituting an alanine in place of the natural leucine using site-directed mutagenesis. As described above, LALA variants (of human IgG1 antibodies) do not bind to Fc-gamma-receptors and complement.

As shown in FIG. 10A and described in Example 5, ZKA190 was tested against a panel of four ZIKV strains. ZKA190 mAb potently neutralized African, Asian and American strains with an IC50 ranging from 0.004 to 0.05 nM (FIG. 10A; 0.6 to 8 ng/ml).

Since ZIKV has been shown to infect human neural progenitor cells (hNPC) leading to heightened cell toxicity, dysregulation of cell-cycle and reduced cell growth, ZKA190 and ZKA190-LALA were tested in hNPCs. To this end, adult male fibroblasts obtained from the Movement Disorders Bio-Bank (Neurogenetics Unit of the Neurological Institute 'Carlo Besta', Milan) were reprogrammed using the CytoTune-iPS 2.0 Sendai kit (Life Technologies). hiPSCs were maintained in feeder-free conditions in mTeSR1 (Stem Cell Technologies). To generate embryoid bodies (EBs), dissociated hiPSCs were plated into low adhesion plates in mTeSR1 supplemented with N2 (0.5×) (ThermoFisher Scientific), human Noggin (0.5 mg/ml, R&D System), SB431542 (5 □M, Sigma), Y27632 (10 □M, Miltenyi Biotec) and penicillin/streptomycin (1%, Sigma) (as described in Marchetto M C N, Carromeu C, Acab A, Yu D, Yeo G W, Mu Y, Chen G, Gage F H, Muotri A R: A model for neural development and treatment of Rett syndrome using human induced pluripotent stem cells. Cell 2010, 143:527-539). To obtain rosettes, EBs were plated after 10 days onto matrigel-coated plates (1:100, matrigel growth factor reduced, Corning) in DMEM/F12 (Sigma) with N2 (1:100), non-essential amino acids (1%, ThermoFisher Scientific) and penicillin/streptomycin. After 10 days, cells were passaged with Accutase (Sigma) and seeded onto matrigel coated-flasks in NPC media containing DMEM/F12, N2 (0.25%), B27 (0.5%, ThermoFisher Scientific), penicillin/streptomycin and FGF2 (20 ng/ml, ThermoFisher Scientific). hNPCs (3×104) were plated on coverslips in 24-well plates 3 days prior to infection with PRVABC59 strain. Virus stock was incubated with the mAbs 1 h prior to addition to hNPCs to obtain an MOI of 0.5. After 4 h of virus adsorption, culture supernatant was removed and fresh medium containing the mAbs was re-added. Supernatant was collected 96 h post-infection to measure virus titers by plaque assay on Vero cells. Cells were fixed in 4% paraformaldehyde (PFA, Sigma) solution in phosphate-buffered saline (PBS, Euroclone) for 30 min for indirect immunofluorescence. Fixed cells were permeabilized for 30 minutes (min) in blocking solution, containing 0.2% Triton X-100 (Sigma) and 10% donkey serum (Sigma), and incubated overnight at 4° C. with the primary antibodies in blocking solution. The following antibody was used for detection: anti-envelope (1:200, Millipore, MAB10216). Then, cells were washed with PBS and incubated for 1 h with Hoechst and anti-mouse Alexa Fluor-488 secondary antibodies (1:1,000 in blocking solution, ThermoFisher Scientific). After PBS washes, cells were washed again and mounted. Results are shown in FIG. 11A. Both, ZKA190 and ZKA190-LALA, fully abolished infection and replication of ZIKV in hNPCs.

Next, the ability of ZKA190 and ZKA190-LALA to cause ADE was tested in the K562 cell line as described in Example 4. Briefly, ADE was measured by a flow based assay using K562 cells. Briefly, for ZKA190, ZKA190 and ZIKV H/PF/2013 (MOI 0.175) were mixed for 1 hour at 37° C. and added to 5000 K562 cells/well. After four days, cells were fixed, permeabilized, and stained with mAb m4G2. The number of infected cells was determined by flow cytometry. For ZKA190-LALA, ZIKV (MOI 0.175) was mixed with plasma from primary ZIKV-infected donors for 30 minutes at 37° C. ZKA190-LALA was added at 50 E g/ml, mixed with 5000 K562 cells/well and incubated for three days. Cells were then stained with 4G2 and analyzed by flow cytometry. Results are shown in FIG. 11B. ZKA190 supports ADE from 0.0001 to 1 nM; as expected, ZKA190-LALA did not show any ADE activity. The ability of ZKA190-LALA to inhibit ADE induced by plasma from four ZIKV-immune donors in K562 cells was also tested. Results are shown in FIG. 11C. It was found that ZKA190-LALA completely inhibited the ADE induced by plasma antibodies (FIG. 11C).

Anti-prM antibodies form part of the predominant antibodies elicited during the human immune response against flaviviruses and have been shown to enhance virus infection in vitro (Dejnirattisai, W., Jumnainsong, A., Onsirisakul, N., Fitton, P., Vasanawathana, S., Limpitikul, W., Puttikhunt, C., Edwards, C., Duangchinda, T., Supasa, S., et al. (2010). Cross-reacting antibodies enhance dengue virus infection in humans. Science 328, 745-748). K562 cells were pre-incubated with serial dilutions of prM cross-reactive antibody DV62 (Beltramello, M., Williams, K. L., Simmons, C. P., Macagno, A., Simonelli, L., Quyen, N. T. H., Sukupolvi-Petty, S., Navarro-Sanchez, E., Young, P. R., de Silva, A. M., et al. (2010). The human immune response to Dengue virus is dominated by highly cross-reactive antibodies endowed with neutralizing and enhancing activity. Cell Host Microbe 8, 271-283) derived from a DENV immune donor. Results are shown in FIG. 11D. DV62 cross-reacted with ZIKV prM protein and caused ADE at a broad range of concentrations (FIG. 11D). ZKA190-LALA can fully block anti-prM DV62 mAb-induced ADE of immature or partially immature ZIKV particles (FIG. 11D).

Finally, the ability of different concentrations of ZKA190, ZKA190-LALA and ZKA190 Fab to cause or block ADE of ZIKV in the presence of enhancing concentrations of human anti-DENV2 plasma or DV62 was tested. Results are shown in FIG. 11E. ZKA190 at low concentrations increased the prM DV62-mediated ADE of ZIKV infection, consistent with its ability to promote the entry of both immature and mature virions, while at concentrations above 1.3 nM (i.e., 200 ng/ml) ZKA190 blocked ADE induced by both DENV plasma and mAb DV62. ZKA190-LALA, as well as its Fab fragment, reduced ADE at concentrations above 0.06 nM, indicating that both inhibited virus infection at a post-attachment step, such as fusion.

Example 7: ZKA190 Binds to a Conserved and Highly Accessible Region of EDIII

To determine the ZKA190 epitope at the residue level, solution NMR spectroscopy was used as described in Bardelli, M., Livoti, E., Simonelli, L., Pedotti, M., Moraes, A., Valente, A. P., and Varani, L. (2015). Epitope mapping by solution NMR spectroscopy. J. Mol. Recognit. 28, 393-400; Simonelli, L., Beltramello, M., Yudina, Z., Macagno, A., Calzolai, L., and Varani, L. (2010). Rapid structural characterization of human antibody-antigen complexes through experimentally validated computational docking. J Mol Biol 396, 1491-1507; and Simonelli, L., Pedotti, M., Beltramello, M., Livoti, E., Calzolai, L., Sallusto, F., Lanzavecchia, A., and Varani, L. (2013). Rational Engineering of a Human Anti-Dengue Antibody through Experimentally Validated Computational Docking. PLoS ONE 8, e55561.

Briefly, spectra were recorded on a Bruker Avance 700 MHz NMR spectrometer at 300 K. For assignments of backbone resonances standard triple resonance experiments (HNCO, HN(CA)CO, HN(CO)CACB, HNCACB were used, while sidechains were annotated using HCCH-TOCSY and HBHA(CO)NH experiments. All NMR experiments were processed using Topspin 2.1 (Bruker Biospin) and analysed with CARA. NOESY cross peaks were automatically assigned using the CYANA "noeassign" macro based on the manually assigned chemical shifts. Upper-distance restraints used for the structure calculations in CYANA using the standard simulated annealing protocol were derived from 70 ms $^{15}$N- and $^{13}$C-resolved NOESY spectra. Backbone dynamics of ZIKV EDIII were derived from $^{15}$N relaxation measurements recorded on 600 and 700 MHz spectrometers. Proton-detected versions of the CPMG (R2), inversion-recovery (R1) and $^{15}$N{$^1$H}-steady-state NOE were utilized. Delay settings for the T2 series were in the range of 0 to 0.25 sec and for the T1 series between 0.02 to 2 sec. The $^{15}$N{$^1$H}-NOE experiment used a relaxation delay of 5 s. The R1 and R2 relaxation rates were derived from least-squares fits of corresponding exponential functions to the measured data using home-written scripts. The relaxation data were analyzed in a model-free approach using the software package DYNAMICS. The program ROTDIF was used to calculate the overall correlation time from the relaxation data (8.5 ns). NMR epitope mapping was performed as previously described (Bardelli et al., 2015; Simonelli et al., 2010; 2013). Briefly, overlay of $^{15}$NHSQC spectra of labelled EDIII free or bound to ZKA190 Fab allowed identification of EDIII residues whose NMR signal changed upon complex formation, indicating that they were affected by ZKA190 binding. Changes were identified by manual inspection and by the Chemical Shift Perturbation (CSP), CSP=$((\Delta\delta_H)^2+(\Delta\delta_N/10)^2)^{1/2}$. NMR samples were typically 800 □M of [$^{15}$N, $^{13}$C]-labeled EDIII in 20 mM sodium phosphate, 50 mM NaCl, pH 6.0. Perdeuterated (nominally 70%) $^2$H,$^{15}$N EDIII samples were used for NMR epitope mapping with a EDIII:ZKA190 Fab ratio of 1:1.1; EDIII concentration was typically 0.4 mM.

Since the NMR signal is strongly dependent on the local chemical environment, changes upon complex formation identify antigen residues that are affected by antibody binding, either directly or through allosteric effects. By comparing the NMR spectra of free and bound EDIII (FIG. 12A), residues affected by ZKA190 were mapped to the LR of EDIII, in particular to the BC, DE and FG loops, as well as to part of the EDI-EDIII hinge (FIG. 13A). These residues are nearly identical among 217 known ZIKV strains, with the exception of substitutions at V341I and E393D in the Uganda 1947 isolate (FIG. 12D). These mutations are also present in the MR766 strain that was efficiently neutralized by ZKA190 (FIG. 10A). Analysis of the ZKA190 epitope on the uncomplexed ZIKV structure showed that the epitope is highly accessible, except for the FG loop in the 5-fold vertex (FIGS. 13B and 12C, molecule A).

Computational docking followed by molecular dynamics simulation, guided and validated by NMR-derived epitope information as well as EDIII mutagenesis, showed that ZKA190 binds through an interface characterized by shape and charge complementarity (FIGS. 13B and 12E). Docking indicates that there are no direct contacts between ZKA190 and the FG loop on EDIII, suggesting that changes in its NMR signals upon antibody binding derive from allosteric effects. This notion is supported by the fact that mutations of FG loop residues in recombinant EDIII, but not in other epitope regions, did not affect the binding affinity of ZKA190 for EDIII (FIGS. 13B and 14).

Example 8: Mechanisms of ZKA190 Neutralization

The ability of ZKA190 to efficiently neutralize the virus may involve inhibition of either cell attachment or membrane fusion. A further mechanism might involve virus inactivation through cross-linking of viral particles.

ZKA190 Fab can neutralize ZIKV, albeit less efficiently than the corresponding IgG. By binding to the EDI-EDIII linker, ZKA190 (both Fab and IgG) might inhibit the ~70 degree rotation of DIII required for viral fusion to the host cell membrane (Bressanelli, S., Stiasny, K., Allison, S. L., Stura, E. A., Duquerroy, S., Lescar, J., Heinz, F. X., and Rey, F. A. (2004). Structure of a flavivirus envelope glycoprotein in its low-pH-induced membrane fusion conformation. Embo J 23, 728-738; Modis, Y., Ogata, S., Clements, D., and Harrison, S. C. (2004). Structure of the dengue virus envelope protein after membrane fusion. Nature 427, 313-319). Alternatively, ZKA190 might prevent the attachment of ZIKV to target cells.

The ability of ZKA190 to inhibit membrane fusion is supported by confocal microscopy analysis. To this end, Vero cells were plated at 7,500 cells/well on 12 mm-diameter coverslips in 24-well plates and incubated overnight. Cells were infected with ZIKV H/PF/2013 (MOI of 100) in the presence or absence of neutralizing concentrations of Alexa-488 conjugated mAbs (0.7 □M) at 37° C. for 3 h, washed with PBS, and fixed with 2% paraformaldehyde in PBS for 30 min at room temperature. Acidified endosome were identified with Lysotracker red (Invitrogen) by adding the dye (50 nM) to the cells for the last 30 min of the incubation prior to fixation. Fixation was followed by extensive washes in PBS and 50 mM glycine and finally the coverslips were prepared for microscopy analysis using Vectashield mounting medium for fluorescence with DAPI (Vector Laboratories). Samples were analyzed by confocal microscopy using a Leica TCS SP5 microscope with a 63×/1.4 N.A. objective. Image analysis and processing was performed with FIJI software.

Results are shown in FIG. 15. Confocal microscopy analysis shows that ZKA190 (Fab or IgG) can enter Vero cells only when complexed with ZIKV, at neutralizing concentrations exceeding the IC50 by 10,000-fold (FIG. 15).

Example 9: In Vivo Characterization of the EDIII-Specific mAb ZKA190

To evaluate their prophylactic and therapeutic properties, ZKA190 and ZKA190-LALA were tested in A129 mice challenged with a lethal dose of ZIKV strain MP1751 (African lineage). To test their prophylactic potencies, ZKA190 and ZKA190-LALA were administered one day before virus challenge.

Female A129 mice (IFN-alpha/beta receptor −/−) and wild-type 129Sv/Ev mice aged 5-8 weeks were administered mAbs (ZKA190, ZKA190-LALA and control antibody MPEG (Corti, D., et al. Cross-neutralization of four paramyxoviruses by a human monoclonal antibody. Nature 501, 439-443 (2013)) diluted in PBS at different doses via the intraperitoneal (i.p.) route in a volume of 500 μl. MAbs were administered either 1 day before or 1, 2, 3 or 4 days after virus challenge. Animals were challenged subcutaneously with 10² pfu ZIKV (strain MP1751) and followed for 14 days. Weights and temperatures were monitored daily and clinical observations were recorded at least twice per day. On day 5 post-challenge, 50 μl of blood was collected from each animal into a RNAprotect tube (Qiagen, UK) and frozen at −80° C. At the end of the study (14 days post-challenge) or when animals met human endpoints, necropsies were undertaken, and blood and sections of brain, spleen, liver, kidney and ovary were collected for virological analysis.

Tissue samples from A129 mice were weighed and homogenized into PBS using ceramic beads and an automated homogenizer (Precellys, UK) using six 5 second cycles of 6500 rpm with a 30 second gap. Two hundred μl of tissue homogenate or blood solution was transferred into 600 μL RLT buffer (Qiagen, UK) for RNA extraction using the RNeasy Mini extraction kit (Qiagen, UK); samples were passed through a QIAshredder (Qiagen, UK) as an initial step. A ZIKV specific realtime RT-PCR assay was utilized for the detection of viral RNA from subject animals. The primer and probe sequences were adopted from Quick et al., 2017 (Quick, J, Grubaugh N D, Pullan S T, Claro I M, Smith A D, Gangavarapu K, Oliveira G, Robles-Sikisaka R, Rogers T F, Beutler N A, et al.: Multiplex PCR method for MinION and Illumina sequencing of Zika and other virus genomes directly from clinical samples. Nat Protoc 2017, 12:1261-1276) with in-house optimization and validation performed to provide optimal mastermix and cycling conditions. Real-time RT-PCR was performed using the SuperScript III Platinum One-step qRT-PCR kit (Life Technologies, UK). The final mastermix (15 μl) was comprised of 10 μl of 2× Reaction Mix, 1.2 μl of PCR-grade water, 0.2 μl of 50 mM MgSO4, 1 μl of each primer (ZIKV 1086 and ZIKV 1162c both at 18 μM working concentration), 0.8 μl of probe (ZIKV 1107-FAM at 25 μM working concentration) and 0.8 μl of SSIII enzyme mix. Five μl of template RNA was added to the mastermix, yielding a final reaction volume of 20 μl. The cycling conditions used were 50° C. for 10 minutes, 95° C. for 2 minutes, followed by 45 cycles of 95° C. for 10 seconds and 60° C. for 40 seconds, plus a final cooling step of 40° C. for 30 seconds. Quantification analysis using fluorescence was performed at the end of each 60° C. step. Reactions were run and analyzed on the 7500 Fast platform (Life Technologies, UK) using 7500 software version 2.0.6. Quantification of viral load in samples was performed using a dilution series of quantified RNA oligonucleotide (Integrated DNA Technologies). The oligonucleotide comprised the 77 bases of ZIKV RNA targeted by the assay, based on GenBank accession AY632535.2 and was synthesized to a scale of 250 nmol with HPLC purification.

Results are shown in FIGS. 16, 17 and 18. ZKA190 and ZKA190-LALA were shown to protect mice from mortality and morbidity at concentrations of 5, 1 or 0.2 mg/kg (FIG. 16A-B). ZKA190-LALA, and to a lesser extent ZKA190, delayed morbidity and mortality as compared to the control group at 0.04 mg/kg. Viral titers in blood and organs were reduced significantly compared to control antibody-treated animals, even in the presence of serum antibody levels below 1 μg/ml (FIG. 17A-D).

To evaluate the therapeutic potential of ZKA190, we administered ZKA190 and ZKA190-LALA at different time-points following ZIKV infection. At a dose of 15 mg/kg, survival rates of 80%-100% were achieved, and the morbidity was greatly reduced even when treatment was given four days post-infection (FIG. 16E-G). ZKA190 and ZKA190-LALA treatment at all post-infection time-points resulted in significantly reduced viral titers, compared to animals treated with control antibody, with a clear trend for greater reduction with earlier treatment (FIG. 18A-16C). Of note, ZKA190-LALA showed a significantly reduced antiviral activity in the blood day 5 sample as compared to ZKA190 when mAbs were given four days post-infection, a result that might be related to the impaired ability of the LALA variant to facilitate rapid clearance of coated virions. Of the 16 treated mice, one in vivo escape mutant (Monoclonal Antibody Resistant Mutant 1, MARM1), containing an amino acid substitution in DIII (T335R, in the center of the epitope) was isolated, while viruses from the other treated mice did not contain any E mutations. Introduction of the T335R mutation into recombinant DIII showed that it abrogated ZKA190 binding, as determined by SPR (FIG. 14; cf Example 7 for experimental methods).

Example 10: In Vitro Selection of ZIKV Escape Mutants

Use of antibody therapeutics may result in the selection of escape mutants. To assess the ability of ZKA190 to select for resistant mutants (MARMs) in vitro, ZIKV (H/PF/2013) was passaged in the presence of sub-neutralizing concentrations of ZKA190.

Briefly, two-thousands TCID50 of H/PF/2013 ZIKV in 500 μl were incubated with 250 μl containing varying concentrations of mAb (8 different concentrations, starting with a final concentration of 200 μg/ml and performing serial 1:4 dilutions). The mixture was incubated for 45 minutes at 37° C., followed by the addition of 250 μl of a Vero cells suspension (3.2×10⁶ cells) and an incubation in a 24 well plate for three-four days at 37° C. to allow virus propagation to occur. After each step of selection, 500 μl of supernatants from three conditions were selected: the lowest concentration of mAb at which full protection of the monolayer was observed, one concentration at which a partial CPE effect on the cell monolayer was observed and one concentration at which 100% of the cell monolayer was destroyed by the ZIKV CPE. The tube was spun down for 5 minutes at 1000×g, aliquoted and stored at −80° C. Half of the volume was again pre-mixed with varying concentrations of mAb to repeat the selection and propagation process. The remaining supernatant was used for micro-neutralization assays and subsequent sequencing of the virus.

To identify the escape mutations of the selected MARMs virus, a genomic RNA extraction was done followed by a one-step-PCR to amplify and sequence the ZIKV E protein amplicon. Cell supernatant (140 μl) from the MARMs selection was used for RNA extraction with the QIAamp Viral RNA mini kit (Qiagen). cDNA synthesis and PCR amplification were performed together using the SuperScript III One-Step RT-PCR with Platinium Taq (Invitrogen). For one reaction 25 μl reaction mix, 8 μl sterile water, 2 μM of each primer, 1 μl RNAse out (Life Technologies), 2 μl Superscript III RT/Platinum TaqMix and 12 μl RNA were used giving a final reaction volume of 50 μl. For the E protein N-terminal part, the primer pair Zika-E-F1 5'-TGCAAACGCGGTCGCAAACCTGGTTG-3' (SEQ ID NO: 266) and ZIKV-E-R1 5'-CGTGCCAAGGTAATG-GAATGTCGTG-3' (SEQ ID NO: 267) and for the C-terminal part the primer pair ZIKV-Ef1530 5'-AGCCTAGGACTTGATTGTGAACCGA-3' (SEQ ID NO: 268) and ZIKV-E-R2769 5'-TTACAGATCC- CACAACGACCGTCAG-3' (SEQ ID NO: 269) were used. The cycling conditions were 54° C. for 40 minutes, 94° C. for 2 min followed by 45 cycles of 94° C. for 45 seconds, 50° C. for 45 seconds and 68° C. for 1.5 minutes with a final elongation step at 68° C. for 5 minutes and a final cooling step at 4° C. The PCR products were analyzed and extracted from a 1.5% agarose gel and further purified with the GFX PCR DNA and Gel Band Purification kit (GE Healthcare). For the sequencing reaction 8 □l of purified PCR product was mixed with 2 □M primer in a final volume of 10 □l and sent for sequencing (Microsynth). E protein N-terminal products were sequenced with ZIKV-E-F2 5'-ACTTGGT-CATGATACTGCTGATTGC-3' (SEQ ID NO: 270) and ZIKV-E-R2 5'-TCGGTTCACAATCAAGTCCTAGGCT-3' (SEQ ID NO: 271), C-terminal PCR products with ZIKV-E-f2058 5'-GCTAACCCCGTAATCACTGAAAGCA-3' (SEQ ID NO: 272) and ZIKV-E-r2248 5'-AAGACTGC-CATTCTCTTGGCACCTC-3' (SEQ ID NO: 273). Sequences were assembled and analyzed using CLC Main Workbench software (CLC Bio, version 5).

Resistant mutant MARM2 was isolated after three rounds of selection, and its E protein showed a E370K mutation in DIII. The mutation abolished neutralization by ZKA190, although the antibody can bind to the mutated DIII (FIG. 14). The mutations in the in vivo (T335R) and in vitro (E370K) MARMS are located on the BC and DE loops of DIII, respectively, and are consistent with the epitope identified by NMR.

Example 11: Development of Bispecific Antibodies According to the Present Invention Viral escape mutants can greatly hinder the efficacy of therapeutic antibodies. To overcome this problem, the present inventors hypothesized that the possibility of virus escaping would be greatly reduced when combining two highly neutralizing antibodies. In view thereof, a series of bispecific antibodies combining ZKA190 with other potently neutralizing mAbs directed towards distinct sites on the E protein was generated. Thereby, it was focused on two mAbs, ZKA185 and ZKA230, that are highly neutralizing and do not compete with ZKA190.

Firstly, their ability to cross-neutralize four ZIKV strains was analyzed as described above. ZKA185, and to a lesser extent ZKA230, potently neutralized African, Asian and American strains with an IC50 ranging from 0.02 to 0.62 nM (FIG. 19A). ZKA185 binds with high affinity to recombinant ZIKV E protein and to Zika virus-like particles (VLP) but not to the isolated DIII (FIG. 19B). Conversely, ZKA230 bound to ZIKV VLPs, but not to recombinant E or DIII, suggesting that it recognizes a quaternary epitope displayed only on the viral surface (FIG. 19B). ZKA185 IgG and Fab were shown to bind to E and VLP antigens with similar high affinity by ELISA.

To identify the ZKA185 and ZKA230 epitopes and also their propensity to generate escape mutants, MARMs against ZKA185 (MARM3) and ZKA230 (MARM4) were isolated by passaging virus in the presence of sub-neutralizing antibody concentrations as described above. MARM3 contained substitutions at K84E and D67H, which are both located on DII (FIG. 19D). MARM4 showed a mixture of different amino acid substitutions at position 84 (from K to G, E or R), confirmed in multiple sequencing experiments. Finally, MARMs 1 to 4 were tested against ZKA190, ZKA185 and ZKA230. ZKA190 neutralized ZKA185 and ZKA230 MARMs as well as the parental virus (FIG. 19C). ZKA185 neutralized both ZKA190 and ZKA230 MARMs.

ZKA230 neutralized only ZKA190 MARM2 and did not neutralize either ZKA190 MARM1 or ZKA185 MARM3.

To gain insight into the development of MARMs capable of escaping from the pressure of multiple antibodies, ZKA190 MARM2 (E370K) were serially passaged in the presence of ZKA185 or ZK230. Thereby, it was found that double MARMs emerged after 3 to 4 passages. ZKA230 introduced an extra K84E mutation while ZKA185, selected for a D76G mutation. These findings indicate that ZIKV can escape the neutralization by multiple antibodies targeting distinct sites when the selection is performed in a stepwise fashion, and confirmed a high plasticity of the ZIKV E protein.

In conclusion, ZKA185 was selected to be used together with ZKA190 for the development of a bispecific antibody since it potently cross-neutralizes ZIKV strains, binds to an alternative site, and does not compete with ZKA190. The bispecific antibody was produced in a tetravalent symmetric format called Fabs-in-tandem-Ig (FIT-Ig). FIT-Igs are described in detail, for example, in WO 2015/103072 A1 and in Gong S, Ren F, Wu D, Wu X, Wu C: Fabs-in-tandem immunoglobulin is a novel and versatile bispecific design for engaging multiple therapeutic targets. MAbs 2017.

FIT-Ig may be produced using three polypeptides. Polypeptide 1 usually comprises the light chain of the outer Fab fused, preferably without linkers, to the N-terminal region of the inner Fab heavy chain. Polypeptide 2 usually comprises the heavy chain variable and CH1 regions of the outer Fab, and polypeptide 3 usually comprises by the light chain of the inner Fab. Accordingly, an antibody of the FIT-Ig format usually comprises an "inner Fab" and an "outer Fab". Two types of FIT-Igs were generated with ZKA190 Fab either in the outer or inner position. Briefly, the three genes encoding for FIT-Ig were codon optimized, synthesized by Genscript and cloned as follows: i) the VL of the outer Fab, followed by the full constant region (lambda or kappa), is fused with the VH of the inner and cloned into the Igγ1 expression vector (modified to encode for the LALA mutation). The resulting polypeptide 1 is formed by VL and CL of the outer Fab, VH of the inner Fab fused to IgG1 CH1-hinge-CH2-CH3 domains; ii) the VH gene of the outer Fab (encoding for polypeptide 2 formed by VH and CH1 of the outer Fab) was cloned into the Fab expression vector (Igγ1 expression vector in which a stop codon is introduced after the codon encoding for the CH1 cysteine residue 220); iii) the VL gene of the inner Fab is cloned into the Igκ or Igλ expression vectors (encoding for polypeptide 3 formed by VL and CL of the inner Fab). Recombinant FIT-Ig mAbs were produced by transient transfection of EXPI293 cells (Invitrogen) using a molar ratio of 1:3:3 of the three constructs described above (as described in WO 2015/103072 A1), purified by Protein A chromatography (GE Healthcare) and desalted against PBS. The proteins were analyzed by SDS-PAGE in both reduced and non-reduced conditions and their concentrations determined by BCA (Pierce, Rockford, IL). In non-reduced conditions, FIT-Ig migrated as a major single band of approximately 250 KDa. In reducing conditions, each of the FIT-Ig proteins yielded two bands, one higher MW band is polypeptide 1 of approximately 75 KDa, and one lower MW band corresponds to both polypeptide 2 and 3 overlapped at approximately 25 KDa. To further study the physical properties of FIT-Ig in solution, size exclusion chromatography (SEC) was used to analyze each protein. Purified FIT-Ig, in PBS, was applied on a Superdex 200 Increase 5/150 GL. All proteins were determined using UV detection at 280 nm and 214 nm. FIT-Ig proteins exhibited a single major peak, demonstrating physical homogeneity as monomeric proteins.

Example 12: In Vitro Characterization of an Antibody According to the Present Invention (FIT-1)

The FIT-Ig bispecific antibody (here designated FIT-1) with ZKA190 in the outer and ZKA185 in the inner Fab positions (FIG. 19E) was selected and further characterized. ELISA showed FIT-1 to bind DIII, E and VLP (FIG. 19F). FIT-1 retained high neutralizing potency against ZIKV strains, with IC50 values largely similar to those of the parental ZKA190 and ZKA185 antibodies (FIG. 19G). FIT-1 was produced using the backbone IgG1 antibody in the LALA format, thereby eliminating any possibility of causing ADE. Several lines of evidence suggest that the ZKA190 and ZKA185 moieties in the FIT-1 format are both active. Firstly, FIT-1 bound to E protein with higher affinity than either the parental ZKA190 and ZKA185 antibodies (KD values: ZKA185 1.8 nM, ZKA190 9.3 nM and FIT-1 KD<1 µM due to slower dissociation rate, presumably through avidity effects). Secondly, FIT-1 effectively neutralized all the ZKA190, ZKA185 and ZKA230 MARMs (FIG. 19H) in contrast to the individual mAbs. The neutralizing activity of the Fab fragment of FIT-1 (each comprising one ZKA190 and one ZKA185) was reduced only by about 6-fold (FIG. 19I, right panel).

Next, the ability of FIT-1 to select MARMs was tested (as described above). However, despite eight rounds of serial passages, no MARMs could be isolated. By contrast, MARMs appeared after 3 to 4 passages when individual mAbs were used. These results suggest that the use of FIT-1 as a therapeutic is safer, since simultaneous mutations in both DIII and DII are less likely to occur.

Confocal microscopy studies using Vero cells also showed that FIT-1, as ZKA190, likely inhibits virus infection at a post-attachment step, likely fusion (FIG. 19J).

Finally, FIT-1, as well as its Fab fragment, blocked ADE of human anti-DENV2 plasma or DV62 at concentrations above 0.1 nM and 10 nM, respectively (FIG. 19K), demonstrating that FIT-1 did not cause ADE and could block ADE of monocytic cells by poorly neutralizing cross-reactive antibodies.

Example 13: In Vivo Therapeutic Potential of FIT-1

To evaluate the therapeutic potential of FIT-1, three different doses (15, 5 and 1 mg/kg) were administered at three different time-points to female A129 mice following ZIKV infection. Briefly, female A129 mice were assigned to 10 distinct groups (control and three different doses with three different administration time points for each dose). All animals were challenged subcutaneously with 102 pfu ZIKV (strain MP17.51) and followed for 14 days. Mice of the nine treatment groups were administered with bispecific antibody FIT-1 diluted in PBS at 15, 5 or 1 mg/kg via the intraperitoneal (i.p.) route in a volume of 500 □l on day 1, day 2, or day 3 after ZIKV virus challenge. Weights and temperatures of all animals were monitored daily and clinical observations were recorded at least twice per day. On day 5 post-challenge, 50 □l of blood was collected from each animal into a RNAprotect tube (Qiagen, UK) and frozen at −80° C. At the end of the study (14 days post-challenge) or when animals met human endpoints, necropsies were undertaken, and blood and sections of brain and ovary were collected for virological analysis.

Results are shown in FIG. 20. The data show that at a dose of 15 mg/kg, survival rates were 100% without signs of morbidity even when treatment was given three days post-infection (FIG. 20A); viral titers were abrogated and no escape mutants were detected, indicating high in vivo efficacy. Administration of 5 mg/kg resulted in survival rates of 70-100%, also no escape mutants were detected on day 5 after infection. The lowest dose tested (i.e., 1 mg/kg) protected when administered on day 1 or 2, but not day 3, after infection.

Example 14: Effect of FIT-1 on Disease in a Congenital Infection Model in AG129 Mice The effect of treatment of infected dams with FIT-1 on the pups born to the infected and treated dams was assessed in a mouse model of congenital infection with ZIKV, which results in live offspring after congenital exposure with ZIKV. In this model, AG-129 mice, deficient in IFN receptors, are used, which results in viral replication in the placenta, transmission of virus to the fetus, and potential long-term implications such as intrauterine growth restriction and hearing deficits.

The effect of FIT-1 treatment on various parameters in the context of intrauterine infection was tested. To this end, mice were infected with ZIKV 7 days post-coitus (dpc) and treated with FIT-1 1 3 days after virus challenge (cf Example 13). Various outcomes of disease, such as virus titer in the fetus and placenta and intrauterine growth restriction, were assessed to determine the effect of FIT-1 treatment.

Materials and Methods:

Animals: 42 female AG-129 mice were used. Groups of animals were randomly assigned to experimental groups and individually marked with ear tags. Hormonal treatment was used to induce estrous in females. Females were individually placed with males and examined for a vaginal plug 0.5 days post-coitus (dpc).

Virus: Zika virus Malaysia (P6-740) was used. A suitable challenge dose was administered via s.c. injection in a volume of 0.1 ml.

Test agent: FIT-1 was administered at a dose of 45 mg/kg. The non-specific control antibody MPEG-LALA Ctr IgG1 was used as an isotype control placebo treatment.

Quantification of virus: The virus titer of various tissues was quantified using a quantitative RT-PCR assay. Total RNA was extracted from tissue samples using TRIzol (ThermoFisher Scientific, Cat #15596018). A volume of 2 μl of the RNA preparation was used for amplification. Serial dilutions of synthetic RNA spanning the amplification region were used to make a positive control; undiluted synthetic ZIKV RNA had $10^{8.0}$ copies/μl. Samples were subjected to 40 cycles of 15 seconds at 95° C. and 60 seconds at 60° C. following an initial single cycle of 30 min at 50° C. and 10 min at 95° C. Samples of unknown quantity were quantified by extrapolation of C(t) values using a curve generated from serial dilutions of synthetic ZIKV RNA.

Experiment Design: Dams were challenged 7 days-post coitus (dpc), and were treated with FIT-1 24 or 72 hours post virus challenge. 2 dams per group were necropsied 11 days after virus challenge. The placenta, fetal tissues, brain tissue, and spleen tissue were collected for determination of virus titer by QRT-PCR. 2 females per group were followed through parturition. Occipito-frontal diameter (OF) of the head and crown rump length (CRL) of pups was recorded with a digital caliper and intrauterine growth restriction was determined by determining the pup size by the formula: CRL X OF. Weights of pups and dams were measured at various times.

Statistical analysis: Survival data were analyzed using the Wilcoxon log-rank survival analysis (Prism 5, GraphPad Software, Inc).

Results and Discussion:

Treatment with FIT-1 was evaluated in a mouse model of congenital infection and disease associated with ZIKV infection. Treatment with FIT-1 was protective to pregnant females with the large majority of treated females being protected from mortality, regardless of when treatment was administered (FIG. 21). Females treated with a non-specific negative control antibody had a mortality rate that was similar to that observed in previous studies.

A trend towards improved measurements in average pup size. The average size of pups from dams treated with FIT-1 were higher than those treated the control MPEG and were similar to sham-infected animals (FIG. 22). This difference was less pronounced in regard to fetal weight, where all groups had similar averages (FIG. 23). There was a trend towards higher placenta weight in dams treated with FIT-1 (FIG. 24).

The virus titer of various tissues is shown in FIG. 25. Significant reduction in viral RNA in the fetus and placenta of dams treated with FIT-1 were observed (FIGS. 25A and 25B, respectively). The reduction was especially evident in placental tissues with an approximate 5-$\log_{10}$ reduction in ZIKV RNA levels. Maternal spleen and brain also had significantly reduced viral RNA in FIT-1-treated animals as compared with MPEG, with several $\log_{10}$ reductions in levels (FIGS. 25C and 25D, respectively).

Conclusions:

Overall, these data support a protective role of FIT-1 in preventing or treating disease in fetuses congenitally exposed to ZIKV. A trend towards improvement in fetal and placental size parameters was observed, with a highly significant reduction in virus titer in various maternal and fetal tissues.

Example 15: Effect of FIT-1 on Disease in a Testis Infection Model in AG129 Mice Sexual transmission and persistent infection of the male reproductive tract has been documented in men infected with ZIKV (D'Ortenzio E, Matheron S, Yazdanpanah Y, et al. Evidence of Sexual Transmission of Zika Virus. N Engl J Med 2016; 374:2195-8). In the AG-129 mouse strain, severe disease is usually observed around 2 weeks after virus challenge, including significant replication of the virus in the testes of mice (Julander J G, Siddharthan V, Evans J, et al. Efficacy of the broad-spectrum antiviral compound BCX4430 against Zika virus in cell culture and in a mouse model. Antiviral Res 2016; 137:14-22). Key sites of virus replication in the reproductive tract of male AG-129 mice include the epididymis and testicle, as well as various accessory sex glands.

In the present study, the effect of FIT-1 on ZIKV infected male mice is assessed in the testis infection model. To this end, male AG129 mice were infected with ZIKV and the pathology in the male reproductive tract after ZIKV infection and treatment with FIT-1 is assessed.

Materials and Methods:

Animals: Male AG129 mice were used. Groups of animals were randomly assigned to experimental groups and individually marked with ear tags.

Virus: Zika virus (Puerto Rican strain, PRVABC-59). A challenge dose of $10^2$ $CCID_{50}$ was administered via s.c. injection in the inguinal fold in a volume of 0.1 ml. This challenge dose is typically lethal in untreated AG129 mice with mortality occurring around 2 weeks after challenge.

Test agent: FIT-1 was administered at a dose of 15 mg/kg. The non-specific control antibody MPEG-LALA Ctr IgG1 was used as an isotype control placebo treatment.

Histopathology: Tissues were collected and incubated for 24 hours in neutral buffered formalin. Following appropriate fixation, all collected tissues were trimmed and held in 70% ethanol until routine processing, paraffin embedding and sectioning were performed. All tissues were blindly analyzed independently by a veterinary anatomic pathology resident and a board certified veterinary anatomic pathologist. A scoring system was developed to grade the severity of inflammation in the reproductive tract.

Experiment Design: Mice were infected with ZIKV and were monitored for 28 days post-virus challenge for survival and weight change. Treatment with 15 mg/kg of FIT-1 was performed 24 or 72 h after virus challenge. A single treatment was administered i.p. in a volume of 0.1 ml. An isotype matched control Ab, MPEG-LALA Crt IgG1, was administered as described above with treatment occurring 24 h after virus challenge. A group of mock-infected, FIT-1-treated mice were included as toxicity controls and a group of normal controls was included. Individual weights were taken on 0, and every other day from 7-21 dpi. Mice were observed daily for signs of disease including conjunctivitis, hunching, and limb weakness or paralysis and initial onset of disease signs was recorded. A cohort of 3 animals was necropsied on 6 dpi and tissue samples were collected for histopathologic analysis.

Statistical analysis: Survival data were analyzed using the Wilcoxon log-rank survival analysis (Prism 5, GraphPad Software, Inc).

Results and Discussion:

Zika virus (ZIKV) can persist in male reproductive tissues for extended periods up to six months, representing a clear target for antiviral treatment. To determine the efficacy of a bispecific anti-ZIKV Ab in preventing or reducing pathology to the male reproductive tract, groups of mice were treated 24 or 72 h after virus challenge with a Puerto Rican isolate of ZIKV. Survival, weight change, and histopathology were used to determine the efficacy of mAb treatment. An isotype control mAb, MPEG-LALA Ctr IgG1, was used as a placebo treatment.

A significant ($P<0.0.5$) improvement in survival was observed as compared with placebo mAb treatment (FIG. 26). Complete survival was observed in mice treated 24 h post-challenge with FIT-1, while mice treated at 72 h post-virus inoculation resulted in one animal that succumbed to virus infection. This single animal was euthanized 24 days after virus challenge, which was much later than animals treated with placebo (FIG. 26). Since infection of AG-129 mice with ZIKV results in lethality, which is much more severe than a typical natural infection with this virus, high levels of protection that are seen with FIT-1 are very promising.

Mean weight change of mice treated with FIT-1 was similar to that of sham-infected treatment controls, while mean weight of mice treated with MPEG declined rapidly after 7 dpi, which further demonstrates potent protection of the mice from disease (FIG. 27).

Since the primary purpose of this study was to evaluate the effects of treatment on the male reproductive tract, and in previous studies the testes and epididymides were the most severely impacted after infection, specific attention was paid to the histopathology of these tissues. No disease was observed in the testicle or epididymis of mice treated with FIT-1, aside from a single animal in the 24 h treatment group (FIG. 28), further demonstrating the efficacy of FIT-1 treatment. FIT-1 also protected mice from disease when treatment was initiated 72 h after virus challenge and none of the mice treated at this time had observable disease in the testicle or epididymis (FIG. 28). The majority of mice in the placebo treatment group had inflammation in the testicle (2/3) and epididymis (3/3) (FIG. 28), although disease severity in this study was fairly mild.

Conclusions:

Treatment with FIT-1 was effective in reducing all evaluated disease parameters. Therapeutic treatment up to 72 h after virus challenge was highly efficacious.

Example 16: Prophylactic and Therapeutic Efficacy of FIT-1 in Rhesus Macaques Challenged with ZIKV This study evaluated the prophylactic and therapeutic efficacy of a bi-specific antibody targeting Zika virus (ZIKV) in Indian Rhesus Macaques (IRM) challenged with ZIKV strain PRVABC59. Sixteen (16) IRMs were randomized into three treatment groups. One group received FIT-1 one day prior to challenge (5 mg/kg) and a second received the treatment one day following challenge (15 mg/kg). A third group was treated with an isotype control (FIT-3, 5 mg/kg) one day prior to challenge. On Day 0, all IRMs were challenged with 1×10⁵ PFU of ZIKV strain PRVABC59 delivered by subcutaneous (SC) injection. Sera, urine, and saliva were collected at predetermined time points and tested for ZIKV load as measured by quantitative RT-PCR.

Methods:

Prior to Study Day 0, sixteen (16) IRMs were randomized into respective groups according to gender/weight using Provantis Software. On Days −1 or 1, animals received either FIT-1 or isotype control FIT-3 delivered intravenously at the dose listed in Table 4 below. On Day 0, all macaques were anesthetized and challenged with 0.5 mL of wild type ZIKV strain PRVABC59 with a target challenge dose of 10×10⁵ PFU per animal by subcutaneous injection. Blood, urine, and saliva samples were collected at predetermined time points as indicated in Table 5 for an assessment of viral load by RT-qPCR.

TABLE 4

Animal Groupings

| Group | Treatment | Treatment Day | Route, Dosage | Challenge[1] |
|---|---|---|---|---|
| 1 (3M/3F) | FIT-1 | Day −1 | i.v., 5 mg/kg | PRVABC59 (1 × 10⁵ PFU) |
| 2 (3M/3F) | FIT-1 | Day +1 | i.v., 15 mg/kg | PRVABC59 (1 × 10⁵ PFU) |
| 3 (2M/2F) | FIT-3 | Day −1 | i.v., 5 mg/kg | PRVABC59 (1 × 10⁵ PFU) |

[1]Subcutaneously challenged on Day 0 with 0.5 mL of wild type ZIKV.

TABLE 5

Key Activities

| Study Day | −1 | 0 | 1 | 5 | 10 | 15 | 20 | 25 | 30 |
|---|---|---|---|---|---|---|---|---|---|
| Treatment | ✓ | | ✓ | | | | | | |
| ZIKV challenge (s.c.) | | ✓ | | | | | | | |
| Daily Observations | | All animals were observed two times daily | | | | | | | |
| Body Weight | | Daily | | | | ✓ | ✓ | ✓ | ✓ |
| Body Temperature | | Daily | | | | ✓ | ✓ | ✓ | ✓ |
| Blood Collections[1] | | Daily | | | | ✓ | ✓ | ✓ | ✓ |
| Urine/Saliva Collections | ✓ | | ✓ | ✓ | ✓ | ✓ | ✓ | ✓ | ✓ |
| Viral Load: RT-qPCR | | Daily | | | | ✓ | ✓ | ✓ | ✓ |
| Blood Volume (mL) | | | | | 2 | 2 | 2 | 2 | 20 |
| Euthanasia | | | | | | | | | ✓ |

[1]Day 0 and 1 blood was collected prior to challenge and treatment

On Study Days −1 (Groups 1 and 3) and 1 (Group 2) anesthetized animals were administered either FIT-1 (stock concentration: 3.67 mg/mL) or FIT-3 (stock concentration: 3.79 mg/mL) via intravenous injection into the right saphenous or cephalic veins.

ZIKV strain PRVABC59; Human/2015/Puerto Rico (American Isolate) was the challenge material used in this study. Preparation of the virus inoculum was performed in a Class II Biological Safety Cabinet under BSL-2 conditions. The virus stock was thawed in a 37±1° C. water bath, vortexed, and diluted with VP-SFM to yield an inoculum of the appropriate concentration of 2×10⁵ PFU/mL. Each syringe was filled with 0.5 mL of virus inoculum and kept on ice until transferred to the animal facility for dosing. On Study Day 0, all animals were anesthetized, the injection site clipped, wiped with alcohol and marked with an indelible marker. Animals were inoculated SC on the anterior surface of the left forearm with 0.5 mL of the ZIKV isolate and dose indicated in Table 4.

All macaques were observed twice daily throughout the quarantine and study periods for signs of morbidity and mortality. Animals were observed twice daily (at no less than 8 hour intervals) for responsiveness and clinical signs including rash, erythema, conjunctivitis, ocular discharge and swelling. For all animals, blood was collected at the time points indicated in Table 5 for in vitro testing via RT-qPCR viral load. During the terminal bleed on Day 30, a volume not exceeding 20 mL per animal was collected. For all animals, urine was collected at the time points indicated in Table 5 for in vitro testing via RT-qPCR for monitoring of virus shedding. Animals were individually housed during the urine collection periods of the study. Urine was collected directly from the cage pans, placed on wet ice following collection, separated into aliquots and stored at −70° C. or below until ready for assay testing. Saliva (drool) was collected from anesthetized animals directly into tubes (up to approximately 0.5 mL). Samples were kept on wet ice following collection and stored at −70° C. or below until ready for assay testing.

Viral loads were measured using a RT-qPCR method for detection of ZIKV genomes in the serum, urine, and saliva samples collected at the time points indicated in Table 5. Samples recovered from virus inoculated animals were tested using primers and probes designed for the detection of ZIKV strain PRVABC59. A description of the PCR methods, including primer and probe sequences, has been published (Goebel et. al., 2016, A Sensitive virus yield assay for evaluation of antivirals against Zika virus. J. Virol. Methods). Viral RNA was isolated from biological fluids using the QIAmp Viral RNA mini kit (Qiagen, 52906). The viral RNA was eluted with sterile RNase and DNase free $H_2O$ and stored at −70° C. or below. The lower limit of quantitation (LLOQ) of this assay was determined to be 10 copies per reaction.

An aliquot of the challenge virus inocula was back-titrated by standard plaque assay on Vero cells to confirm the actual delivered dose. Ten-fold serial dilutions of the challenge inocula were used to infect confluent monolayers of Vero cells in 6-well plates that were plated the day before. Plates were incubated at 37° C. and 5% CO2 for 1 hour before the addition of overlay media containing 0.5% agarose. Plates were incubated for 3 days until discernable plaques form after which they were fixed, stained with crystal violet and counted.

Results:

Macaques were monitored twice daily for signs of mortality and morbidity for the duration of the study. All animals survived to the scheduled termination. Body weights and temperatures of all animals were measured at the time points indicated in Table 5. There was no significant body weight loss during the course of the study. All animals maintained a normal range of body temperatures throughout the study. Clinical observations were limited to mild redness at the challenge site in a few animals.

Viral loads were measured using a RT-qPCR method for detection of ZIKV genomes in serum, urine, and saliva samples collected at the time points indicated in Table 5. Viral load in the serum is presented in FIG. 29.

Animals in Group 3, treated with the isotype control, had detectable viral load in the serum the day following challenge. Viral load in three of the four animals peaked above $1 \times 10^5$ genome copies/mL (GC/mL) on either Day 2 or 3. The average serum viral load peaked in this group on Day 3 at $1.15 \times 10^5$ GC/mL. Viral loads decreased below the LLOQ of the assay (860 GC/mL) by Day 4 in one animal and by Day 5 in the remaining three.

Group 2 animals, treated with 15 mg/kg of FIT-1 the day after challenge, had an average viral load of $3.99 \times 10^3$ GC/mL prior to treatment. On Day 2, average serum viral load decreased to only 96.5 GC/mL. While low levels of viral RNA were sporadically detected after Day 1, at no point following treatment were viral loads detected in Group 2 animals at or above the LLOQ of the RT-qPCR assay.

Pretreatment with 5 mg/kg of FIT-1 decreased Day 1 average serum viral loads by greater than 50-fold compared to Group 3. At no time point after challenge were viral loads detected at or above the LLOQ of the assay, and by Day 2 no viral RNA was detected in the serum of any of the Group 1 animals.

Only sporadic, low levels of ZIKV RNA were detected in the urine or saliva from any of the animals. At no point were viral loads detected at or above the LLOQ of the assay in urine or saliva from any animal.

An aliquot of the challenge virus inocula was back-titrated by standard plaque assay on Vero cells to confirm the actual delivered dose. The plaque assay yielded a titer of $1.7 \times 10^5$ PFU/mL.

SUMMARY AND CONCLUSIONS

This study evaluated the prophylactic and therapeutic efficacy of FIT-1 in IRMs challenged with ZIKV. There was no mortality throughout the course of the study and clinical observations were limited to mild redness at the challenge site in a few animals. Viral load as detected by RT-qPCR in serum collected following challenge was the primary end point of the study. Viral RNA was readily detected in the serum of all animals treated with the isotype control, with viral loads peaking on Days 2 or 3 and sustaining at levels above the LLOQ of 860 GC/mL until Days 4 or 5. Average peak load was $1.1.5 \times 10^5$ GC/mL on Day 3. In contrast, prophylactic treatment with 5 mg/kg of FIT-1 effectively reduced peak viral loads and time to viral clearance in ZIKV challenged IRMs. Low levels of viral RNA were detected in all six animals from this group on Day 1 but by Day 2, no viral RNA was detected in any animal. At no point was ZIKV RNA detected above the LLOQ of 860 GC/mL in the serum of any animal from this group. Similarly, therapeutic treatment with 15 mg/kg of FIT-1 the day following challenge reduced both peak viral loads and time to viral clearance from the serum compared to animals treated with the isotype control. Group 2 macaques had a mean peak viral load of $3.99 \times 10^3$ GC/mL on Day 1 but after treatment on Day 1, average viral loads in the serum of this group decreased to only 96.5 GC/mL by Day 2. No animals in this group had viral loads above the LLOQ of 860 GC/mL for the remainder of the observation period.

Tables of Sequences and SEQ ID Numbers

| ZKA190 | SEQ ID NO. | Amino acid sequence |
|---|---|---|
| CDRH1 | 1 | GFTFSKYG |
| CDRH2 | 2 | ISYEGSNK |
| CDRH3 | 3 | AKSGTQYYDTTGYEYRGLEYFGY |
| CDRL1 | 4 | QSVSSSY |
| CDRL2 | 5 | DAS |
| CDRL2 long | 6 | LIYDASSRA |
| CDRL3 | 7 | QQYGRSRWT |
| VH | 8 | QVQLVESGGGVVQPGRSLRLSCAASGFTFSKYGMHWVRQAPGKGLE WVAVISYEGSNKYYADSVKGRFTISRDNSKNTLYLQMNSLRAEDTA VYYCAKSGTQYYDTTGYEYRGLEYFGYWGQGTLVTVSS |
| VL | 9 | EIVLTQSPGTLSLSPGERATLSCRASQSVSSSYLAWYQQKRGQAPR LLIYDASSRATGIPDRFSGSGSGTDFTLTISRLEPEDFAVYYCQQY GRSRWTFGQGTKVEIK |

Tables of Sequences and SEQ ID Numbers

| ZKA190 | SEQ ID NO. | Nucleic acid sequence |
|---|---|---|
| CDRH1 | 10 | ggattcaccttcagtaaatatggc |
| CDRH2 | 11 | atatcatatgagggaagtaataaa |
| CDRH3 | 12 | gcgaaatcggggacccaatactatgatactactggttatgagtataggggtttggaatactttggctac |
| CDRL1 | 13 | cagagtgttagtagcagttac |
| CDRL2 | 14 | gatgcatcc |
| CDRL2 long | 15 | ctcatctatgatgcatccagcagggcc |
| CDRL3 | 16 | cagcagtatggtaggtcaaggtggaca |
| VH | 17 | caggtgcagctggtggagtctggggg aggcgtggtccagcctgggaggtccctgagactctcctgtgcagcctctggattcaccttcagtaaatatggcatgcactgggtccgccaggctccaggcaaggggctggagtgggtggcagttatatcatatgagggaagtaataaatattatgcagactccgtgaagggccgattcaccatctccagagacaattccaagaacacgctgtatctgcaaatgaacagcctgagagctgaggacacggcagtgtattactgtgcgaaatcggggacccaatactatgatactactggttatgagtataggggtttggaatactttggctactggggccagggaaccctggtcaccgtctcctcag |
| VL | 18 | gaaattgtgttgacgcagtctccaggcaccctgtctttgtctccaggggaaagagccaccctctcctgcagggccagtcagagtgttagtagcagttacttagcctggtaccagcagaaacgtggccaggctcccaggctcctcatctatgatgcatccagcagggccactggcatcccagacaggttcagtggcagtggttctgggacagacttcactctcaccatcagcagactggagcctgaagattttgcagtgtattactgtcagcagtatggtaggtcaaggtggacattcggccaagggaccaaggtggaaatcaaac |

| ZKA185 | SEQ ID NO. | Amino acid sequence |
|---|---|---|
| CDRH1 | 19 | GYSFTSYW |
| CDRH2 | 20 | FDPSDSQT |
| CDRH3 | 21 | ARRYCSSSSCYVDN |
| CDRL1 | 22 | ALPNKF |
| CDRL2 | 23 | EDN |
| CDRL2 long | 24 | VIYEDNKRP |
| CDRL3 | 25 | YSTDSSSNPLGV |
| VH | 26 | EVQLVQSGAEVKKPGESLRISCKGSGYSFTSYWITWVRQMPGKGLEWMAKFDPSDSQTNYSPSFQGHVTISVDKSISTAYLQWSSLKASDTAMYYCARRYCSSSSCYVDNWGQGTLVTIFS |
| VL | 27 | SYELTQPPSVSVSPGQTARITCSGDALPNKFAYWYRQKSGQAPVLVIYEDNKRPSGIPERFSGSSSGTMATLTISGAQVEDADYHCYSTDSSSNPLGVFGGGTKLTVL |

| ZKA185 | SEQ ID NO. | Nucleic acid sequence |
|---|---|---|
| CDRH1 | 28 | ggatatagttttaccagttactgg |
| CDRH2 | 29 | tttgatcctagtgactctcaaacc |
| CDRH3 | 30 | gcgagaagatattgtagtagtagtagttgttatgtggacaat |
| CDRL1 | 31 | gcattgccaaataaattt |

Tables of Sequences and SEQ ID Numbers

| | | |
|---|---|---|
| CDRL2 | 32 | gaggacaac |
| CDRL2 long | 33 | gtcatctatgaggacaacaaacgaccc |
| CDRL3 | 34 | tactcaacagacagcagttctaatccctgggagta |
| VH | 35 | gaagtgcagctggtgcagtccggagcagaggtgaaaaagcc cggggagtctctgaggatctcctgtaaggggttctggatata gttttaccagttactggatcacctgggtgcgccagatgccc gggaaaggcctggagtggatggcgaagtttgatcctagtga ctctcaaaccaactacagcccgtccttccaaggccacgtca ccatctcagttgacaagtccatcagcactgcctacttgcag tggagcagcctgaaggcctcggacaccgccatgtattactg tgcgagaagatattgtagtagtagtagttgttatgtggaca attggggccagggaaccctggtcaccatcttctcag |
| VL | 36 | tcctatgagctgacacagccaccctcggtgtcagtgtccc aggacaaacggccaggatcacctgctctggagatgcattgc caaataaatttgcttattggtaccggcagaagtcaggccag gccctgttctggtcatctatgaggacaacaaacgaccctc cgggatccctgagagattctctggctccagctcagggacaa tggccaccttgactatcagtggggcccaggtggaggatgaa gctgactaccactgttactcaacagacagcagttctaatcc cctgggagtattcggcggagggaccaagctgaccgtcctag |

| ZKA230 | SEQ ID NO. | Amino acid sequence |
|---|---|---|
| CDRH1 | 37 | GGSISSDY |
| CDRH2 | 38 | IYYSGST |
| CDRH3 | 39 | ARRRKYDSLWGSFAFDI |
| CDRL1 | 40 | SSNIGGNY |
| CDRL2 | 41 | IND |
| CDRL2 long | 42 | LICINDHRP |
| CDRL3 | 43 | ATWDDSLGGLV |
| VH | 44 | QVQLQESGPGLVKPSETLSLTCAVSGGSISSDYWSWIRQPPGKGLE WIGYIYYSGSTNYNPSLKSRVTISVDTSKNHFSLKLNSVTAADTAV YYCARRRKYDSLWGSFAFDIWGQGTMVTSS |
| VL | 45 | QSVLTQPPSASGTPGQRVTISCSGSSSNIGGNYVYWYQQLPGTAPK LLICINDHRPSGVPDRFSGSKSGTSASLAISGLQSEDEADYYCATW DDSLGGLVFGGGTKLTVL |

| ZKA230 | SEQ ID NO. | Nucleic acid sequence |
|---|---|---|
| CDRH1 | 46 | ggtggctccatcagtagtgactac |
| CDRH2 | 47 | atctattacagtgggagcacc |
| CDRH3 | 48 | gcgaggaggaggaagtatgattccctttgggggagttttgc ttttgatatc |
| CDRL1 | 49 | agctccaacatcggaggtaattat |
| CDRL2 | 50 | attaatgat |
| CDRL2 long | 51 | ctcatctgtattaatgatcaccggccc |
| CDRL3 | 52 | gcaacatgggatgacagcctgggtggccttgta |
| VH | 53 | caggtgcagctgcaggagtcgggcccaggcctggtgaagcc ttcggagaccctgtccctcacctgcgcagtctctggtggct ccatcagtagtgactactggagctggatccggcagccca gggaagggactggagtggattgggtatatctattacagtgg gagcaccaactacaacccctccctcaagagtcgagtcacca tatcagtagacacgtccaagaaccacttctccctgaagctg aactctgtgaccgctgcggacacggccgtgtattactgtgc gaggaggaggaagtatgattcccttgggggagttttgctt |

Tables of Sequences and SEQ ID Numbers

| | | |
|---|---|---|
| | | ttgatatctggggccaagggacaatggtcaccgtctcttca g |
| VL | 54 | cagtctgtgctgactcagccaccctcagcgtctgggacccc cgggcagagggtcaccatctcttgttctggaagcagctcca acatcggaggtaattatgtatactggtaccagcagctccca ggaacggccccccaaactcctcatctgtattaatgatcaccg gccctcaggggtcccctgaccgattctctggctccaagtctg gcacctcagcctcctggccatcagtgggctccagtccgag gatgaggctgattattactgtgcaacatgggatgacagcct ggtggccttgtattcggcggagggaccaagctgaccgtcc tag |
| ZKA78 | SEQ ID NO. | Amino acid sequence |
| CDRH1 | 55 | GFTFSNYA |
| CDRH2 | 56 | IGRNGDSI |
| CDRH3 | 57 | VKDLAIPESYRIEADY |
| CDRL1 | 58 | QSVLYRSNNKNY |
| CDRL2 | 59 | WAS |
| CDRL2 long | 60 | LIYWASTRE |
| CDRL3 | 61 | QQYYSSPRT |
| VH | 62 | EVQLAESGGGLVQPGGSLTLSCSGSGFTFSNYAMVWARQAPGKGLE YVSGIGRNGDSIYYTDSVKGRFTISRDNSKSMVYLQMSSLRTEDTA VYYCVKDLAIPESYRIEADYWGQGTLVIVSA |
| VL | 63 | DIVMTQSPDSLAVSLGERATINCKSSQSVLYRSNNKNYLSWYQQKP GQPPKLLIYWASTRESGVPDRFSGSGSGTDFTLTISPLQAEDVAVY YCQQYYSSPRTFGQGTKVEIK |
| ZKA78 | SEQ ID NO. | Nucleic acid sequence |
| CDRH1 | 64 | ggcttcacttttagtaactatgca |
| CDRH2 | 65 | atcgggcgcaacggggactctatc |
| CDRH3 | 66 | gtgaaagatctggccatccccgagtcctacagaattgaag ctgattat |
| CDRL1 | 67 | cagtccgtgctgtaccgctctaacaacaagaattac |
| CDRL2 | 68 | tgggcttca |
| CDRL2 long | 69 | ctgatctattgggcttcaacccgggaa |
| CDRL3 | 70 | cagcagtactattctagtcctcgaact |
| VH | 71 | gaggtgcagctggcagaatcaggcgggggactggtccagc ctggcggcagcctgacactgtcttgcagtggatcaggctt cacttttagtaactatgcaatggtgtgggcaaggcaggct cctgggaagggactggagtatgtctctggcatcgggcgca acggggactctatctactatactgatagtgtgaagggccg gttcaccatcagcagagacaatagcaaatccatggtgtac ctgcagatgagctccctgcgaaccgaagacacagcagtgt actattgcgtgaaagatctggccatccccgagtcctacag aattgaagctgattattggggacagggcaccctggtcatc gtgagcgccg |
| VL | 72 | gacatcgtgatgacacagtctccagatagtctggcagtca gtctgggggagagggccactattaactgcaagagctccca gtccgtgctgtaccgctctaacaacaagaattacctgtct tggtatcagcagaagcccggacagccccctaaactgctga tctattgggcttcaacccggggaaagcggcgtcccagacga attctcaggcagcgggtccggaacagacttcaccctgaca attagccccctgcaggcagaggacgtggctgtctactatt gtcagcagtactattctagtcctcgaactttcggccaggg gaccaaggtggaaatcaaac |

-continued

Tables of Sequences and SEQ ID Numbers

| ZKA64 | SEQ ID NO. | Amino acid sequence |
|---|---|---|
| CDRH1 | 73 | GYTFTGYH |
| CDRH2 | 74 | INPNSGGT |
| CDRH3 | 75 | ARMSSSIWGFDH |
| CDRL1 | 76 | QSVLIN |
| CDRL2 | 77 | GAS |
| CDRL2 long | 78 | LIYGASSRA |
| CDRL3 | 79 | QQYNDWPPIT |
| VH | 80 | QVQLVQSGAEVKKPGASVKVSCKASGYTFTGYHIDWVRQARGQGLEWMGRINPNSGGTNYAQKFQGRVTMTRDTSISTAYMQLSRLRSDDSAVYYCARMSSSIWGFDHWGQGTLVTVSS |
| VL | 81 | EIVMTQSPATLSVSPGERATLSCRASQSVLINLAWYQQKPGQAPRLLIYGASSRATGIPARFSGSGSGTEFTLTISSLQSEDFAVYYCQQYNDWPPITFGQGTRLEIK |

| ZKA64 | SEQ ID NO. | Nucleic acid sequence |
|---|---|---|
| CDRH1 | 82 | ggctacaccttcacagggtatcac |
| CDRH2 | 83 | attaaccctaattctggcgggacc |
| CDRH3 | 84 | gctcggatgagctcctctatttggggcttcgatcat |
| CDRL1 | 85 | cagtctgtgctgattaac |
| CDRL2 | 86 | ggagcatcc |
| CDRL2 long | 87 | ctgatctatggagcatcctccagggct |
| CDRL3 | 88 | cagcagtacaatgattggccccctatcaca |
| VH | 89 | caggtgcagctggtccagagcggagcagaggtgaagaaacccggcgcctcagtgaaggtcagctgcaaagcttccggctacaccttcacagggtatcacatcgactgggtgaggcaggaagaggacagggactggaatggatgggacggattaaccctaattctggcgggaccaactacgcccagaagtttcagggccgagtgactatgaccagagacaccagctcatctcacagcttatatgcagctgtcccggctgagatctgacgatagtgccgtctactattgtgctcggatgagctcctctatttggggcttcgatcattgggggcagggaacactggtgactgtcagttcag |
| VL | 90 | gagatcgtgatgactcagtctccagccaccctgtcagtcagcccaggagaacgggcaaccctgtcttgcagagcctcccagtctgtgctgattaacctggcttggtaccagcagaagccaggccaggcaccccgactgctgatctatggagcatcctccagggctaccggcattcctgcacgcttcagtggatcaggaagcggaacagagtttaccctgacaatctctagtctgcagtccgaagacttcgctgtctactattgtcagcagtacaatgattggccccctatcacatttggccaggggactagactggagatcaagc |

| Constant regions | SEQ ID NO. | Sequence |
|---|---|---|
| IgG1 CH1-CH2-CH3 aa | 91 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |

| Tables of Sequences and SEQ ID Numbers | | |
|---|---|---|
| IgG1 CH1-CH2-CH3 LALA aa | 92 | ASTKGPSVFPLAPSSKSTSGGTAALGCLVKDYFPEPV<br>TVSWNSGALTSGVHTFPAVLQSSGLYSLSSVVTVPSSS<br>LGTQTYICNVNHKPSNTKVDKKVEPKSCDKTHTCPP<br>CPAPEAAGGPSVFLFPPKPKDTLMISRTPEVTCVVVD<br>VSHEDPEVKFNWYVDGVEVHNAKTKPREEQYNSTY<br>RVVSVLTVLHQDWLNGKEYKCKVSNKALPAPIEKTIS<br>KAKGQPREPQVYTLPPSRDELTKNQVSLTCLVKGFYP<br>SDIAVEWESNGQPENNYKTTPPVLDSDGSFFLYSKLT<br>VDKSRWQQGNVFSCSVMHEALHNHYTQKSLSLSPGK |
| IgG CK aa | 93 | RTVAAPSVFIFPPSDEQLKSGTASVVCLLNNFYPREAK<br>VQWKVDNALQSGNSQESVTEQDSKDSTYSLSSTLTLS<br>KADYEKHKVYACEVTHQGLSSPVTKSFNRGEC |
| IgG CL aa | 94 | GQPKAAPSVTLFPPSSEELQANKATLVCLISDFYPGAV<br>TVAWKADSSPVKAGVETTTPSKQSNNKYAASSYLSLT<br>PEQWKSHRSYSCQVTHEGSTVEKTVAPTECS |
| IgG1 CH1-CH2-CH3 nucl | 95 | gcgtcgaccaagggcccatcggtcttccccctggcaccctcctccaagagcacctct<br>ggggggcacagcggccctgggctgcctggtcaaggactacttccccgaacctgtg<br>acggtctcgtggaactcaggcgccctgaccagcggcgtgcacaccttcccggctg<br>tcctacagtcctcaggactctactccctcagcagcgtggtgaccgtgccctccagca<br>gcttgggcacccagacctacatctgcaacgtgaatcacaagcccagcaacaccaag<br>gtggacaagagagttgagcccaaatcttgtgacaaaactcacacatgcccaccgtg<br>cccagcacctgaactcctggggggaccgtcagtcttcctcttccccccaaaacccaa<br>ggacaccctcatgatctcccggacccctgaggtcacatgcgtggtggtggacgtg<br>agccacgaAgaCcctgaggtcaagttcaactggtacgtggacggcgtggaggt<br>gcataatgccaagacaaagccgcgggaggagcagtacaacagcacgtaccgtgt<br>ggtcagcgtcctcaccgtcctgcaccaggactggctgaatggcaaggagtacaag<br>tgcaaggtctccaacaaagcccccagccccatcgagaaaaccatctccaaagcc<br>aaagggcagccccgagaaccacaggtgtacaccctgcccccatcccgggaggag<br>atgaccaagaaccaggtcagcctgacctgcctggtcaaaggcttctatcccagcga<br>catcgccgtggagtgggagagcaatgggcagccggagaacaactacaagaccac<br>gcctcccgtgctggactccgacggctccttcttcctctatagcaagctcaccgtgga<br>caagagcaggtggcagcaggggaacgtcttctcatgctccgtgatgcatgaggct<br>ctgcacaaccactacacgcagaagagcctctccctgtccccgggtaaa |
| IgG1 CH1-CH2-CH3 LALA nucl | 96 | gcgtcgaccaagggcccatcggtcttccccctggcaccctcctccaagagcacctct<br>ggggggcacagcggccctgggctgcctggtcaaggactacttccccgaacctgtg<br>acggtctcgtggaactcaggcgccctgaccagcggcgtgcacaccttcccggctg<br>tcctacagtcctcaggactctactccctcagcagcgtggtgaccgtgccctccagca<br>gcttgggcacccagacctacatctgcaacgtgaatcacaagcccagcaacaccaag<br>gtggacaagagagttgagcccaaatcttgtgacaaaactcacacatgcccaccgtg<br>cccagcacctgaaGCCGCGgggggaccgtcagtcttcctcttccccccaaaac<br>ccaaggacaccctcatgatctcccggacccctgaggtcacatgcgtggtggtgga<br>cgtgagccacgaagaccctgaggtcaagttcaactggtacgtggacggcgtgga<br>ggtgcataatgccaagacaaagccgcgggaggagcagtacaacagcacgtaccg<br>tgtggtcagcgtcctcaccgtcctgcaccaggactggctgaatggcaaggagtac<br>aagtgcaaggtctccaacaaagcccccagccccatcgagaaaaccatctccaaa<br>gccaaagggcagccccgagaaccacaggtgtacaccctgcccccatcccgggag<br>gagatgaccaagaaccaggtcagcctgacctgcctggtcaaaggcttctatcccag<br>cgacatcgccgtggagtgggagagcaatgggcagccggagaacaactacaaga<br>ccacgcctcccgtgctggactccgacggctccttcttcctctatagcaagctcaccgt<br>ggacaagagcaggtggcagcaggggaacgtcttctcatgctccgtgatgcatga<br>ggctctgcacaaccactacacgcagaagagcctctccctgtccccgggtaaa |
| IgG CK nucl | 97 | cgTacGgtggctgcaccatctgtcttcatcttcccgccatctgatgagcagttgaa<br>atctggaactgcctctgttgtgtgcctgctgaataacttctatcccagagaggccaa<br>agtacagtggaaggtggataacgccctccaatcgggtaactcccaggagagtgtc<br>acagagcaggacagcaaggacagcacctacagcctcagcagcaccctgacgctga<br>gcaaagcagactacgagaaacacaaagtctacgcctgcgaagtcacccatcaggg<br>cctgagctcgcccgtcacaaagagcttcaacaggggagagtgt |
| IgG CL nucl | 98 | ggtcagcccaaggctgccccctcggtcactctgttcccgccctcctctgaggagctt<br>caagccaacaaggccacactggtgtgtctcataagtgacttctacccgggagccgt<br>gacagtggcttggaaagcagatagcagccccgtcaaggcggagtggagacca<br>ccacaccctccaaacaaagcaacaacaagtacgcggccagcagctatctgagcctg<br>acgcctgagcagtggaagtcccacagaagctacagctgccaggtcacgcatgaag<br>ggagcaccgtggagaagacagtggcccctacagaatgttca |
| ZKA3 | SEQ ID NO. | Amino acid sequence |
| CDRH1 | 99 | GFIFSNYA |
| CDRH2 | 100 | IGGKGDSI |

| | | Tables of Sequences and SEQ ID Numbers |
|---|---|---|
| CDRH3 | 101 | VKDLAVLESDRLEVDQ |
| VH | 102 | EVQLAESGGGLVQPGGSLRLSCSGSGFIFSNYAMVWARQAP GKGLEYVSGIGGKGDSIYHIDSVKGRFTISRDNSKRTVYLQ MSRLRTEDTAVYYCVKDLAVLESDRLEVDQWGQGTLVIVSA |
| ZKA4 | SEQ ID NO. | Amino acid sequence |
| CDRH1 | 103 | GFTFSSYV |
| CDRH2 | 104 | TSYDGSNK |
| CDRH3 | 105 | ARGPVPYWSGESYSGAYFDF |
| VH | 106 | QVQLVESGGGVVQPGRSLRLSCAASGFTFSSYVMHWVRQAP GKGLEWVTTSYDGSNKYYADSVKGRFTISRDNAKNTLYLQ MNSLRGEDTAIYYCARGPVPYWSGESYSGAYFDWGQGILV TVSS |
| ZKA5 | SEQ ID NO. | Amino acid sequence |
| CDRH1 | 107 | GFTFSNYY |
| CDRH2 | 108 | MSSSETIK |
| CDRH3 | 109 | ARSGIETVAGSIDYYGMDV |
| VH | 110 | QVQLVESGGGLVKPGGSLRLSCAGSGFTFSNYYMTWIRQAP GKGLELVSYMSSSETIKYYADSVKGRFTISRDNAKNSLYLQ MNSLRADDTARYYCARSGIETVAGSIDYYGMDVWGHGTPVT VSS |
| ZKA6 | SEQ ID NO. | Amino acid sequence |
| CDRH1 | 111 | DFTVSNYA |
| CDRH2 | 112 | VSYDGSNK |
| CDRH3 | 113 | ATGVTMFQGAQTNAEYLHY |
| VH | 114 | QVHLVESGGGVVQPGRSLRLSCEASDFTVSNYAMHWVRQAP GKGLEWVAVVSYDGSNKYYADSVKGRFTISRDNSKNTLYLQ MNSLRAEDTALYYCATGVTMFQGAQTNAEYLHYWGQGSLVT ISS |
| ZKA7 | SEQ ID NO. | Amino acid sequence |
| CDRH1 | 115 | GFTFSRYG |
| CDRH2 | 116 | VSGDGSST |
| CDRH3 | 117 | VKDFWSGDQSLESDF |
| VH | 118 | EVQLVESGGGLVQPGGSLRLSCSASGFTFSRYGMVWARQAP GKGLEYLSGVSGDGSSTYYANSVKGRFTISRDNSKNTLYLH MSRLRDEDTAMYYCVKDFWSGDQSLESDFWGQGALVTVSS |
| ZKA8 | SEQ ID NO. | Amino acid sequence |
| CDRH1 | 119 | GFTFSAHA |
| CDRH2 | 120 | ISRNEDYT |
| CDRH3 | 121 | VKDFGTSPQTDF |
| VH | 122 | DERLVESGGGLVQPGGSLRLVCSASGFTFSAHAMHWVRQPP GKGLEYVSTISRNEDYTYYADSVKGRFTISRDNSKNSLYLQ MRRLRPEDTAIYYCVKDFGTSPQTDFWGQGTLVAVSS |
| ZKA76 | SEQ ID NO. | Amino acid sequence |
| CDRH1 | 123 | GFTFSTYF |
| CDRH2 | 124 | ISSTGSYK |
| CDRH3 | 125 | ARPFHSEYTYGLDAFDI |

Tables of Sequences and SEQ ID Numbers

| | | |
|---|---|---|
| VH | 126 | EVQLVESGGGLVKPGGSLRLSCAASGFTFSTYFMHWVRQAPGKGLEWVASISSTGSYKFYADSVKGRFTISRDNTKNSLFLQMNSLRAEDTAVFYCARPFHSEYTYGLDAFDIWGQGTMLTVSS |
| ZKA117 | SEQ ID NO. | Amino acid sequence |
| CDRH1 | 127 | GGSIRRTNSY |
| CDRH2 | 128 | ISYSGST |
| CDRH3 | 129 | ARLNDGSTVTTSSYFDY |
| VH | 130 | QLQLQESGPGLVKPSETLSLTCTVSGGSIRRTNSYWGWIRQTTGKGLQWIGSISYSGSTFYNPSLKSRVTISLDTSKDHFSLELSSVTAADTAIYYCARLNDGSTVTTSSYFDYWGQGTLVTVSS |
| ZKB27 | SEQ ID NO. | Amino acid sequence |
| CDRH1 | 131 | GYSFTSSW |
| CDRH2 | 132 | IDPSDSYT |
| CDRH3 | 133 | ARHDYSVSENGMDV |
| VH | 134 | EVQLVQSGAEVKKPGESLRISCKASGYSFTSSWINWVRQMPGKGLEWMGRIDPSDSYTTYNPSFQGHVTISVDKSIGTAYLQWNSLRASDTAMYYCARHDYSVSENGMDVWGQGTTVIVSS |
| ZKB29 | SEQ ID NO. | Amino acid sequence |
| CDRH1 | 135 | GFTFSSYT |
| CDRH2 | 136 | ISYDGSHK |
| CDRH3 | 137 | ARRSYSISCFDY |
| VH | 138 | QVQLVESGGGVVQPGRSLRLSCAASGFTFSSYTMHWVRQAPGKGLEWVAVISYDGSHKFYADSVKGRFTISRDNSKDTLYLQMNSLRAEDTALYYCARRSYSISCFDYWGQGTLVTISS |
| ZKB34 | SEQ ID NO. | Amino acid sequence |
| CDRH1 | 139 | GFTFSRSG |
| CDRH2 | 140 | VSYDGSNK |
| CDRH3 | 141 | AKDLTMVRGVHYYYYVMDV |
| VH | 142 | QVQLVESGGGVVQPGRSLRLSCAASGFTFSRSGMHWVRQAPGKGLEWVAVVSYDGSNKYYSDVKGRFTISRDNSKNTLYLQMNSLRVEDTAVYYCAKDLTMVRGVHYYYYVMDVWGQGTIVTVSS |
| ZKB39 | SEQ ID NO. | Amino acid sequence |
| CDRH1 | 143 | GYTFDDYY |
| CDRH2 | 144 | INPHRGGT |
| CDRH3 | 145 | VRDQYCDGGNCYGIHQPHYGMDV |
| VH | 146 | QVQLVQSGAEVKKPGASLKVSCKASGYTFDDYYIHWVRQAPGQGLEWLGRINPHRGGTNYAQKFQGRVIMTLDMSISTTYMELRRITSDDAAVYYCVRDQYCDGGNCYGIHQPHYGMDVWGQGTTVTVSS |
| ZKB46 | SEQ ID NO. | Amino acid sequence |
| CDRH1 | 147 | GYSFTSYW |
| CDRH2 | 148 | IDPSDSYT |
| CDRH3 | 149 | ARREYSSSGQEDWFDP |

| | | Tables of Sequences and SEQ ID Numbers |
|---|---|---|
| VH | 150 | EVQLVQSGAEVKKPGESLRISCKGSGYSFTSYWISWVRQMPGKGLEWMGRIDPSDSYTNYSPSFQGHVTISADKSISTAYLQWSSLKASDTAMYYCARREYSSSSGQEDWFDPWGQGTLVTVSS |
| ZKB53 | SEQ ID NO. | Amino acid sequence |
| CDRH1 | 151 | GFTFSSYA |
| CDRH2 | 152 | ISYDGSNR |
| CDRH3 | 153 | ARHVEQLPSSGYFQH |
| VH | 154 | QVQLVESGGGVVQPGRSLRLSCAASGFTFSSYAMHWVRQTPGKGLEWVTISYDGSNRYYADSVKGRFTISRDNSKNTLYLQMNSLRSEDTAVYYCARHVEQLPSSGYFQHWGQGTLVTVSS |
| ZKC26 | SEQ ID NO. | Amino acid sequence |
| CDRH1 | 155 | GFIFSDFY |
| CDRH2 | 156 | IGHDGSYI |
| CDRH3 | 157 | ARAHGGFRH |
| VH | 158 | QVQVVESGGGLVKPGGSLRLSCAASGFIFSDFYMSWMRQAPGKGLEWVAYIGHDGSYILYADSVKGRFTISRDNAKNSLFLRMNSLRVEDTAVYYCARAHGGFRHWGQGTVVAVSP |
| ZKD5 | SEQ ID NO. | Amino acid sequence |
| CDRH1 | 159 | GFTFTSYG |
| CDRH2 | 160 | ISYDGSNK |
| CDRH3 | 161 | ARDRDHYDLWNAYTFDY |
| VH | 162 | QVQLVESGGGVVQPGRSLRLSCAASGFTFTSYGMHWVRQTPGKGLDWVAVISYDGSNKYYADSVKGRFTISRDNSKDTLYLQMNSLRAADTALYYCARDRDHYDLWNAYTFDYWGQGTLVTVSS |
| ZKD7 | SEQ ID NO. | Amino acid sequence |
| CDRH1 | 163 | GFTFSNYA |
| CDRH2 | 164 | ISYDVSDK |
| CDRH3 | 165 | AGGPLGVVVIKPSNAEHFHH |
| VH | 166 | QVQLVESGGGVVQPGRSLRLSCAASGFTFSNYAMHWVRQAPGKGLEWVAVISYDVSDKYYADSVKGRFTISRDNSKNTLFLQMNSLRAEDTAAYYCAGGPLGVVVIKPSNAEHFHHWGQGTLVTVSS |
| ZKD8 | SEQ ID NO. | Amino acid sequence |
| CDRH1 | 167 | GFTFINYA |
| CDRH2 | 168 | ISYDGSNK |
| CDRH3 | 169 | ATDADAYGDSGANFHY |
| VH | 170 | QVQLVESGGGVVQPGKSLRLSCAASGFTFINYAIHWVRQAPGKGLEWVAVISYDGSNKFYTDSVKGRFTISRDNSKNTLYLQMNSLRADDTAVYYCATDADAYGDSGANFHYWGQGTLVTVSS |
| ZKD15 | SEQ ID NO. | Amino acid sequence |
| CDRH1 | 171 | DASISSGGFS |
| CDRH2 | 172 | IYSSGDT |
| CDRH3 | 173 | ARAHTPTSKFYYYAMDV |

| | | Tables of Sequences and SEQ ID Numbers |
|---|---|---|
| VH | 174 | QLQLQESGSGLVKPSQTLSLTCTVSDASISSGGFSWSWIRQ PLGKGLEWLGYIYSSGDTFYNPSLQGRVTMSVDIFRSQFSL KLTSVTAADTAMYYCARAHTPTSKFYYYYAMDWGQGTTVT VSS |
| ZKD16 | SEQ ID NO. | Amino acid sequence |
| CDRH1 | 175 | GFTFSDHF |
| CDRH2 | 176 | SRNKPNSYTT |
| CDRH3 | 177 | AKVGGCYGGDCHVENDY |
| VH | 178 | EVQLVESGGDLVQPGGSLRLSCVASGFTFSDHFMDWVRQAP GKGLEWVGRSRNKPNSYTTEYAASVKGRFSISRDDSKKALY LQMNSLQTEDTAVYYCAKVGGCYGGDCHVENDYWGQGTLVT VSS |
| ZKD17 | SEQ ID NO. | Amino acid sequence |
| CDRH1 | 179 | GFIFSDYA |
| CDRH2 | 180 | ISYDGSSR |
| CDRH3 | 181 | ARGYCSSGTCFSTNAEYFHP |
| VH | 182 | QVQMVESGGGVVQPGTSLRLSCATSGFIFSDYAMHWVRQAP GKGLEWVAVISYDGSSRLYADSVKGRFTVSRDNSKNTLYLQ MHSLRAGDTAVYYCARGYCSSGTCFSTNAEYFHPWGQGTLA TISS |
| ZKD20 | SEQ ID NO. | Amino acid sequence |
| CDRH1 | 183 | GFTFSDHF |
| CDRH2 | 184 | SRNKPNSYTT |
| CDRH3 | 185 | ARVGGCNGGDCHVENDY |
| VH | 186 | EVQLVESGGGLVQPGGSLRLSCVASGFTFSDHFMDWVRQAP GKGLEWVGRSRNKPNSYTTEYAASVKGRFTISRDDSKNSLY LQMNSLQTEDTAVYYCARVGGCNGGDCHVENDYWGQGTLVT VSS |
| ZKA134 | SEQ ID NO. | Amino acid sequence |
| CDRH1 | 187 | GGTFSAYA |
| CDRH2 | 188 | IIPFFGTA |
| CDRH3 | 189 | ARSDIVSTTRGYHHYGMDV |
| VH | 190 | QVHLVQSGAEVKKPGSSVNVSCKASGGTFSAYAISWVRQAP GQGLEWMGIIPFFGTAYYAQKFKGRVTVTADKSISTVYME MISLRSEDTAVYYCARSDIVSTTRGYHHYGMDVWGQGTTVT VSS |
| ZKA246 | SEQ ID NO. | Amino acid sequence |
| CDRH1 | 191 | GYTFSDYY |
| CDRH2 | 192 | INPYSGGT |
| CDRH3 | 193 | ARGFTMISDREFDP |
| VH | 194 | QVQLVQSGAEVKRPGASVKVSCKASGYTFSDYYMHWVRQAP GQGLEWMGRINPYSGGTNYAQKFHGRVTVTRDTSISTVYME LRGLRSDDTAVYYCARGFTMISDREFDPWGQGTLVTVSS |
| ZKA256 | SEQ ID NO. | Amino acid sequence |
| CDRH1 | 195 | GFTFSTYW |
| CDRH2 | 196 | IKQDGSEK |
| CDRH3 | 197 | ARDPGYDDFWSGSYSGSFDI |

Tables of Sequences and SEQ ID Numbers

| | | |
|---|---|---|
| VH | 198 | EVQLVESGGGLVQPGGSLRLSCAASGFTFSTYWMTWVRQAP<br>GKGLEWVANIKQDGSEKYYVDSVKGRFTISRDNTKNSLYLQ<br>VNSLRAEDTAIYYCARDPGYDDFWSGSYSGSFDIWGQGTMV<br>TVSS |
| ZKB42 | SEQ ID NO. | Amino acid sequence |
| CDRH1 | 199 | GFTFNNYG |
| CDRH2 | 200 | ISYDGNKK |
| CDRH3 | 201 | VKYGERINGYSDPFDH |
| VH | 202 | QVQVVESGGGVVQPGRSLRLFCAASGFTFNNYGMHWVRQAP<br>GKGLEWVALISYDGNKKYYADSVKGRFSISRDNSKNTLYLQ<br>MNRLRSGDTAVYHCVKYGERINGYSDPFDHWGQGTLVTVSS |
| ZKB85 | SEQ ID NO. | Amino acid sequence |
| CDRH1 | 203 | GYTFTTYA |
| CDRH2 | 204 | INTNTGNP |
| CDRH3 | 205 | ARVIVPYAFDI |
| VH | 206 | QVQLVQSGSELKKPGASVKVSCKASGYTFTTYAMNWVRQAP<br>GQGPEWVGWINTNTGNPTYAQGFTGRFVLSLDTSVSTAFLQ<br>ISSLKAEDTAVYYCARVIVPYAFDIWGQGTMVTVSS |
| ZKB47 | SEQ ID NO. | Amino acid sequence |
| CDRH1 | 207 | GYTFTNYY |
| CDRH2 | 208 | INPSGGPT |
| CDRH3 | 209 | ARDQYGGYARYGMDV |
| VH | 210 | QVQLVQSGAEVKKPGASVKVSCQASGYTFTNYYMHWVRQAP<br>GQGLEWMGIINPSGGPTSYAQKFQGRVTMTTDTSTSTVYME<br>LSSLRSEDTAVYYCARDQYGGYARYGMDVWGQGTTVIVSS |
| ZKC6 | SEQ ID NO. | Amino acid sequence |
| CDRH1 | 211 | GYTFTGYY |
| CDRH2 | 212 | INPNSGGT |
| CDRH3 | 213 | ARVSDWGFAFDI |
| VH | 214 | QVQLVQSGTEVKKPGASVKVSCKASGYTFTGYYMHWVRQAP<br>GQGLEWMGRINPNSGGTNYAQKFQGRVTMTRDTSISTAYME<br>LSGLRSDDTAVYYCARVSDWGFAFDIWGQGTMVTVSQ |
| ZKA160 | SEQ ID NO. | Amino acid sequence |
| CDRH1 | 215 | GGSITSYS |
| CDRH2 | 216 | IFYSGST |
| CDRH3 | 217 | ARDQTMPVWVGGMDV |
| VH | 218 | QVQLQESGPGLVKPSETLSLTCTVSGGSITSYSWSWIRQPP<br>GKGLEWIGYIFYSGSTDYNPSLKSRVTISVDTSKDQFSLRL<br>RSVTAADTAVYYCARDQTMPVWVGGMDVWGQGTTVTVSS |
| ZKA172 | SEQ ID NO. | Amino acid sequence |
| CDRH1 | 219 | GYIFTRYW |
| CDRH2 | 220 | IDPSDSYT |
| CDRH3 | 221 | ARQETAREDGMAV |

Tables of Sequences and SEQ ID Numbers

| | | |
|---|---|---|
| VH | 222 | EVQLVQSGAEVKKPGKSLRISCKGSGYIFTRYWISWVRQMPGKGLEWMGRIDPSDSYTNYSPSFQGHVTISADKSISTAYLQWSSLKASDTAMYYCARQETAREDGMAVWGQGTTVTVSS |
| ZKA174 | SEQ ID NO. | Amino acid sequence |
| CDRH1 | 223 | GGSMSNSYYH |
| CDRH2 | 224 | IYYSGST |
| CDRH3 | 225 | ARNPVFNPLTLTHDAFDI |
| VH | 226 | QLQLQESGPGLVKPSETLSLTCTVSGGSMSNSYYHWGWIRQPPGKGLEWIGSIYYSGSTYYNPSLKSRVTISVDTSKNQFSLKLNSVTAADTAVYYCARNPVFNPLTLTHDAFDIWGQGTMVTVSS |
| ZKA189 | SEQ ID NO. | Amino acid sequence |
| CDRH1 | 227 | GFTFSSYA |
| CDRH2 | 228 | ISGSGDNT |
| CDRH3 | 229 | AKWPYYDFWSGSESYFDP |
| VH | 230 | GVQLLESGGALVQPGKSLRLSCAASGFTFSSYALTWVRQAPGKGLQWVSAISGSGDNTYYADSVKGRFTISRDNSKNTLYLQMNSLRAEDTAVYYCAKWPYYDFWSGSESYFDPWGQGTLVTVSS |
| ZKA195 | SEQ ID NO. | Amino acid sequence |
| CDRH1 | 231 | GYNFPSYW |
| CDRH2 | 232 | IDPSDSYT |
| CDRH3 | 233 | ARADCRSTSCYLVFE |
| VH | 234 | EVQLVQSGAEVKKPGESLRISCKDSGYNFPSYWIHWVRQMPGKGLEWMGTIDPSDSYTNYSPSFQGHVTISADKSISTAYLQWSSLKASDTAMYYCARADCRSTSCYLVFEGQGTLVTVSS |
| ZKA215 | SEQ ID NO. | Amino acid sequence |
| CDRH1 | 235 | GYTFTSYW |
| CDRH2 | 236 | IDPSDSHT |
| CDRH3 | 237 | ARHALPNYFDS |
| VH | 238 | EVQLVQSGAEVKKPGESLRISCKGSGYTFTSYWISWVRQMPGKGLEWMGRIDPSDSHTDYSPSFQGHVTISADKSISAAYLQWSSLKASDTAMYYCARHALPNYFDSWGQGTLVTVSS |
| ZKA218 | SEQ ID NO. | Amino acid sequence |
| CDRH1 | 239 | GFPFSSYW |
| CDRH2 | 240 | INSDGRNT |
| CDRH3 | 241 | ARGGYDYDSSGCFDY |
| VH | 242 | EVQLVESGGGLVQPGGSLRLSCAASGFPFSSYWMHWVRQAPGKGLVWVSRINSDGRNTNYADSVKGRFTISRDNAENTVYLQMNSLRAEDTAVYYCARGGYDYDSSGCFDYWGQGTLVTVSS |
| ZKB75 | SEQ ID NO. | Amino acid sequence |
| CDRH1 | 243 | GFTFSNYA |
| CDRH2 | 244 | ISGTGGST |
| CDRH3 | 245 | AKDSASRGGYCSGGVCYLNPGHHDY |

| | | Tables of Sequences and SEQ ID Numbers |
|---|---|---|
| VH | 246 | EVQVLESGGGLLQPGGSLRLSCAASGFTFSNYAMSWVRQAP GKGLEWVSTISGTGGSTYYADSVKGRFTISRDNSKNTLYLQ MNSLRAEDTAVYYCAKDSASRGGYCSGGVCYLNPGHHDYWG QGTLVTVSS |
| ZKB83 | SEQ ID NO. | Amino acid sequence |
| CDRH1 | 247 | GYSFTNYW |
| CDRH2 | 248 | IDPSDSYT |
| CDRH3 | 249 | ARLRGSLYCSGGRCYSVPGETPNWFDP |
| VH | 250 | EVQLVQSGAEVKKPGESLRISCKGSGYSFTNYWITWVRQMP GKGLEWMGSIDPSDSYTNYSPSFQGHVTISADWSINTAYLQ WSSLKASDTAKYYCARLRGSLYCSGGRCYSVPGETPNWFDP WGQGTLVTVSS |
| ZKC3 | SEQ ID NO. | Amino acid sequence |
| CDRH1 | 251 | GGSITSYY |
| CDRH2 | 252 | IYYSGST |
| CDRH3 | 253 | ARVGGAPYYYYGMDV |
| VH | 254 | QVQLQESGPGLVKPSETLSLTCTVSGGSITSYYWSWIRQPP GKGLEWIGYIYYSGSTNYNPSLKSRVTISVDTSKNQFSLKL SSVTAADTAVYYCARVGGAPYYYYGMDVWGQGTTVTVSS |
| ZKC18 | SEQ ID NO. | Amino acid sequence |
| CDRH1 | 255 | GFTFGDYA |
| CDRH2 | 256 | IRSKAYGGTT |
| CDRH3 | 257 | SRDHTGTTYAFDI |
| VH | 258 | EVQLVESGGGLVQPGRSLRLSCTASGFTFGDYAMSWFRQAP GKGLEWVGFIRSKAYGGTTEYAASVKGRFTISRDDSKSIAY LQMNSLKTEDTAVYYCSRDHTGTTYAFDIWGQGTMVTVSQ |
| ZKD1 | SEQ ID NO. | Amino acid sequence |
| CDRH1 | 259 | GFTFSSYG |
| CDRH2 | 260 | IWYDGSNK |
| CDRH3 | 261 | ARDRRGYGDYVGYYYGMDV |
| VH | 262 | QVQLVESGGGVVQPGRSLRLSCASGFTFSSYGMHWVRQAP GKGLEWVAVIWYDGSNKYYADSVKGRFTISRDNSKNTLYLQ MNSLRAEDTAVYYCARDRRGYGDYVGYYYGMDVWGQGTTVT VSS |
| Name | SEQ ID NO. | Amino acid sequence |
| ZIKV EDIII generic | 263 | TAAFTFTKXPAEXXHGTVTVEXQYXGXDGPCKXPXQ MAVDXQTLTPVGRLITANPVITEXTENSKMMLELDPP FGDSYIVIGXGXKKITHHWHRS |
| ZIKV H/PF/2013 EDIII | 264 | TAAFTFTKIPAETLHGTVTVEVQYAGTDGPCKVPAQM AVDMQTLTPVGRLITANPVITESTENSKMMLELDPPF GDSYIVIGVGEKKITHHWHRS |
| ZIKV EDIII generic | 265 | $X_1GX_2X_3$YSLCTAAFTFTK$X_4$PAEX$X_5X_6$HGTVTVEX$_

| | | |
|---|---|---|
| | | X4 may be any (naturally occurring) amino acid, preferably I or V; X5 may be any (naturally occurring) amino acid, preferably T or V; X6 may be any (naturally occurring) amino acid, preferably L or D; X7 may be any (naturally occurring) amino acid, preferably V or G; X8 may be any (naturally occurring) amino acid, preferably A or G; X9 may be any (naturally occurring) amino acid except R, preferably T or A; X10 may be any (naturally occurring) amino acid, preferably V or I; X11 may be any (naturally occurring) amino acid, preferably A or V; X12 may be any (naturally occurring) amino acid, preferably M or T; X13 may be any (naturally occurring) amino acid, preferably S or G; X14 may be any (naturally occurring) amino acid, preferably E or K; X15 may be any (naturally occurring) amino acid, preferably V or I; X16 may be any (naturally occurring) amino acid, preferably E, A, K, or D; and X17 may be any (naturally occurring) amino acid, preferably E, A, or K, more preferably K or A |
| Zika-E-F1 primer | 266 | TGCAAACGCGGTCGCAAACCTGGTTG |
| ZIKV-E-R1 primer | 267 | CGTGCCAAGGTAATGGAATGTCGTG |
| ZIKV-Ef1530 primer | 268 | AGCCTAGGACTTGATTGTGAACCGA |
| ZIKV-E-R2769 primer | 269 | TTACAGATCCCACAACGACCGTCAG |
| ZIKV-E-F2 | 270 | ACTTGGTCATGATACTGCTGATTGC |
| ZIKV-E-R2 | 271 | TCGGTTCACAATCAAGTCCTAGGCT |
| ZIKV-E-f2058 | 272 | GCTAACCCCGTAATCACTGAAAGCA |
| ZIKV-E-r2248 | 273 | AAGACTGCCATTCTCTTGGCACCTC |

*the sequences highlighted in bold are CDR regions (nucleotide or aa) and the underlined residues are mutated residues as compared to the "germline" sequence.

---

The invention claimed is:

1. An isolated multispecific antibody, or an antigen binding fragment thereof, specifically binding to at least two distinct Zika virus epitopes, that comprises a first heavy chain comprising CDRH1, CDRH2, and CDRH3 amino acid sequences and a first light chain comprising CDRL1, CDRL2, and CDRL3 amino acid sequences, and a second heavy chain comprising CDRH1, CDRH2, and CDRH3 amino acid sequences and a second light chain comprising CDRL1, CDRL2, and CDRL3 amino acid sequences, each according to one of:
  (a) SEQ ID NOs: 1-5 and 7, respectively;
  (b) SEQ ID NOs: 1-4 and 6-7, respectively;
  (c) SEQ ID NOs: 19-23 and 25, respectively;
  (d) SEQ ID NOs: 19-22 and 24-25, respectively;
  (e) SEQ ID NOs: 37-41 and 34, respectively;
  (f) SEQ ID NOs: 37-40 and 42-43, respectively;
  (g) SEQ ID NOs: 55-59 and 61, respectively;
  (h) SEQ ID NOs: 55-58 and 60-61, respectively;
  (i) SEQ ID NOs: 73-77 and 79, respectively; or
  (j) SEQ ID NOs: 73-76 and 78-79, respectively,
wherein the first heavy chain and first light chain and the second heavy chain and second light chain are different.

2. The antibody, or the antigen binding fragment thereof, according to claim 1, wherein the antibody, or the antigen binding fragment thereof, neutralizes Zika virus infection.

3. The antibody, or the antigen binding fragment thereof, according to claim 1, characterized in that the antibody, or antigen binding fragment thereof, is bispecific, trispecific, tetraspecific or pentaspecific.

4. The antibody, or the antigen binding fragment thereof, according to claim 1, characterized in that the antibody, or antigen binding fragment thereof, is bivalent, trivalent, tetravalent, hexavalent or octavalent.

5. The antibody, or the antigen binding fragment thereof, according to claim 1, characterized in that the antibody, or antigen binding fragment thereof, comprises an Fc moiety.

6. The antibody, or the antigen binding fragment thereof, according to claim 1, characterized in that the antibody, or antigen binding fragment thereof, is of the Fabs-in-tandem-Ig antibody format, or is of the of the DVD-Ig antibody format.

7. The antibody, or the antigen binding fragment thereof, according to claim 1, characterized in that the antibody, or the antigen binding fragment thereof, comprises:
  (a) a first epitope binding site comprising CDRH1, CDRH2, and CDRH3 amino acid sequences and CDRL1, CDRL2, and CDRL3 amino acid sequences
    (i) according to SEQ ID NOs: 1-5 and 7; or (ii) according to SEQ ID NOs: 1-4 and 6-7; and
  (b) a second epitope binding site comprising CDRH1, CDRH2, and CDRH3 amino acid sequences and CDRL1, CDRL2, and CDRL3 amino acid sequences
    (i) according to SEQ ID NOs: 19-23 and 25; or (ii) according to SEQ ID NOs: 19-22 and 24-25.

8. The antibody, or the antigen binding fragment thereof, according to claim 1, characterized in that the antibody, or the antigen binding fragment thereof, comprises
  (a) a first epitope binding site comprising CDRH1, CDRH2, and CDRH3 amino acid sequences and CDRL1, CDRL2, and CDRL3 amino acid sequences
    (i) according to SEQ ID NOs: 1-5 and 7; or (ii) according to SEQ ID NOs: 1-4 and 6-7; and
  (b) a second epitope binding site comprising CDRH1, CDRH2, and CDRH3 amino acid sequences and CDRL1, CDRL2, and CDRL3 amino acid sequences
    (i) according to SEQ ID NOs: 37-41 and 43; or (ii) according to SEQ ID NOs: 37-40 and 42-43.

9. The antibody, or the antigen binding fragment thereof, according to claim 1, characterized in that the antibody, or the antigen binding fragment thereof, comprises (i) a heavy chain variable region (VH) amino acid sequence according to SEQ ID NO: 8 or a functional sequence variant thereof having at least 70% sequence identity and a light chain variable region (VL) amino acid sequence according to SEQ ID NO: 9 or a functional sequence variant thereof having at least 70% sequence identity; (ii) a heavy chain variable region (VH) amino acid sequence according to SEQ ID NO: 26 or a functional sequence variant thereof having at least 70% sequence identity and a light chain variable region (VL) amino acid sequence according to SEQ ID NO: 27 or a functional sequence variant thereof having at least 70% sequence identity; (iii) a heavy chain variable region (VH) amino acid sequence according to SEQ ID NO: 44 or a functional sequence variant thereof having at least 70% sequence identity and a light chain variable region (VL) amino acid sequence according to SEQ ID NO: 45 or a functional sequence variant thereof having at least 70% sequence identity; (iv) a heavy chain variable region (VH) amino acid sequence according to SEQ ID NO: 62 or a functional sequence variant thereof having at least 70% sequence identity and a light chain variable region (VL) amino acid sequence according to SEQ ID NO: 63 or a functional sequence variant thereof having at least 70% sequence identity; or (v) a heavy chain variable region (VH) amino acid sequence according to SEQ ID NO: 80 or a functional sequence variant thereof having at least 70% sequence identity and a light chain variable region (VL) amino acid sequence according to SEQ ID NO: 81 or a functional sequence variant thereof having at least 70% sequence identity.

10. The antibody, or the antigen binding fragment thereof, according to claim 1, characterized in that the antibody, or the antigen binding fragment thereof, comprises
  (a) a first epitope binding site comprising a heavy chain variable region (VH) amino acid sequence according to SEQ ID NO: 8 or a functional sequence variant thereof having at least 70% sequence identity and a light chain variable region (VL) amino acid sequence according to SEQ ID NO: 9 or a functional sequence variant thereof having at least 70% sequence identity; and (b) a second epitope binding site comprising a heavy chain variable region (VH) amino acid sequence according to SEQ ID NO: 26 or a functional sequence variant thereof having at least 70% sequence identity and a light chain variable region (VL) amino acid sequence according to SEQ ID NO: 27 or a functional sequence variant thereof having at least 70% sequence identity.

11. The antibody, or the antigen binding fragment thereof, according to claim 1, characterized in that the antibody, or the antigen binding fragment thereof, comprises
(a) a first epitope binding site comprising a heavy chain variable region (VH) amino acid sequence according to SEQ ID NO: 8 or a functional sequence variant thereof having at least 70% sequence identity and a light chain variable region (VL) amino acid sequence according to SEQ ID NO: 9 or a functional sequence variant thereof having at least 70% sequence identity; and
(b) a second epitope binding site comprising a heavy chain variable region (VH) amino acid sequence according to SEQ ID NO: 44 or a functional sequence variant thereof having at least 70% sequence identity and a light chain variable region (VL) amino acid sequence according to SEQ ID NO: 45 or a functional sequence variant thereof having at least 70% sequence identity.

12. The antibody, or the antigen binding fragment thereof, according to claim 1, characterized in that the antibody, or the antigen binding fragment thereof, is in the Fabs-in-tandem-Ig (FIT-Ig) format and an outer Fab of the FIT-Ig format comprises an epitope binding site comprising CDRH1, CDRH2, and CDRH3 amino acid sequences and CDRL1, CDRL2, and CDRL3 amino acid sequences (i) according to SEQ ID NOs: 1-5 and 7; or (ii) according to SEQ ID NOs: 1-4 and 6-7.

13. The antibody, or the antigen binding fragment thereof, according to claim 12, characterized in that the outer Fab of the FIT-Ig format comprises an epitope binding site comprising a heavy chain variable region (VH) amino acid sequence according to SEQ ID NO: 8 or a functional sequence variant thereof having at least 70% sequence identity and a light chain variable region (VL) amino acid sequence according to SEQ ID NO: 9 or a functional sequence variant thereof having at least 70% sequence identity.

14. The antibody, or the antigen binding fragment thereof, according to claim 12, characterized in that the inner Fab of the FIT-Ig format comprises an epitope binding site comprising CDRH1, CDRH2, and CDRH3 amino acid sequences and CDRL1, CDRL2, and CDRL3 amino acid sequences (i) according to SEQ ID NOs: 19-23 and 25; or (ii) according to SEQ ID NOs: 19-22 and 24-25.

15. The antibody, or the antigen binding fragment thereof, according to claim 14, characterized in that the inner Fab of the FIT-Ig format comprises an epitope binding site comprising a heavy chain variable region (VH) amino acid sequence according to SEQ ID NO: 26 or a functional sequence variant thereof having at least 70% sequence identity and a light chain variable region (VL) amino acid sequence according to SEQ ID NO: 27 or a functional sequence variant thereof having at least 70% sequence identity.

16. The antibody, or the antigen binding fragment thereof, according to claim 3, characterized in that the antibody, or the antigen binding fragment thereof, is bispecific.

17. The antibody, or the antigen binding fragment thereof, according to claim 4, characterized in that the antibody, or the antigen binding fragment thereof, is tetravalent.

18. The antibody, or the antigen binding fragment thereof, according to claim 1, characterized in that the antibody, or the antigen binding fragment thereof, is bispecific, trispecific or tetraspecific.

19. A pharmaceutical composition comprising the antibody, or the antigen binding fragment thereof, according to claim 1.

20. A kit of parts comprising at least one antibody, or the antigen binding fragment thereof, according to claim 1, and at least one means for administration of the antibody or the antigen binding fragment thereof.

21. An isolated multispecific antibody, or an antigen binding fragment thereof, specifically binding to at least two distinct Zika virus epitopes, that comprises a heavy chain comprising CDRH1, CDRH2, and CDRH3 amino acid sequences and a light chain comprising CDRL1, CDRL2, and CDRL3 amino acid sequences according to:
(a) SEQ ID NOs: 1-5 and 7, respectively;
(b) SEQ ID NOs: 1-4 and 6-7, respectively;
(c) SEQ ID NOs: 19-23 and 25, respectively;
(d) SEQ ID NOs: 19-22 and 24-25, respectively;
(e) SEQ ID NOs: 37-41 and 34, respectively;
(f) SEQ ID NOs: 37-40 and 42-43, respectively;
(g) SEQ ID NOs: 55-59 and 61, respectively;
(h) SEQ ID NOs: 55-58 and 60-61, respectively;
(i) SEQ ID NOs: 73-77 and 79, respectively; or
(j) SEQ ID NOs: 73-76 and 78-79, respectively.

* * * * *

SEQUENCE LISTING

<160> NUMBER OF SEQ ID NOS: 273

<210> SEQ ID NO 1
<211> LENGTH: 8
<212> TYPE: PRT
<213> ORGANISM: Artificial Sequence
<220> FEATURE:
<223> OTHER INFORMATION: ZKA190 CDRH1

<400> SEQUENCE: 1

Gly Phe Thr Phe Ser Lys Tyr Gly
1               5

<210> SEQ ID NO 2
<211> LENGTH: 8
<212> TYPE: PRT
<213> ORGANISM: Artificial Sequence
<220> FEATURE:

```
<223> OTHER INFORMATION: ZKA190 CDRH2

<400> SEQUENCE: 2

Ile Ser Tyr Glu Gly Ser Asn Lys
1               5

<210> SEQ ID NO 3
<211> LENGTH: 23
<212> TYPE: PRT
<213> ORGANISM: Artificial Sequence
<220> FEATURE:
<223> OTHER INFORMATION: ZKA190 CDRH3

<400> SEQUENCE: 3

Ala Lys Ser Gly Thr Gln Tyr Tyr Asp Thr Thr Gly Tyr Glu Tyr Arg
1               5                   10                  15

Gly Leu Glu Tyr Phe Gly Tyr
            20

<210> SEQ ID NO 4
<211> LENGTH: 7
<212> TYPE: PRT
<213> ORGANISM: Artificial Sequence
<220> FEATURE:
<223> OTHER INFORMATION: ZKA190 CDRL1

<400> SEQUENCE: 4

Gln Ser Val Ser Ser Ser Tyr
1               5

<210> SEQ ID NO 5

<400> SEQUENCE: 5

000

<210> SEQ ID NO 6
<211> LENGTH: 9
<212> TYPE: PRT
<213> ORGANISM: Artificial Sequence
<220> FEATURE:
<223> OTHER INFORMATION: ZKA190 CDRL2 long

<400> SEQUENCE: 6

Leu Ile Tyr Asp Ala Ser Ser Arg Ala
1               5

<210> SEQ ID NO 7
<211> LENGTH: 9
<212> TYPE: PRT
<213> ORGANISM: Artificial Sequence
<220> FEATURE:
<223> OTHER INFORMATION: ZKA190 CDRL3

<400> SEQUENCE: 7

Gln Gln Tyr Gly Arg Ser Arg Trp Thr
1               5

<210> SEQ ID NO 8
<211> LENGTH: 130
<212> TYPE: PRT
<213> ORGANISM: Artificial Sequence
<220> FEATURE:
<223> OTHER INFORMATION: ZKA190 VH

<400> SEQUENCE: 8
```

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Lys Tyr
            20                  25                  30

Gly Met His Trp Val Arg Gln Ala Pro Gly Lys Gly Leu Glu Trp Val
            35                  40                  45

Ala Val Ile Ser Tyr Glu Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Thr Gln Tyr Tyr Asp Thr Thr Gly Tyr Glu Tyr Arg
            100                 105                 110

Gly Leu Glu Tyr Phe Gly Tyr Trp Gly Gln Gly Thr Leu Val Thr Val
            115                 120                 125

Ser Ser
    130

<210> SEQ ID NO 9
<211> LENGTH: 108
<212> TYPE: PRT
<213> ORGANISM: Artificial Sequence
<220> FEATURE:
<223> OTHER INFORMATION: ZKA190 VL

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Arg Gly Gln Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Arg
                85                  90                  95

Trp Thr Phe Gly Gln Gly Thr Lys Val Glu Ile Lys
            100                 105

<210> SEQ ID NO 10
<211> LENGTH: 24
<212> TYPE: DNA
<213> ORGANISM: Artificial Sequence
<220> FEATURE:
<223> OTHER INFORMATION: ZKA190 CDRH1

<400> SEQUENCE: 10
ggattcacct tcagtaaata tggc                                          24

<210> SEQ ID NO 11
<211> LENGTH: 24
<212> TYPE: DNA
<213> ORGANISM: Artificial Sequence
<220> FEATURE:
<223> OTHER INFORMATION: ZKA190 CDRH2

<400> SEQUENCE: 11
```

```
atatcatatg agggaagtaa taaa                                           24

<210> SEQ ID NO 12
<211> LENGTH: 69
<212> TYPE: DNA
<213> ORGANISM: Artificial Sequence
<220> FEATURE:
<223> OTHER INFORMATION: ZKA190 CDRH3

<400> SEQUENCE: 12
gcgaaatcgg ggacccaata ctatgatact actggttatg agtataggg tttggaatac    60 tttggctac                                                           69

<210> SEQ ID NO 13
<211> LENGTH: 21
<212> TYPE: DNA
<213> ORGANISM: Artificial Sequence
<220> FEATURE:
<223> OTHER INFORMATION: ZKA190 CDRL1

<400> SEQUENCE: 13
cagagtgtta gtagcagtta c                                             21

<210> SEQ ID NO 14

<400> SEQUENCE: 14

000

<210> SEQ ID NO 15
<211> LENGTH: 27
<212> TYPE: DNA
<213> ORGANISM: Artificial Sequence
<220> FEATURE:
<223> OTHER INFORMATION: ZKA190 CDRL2 long

<400> SEQUENCE: 15
ctcatctatg atgcatccag cagggcc                                       27

<210> SEQ ID NO 16
<211> LENGTH: 27
<212> TYPE: DNA
<213> ORGANISM: Artificial Sequence
<220> FEATURE:
<223> OTHER INFORMATION: ZKA190 CDRL3

<400> SEQUENCE: 16
cagcagtatg gtaggtcaag gtggaca                                       27

<210> SEQ ID NO 17
<211> LENGTH: 391
<212> TYPE: DNA
<213> ORGANISM: Artificial Sequence
<220> FEATURE:
<223> OTHER INFORMATION: ZKA190 VH

<400> SEQUENCE: 17
caggtgcagc tggtggagtc tgggggaggc gtggtccagc ctggggagtc cctgagactc    60
tcctgtgcag cctctggatt caccttcagt aaatatggca tgcactgggt ccgccaggct   120
ccaggcaagg ggctggagtg ggtggcagtt atatcatatg agggaagtaa taaatattat   180
gcagactccg tgaagggccg attcaccatc tccagagaca attccaagaa cacgctgtat   240
ctgcaaatga acagcctgag agctgaggac acggcagtgt attactgtgc gaaatcgggg   300
```

```
acccaatact atgatactac tggttatgag tatagggggtt tggaatactt tggctactgg    360
ggccagggaa ccctggtcac cgtctcctca g                                    391
```

<210> SEQ ID NO 18
<211> LENGTH: 325
<212> TYPE: DNA
<213> ORGANISM: Artificial Sequence
<220> FEATURE:
<223> OTHER INFORMATION: ZKA190 VL

<400> SEQUENCE: 18

```
gaaattgtgt tgacgcagtc tccaggcacc ctgtctttgt ctccagggga aagagccacc     60
ctctcctgca gggccagtca gagtgttagt agcagttact tagcctggta ccagcagaaa    120
cgtggccagg ctcccaggct cctcatctat gatgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta ggtcaaggtg gacattcggc    300
caagggacca aggtggaaat caaac                                          325
```

<210> SEQ ID NO 19
<211> LENGTH: 8
<212> TYPE: PRT
<213> ORGANISM: Artificial Sequence
<220> FEATURE:
<223> OTHER INFORMATION: ZKA185 CDRH1

<400> SEQUENCE: 19

Gly Tyr Ser Phe Thr Ser Tyr Trp
1               5

<210> SEQ ID NO 20
<211> LENGTH: 8
<212> TYPE: PRT
<213> ORGANISM: Artificial Sequence
<220> FEATURE:
<223> OTHER INFORMATION: ZKA185 CDRH2

<400> SEQUENCE: 20

Phe Asp Pro Ser Asp Ser Gln Thr
1               5

<210> SEQ ID NO 21
<211> LENGTH: 14
<212> TYPE: PRT
<213> ORGANISM: Artificial Sequence
<220> FEATURE:
<223> OTHER INFORMATION: ZKA185 CDRH3

<400> SEQUENCE: 21

Ala Arg Arg Tyr Cys Ser Ser Ser Ser Cys Tyr Val Asp Asn
1               5                   10

<210> SEQ ID NO 22
<211> LENGTH: 6
<212> TYPE: PRT
<213> ORGANISM: Artificial Sequence
<220> FEATURE:
<223> OTHER INFORMATION: ZKA185 CDRL1

<400> SEQUENCE: 22

Ala Leu Pro Asn Lys Phe
1               5

<210> SEQ ID NO 23

<400> SEQUENCE: 23

000

<210> SEQ ID NO 24
<211> LENGTH: 9
<212> TYPE: PRT
<213> ORGANISM: Artificial Sequence
<220> FEATURE:
<223> OTHER INFORMATION: ZKA185 CDRL2 long

<400> SEQUENCE: 24

Val Ile Tyr Glu Asp Asn Lys Arg Pro
1               5

<210> SEQ ID NO 25
<211> LENGTH: 12
<212> TYPE: PRT
<213> ORGANISM: Artificial Sequence
<220> FEATURE:
<223> OTHER INFORMATION: ZKA185 CDRL3

<400> SEQUENCE: 25

Tyr Ser Thr Asp Ser Ser Ser Asn Pro Leu Gly Val
1               5                   10

<210> SEQ ID NO 26
<211> LENGTH: 121
<212> TYPE: PRT
<213> ORGANISM: Artificial Sequence
<220> FEATURE:
<223> OTHER INFORMATION: ZKA185 VH

<400> SEQUENCE: 26

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Thr Trp Val Arg Gln Met Pro Gly Lys Gly Leu Glu Trp Met
            35                  40                  45

Ala Lys Phe Asp Pro Ser Asp Ser Gln Thr Asn Tyr Ser Pro Ser Phe
    50                  55                  60

Gln Gly His Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Tyr Cys Ser Ser Ser Cys Tyr Val Asp Asn Trp Gly
                100                 105                 110

Gln Gly Thr Leu Val Thr Ile Phe Ser
        115                 120

<210> SEQ ID NO 27
<211> LENGTH: 109
<212> TYPE: PRT
<213> ORGANISM: Artificial Sequence
<220> FEATURE:
<223> OTHER INFORMATION: ZKA185 VL

<400> SEQUENCE: 27

Ser Tyr Glu Leu Thr Gln Pro Pro Ser Val Ser Val Ser Pro Gly Gln
1               5                   10                  15

```
Thr Ala Arg Ile Thr Cys Ser Gly Asp Ala Leu Pro Asn Lys Phe Ala
            20                  25                  30

Tyr Trp Tyr Arg Gln Lys Ser Gly Gln Ala Pro Val Leu Val Ile Tyr
        35                  40                  45

Glu Asp Asn Lys Arg Pro Ser Gly Ile Pro Glu Arg Phe Ser Gly Ser
50                  55                  60

Ser Ser Gly Thr Met Ala Thr Leu Thr Ile Ser Gly Ala Gln Val Glu
65                  70                  75                  80

Asp Glu Ala Asp Tyr His Cys Tyr Ser Thr Asp Ser Ser Asn Pro
                85                  90                  95

Leu Gly Val Phe Gly Gly Gly Thr Lys Leu Thr Val Leu
            100                 105

<210> SEQ ID NO 28
<211> LENGTH: 24
<212> TYPE: DNA
<213> ORGANISM: Artificial Sequence
<220> FEATURE:
<223> OTHER INFORMATION: ZKA185 CDRH1

<400> SEQUENCE: 28
ggatatagtt ttaccagtta ctgg                                          24

<210> SEQ ID NO 29
<211> LENGTH: 24
<212> TYPE: DNA
<213> ORGANISM: Artificial Sequence
<220> FEATURE:
<223> OTHER INFORMATION: ZKA185 CDRH2

<400> SEQUENCE: 29
tttgatccta gtgactctca aacc                                          24

<210> SEQ ID NO 30
<211> LENGTH: 42
<212> TYPE: DNA
<213> ORGANISM: Artificial Sequence
<220> FEATURE:
<223> OTHER INFORMATION: ZKA185 CDRH3

<400> SEQUENCE: 30
gcgagaagat attgtagtag tagtagttgt tatgtggaca at                      42

<210> SEQ ID NO 31
<211> LENGTH: 18
<212> TYPE: DNA
<213> ORGANISM: Artificial Sequence
<220> FEATURE:
<223> OTHER INFORMATION: ZKA185 CDRL1

<400> SEQUENCE: 31
gcattgccaa ataaattt                                                 18

<210> SEQ ID NO 32

<400> SEQUENCE: 32

000

<210> SEQ ID NO 33
<211> LENGTH: 27
<212> TYPE: DNA
<213> ORGANISM: Artificial Sequence
```

```
<220> FEATURE:
<223> OTHER INFORMATION: ZKA185 CDRL2 long

<400> SEQUENCE: 33
gtcatctatg aggacaacaa acgaccc                                            27

<210> SEQ ID NO 34
<211> LENGTH: 36
<212> TYPE: DNA
<213> ORGANISM: Artificial Sequence
<220> FEATURE:
<223> OTHER INFORMATION: ZKA185 CDRL3

<400> SEQUENCE: 34
tactcaacag acagcagttc taatcccctg ggagta                                  36

<210> SEQ ID NO 35
<211> LENGTH: 364
<212> TYPE: DNA
<213> ORGANISM: Artificial Sequence
<220> FEATURE:
<223> OTHER INFORMATION: ZKA185 VH

<400> SEQUENCE: 35
gaagtgcagc tggtgcagtc cggagcagag gtgaaaaagc ccggggagtc tctgaggatc         60
tcctgtaagg gttctggata tagttttacc agttactgga tcacctgggt gcgccagatg        120 cccggggaaag gcctggagtg gatggcgaag tttgatccta gtgactctca aaccaactac        180
agcccgtcct ccaaggcca cgtcaccatc tcagttgaca agtccatcag cactgcctac         240
ttgcagtgga gcagcctgaa ggcctcggac accgccatgt attactgtgc gagaagatat        300
tgtagtagta gtagttgtta tgtggacaat gggggccagg gaaccctggt caccatcttc        360
tcag                                                                    364

<210> SEQ ID NO 36
<211> LENGTH: 328
<212> TYPE: DNA
<213> ORGANISM: Artificial Sequence
<220> FEATURE:
<223> OTHER INFORMATION: ZKA185 VL

<400> SEQUENCE: 36
tcctatgagc tgacacagcc accctcggtg tcagtgtccc caggacaaac ggccaggatc         60
acctgctctg gagatgcatt gccaaataaa tttgcttatt ggtaccggca gaagtcaggc        120
caggcccctg ttctggtcat ctatgaggac aacaaacgac cctccgggat ccctgagaga        180
ttctctggct ccagctcagg gacaatggcc accttgacta tcagtggggc caggtggag         240 gatgaagctg actaccactg ttactcaaca gacagcagtt ctaatcccct gggagtattc        300
ggcggaggga ccaagctgac cgtcctag                                           328

<210> SEQ ID NO 37
<211> LENGTH: 8
<212> TYPE: PRT
<213> ORGANISM: Artificial Sequence
<220> FEATURE:
<223> OTHER INFORMATION: ZKA230 CDRH1

<400> SEQUENCE: 37

Gly Gly Ser Ile Ser Ser Asp Tyr
1               5
```

<210> SEQ ID NO 38
<211> LENGTH: 7
<212> TYPE: PRT
<213> ORGANISM: Artificial Sequence
<220> FEATURE:
<223> OTHER INFORMATION: ZKA230 CDRH2

<400> SEQUENCE: 38

Ile Tyr Tyr Ser Gly Ser Thr
1               5

<210> SEQ ID NO 39
<211> LENGTH: 17
<212> TYPE: PRT
<213> ORGANISM: Artificial Sequence
<220> FEATURE:
<223> OTHER INFORMATION: ZKA230 CDRH3

<400> SEQUENCE: 39

Ala Arg Arg Arg Lys Tyr Asp Ser Leu Trp Gly Ser Phe Ala Phe Asp
1               5                   10                  15

Ile

<210> SEQ ID NO 40
<211> LENGTH: 8
<212> TYPE: PRT
<213> ORGANISM: Artificial Sequence
<220> FEATURE:
<223> OTHER INFORMATION: ZKA230 CDRL1

<400> SEQUENCE: 40

Ser Ser Asn Ile Gly Gly Asn Tyr
1               5

<210> SEQ ID NO 41

<400> SEQUENCE: 41

000

<210> SEQ ID NO 42
<211> LENGTH: 9
<212> TYPE: PRT
<213> ORGANISM: Artificial Sequence
<220> FEATURE:
<223> OTHER INFORMATION: ZKA230 CDRL2 long

<400> SEQUENCE: 42

Leu Ile Cys Ile Asn Asp His Arg Pro
1               5

<210> SEQ ID NO 43
<211> LENGTH: 11
<212> TYPE: PRT
<213> ORGANISM: Artificial Sequence
<220> FEATURE:
<223> OTHER INFORMATION: ZKA230 CDRL3

<400> SEQUENCE: 43

Ala Thr Trp Asp Asp Ser Leu Gly Gly Leu Val
1               5                   10

<210> SEQ ID NO 44
<211> LENGTH: 123
<212> TYPE: PRT
<213> ORGANISM: Artificial Sequence
<220> FEATURE:

<223> OTHER INFORMATION: ZKA230 VH

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Asp
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn His Phe Ser Leu
65                  70                  75                  80

Lys Leu Asn Ser Val Thr Ala Ala Asp Thr Ala Val Tyr Tyr Cys Ala
                85                  90                  95

Arg Arg Arg Lys Tyr Asp Ser Leu Trp Gly Ser Phe Ala Phe Asp Ile
            100                 105                 110

Trp Gly Gln Gly Thr Met Val Thr Val Ser Ser
        115                 120

<210> SEQ ID NO 45
<211> LENGTH: 110
<212> TYPE: PRT
<213> ORGANISM: Artificial Sequence
<220> FEATURE:
<223> OTHER INFORMATION: ZKA230 VL

<400> SEQUENCE: 45

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Tyr Val Tyr Trp Tyr Gln Gln Leu Pro Gly Thr Ala Pro Lys Leu Leu
        35                  40                  45

Ile Cys Ile Asn Asp His Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Gly Gly Leu Val Phe Gly Gly Gly Thr Lys Leu Thr Val Leu
            100                 105                 110

<210> SEQ ID NO 46
<211> LENGTH: 24
<212> TYPE: DNA
<213> ORGANISM: Artificial Sequence
<220> FEATURE:
<223> OTHER INFORMATION: ZKA230 CDRH1

<400> SEQUENCE: 46
ggtggctcca tcagtagtga ctac                                      24

<210> SEQ ID NO 47
<211> LENGTH: 21
<212> TYPE: DNA
<213> ORGANISM: Artificial Sequence
<220> FEATURE:
<223> OTHER INFORMATION: ZKA230 CDRH2

-continued

<400> SEQUENCE: 47
atctattaca gtgggagcac c                                              21

<210> SEQ ID NO 48
<211> LENGTH: 51
<212> TYPE: DNA
<213> ORGANISM: Artificial Sequence
<220> FEATURE:
<223> OTHER INFORMATION: ZKA230 CDRH3

<400> SEQUENCE: 48
gcgaggagga ggaagtatga ttcccttttgg gggagttttg cttttgatat c            51

<210> SEQ ID NO 49
<211> LENGTH: 24
<212> TYPE: DNA
<213> ORGANISM: Artificial Sequence
<220> FEATURE:
<223> OTHER INFORMATION: ZKA230 CDRL1

<400> SEQUENCE: 49
agctccaaca tcggaggtaa ttat                                           24

<210> SEQ ID NO 50

<400> SEQUENCE: 50

000

<210> SEQ ID NO 51
<211> LENGTH: 27
<212> TYPE: DNA
<213> ORGANISM: Artificial Sequence
<220> FEATURE:
<223> OTHER INFORMATION: ZKA230 CDRL2 long

<400> SEQUENCE: 51
ctcatctgta ttaatgatca ccggccc                                        27

<210> SEQ ID NO 52
<211> LENGTH: 33
<212> TYPE: DNA
<213> ORGANISM: Artificial Sequence
<220> FEATURE:
<223> OTHER INFORMATION: ZKA230 CDRL3

<400> SEQUENCE: 52
gcaacatggg atgacagcct gggtggcctt gta                                 33

<210> SEQ ID NO 53
<211> LENGTH: 370
<212> TYPE: DNA
<213> ORGANISM: Artificial Sequence
<220> FEATURE:
<223> OTHER INFORMATION: ZKA230 VH

<400> SEQUENCE: 53
caggtgcagc tgcaggagtc gggcccaggc ctggtgaagc cttcggagac cctgtccctc     60
acctgcgcag tctctggtgg ctccatcagt agtgactact ggagctggat ccggcagccc    120
ccagggaagg gactggagtg gattgggtat atctattaca gtgggagcac caactacaac    180
ccctccctca agagtcgagt caccatatca gtagacacgt ccaagaacca cttctccctg    240
aagctgaact ctgtgaccgc tgcggacacg gccgtgtatt actgtgcgag gaggaggaag    300

```
tatgattccc tttgggggag ttttgctttt gatatctggg gccaagggac aatggtcacc    360
gtctcttcag                                                           370
```

```
<210> SEQ ID NO 54
<211> LENGTH: 331
<212> TYPE: DNA
<213> ORGANISM: Artificial Sequence
<220> FEATURE:
<223> OTHER INFORMATION: ZKA230 VL

<400> SEQUENCE: 54
cagtctgtgc tgactcagcc accctcagcg tctgggaccc ccgggcagag ggtcaccatc     60
tcttgttctg gaagcagctc caacatcgga ggtaattatg tatactggta ccagcagctc   120
ccaggaacgg cccccaaact cctcatctgt attaatgatc accggcctc aggggtccct    180 gaccgattct ctggctccaa gtctggcacc tcagcctccc tggccatcag tgggctccag   240
tccgaggatg aggctgatta ttactgtgca acatgggatg acagcctggg tggccttgta   300
ttcggcggag ggaccaagct gaccgtccta g                                  331
```

```
<210> SEQ ID NO 55
<211> LENGTH: 8
<212> TYPE: PRT
<213> ORGANISM: Artificial Sequence
<220> FEATURE:
<223> OTHER INFORMATION: ZKA78 CDRH1

<400> SEQUENCE: 55

Gly Phe Thr Phe Ser Asn Tyr Ala
1               5
```

```
<210> SEQ ID NO 56
<211> LENGTH: 8
<212> TYPE: PRT
<213> ORGANISM: Artificial Sequence
<220> FEATURE:
<223> OTHER INFORMATION: ZKA78 CDRH2

<400> SEQUENCE: 56

Ile Gly Arg Asn Gly Asp Ser Ile
1               5
```

```
<210> SEQ ID NO 57
<211> LENGTH: 16
<212> TYPE: PRT
<213> ORGANISM: Artificial Sequence
<220> FEATURE:
<223> OTHER INFORMATION: ZKA78 CDRH3

<400> SEQUENCE: 57

Val Lys Asp Leu Ala Ile Pro Glu Ser Tyr Arg Ile Glu Ala Asp Tyr
1               5                   10                  15
```

```
<210> SEQ ID NO 58
<211> LENGTH: 12
<212> TYPE: PRT
<213> ORGANISM: Artificial Sequence
<220> FEATURE:
<223> OTHER INFORMATION: ZKA78 CDRL1

<400> SEQUENCE: 58

Gln Ser Val Leu Tyr Arg Ser Asn Asn Lys Asn Tyr
1               5                   10
```

```
<210> SEQ ID NO 59
<400> SEQUENCE: 59

000

<210> SEQ ID NO 60
<211> LENGTH: 9
<212> TYPE: PRT
<213> ORGANISM: Artificial Sequence
<220> FEATURE:
<223> OTHER INFORMATION: ZKA78 CDRL2 long

<400> SEQUENCE: 60

Leu Ile Tyr Trp Ala Ser Thr Arg Glu
1               5

<210> SEQ ID NO 61
<211> LENGTH: 9
<212> TYPE: PRT
<213> ORGANISM: Artificial Sequence
<220> FEATURE:
<223> OTHER INFORMATION: ZKA78 CDRL3

<400> SEQUENCE: 61

Gln Gln Tyr Tyr Ser Ser Pro Arg Thr
1               5

<210> SEQ ID NO 62
<211> LENGTH: 123
<212> TYPE: PRT
<213> ORGANISM: Artificial Sequence
<220> FEATURE:
<223> OTHER INFORMATION: ZKA78 VH

<400> SEQUENCE: 62

Glu Val Gln Leu Ala Glu Ser Gly Gly Gly Leu Val Gln Pro Gly Gly
1               5                   10                  15

Ser Leu Thr Leu Ser Cys Ser Gly Ser Gly Phe Thr Phe Ser Asn Tyr
            20                  25                  30

Ala Met Val Trp Ala Arg Gln Ala Pro Gly Lys Gly Leu Glu Tyr Val
        35                  40                  45

Ser Gly Ile Gly Arg Asn Gly Asp Ser Ile Tyr Tyr Thr Asp Ser Val
    50                  55                  60

Lys Gly Arg Phe Thr Ile Ser Arg Asp Asn Ser Lys Ser Met Val Tyr
65                  70                  75                  80

Leu Gln Met Ser Ser Leu Arg Thr Glu Asp Thr Ala Val Tyr Tyr Cys
                85                  90                  95

Val Lys Asp Leu Ala Ile Pro Glu Ser Tyr Arg Ile Glu Ala Asp Tyr
            100                 105                 110

Trp Gly Gln Gly Thr Leu Val Ile Val Ser Ala
        115                 120

<210> SEQ ID NO 63
<211> LENGTH: 113
<212> TYPE: PRT
<213> ORGANISM: Artificial Sequence
<220> FEATURE:
<223> OTHER INFORMATION: ZKA78 VL

<400> SEQUENCE: 63

Asp Ile Val Met Thr Gln Ser Pro Asp Ser Leu Ala Val Ser Leu Gly
1               5                   10                  15
```

```
              Glu Arg Ala Thr Ile Asn Cys Lys Ser Ser Gln Ser Val Leu Tyr Arg
                               20                  25                  30

Ser Asn Asn Lys Asn Tyr Leu Ser Trp Tyr Gln Gln Lys Pro Gly Gln
                           35                  40                  45

Pro Pro Lys Leu Leu Ile Tyr Trp Ala Ser Thr Arg Glu Ser Gly Val
              50                  55                  60

Pro Asp Arg Phe Ser Gly Ser Gly Ser Gly Thr Asp Phe Thr Leu Thr
              65                  70                  75                  80

Ile Ser Pro Leu Gln Ala Glu Asp Val Ala Val Tyr Tyr Cys Gln Gln
                               85                  90                  95

Tyr Tyr Ser Ser Pro Arg Thr Phe Gly Gln Gly Thr Lys Val Glu Ile
                          100                 105                 110

Lys
```

```
<210> SEQ ID NO 64
<211> LENGTH: 24
<212> TYPE: DNA
<213> ORGANISM: Artificial Sequence
<220> FEATURE:
<223> OTHER INFORMATION: ZKA78 CDRH1

<400> SEQUENCE: 64
ggcttcactt ttagtaacta tgca                                          24

<210> SEQ ID NO 65
<211> LENGTH: 24
<212> TYPE: DNA
<213> ORGANISM: Artificial Sequence
<220> FEATURE:
<223> OTHER INFORMATION: ZKA78 CDRH2

<400> SEQUENCE: 65
atcgggcgca acggggactc tatc                                          24

<210> SEQ ID NO 66
<211> LENGTH: 48
<212> TYPE: DNA
<213> ORGANISM: Artificial Sequence
<220> FEATURE:
<223> OTHER INFORMATION: ZKA78 CDRH3

<400> SEQUENCE: 66
gtgaaagatc tggccatccc cgagtcctac agaattgaag ctgattat                48

<210> SEQ ID NO 67
<211> LENGTH: 36
<212> TYPE: DNA
<213> ORGANISM: Artificial Sequence
<220> FEATURE:
<223> OTHER INFORMATION: ZKA78 CDRL1

<400> SEQUENCE: 67
cagtccgtgc tgtaccgctc taacaacaag aattac                             36

<210> SEQ ID NO 68

<400> SEQUENCE: 68

000

<210> SEQ ID NO 69
<211> LENGTH: 27
<212> TYPE: DNA
```

```
<213> ORGANISM: Artificial Sequence
<220> FEATURE:
<223> OTHER INFORMATION: ZKA78 CDRL2 long

<400> SEQUENCE: 69
ctgatctatt gggcttcaac ccgggaa                                          27

<210> SEQ ID NO 70
<211> LENGTH: 27
<212> TYPE: DNA
<213> ORGANISM: Artificial Sequence
<220> FEATURE:
<223> OTHER INFORMATION: ZKA78 CDRL3

<400> SEQUENCE: 70
cagcagtact attctagtcc tcgaact                                          27

<210> SEQ ID NO 71
<211> LENGTH: 370
<212> TYPE: DNA
<213> ORGANISM: Artificial Sequence
<220> FEATURE:
<223> OTHER INFORMATION: ZKA78 VH

<400> SEQUENCE: 71
gaggtgcagc tggcagaatc aggcggggga ctggtccagc ctggcggcag cctgacactg      60
tcttgcagtg atcaggctt cacttttagt aactatgcaa tggtgtgggc aaggcaggct     120
cctgggaagg gactggagta tgtctctggc atcgggcgca acggggactc tatctactat    180
actgatagtg tgaagggccg gttcaccatc agcagagaca atagcaaatc catggtgtac    240
ctgcagatga gctccctgcg aaccgaagac acagcagtgt actattgcgt gaaagatctg    300
gccatccccg agtcctacag aattgaagct gattattggg gacagggcac cctggtcatc    360
gtgagcgccg                                                           370

<210> SEQ ID NO 72
<211> LENGTH: 340
<212> TYPE: DNA
<213> ORGANISM: Artificial Sequence
<220> FEATURE:
<223> OTHER INFORMATION: ZKA78 VL

<400> SEQUENCE: 72
gacatcgtga tgacacagtc tccagatagt ctggcagtca gtctggggga gagggccact     60
attaactgca agagctccca gtccgtgctg taccgctcta acaacaagaa ttacctgtct    120
tggtatcagc agaagcccgg acagccccct aaactgctga tctattgggc ttcaacccgg    180
gaaagcggcg tcccagacag attctcaggc agcgggtccg gaacagactt caccctgaca    240
attagccccc tgcaggcaga ggacgtggct gtctactatt gtcagcagta ctattctagt    300
cctcgaactt tcggccaggg gaccaaggtg gaaatcaaac                          340

<210> SEQ ID NO 73
<211> LENGTH: 8
<212> TYPE: PRT
<213> ORGANISM: Artificial Sequence
<220> FEATURE:
<223> OTHER INFORMATION: ZKA64 CDRH1

<400> SEQUENCE: 73

Gly Tyr Thr Phe Thr Gly Tyr His
1               5
```

<210> SEQ ID NO 74
<211> LENGTH: 8
<212> TYPE: PRT
<213> ORGANISM: Artificial Sequence
<220> FEATURE:
<223> OTHER INFORMATION: ZKA64 CDRH2

<400> SEQUENCE: 74

Ile Asn Pro Asn Ser Gly Gly Thr
1               5

<210> SEQ ID NO 75
<211> LENGTH: 12
<212> TYPE: PRT
<213> ORGANISM: Artificial Sequence
<220> FEATURE:
<223> OTHER INFORMATION: ZKA64 CDRH3

<400> SEQUENCE: 75

Ala Arg Met Ser Ser Ser Ile Trp Gly Phe Asp His
1               5                   10

<210> SEQ ID NO 76
<211> LENGTH: 6
<212> TYPE: PRT
<213> ORGANISM: Artificial Sequence
<220> FEATURE:
<223> OTHER INFORMATION: ZKA64 CDRL1

<400> SEQUENCE: 76

Gln Ser Val Leu Ile Asn
1               5

<210> SEQ ID NO 77

<400> SEQUENCE: 77

000

<210> SEQ ID NO 78
<211> LENGTH: 9
<212> TYPE: PRT
<213> ORGANISM: Artificial Sequence
<220> FEATURE:
<223> OTHER INFORMATION: ZKA64 CDRL2 long

<400> SEQUENCE: 78

Leu Ile Tyr Gly Ala Ser Ser Arg Ala
1               5

<210> SEQ ID NO 79
<211> LENGTH: 10
<212> TYPE: PRT
<213> ORGANISM: Artificial Sequence
<220> FEATURE:
<223> OTHER INFORMATION: ZKA64 CDRL3

<400> SEQUENCE: 79

Gln Gln Tyr Asn Asp Trp Pro Pro Ile Thr
1               5                   10

<210> SEQ ID NO 80
<211> LENGTH: 119
<212> TYPE: PRT
<213> ORGANISM: Artificial Sequence
<220> FEATURE:
<223> OTHER INFORMATION: ZKA64 VH

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Ile Asp Trp Val Arg Gln Ala Arg Gly Gln Gly Leu Glu Trp Met
        35                  40                  45

Gly Arg Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Gln Leu Ser Arg Leu Arg Ser Asp Ser Ala Val Tyr Tyr Cys
                85                  90                  95

Ala Arg Met Ser Ser Ser Ile Trp Gly Phe Asp His Trp Gly Gln Gly
            100                 105                 110

Thr Leu Val Thr Val Ser Ser
            115

<210> SEQ ID NO 81
<211> LENGTH: 108
<212> TYPE: PRT
<213> ORGANISM: Artificial Sequence
<220> FEATURE:
<223> OTHER INFORMATION: ZKA64 VL

<400> SEQUENCE: 81

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Leu Ile Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Pro
                85                  90                  95

Ile Thr Phe Gly Gln Gly Thr Arg Leu Glu Ile Lys
            100                 105

<210> SEQ ID NO 82
<211> LENGTH: 24
<212> TYPE: DNA
<213> ORGANISM: Artificial Sequence
<220> FEATURE:
<223> OTHER INFORMATION: ZKA64 CDRH1

<400> SEQUENCE: 82
ggctacacct tcacagggta tcac                                          24

<210> SEQ ID NO 83
<211> LENGTH: 24
<212> TYPE: DNA
<213> ORGANISM: Artificial Sequence
<220> FEATURE:
<223> OTHER INFORMATION: ZKA64 CDRH2

<400> SEQUENCE: 83

-continued attaacccta attctggcgg gacc                                              24

<210> SEQ ID NO 84
<211> LENGTH: 36
<212> TYPE: DNA
<213> ORGANISM: Artificial Sequence
<220> FEATURE:
<223> OTHER INFORMATION: ZKA64 CDRH3

<400> SEQUENCE: 84
gctcggatga gctcctctat ttggggcttc gatcat                                 36

<210> SEQ ID NO 85
<211> LENGTH: 18
<212> TYPE: DNA
<213> ORGANISM: Artificial Sequence
<220> FEATURE:
<223> OTHER INFORMATION: ZKA64 CDRL1

<400> SEQUENCE: 85
cagtctgtgc tgattaac                                                     18

<210> SEQ ID NO 86

<400> SEQUENCE: 86

000

<210> SEQ ID NO 87
<211> LENGTH: 27
<212> TYPE: DNA
<213> ORGANISM: Artificial Sequence
<220> FEATURE:
<223> OTHER INFORMATION: ZKA64 CDRL2 long

<400> SEQUENCE: 87
ctgatctatg gagcatcctc cagggct                                           27

<210> SEQ ID NO 88
<211> LENGTH: 30
<212> TYPE: DNA
<213> ORGANISM: Artificial Sequence
<220> FEATURE:
<223> OTHER INFORMATION: ZKA64 CDRL3

<400> SEQUENCE: 88
cagcagtaca atgattggcc ccctatcaca                                        30

<210> SEQ ID NO 89
<211> LENGTH: 358
<212> TYPE: DNA
<213> ORGANISM: Artificial Sequence
<220> FEATURE:
<223> OTHER INFORMATION: ZKA64 VH

<400> SEQUENCE: 89
caggtgcagc tggtccagag cggagcagag gtgaagaaac ccggcgcctc agtgaaggtc        60
agctgcaaag cttccggcta caccttcaca gggtatcaca tcgactgggt gaggcaggca      120
agaggacagg gactggaatg gatgggacgg attaaccccta attctggcgg gaccaactac     180
gcccagaagt ttcagggccg agtgactatg accagagaca ccagcatctc cacagcttat     240
atgcagctgt cccggctgag atctgacgat agtgccgtct actattgtgc tcggatgagc     300
tcctctattt ggggcttcga tcattggggg cagggaacac tggtgactgt cagttcag       358

<210> SEQ ID NO 90
<211> LENGTH: 325
<212> TYPE: DNA
<213> ORGANISM: Artificial Sequence
<220> FEATURE:
<223> OTHER INFORMATION: ZKA64 VL

<400> SEQUENCE: 90

```
gagatcgtga tgactcagtc tccagccacc ctgtcagtca gcccaggaga acgggcaacc      60
ctgtcttgca gagcctccca gtctgtgctg attaacctgg cttggtacca gcagaagcca     120
ggccaggcac cccgactgct gatctatgga gcatcctcca gggctaccgg cattcctgca     180
cgcttcagtg gatcaggaag cggaacagag tttaccctga caatctctag tctgcagtcc     240
gaagacttcg ctgtctacta ttgtcagcag tacaatgatt ggccccctat cacatttggc     300
caggggacta gactggagat caagc                                           325
```

<210> SEQ ID NO 91
<211> LENGTH: 330
<212> TYPE: PRT
<213> ORGANISM: Artificial Sequence
<220> FEATURE:
<223> OTHER INFORMATION: IgG1 CH1-CH2-CH3 aa

<400> SEQUENCE: 91

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 92
<211> LENGTH: 330
<212> TYPE: PRT
<213> ORGANISM: Artificial Sequence
<220> FEATURE:
<223> OTHER INFORMATION: IgG1 CH1-CH2-CH3 LALA aa

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 93
<211> LENGTH: 107
<212> TYPE: PRT
<213> ORGANISM: Artificial Sequence
<220> FEATURE:
<223> OTHER INFORMATION: IgG CK aa

<400> SEQUENCE: 93

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 94
<211> LENGTH: 106
<212> TYPE: PRT
<213> ORGANISM: Artificial Sequence
<220> FEATURE:
<223> OTHER INFORMATION: IgG CL aa

<400> SEQUENCE: 94

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 95
<211> LENGTH: 990
<212> TYPE: DNA
<213> ORGANISM: Artificial Sequence
<220> FEATURE:
```

<223> OTHER INFORMATION: IgG1 CH1-CH2-CH3 nucl

<400> SEQUENCE: 95

```
gcgtcgacca agggcccatc ggtcttcccc ctggcaccct cctccaagag cacctctggg    60
ggcacagcgg ccctgggctg cctggtcaag gactacttcc ccgaacctgt gacggtctcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc cccgggtaaa                                   990
```

<210> SEQ ID NO 96
<211> LENGTH: 990
<212> TYPE: DNA
<213> ORGANISM: Artificial Sequence
<220> FEATURE:
<223> OTHER INFORMATION: IgG1 CH1-CH2-CH3 LALA nucl

<400> SEQUENCE: 96

```
gcgtcgacca agggcccatc ggtcttcccc ctggcaccct cctccaagag cacctctggg    60
ggcacagcgg ccctgggctg cctggtcaag gactacttcc ccgaacctgt gacggtctcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaagc cgcgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
```

```
cagaagagcc tctccctgtc cccgggtaaa                                      990
```

<210> SEQ ID NO 97
<211> LENGTH: 321
<212> TYPE: DNA
<213> ORGANISM: Artificial Sequence
<220> FEATURE:
<223> OTHER INFORMATION: IgG CK nucl

<400> SEQUENCE: 97

```
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321
```

<210> SEQ ID NO 98
<211> LENGTH: 318
<212> TYPE: DNA
<213> ORGANISM: Artificial Sequence
<220> FEATURE:
<223> OTHER INFORMATION: IgG CL nucl

<400> SEQUENCE: 98

```
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcttggaaag cagatagcag ccccgtcaag gcgggagtgg agaccaccac accctccaaa     180
caaagcaaca acaagtacgc ggccagcagc tatctgagcc tgacgcctga gcagtggaag     240
tcccacagaa gctacagctg ccaggtcacg catgaaggga gcaccgtgga agacagtg      300
gcccctacag aatgttca                                                   318
```

<210> SEQ ID NO 99
<211> LENGTH: 8
<212> TYPE: PRT
<213> ORGANISM: Artificial Sequence
<220> FEATURE:
<223> OTHER INFORMATION: ZKA3 CDRH1

<400> SEQUENCE: 99

Gly Phe Ile Phe Ser Asn Tyr Ala
1               5

<210> SEQ ID NO 100
<211> LENGTH: 8
<212> TYPE: PRT
<213> ORGANISM: Artificial Sequence
<220> FEATURE:
<223> OTHER INFORMATION: ZKA3 CDRH2

<400> SEQUENCE: 100

Ile Gly Gly Lys Gly Asp Ser Ile
1               5

<210> SEQ ID NO 101
<211> LENGTH: 16
<212> TYPE: PRT
<213> ORGANISM: Artificial Sequence
<220> FEATURE:

<223> OTHER INFORMATION: ZKA3 CDRH3

<400> SEQUENCE: 101

Val Lys Asp Leu Ala Val Leu Glu Ser Asp Arg Leu Glu Val Asp Gln
1               5                   10                  15

<210> SEQ ID NO 102
<211> LENGTH: 123
<212> TYPE: PRT
<213> ORGANISM: Artificial Sequence
<220> FEATURE:
<223> OTHER INFORMATION: ZKA3 VH

<400> SEQUENCE: 102

Glu Val Gln Leu Ala Glu Ser Gly Gly Gly Leu Val Gln Pro Gly Gly
1               5                   10                  15

Ser Leu Arg Leu Ser Cys Ser Gly Ser Gly Phe Ile Phe Ser Asn Tyr
            20                  25                  30

Ala Met Val Trp Ala Arg Gln Ala Pro Gly Lys Gly Leu Glu Tyr Val
        35                  40                  45

Ser Gly Ile Gly Gly Lys Gly Asp Ser Ile Tyr His Ile Asp Ser Val
    50                  55                  60

Lys Gly Arg Phe Thr Ile Ser Arg Asp Asn Ser Lys Arg Thr Val Tyr
65                  70                  75                  80

Leu Gln Met Ser Arg Leu Arg Thr Glu Asp Thr Ala Val Tyr Tyr Cys
                85                  90                  95

Val Lys Asp Leu Ala Val Leu Glu Ser Asp Arg Leu Glu Val Asp Gln
            100                 105                 110

Trp Gly Gln Gly Thr Leu Val Ile Val Ser Ala
        115                 120

<210> SEQ ID NO 103
<211> LENGTH: 8
<212> TYPE: PRT
<213> ORGANISM: Artificial Sequence
<220> FEATURE:
<223> OTHER INFORMATION: ZKA4 CDRH1

<400> SEQUENCE: 103

Gly Phe Thr Phe Ser Ser Tyr Val
1               5

<210> SEQ ID NO 104
<211> LENGTH: 8
<212> TYPE: PRT
<213> ORGANISM: Artificial Sequence
<220> FEATURE:
<223> OTHER INFORMATION: ZKA4 CDRH2

<400> SEQUENCE: 104

Thr Ser Tyr Asp Gly Ser Asn Lys
1               5

<210> SEQ ID NO 105
<211> LENGTH: 20
<212> TYPE: PRT
<213> ORGANISM: Artificial Sequence
<220> FEATURE:
<223> OTHER INFORMATION: ZKA4 CDRH3

<400> SEQUENCE: 105

Ala Arg Gly Pro Val Pro Tyr Trp Ser Gly Glu Ser Tyr Ser Gly Ala
1               5                   10                  15

Tyr Phe Asp Phe
            20

<210> SEQ ID NO 106
<211> LENGTH: 127
<212> TYPE: PRT
<213> ORGANISM: Artificial Sequence
<220> FEATURE:
<223> OTHER INFORMATION: ZKA4 VH

<400> SEQUENCE: 106

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Thr Val Thr Ser Tyr Asp Gly Ser Asn Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Gly Glu Asp Thr Ala Ile Tyr Tyr Cys
                85                  90                  95

Ala Arg Gly Pro Val Pro Tyr Trp Ser Gly Glu Ser Tyr Ser Gly Ala
            100                 105                 110

Tyr Phe Asp Phe Trp Gly Gln Gly Ile Leu Val Thr Val Ser Ser
        115                 120                 125

<210> SEQ ID NO 107
<211> LENGTH: 8
<212> TYPE: PRT
<213> ORGANISM: Artificial Sequence
<220> FEATURE:
<223> OTHER INFORMATION: ZKA5 CDRH1

<400> SEQUENCE: 107

Gly Phe Thr Phe Ser Asn Tyr Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: ZKA5 CDRH2

<400> SEQUENCE: 108

Met Ser Ser Ser Glu Thr Ile Lys
1               5

<210> SEQ ID NO 109
<211> LENGTH: 19
<212> TYPE: PRT
<213> ORGANISM: Artificial Sequence
<220> FEATURE:
<223> OTHER INFORMATION: ZKA5 CDRH3

<400> SEQUENCE: 109

Ala Arg Ser Gly Ile Glu Thr Val Ala Gly Ser Ile Asp Tyr Tyr Gly
1               5                   10                  15

Met Asp Val

<210> SEQ ID NO 110
<211> LENGTH: 126
<212> TYPE: PRT
<213> ORGANISM: Artificial Sequence
<220> FEATURE:
<223> OTHER INFORMATION: ZKA5 VH

<400> SEQUENCE: 110

```
Gln Val Gln Leu Val Glu Ser Gly Gly Gly Leu Val Lys Pro Gly Gly
1               5                   10                  15

Ser Leu Arg Leu Ser Cys Ala Gly Ser Gly Phe Thr Phe Ser Asn Tyr
            20                  25                  30

Tyr Met Thr Trp Ile Arg Gln Ala Pro Gly Lys Gly Leu Glu Leu Val
        35                  40                  45

Ser Tyr Met Ser Ser Ser Glu Thr Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Arg Tyr Tyr Cys
                85                  90                  95

Ala Arg Ser Gly Ile Glu Thr Val Ala Gly Ser Ile Tyr Tyr Gly
            100                 105                 110

Met Asp Val Trp Gly His Gly Thr Pro Val Thr Val Ser Ser
        115                 120                 125
```

<210> SEQ ID NO 111
<211> LENGTH: 8
<212> TYPE: PRT
<213> ORGANISM: Artificial Sequence
<220> FEATURE:
<223> OTHER INFORMATION: ZKA6 CDRH1

<400> SEQUENCE: 111

```
Asp Phe Thr Val Ser Asn Tyr Ala
1               5
```

<210> SEQ ID NO 112
<211> LENGTH: 8
<212> TYPE: PRT
<213> ORGANISM: Artificial Sequence
<220> FEATURE:
<223> OTHER INFORMATION: ZKA6 CDRH2

<400> SEQUENCE: 112

```
Val Ser Tyr Asp Gly Ser Asn Lys
1               5
```

<210> SEQ ID NO 113
<211> LENGTH: 19
<212> TYPE: PRT
<213> ORGANISM: Artificial Sequence
<220> FEATURE:
<223> OTHER INFORMATION: ZKA6 CDRH3

<400> SEQUENCE: 113

```
Ala Thr Gly Val Thr Met Phe Gln Gly Ala Gln Thr Asn Ala Glu Tyr
1               5                   10                  15

Leu His Tyr
```

<210> SEQ ID NO 114
<211> LENGTH: 126
<212> TYPE: PRT

```
<213> ORGANISM: Artificial Sequence
<220> FEATURE:
<223> OTHER INFORMATION: ZKA6 VH

<400> SEQUENCE: 114

Gln Val His Leu Val Glu Ser Gly Gly Val Val Gln Pro Gly Arg
1               5                   10                  15

Ser Leu Arg Leu Ser Cys Glu Ala Ser Asp Phe Thr Val Ser Asn Tyr
            20                  25                  30

Ala Met His Trp Val Arg Gln Ala Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Thr Gly Val Thr Met Phe Gly Ala Gln Thr Asn Ala Glu Tyr
            100                 105                 110

Leu His Tyr Trp Gly Gln Gly Ser Leu Val Thr Ile Ser Ser
        115                 120                 125

<210> SEQ ID NO 115
<211> LENGTH: 8
<212> TYPE: PRT
<213> ORGANISM: Artificial Sequence
<220> FEATURE:
<223> OTHER INFORMATION: ZKA7 CDRH1

<400> SEQUENCE: 115

Gly Phe Thr Phe Ser Arg Tyr Gly
1               5

<210> SEQ ID NO 116
<211> LENGTH: 8
<212> TYPE: PRT
<213> ORGANISM: Artificial Sequence
<220> FEATURE:
<223> OTHER INFORMATION: ZKA7 CDRH2

<400> SEQUENCE: 116

Val Ser Gly Asp Gly Ser Ser Thr
1               5

<210> SEQ ID NO 117
<211> LENGTH: 15
<212> TYPE: PRT
<213> ORGANISM: Artificial Sequence
<220> FEATURE:
<223> OTHER INFORMATION: ZKA7 CDRH3

<400> SEQUENCE: 117

Val Lys Asp Phe Trp Ser Gly Asp Gln Ser Leu Glu Ser Asp Phe
1               5                   10                  15

<210> SEQ ID NO 118
<211> LENGTH: 122
<212> TYPE: PRT
<213> ORGANISM: Artificial Sequence
<220> FEATURE:
<223> OTHER INFORMATION: ZKA7 VH

<400> SEQUENCE: 118
```

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Arg Tyr
            20                  25                  30

Gly Met Val Trp Ala Arg Gln Ala Pro Gly Lys Gly Leu Glu Tyr Leu
        35                  40                  45

Ser Gly Val Ser Gly Asp Gly Ser Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu His Met Ser Arg Leu Arg Asp Glu Asp Thr Ala Met Tyr Tyr Cys
                85                  90                  95

Val Lys Asp Phe Trp Ser Gly Asp Gln Ser Leu Glu Ser Asp Phe Trp
            100                 105                 110

Gly Gln Gly Ala Leu Val Thr Val Ser Ser
        115                 120
```

<210> SEQ ID NO 119
<211> LENGTH: 8
<212> TYPE: PRT
<213> ORGANISM: Artificial Sequence
<220> FEATURE:
<223> OTHER INFORMATION: ZKA8 CDRH1

<400> SEQUENCE: 119

```
Gly Phe Thr Phe Ser Ala His Ala
1               5
```

<210> SEQ ID NO 120
<211> LENGTH: 8
<212> TYPE: PRT
<213> ORGANISM: Artificial Sequence
<220> FEATURE:
<223> OTHER INFORMATION: ZKA8 CDRH2

<400> SEQUENCE: 120

```
Ile Ser Arg Asn Glu Asp Tyr Thr
1               5
```

<210> SEQ ID NO 121
<211> LENGTH: 12
<212> TYPE: PRT
<213> ORGANISM: Artificial Sequence
<220> FEATURE:
<223> OTHER INFORMATION: ZKA8 CDRH3

<400> SEQUENCE: 121

```
Val Lys Asp Phe Gly Thr Ser Pro Gln Thr Asp Phe
1               5                   10
```

<210> SEQ ID NO 122
<211> LENGTH: 119
<212> TYPE: PRT
<213> ORGANISM: Artificial Sequence
<220> FEATURE:
<223> OTHER INFORMATION: ZKA8 VH

<400> SEQUENCE: 122

```
Asp Glu Arg Leu Val Glu Ser Gly Gly Gly Leu Val Gln Pro Gly Gly
1               5                   10                  15

Ser Leu Arg Leu Val Cys Ser Ala Ser Gly Phe Thr Phe Ser Ala His
            20                  25                  30
```

```
Ala Met His Trp Val Arg Gln Pro Pro Gly Lys Gly Leu Glu Tyr Val
         35                  40                  45

Ser Thr Ile Ser Arg Asn Glu Asp Tyr Thr Tyr Ala Asp Ser Val
 50                  55                  60

Lys Gly Arg Phe Thr Ile Ser Arg Asp Asn Ser Lys Asn Ser Leu Tyr
 65                  70                  75                  80

Leu Gln Met Arg Arg Leu Arg Pro Glu Asp Thr Ala Ile Tyr Tyr Cys
                 85                  90                  95

Val Lys Asp Phe Gly Thr Ser Pro Gln Thr Asp Phe Trp Gly Gln Gly
            100                 105                 110

Thr Leu Val Ala Val Ser Ser
        115
```

<210> SEQ ID NO 123
<211> LENGTH: 8
<212> TYPE: PRT
<213> ORGANISM: Artificial Sequence
<220> FEATURE:
<223> OTHER INFORMATION: ZKA76 CDRH1

<400> SEQUENCE: 123

```
Gly Phe Thr Phe Ser Thr Tyr Phe
 1               5
```

<210> SEQ ID NO 124
<211> LENGTH: 8
<212> TYPE: PRT
<213> ORGANISM: Artificial Sequence
<220> FEATURE:
<223> OTHER INFORMATION: ZKA76 CDRH2

<400> SEQUENCE: 124

```
Ile Ser Ser Thr Gly Ser Tyr Lys
 1               5
```

<210> SEQ ID NO 125
<211> LENGTH: 17
<212> TYPE: PRT
<213> ORGANISM: Artificial Sequence
<220> FEATURE:
<223> OTHER INFORMATION: ZKA76 CDRH3

<400> SEQUENCE: 125

```
Ala Arg Pro Phe His Ser Glu Tyr Thr Tyr Gly Leu Asp Ala Phe Asp
 1               5                  10                  15

Ile
```

<210> SEQ ID NO 126
<211> LENGTH: 124
<212> TYPE: PRT
<213> ORGANISM: Artificial Sequence
<220> FEATURE:
<223> OTHER INFORMATION: ZKA76 VH

<400> SEQUENCE: 126

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
                20                  25                  30

Phe Met His Trp Val Arg Gln Ala Pro Gly Lys Gly Leu Glu Trp Val
             35                  40                  45

Ala Ser Ile Ser Ser Thr Gly Ser Tyr Lys Phe Tyr Ala Asp Ser Val
```

```
                50                  55                  60
Lys Gly Arg Phe Thr Ile Ser Arg Asp Asn Thr Lys Asn Ser Leu Phe
 65                  70                  75                  80

Leu Gln Met Asn Ser Leu Arg Ala Glu Asp Thr Ala Val Phe Tyr Cys
                 85                  90                  95

Ala Arg Pro Phe His Ser Glu Tyr Thr Tyr Gly Leu Asp Ala Phe Asp
            100                 105                 110

Ile Trp Gly Gln Gly Thr Met Leu Thr Val Ser Ser
        115                 120

<210> SEQ ID NO 127
<211> LENGTH: 10
<212> TYPE: PRT
<213> ORGANISM: Artificial Sequence
<220> FEATURE:
<223> OTHER INFORMATION: ZKA117 CDRH1

<400> SEQUENCE: 127

Gly Gly Ser Ile Arg Arg Thr Asn Ser Tyr
 1               5                  10

<210> SEQ ID NO 128
<211> LENGTH: 7
<212> TYPE: PRT
<213> ORGANISM: Artificial Sequence
<220> FEATURE:
<223> OTHER INFORMATION: ZKA117 CDRH2

<400> SEQUENCE: 128

Ile Ser Tyr Ser Gly Ser Thr
 1               5

<210> SEQ ID NO 129
<211> LENGTH: 17
<212> TYPE: PRT
<213> ORGANISM: Artificial Sequence
<220> FEATURE:
<223> OTHER INFORMATION: ZKA117 CDRH3

<400> SEQUENCE: 129

Ala Arg Leu Asn Asp Gly Ser Thr Val Thr Thr Ser Ser Tyr Phe Asp
 1               5                  10                  15

Tyr

<210> SEQ ID NO 130
<211> LENGTH: 125
<212> TYPE: PRT
<213> ORGANISM: Artificial Sequence
<220> FEATURE:
<223> OTHER INFORMATION: ZKA117 VH

<400> SEQUENCE: 130

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Arg Arg Thr
                20                  25                  30

Asn Ser Tyr Trp Gly Trp Ile Arg Gln Thr Thr Gly Lys Gly Leu Gln
             35                  40                  45

Trp Ile Gly Ser Ile Ser Tyr Ser Gly Ser Thr Phe Tyr Asn Pro Ser
     50                  55                  60

Leu Lys Ser Arg Val Thr Ile Ser Leu Asp Thr Ser Lys Asp His Phe
 65                  70                  75                  80
```

```
Ser Leu Glu Leu Ser Ser Val Thr Ala Ala Asp Thr Ala Ile Tyr Tyr
                85                  90                  95

Cys Ala Arg Leu Asn Asp Gly Ser Val Thr Thr Ser Ser Tyr Phe
            100                 105                 110

Asp Tyr Trp Gly Gln Gly Thr Leu Val Thr Val Ser Ser
        115                 120                 125

<210> SEQ ID NO 131
<211> LENGTH: 8
<212> TYPE: PRT
<213> ORGANISM: Artificial Sequence
<220> FEATURE:
<223> OTHER INFORMATION: ZKB27 CDRH1

<400> SEQUENCE: 131

Gly Tyr Ser Phe Thr Ser Ser Trp
1               5

<210> SEQ ID NO 132
<211> LENGTH: 8
<212> TYPE: PRT
<213> ORGANISM: Artificial Sequence
<220> FEATURE:
<223> OTHER INFORMATION: ZKB27 CDRH2

<400> SEQUENCE: 132

Ile Asp Pro Ser Asp Ser Tyr Thr
1               5

<210> SEQ ID NO 133
<211> LENGTH: 14
<212> TYPE: PRT
<213> ORGANISM: Artificial Sequence
<220> FEATURE:
<223> OTHER INFORMATION: ZKB27 CDRH3

<400> SEQUENCE: 133

Ala Arg His Asp Tyr Ser Val Ser Glu Asn Gly Met Asp Val
1               5                   10

<210> SEQ ID NO 134
<211> LENGTH: 121
<212> TYPE: PRT
<213> ORGANISM: Artificial Sequence
<220> FEATURE:
<223> OTHER INFORMATION: ZKB27 VH

<400> SEQUENCE: 134

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Ser
                20                  25                  30

Trp Ile Asn Trp Val Arg Gln Met Pro Gly Lys Gly Leu Glu Trp Met
            35                  40                  45

Gly Arg Ile Asp Pro Ser Asp Ser Tyr Thr Thr Tyr Asn Pro Ser Phe
        50                  55                  60

Gln Gly His Val Thr Ile Ser Val Asp Lys Ser Ile Gly Thr Ala Tyr
65                  70                  75                  80

Leu Gln Trp Asn Ser Leu Arg Ala Ser Asp Thr Ala Met Tyr Tyr Cys
                85                  90                  95

Ala Arg His Asp Tyr Ser Val Ser Glu Asn Gly Met Asp Val Trp Gly
            100                 105                 110
```

```
Gln Gly Thr Thr Val Thr Val Ser Ser
        115                 120

<210> SEQ ID NO 135
<211> LENGTH: 8
<212> TYPE: PRT
<213> ORGANISM: Artificial Sequence
<220> FEATURE:
<223> OTHER INFORMATION: ZKB29 CDRH1

<400> SEQUENCE: 135

Gly Phe Thr Phe Ser Ser Tyr Thr
1               5

<210> SEQ ID NO 136
<211> LENGTH: 8
<212> TYPE: PRT
<213> ORGANISM: Artificial Sequence
<220> FEATURE:
<223> OTHER INFORMATION: ZKB29 CDRH2

<400> SEQUENCE: 136

Ile Ser Tyr Asp Gly Ser His Lys
1               5

<210> SEQ ID NO 137
<211> LENGTH: 12
<212> TYPE: PRT
<213> ORGANISM: Artificial Sequence
<220> FEATURE:
<223> OTHER INFORMATION: ZKB29 CDRH3

<400> SEQUENCE: 137

Ala Arg Arg Ser Tyr Ser Ile Ser Cys Phe Asp Tyr
1               5                   10

<210> SEQ ID NO 138
<211> LENGTH: 119
<212> TYPE: PRT
<213> ORGANISM: Artificial Sequence
<220> FEATURE:
<223> OTHER INFORMATION: ZKB29 VH

<400> SEQUENCE: 138

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Ala Val Ile Ser Tyr Asp Gly Ser His Lys Phe Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Leu Tyr Tyr Cys
                85                  90                  95

Ala Arg Arg Ser Tyr Ser Ile Ser Cys Phe Asp Tyr Trp Gly Gln Gly
            100                 105                 110

Thr Leu Val Thr Ile Ser Ser
        115

<210> SEQ ID NO 139
```

```
<211> LENGTH: 8
<212> TYPE: PRT
<213> ORGANISM: Artificial Sequence
<220> FEATURE:
<223> OTHER INFORMATION: ZKB34 CDRH1

<400> SEQUENCE: 139

Gly Phe Thr Phe Ser Arg Ser Gly
1               5

<210> SEQ ID NO 140
<211> LENGTH: 8
<212> TYPE: PRT
<213> ORGANISM: Artificial Sequence
<220> FEATURE:
<223> OTHER INFORMATION: ZKB34 CDRH2

<400> SEQUENCE: 140

Val Ser Tyr Asp Gly Ser Asn Lys
1               5

<210> SEQ ID NO 141
<211> LENGTH: 19
<212> TYPE: PRT
<213> ORGANISM: Artificial Sequence
<220> FEATURE:
<223> OTHER INFORMATION: ZKB34 CDRH3

<400> SEQUENCE: 141

Ala Lys Asp Leu Thr Met Val Arg Gly Val His Tyr Tyr Tyr Val
1               5                   10                  15

Met Asp Val

<210> SEQ ID NO 142
<211> LENGTH: 126
<212> TYPE: PRT
<213> ORGANISM: Artificial Sequence
<220> FEATURE:
<223> OTHER INFORMATION: ZKB34 VH

<400> SEQUENCE: 142

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg Ser
            20                  25                  30

Gly Met His Trp Val Arg Gln Ala Pro Gly Lys Gly Leu Glu Trp Val
        35                  40                  45

Ala Val Val Ser Tyr Asp Gly Ser Asn Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Leu Thr Met Val Arg Gly Val His Tyr Tyr Tyr Val
            100                 105                 110

Met Asp Val Trp Gly Gln Gly Thr Thr Val Thr Val Ser Ser
        115                 120                 125

<210> SEQ ID NO 143
<211> LENGTH: 8
<212> TYPE: PRT
<213> ORGANISM: Artificial Sequence
<220> FEATURE:
```

<223> OTHER INFORMATION: ZKB39 CDRH1

<400> SEQUENCE: 143

Gly Tyr Thr Phe Asp Asp Tyr Tyr
1               5

<210> SEQ ID NO 144
<211> LENGTH: 8
<212> TYPE: PRT
<213> ORGANISM: Artificial Sequence
<220> FEATURE:
<223> OTHER INFORMATION: ZKB39 CDRH2

<400> SEQUENCE: 144

Ile Asn Pro His Arg Gly Gly Thr
1               5

<210> SEQ ID NO 145
<211> LENGTH: 23
<212> TYPE: PRT
<213> ORGANISM: Artificial Sequence
<220> FEATURE:
<223> OTHER INFORMATION: ZKB39 CDRH3

<400> SEQUENCE: 145

Val Arg Asp Gln Tyr Cys Asp Gly Gly Asn Cys Tyr Gly Ile His Gln
1               5                   10                  15

Pro His Tyr Gly Met Asp Val
            20

<210> SEQ ID NO 146
<211> LENGTH: 130
<212> TYPE: PRT
<213> ORGANISM: Artificial Sequence
<220> FEATURE:
<223> OTHER INFORMATION: ZKB39 VH

<400> SEQUENCE: 146

Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Thr Phe Asp Asp Tyr
            20                  25                  30

Tyr Ile His Trp Val Arg Gln Ala Pro Gly Gln Gly Leu Glu Trp Leu
        35                  40                  45

Gly Arg Ile Asn Pro His Arg Gly Gly Thr Asn Tyr Ala Gln Lys Phe
    50                  55                  60

Gln Gly Arg Val Ile Met Thr Leu Asp Met Ser Ile Ser Thr Thr Tyr
65                  70                  75                  80

Met Glu Leu Arg Arg Ile Thr Ser Asp Asp Ala Ala Val Tyr Tyr Cys
                85                  90                  95

Val Arg Asp Gln Tyr Cys Asp Gly Gly Asn Cys Tyr Gly Ile His Gln
            100                 105                 110

Pro His Tyr Gly Met Asp Val Trp Gly Gln Gly Thr Thr Val Thr Val
        115                 120                 125

Ser Ser
    130

<210> SEQ ID NO 147
<211> LENGTH: 8
<212> TYPE: PRT
<213> ORGANISM: Artificial Sequence
<220> FEATURE:

<223> OTHER INFORMATION: ZKB46 CDRH1

<400> SEQUENCE: 147

Gly Tyr Ser Phe Thr Ser Tyr Trp
1               5

<210> SEQ ID NO 148
<211> LENGTH: 8
<212> TYPE: PRT
<213> ORGANISM: Artificial Sequence
<220> FEATURE:
<223> OTHER INFORMATION: ZKB46 CDRH2

<400> SEQUENCE: 148

Ile Asp Pro Ser Asp Ser Tyr Thr
1               5

<210> SEQ ID NO 149
<211> LENGTH: 17
<212> TYPE: PRT
<213> ORGANISM: Artificial Sequence
<220> FEATURE:
<223> OTHER INFORMATION: ZKB46 CDRH3

<400> SEQUENCE: 149

Ala Arg Arg Glu Tyr Ser Ser Ser Ser Gly Gln Glu Asp Trp Phe Asp
1               5                   10                  15
Pro

<210> SEQ ID NO 150
<211> LENGTH: 124
<212> TYPE: PRT
<213> ORGANISM: Artificial Sequence
<220> FEATURE:
<223> OTHER INFORMATION: ZKB46 VH

<400> SEQUENCE: 150

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Glu Tyr Ser Ser Ser Ser Gly Gln Glu Asp Trp Phe Asp
            100                 105                 110

Pro Trp Gly Gln Gly Thr Leu Val Thr Val Ser Ser
        115                 120

<210> SEQ ID NO 151
<211> LENGTH: 8
<212> TYPE: PRT
<213> ORGANISM: Artificial Sequence
<220> FEATURE:
<223> OTHER INFORMATION: ZKB53 CDRH1

<400> SEQUENCE: 151

```
Gly Phe Thr Phe Ser Ser Tyr Ala
1               5

<210> SEQ ID NO 152
<211> LENGTH: 8
<212> TYPE: PRT
<213> ORGANISM: Artificial Sequence
<220> FEATURE:
<223> OTHER INFORMATION: ZKB53 CDRH2

<400> SEQUENCE: 152

Ile Ser Tyr Asp Gly Ser Asn Arg
1               5

<210> SEQ ID NO 153
<211> LENGTH: 15
<212> TYPE: PRT
<213> ORGANISM: Artificial Sequence
<220> FEATURE:
<223> OTHER INFORMATION: ZKB53 CDRH3

<400> SEQUENCE: 153

Ala Arg His Val Glu Gln Leu Pro Ser Ser Gly Tyr Phe Gln His
1               5                   10                  15

<210> SEQ ID NO 154
<211> LENGTH: 122
<212> TYPE: PRT
<213> ORGANISM: Artificial Sequence
<220> FEATURE:
<223> OTHER INFORMATION: ZKB53 VH

<400> SEQUENCE: 154

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Thr Pro Gly Lys Gly Leu Glu Trp Val
            35                  40                  45

Thr Val Ile Ser Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg His Val Glu Gln Leu Pro Ser Ser Gly Tyr Phe Gln His Trp
            100                 105                 110

Gly Gln Gly Thr Leu Val Thr Val Ser Ser
        115                 120

<210> SEQ ID NO 155
<211> LENGTH: 8
<212> TYPE: PRT
<213> ORGANISM: Artificial Sequence
<220> FEATURE:
<223> OTHER INFORMATION: ZKC26 CDRH1

<400> SEQUENCE: 155

Gly Phe Ile Phe Ser Asp Phe Tyr
1               5

<210> SEQ ID NO 156
<211> LENGTH: 8
```

```
<212> TYPE: PRT
<213> ORGANISM: Artificial Sequence
<220> FEATURE:
<223> OTHER INFORMATION: ZKC26 CDRH2

<400> SEQUENCE: 156

Ile Gly His Asp Gly Ser Tyr Ile
1               5

<210> SEQ ID NO 157
<211> LENGTH: 9
<212> TYPE: PRT
<213> ORGANISM: Artificial Sequence
<220> FEATURE:
<223> OTHER INFORMATION: ZKC26 CDRH3

<400> SEQUENCE: 157

Ala Arg Ala His Gly Gly Phe Arg His
1               5

<210> SEQ ID NO 158
<211> LENGTH: 116
<212> TYPE: PRT
<213> ORGANISM: Artificial Sequence
<220> FEATURE:
<223> OTHER INFORMATION: ZKC26 VH

<400> SEQUENCE: 158

Gln Val Gln Val Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Phe
            20                  25                  30

Tyr Met Ser Trp Met Arg Gln Ala Pro Gly Lys Gly Leu Glu Trp Val
        35                  40                  45

Ala Tyr Ile Gly His Asp Gly Ser Tyr Ile Leu Tyr Ala Asp Ser Val
    50                  55                  60

Lys Gly Arg Phe Thr Ile Ser Arg Asp Asn Ala Lys Asn Ser Leu Phe
65                  70                  75                  80

Leu Arg Met Asn Ser Leu Arg Val Glu Asp Thr Ala Val Tyr Tyr Cys
                85                  90                  95

Ala Arg Ala His Gly Gly Phe Arg His Trp Gly Gln Gly Thr Val Val
            100                 105                 110

Ala Val Ser Pro
        115

<210> SEQ ID NO 159
<211> LENGTH: 8
<212> TYPE: PRT
<213> ORGANISM: Artificial Sequence
<220> FEATURE:
<223> OTHER INFORMATION: ZKD5 CDRH1

<400> SEQUENCE: 159

Gly Phe Thr Phe Thr Ser Tyr Gly
1               5

<210> SEQ ID NO 160
<211> LENGTH: 8
<212> TYPE: PRT
<213> ORGANISM: Artificial Sequence
<220> FEATURE:
<223> OTHER INFORMATION: ZKD5 CDRH2

<400> SEQUENCE: 160
```

```
Ile Ser Tyr Asp Gly Ser Asn Lys
1               5

<210> SEQ ID NO 161
<211> LENGTH: 17
<212> TYPE: PRT
<213> ORGANISM: Artificial Sequence
<220> FEATURE:
<223> OTHER INFORMATION: ZKD5 CDRH3

<400> SEQUENCE: 161

Ala Arg Asp Arg Asp His Tyr Asp Leu Trp Asn Ala Tyr Thr Phe Asp
1               5                   10                  15

Tyr

<210> SEQ ID NO 162
<211> LENGTH: 124
<212> TYPE: PRT
<213> ORGANISM: Artificial Sequence
<220> FEATURE:
<223> OTHER INFORMATION: ZKD5 VH

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met His Trp Val Arg Gln Thr Pro Gly Lys Gly Leu Asp Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Thr Leu Tyr
65                  70                  75                  80

Leu Gln Met Asn Ser Leu Arg Ala Ala Asp Thr Ala Leu Tyr Tyr Cys
                85                  90                  95

Ala Arg Asp Arg Asp His Tyr Asp Leu Trp Asn Ala Tyr Thr Phe Asp
            100                 105                 110

Tyr Trp Gly Gln Gly Thr Leu Val Thr Val Ser Ser
        115                 120

<210> SEQ ID NO 163
<211> LENGTH: 8
<212> TYPE: PRT
<213> ORGANISM: Artificial Sequence
<220> FEATURE:
<223> OTHER INFORMATION: ZKD7 CDRH1

<400> SEQUENCE: 163

Gly Phe Thr Phe Ser Asn Tyr Ala
1               5

<210> SEQ ID NO 164
<211> LENGTH: 8
<212> TYPE: PRT
<213> ORGANISM: Artificial Sequence
<220> FEATURE:
<223> OTHER INFORMATION: ZKD7 CDRH2

<400> SEQUENCE: 164

Ile Ser Tyr Asp Val Ser Asp Lys
1               5
```

<210> SEQ ID NO 165
<211> LENGTH: 20
<212> TYPE: PRT
<213> ORGANISM: Artificial Sequence
<220> FEATURE:
<223> OTHER INFORMATION: ZKD7 CDRH3

<400> SEQUENCE: 165

Ala Gly Gly Pro Leu Gly Val Val Ile Lys Pro Ser Asn Ala Glu
1               5                   10                  15

His Phe His His
            20

<210> SEQ ID NO 166
<211> LENGTH: 127
<212> TYPE: PRT
<213> ORGANISM: Artificial Sequence
<220> FEATURE:
<223> OTHER INFORMATION: ZKD7 VH

<400> SEQUENCE: 166

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Ala Met His Trp Val Arg Gln Ala Pro Gly Lys Gly Leu Glu Trp Val
            35                  40                  45

Ala Val Ile Ser Tyr Asp Val Ser Asp Lys Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Ala Tyr Tyr Cys
                85                  90                  95

Ala Gly Gly Pro Leu Gly Val Val Val Ile Lys Pro Ser Asn Ala Glu
            100                 105                 110

His Phe His His Trp Gly Gln Gly Thr Leu Val Thr Val Ser Ser
        115                 120                 125

<210> SEQ ID NO 167
<211> LENGTH: 8
<212> TYPE: PRT
<213> ORGANISM: Artificial Sequence
<220> FEATURE:
<223> OTHER INFORMATION: ZKD8 CDRH1

<400> SEQUENCE: 167

Gly Phe Thr Phe Ile Asn Tyr Ala
1               5

<210> SEQ ID NO 168
<211> LENGTH: 8
<212> TYPE: PRT
<213> ORGANISM: Artificial Sequence
<220> FEATURE:
<223> OTHER INFORMATION: ZKD8 CDRH2

<400> SEQUENCE: 168

Ile Ser Tyr Asp Gly Ser Asn Lys
1               5

<210> SEQ ID NO 169
<211> LENGTH: 16

```
<212> TYPE: PRT
<213> ORGANISM: Artificial Sequence
<220> FEATURE:
<223> OTHER INFORMATION: ZKD8 CDRH3

<400> SEQUENCE: 169

Ala Thr Asp Ala Asp Ala Tyr Gly Asp Ser Gly Ala Asn Phe His Tyr
1               5                   10                  15

<210> SEQ ID NO 170
<211> LENGTH: 123
<212> TYPE: PRT
<213> ORGANISM: Artificial Sequence
<220> FEATURE:
<223> OTHER INFORMATION: ZKD8 VH

<400> SEQUENCE: 170

Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ile Asn Tyr
            20                  25                  30

Ala Ile His Trp Val Arg Gln Ala Pro Gly Lys Gly Leu Glu Trp Val
        35                  40                  45

Ala Val Ile Ser Tyr Asp Gly Ser Asn Lys Phe Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Thr Asp Ala Asp Ala Tyr Gly Asp Ser Gly Ala Asn Phe His Tyr
            100                 105                 110

Trp Gly Gln Gly Thr Leu Val Thr Val Ser Ser
        115                 120

<210> SEQ ID NO 171
<211> LENGTH: 10
<212> TYPE: PRT
<213> ORGANISM: Artificial Sequence
<220> FEATURE:
<223> OTHER INFORMATION: ZKD15 CDRH1

<400> SEQUENCE: 171

Asp Ala Ser Ile Ser Ser Gly Gly Phe Ser
1               5                   10

<210> SEQ ID NO 172
<211> LENGTH: 7
<212> TYPE: PRT
<213> ORGANISM: Artificial Sequence
<220> FEATURE:
<223> OTHER INFORMATION: ZKD15 CDRH2

<400> SEQUENCE: 172

Ile Tyr Ser Ser Gly Asp Thr
1               5

<210> SEQ ID NO 173
<211> LENGTH: 18
<212> TYPE: PRT
<213> ORGANISM: Artificial Sequence
<220> FEATURE:
<223> OTHER INFORMATION: ZKD15 CDRH3

<400> SEQUENCE: 173
```

Ala Arg Ala His Thr Pro Thr Ser Lys Phe Tyr Tyr Tyr Ala Met
1               5                   10                  15

Asp Val

<210> SEQ ID NO 174
<211> LENGTH: 126
<212> TYPE: PRT
<213> ORGANISM: Artificial Sequence
<220> FEATURE:
<223> OTHER INFORMATION: ZKD15 VH

<400> SEQUENCE: 174

Gln Leu Gln Leu Gln Glu Ser Gly Ser Gly Leu Val Lys Pro Ser Gln
1               5                   10                  15

Thr Leu Ser Leu Thr Cys Thr Val Ser Asp Ala Ser Ile Ser Ser Gly
            20                  25                  30

Gly Phe Ser Trp Ser Trp Ile Arg Gln Pro Leu Gly Lys Gly Leu Glu
        35                  40                  45

Trp Leu Gly Tyr Ile Tyr Ser Ser Gly Asp Thr Phe Tyr Asn Pro Ser
    50                  55                  60

Leu Gln Gly Arg Val Thr Met Ser Val Asp Ile Phe Arg Ser Gln Phe
65                  70                  75                  80

Ser Leu Lys Leu Thr Ser Val Thr Ala Ala Asp Thr Ala Met Tyr Tyr
                85                  90                  95

Cys Ala Arg Ala His Thr Pro Thr Ser Lys Phe Tyr Tyr Tyr Ala
            100                 105                 110

Met Asp Val Trp Gly Gln Gly Thr Thr Val Thr Val Ser Ser
        115                 120                 125

<210> SEQ ID NO 175
<211> LENGTH: 8
<212> TYPE: PRT
<213> ORGANISM: Artificial Sequence
<220> FEATURE:
<223> OTHER INFORMATION: ZKD16 CDRH1

<400> SEQUENCE: 175

Gly Phe Thr Phe Ser Asp His Phe
1               5

<210> SEQ ID NO 176
<211> LENGTH: 10
<212> TYPE: PRT
<213> ORGANISM: Artificial Sequence
<220> FEATURE:
<223> OTHER INFORMATION: ZKD16 CDRH2

<400> SEQUENCE: 176

Ser Arg Asn Lys Pro Asn Ser Tyr Thr Thr
1               5                   10

<210> SEQ ID NO 177
<211> LENGTH: 17
<212> TYPE: PRT
<213> ORGANISM: Artificial Sequence
<220> FEATURE:
<223> OTHER INFORMATION: ZKD16 CDRH3

<400> SEQUENCE: 177

Ala Lys Val Gly Gly Cys Tyr Gly Gly Asp Cys His Val Glu Asn Asp
1               5                   10                  15

Tyr

<210> SEQ ID NO 178
<211> LENGTH: 126
<212> TYPE: PRT
<213> ORGANISM: Artificial Sequence
<220> FEATURE:
<223> OTHER INFORMATION: ZKD16 VH

<400> SEQUENCE: 178

Glu Val Gln Leu Val Glu Ser Gly Gly Asp Leu Val Gln Pro Gly Gly
1               5                   10                  15

Ser Leu Arg Leu Ser Cys Val Ala Ser Gly Phe Thr Phe Ser Asp His
            20                  25                  30

Phe Met Asp Trp Val Arg Gln Ala Pro Gly Lys Gly Leu Glu Trp Val
        35                  40                  45

Gly Arg Ser Arg Asn Lys Pro Asn Ser Tyr Thr Thr Glu Tyr Ala Ala
    50                  55                  60

Ser Val Lys Gly Arg Phe Ser Ile Ser Arg Asp Asp Ser Lys Lys Ala
65                  70                  75                  80

Leu Tyr Leu Gln Met Asn Ser Leu Gln Thr Glu Asp Thr Ala Val Tyr
                85                  90                  95

Tyr Cys Ala Lys Val Gly Gly Cys Tyr Gly Gly Asp Cys His Val Glu
            100                 105                 110

Asn Asp Tyr Trp Gly Gln Gly Thr Leu Val Thr Val Ser Ser
        115                 120                 125

<210> SEQ ID NO 179
<211> LENGTH: 8
<212> TYPE: PRT
<213> ORGANISM: Artificial Sequence
<220> FEATURE:
<223> OTHER INFORMATION: ZKD17 CDRH1

<400> SEQUENCE: 179

Gly Phe Ile Phe Ser Asp Tyr Ala
1               5

<210> SEQ ID NO 180
<211> LENGTH: 8
<212> TYPE: PRT
<213> ORGANISM: Artificial Sequence
<220> FEATURE:
<223> OTHER INFORMATION: ZKD17 CDRH2

<400> SEQUENCE: 180

Ile Ser Tyr Asp Gly Ser Ser Arg
1               5

<210> SEQ ID NO 181
<211> LENGTH: 20
<212> TYPE: PRT
<213> ORGANISM: Artificial Sequence
<220> FEATURE:
<223> OTHER INFORMATION: ZKD17 CDRH3

<400> SEQUENCE: 181

Ala Arg Gly Tyr Cys Ser Ser Gly Thr Cys Phe Ser Thr Asn Ala Glu
1               5                   10                  15

Tyr Phe His Pro
            20

```
<210> SEQ ID NO 182
<211> LENGTH: 127
<212> TYPE: PRT
<213> ORGANISM: Artificial Sequence
<220> FEATURE:
<223> OTHER INFORMATION: ZKD17 VH

<400> SEQUENCE: 182

Gln Val Gln Met Val Glu Ser Gly Gly Val Val Gln Pro Gly Thr
1               5                   10                  15

Ser Leu Arg Leu Ser Cys Ala Thr Ser Gly Phe Ile Phe Ser Asp Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Ser Arg Leu Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met His Ser Leu Arg Ala Gly Asp Thr Ala Val Tyr Tyr Cys
                85                  90                  95

Ala Arg Gly Tyr Cys Ser Ser Gly Thr Cys Phe Ser Thr Asn Ala Glu
            100                 105                 110

Tyr Phe His Pro Trp Gly Gln Gly Thr Leu Ala Thr Ile Ser Ser
        115                 120                 125

<210> SEQ ID NO 183
<211> LENGTH: 8
<212> TYPE: PRT
<213> ORGANISM: Artificial Sequence
<220> FEATURE:
<223> OTHER INFORMATION: ZKD20 CDRH1

<400> SEQUENCE: 183

Gly Phe Thr Phe Ser Asp His Phe
1               5

<210> SEQ ID NO 184
<211> LENGTH: 10
<212> TYPE: PRT
<213> ORGANISM: Artificial Sequence
<220> FEATURE:
<223> OTHER INFORMATION: ZKD20 CDRH2

<400> SEQUENCE: 184

Ser Arg Asn Lys Pro Asn Ser Tyr Thr Thr
1               5                   10

<210> SEQ ID NO 185
<211> LENGTH: 17
<212> TYPE: PRT
<213> ORGANISM: Artificial Sequence
<220> FEATURE:
<223> OTHER INFORMATION: ZKD20 CDRH3

<400> SEQUENCE: 185

Ala Arg Val Gly Gly Cys Asn Gly Gly Asp Cys His Val Glu Asn Asp
1               5                   10                  15

Tyr

<210> SEQ ID NO 186
<211> LENGTH: 126
<212> TYPE: PRT
<213> ORGANISM: Artificial Sequence
```

```
<220> FEATURE:
<223> OTHER INFORMATION: ZKD20 VH

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asp His
            20                  25                  30

Phe Met Asp Trp Val Arg Gln Ala Pro Gly Lys Gly Leu Glu Trp Val
        35                  40                  45

Gly Arg Ser Arg Asn Lys Pro Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Gln Thr Glu Asp Thr Ala Val Tyr
                85                  90                  95

Tyr Cys Ala Arg Val Gly Gly Cys Asn Gly Asp Cys His Val Glu
            100                 105                 110

Asn Asp Tyr Trp Gly Gln Gly Thr Leu Val Thr Val Ser Ser
        115                 120                 125

<210> SEQ ID NO 187
<211> LENGTH: 8
<212> TYPE: PRT
<213> ORGANISM: Artificial Sequence
<220> FEATURE:
<223> OTHER INFORMATION: ZKA134 CDRH1

<400> SEQUENCE: 187

Gly Gly Thr Phe Ser Ala Tyr Ala
1               5

<210> SEQ ID NO 188
<211> LENGTH: 8
<212> TYPE: PRT
<213> ORGANISM: Artificial Sequence
<220> FEATURE:
<223> OTHER INFORMATION: ZKA134 CDRH2

<400> SEQUENCE: 188

Ile Ile Pro Phe Phe Gly Thr Ala
1               5

<210> SEQ ID NO 189
<211> LENGTH: 19
<212> TYPE: PRT
<213> ORGANISM: Artificial Sequence
<220> FEATURE:
<223> OTHER INFORMATION: ZKA134 CDRH3

<400> SEQUENCE: 189

Ala Arg Ser Asp Ile Val Ser Thr Thr Arg Gly Tyr His His Tyr Gly
1               5                   10                  15

Met Asp Val

<210> SEQ ID NO 190
<211> LENGTH: 126
<212> TYPE: PRT
<213> ORGANISM: Artificial Sequence
<220> FEATURE:
<223> OTHER INFORMATION: ZKA134 VH

<400> SEQUENCE: 190
```

```
Gln Val His Leu Val Gln Ser Gly Ala Glu Val Lys Lys Pro Gly Ser
1               5                   10                  15

Ser Val Asn Val Ser Cys Lys Ala Ser Gly Gly Thr Phe Ser Ala Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Gly Thr Ala Tyr Tyr Ala Gln Lys Phe
50                  55                  60

Lys Gly Arg Val Thr Val Thr Ala Asp Lys Ser Ser Thr Val Tyr
65                  70                  75                  80

Met Glu Met Thr Ser Leu Arg Ser Glu Asp Thr Ala Val Tyr Tyr Cys
                85                  90                  95

Ala Arg Ser Asp Ile Val Ser Thr Thr Arg Gly Tyr His His Tyr Gly
                100                 105                 110

Met Asp Val Trp Gly Gln Gly Thr Thr Val Thr Val Ser Ser
            115                 120                 125
```

<210> SEQ ID NO 191
<211> LENGTH: 8
<212> TYPE: PRT
<213> ORGANISM: Artificial Sequence
<220> FEATURE:
<223> OTHER INFORMATION: ZKA246 CDRH1

<400> SEQUENCE: 191

```
Gly Tyr Thr Phe Ser Asp Tyr Tyr
1               5
```

<210> SEQ ID NO 192
<211> LENGTH: 8
<212> TYPE: PRT
<213> ORGANISM: Artificial Sequence
<220> FEATURE:
<223> OTHER INFORMATION: ZKA246 CDRH2

<400> SEQUENCE: 192

```
Ile Asn Pro Tyr Ser Gly Gly Thr
1               5
```

<210> SEQ ID NO 193
<211> LENGTH: 14
<212> TYPE: PRT
<213> ORGANISM: Artificial Sequence
<220> FEATURE:
<223> OTHER INFORMATION: ZKA246 CDRH3

<400> SEQUENCE: 193

```
Ala Arg Gly Phe Thr Met Ile Ser Asp Arg Glu Phe Asp Pro
1               5                   10
```

<210> SEQ ID NO 194
<211> LENGTH: 121
<212> TYPE: PRT
<213> ORGANISM: Artificial Sequence
<220> FEATURE:
<223> OTHER INFORMATION: ZKA246 VH

<400> SEQUENCE: 194

```
Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Ser Asp Tyr
            20                  25                  30
```

```
Tyr Met His Trp Val Arg Gln Ala Pro Gly Gln Gly Leu Glu Trp Met
        35                  40                  45

Gly Arg Ile Asn Pro Tyr Ser Gly Gly Thr Asn Tyr Ala Gln Lys Phe
    50                  55                  60

His Gly Arg Val Thr Val Thr Arg Asp Thr Ser Ile Ser Thr Val Tyr
 65                  70                  75                  80

Met Glu Leu Arg Gly Leu Arg Ser Asp Thr Ala Val Tyr Tyr Cys
                85                  90                  95

Ala Arg Gly Phe Thr Met Ile Ser Asp Arg Glu Phe Asp Pro Trp Gly
            100                 105                 110

Gln Gly Thr Leu Val Thr Val Ser Ser
        115                 120

<210> SEQ ID NO 195
<211> LENGTH: 8
<212> TYPE: PRT
<213> ORGANISM: Artificial Sequence
<220> FEATURE:
<223> OTHER INFORMATION: ZKA256 CDRH1

<400> SEQUENCE: 195

Gly Phe Thr Phe Ser Thr Tyr Trp
1               5

<210> SEQ ID NO 196
<211> LENGTH: 8
<212> TYPE: PRT
<213> ORGANISM: Artificial Sequence
<220> FEATURE:
<223> OTHER INFORMATION: ZKA256 CDRH2

<400> SEQUENCE: 196

Ile Lys Gln Asp Gly Ser Glu Lys
1               5

<210> SEQ ID NO 197
<211> LENGTH: 20
<212> TYPE: PRT
<213> ORGANISM: Artificial Sequence
<220> FEATURE:
<223> OTHER INFORMATION: ZKA256 CDRH3

<400> SEQUENCE: 197

Ala Arg Asp Pro Gly Tyr Asp Asp Phe Trp Ser Gly Ser Tyr Ser Gly
1               5                   10                  15

Ser Phe Asp Ile
            20

<210> SEQ ID NO 198
<211> LENGTH: 127
<212> TYPE: PRT
<213> ORGANISM: Artificial Sequence
<220> FEATURE:
<223> OTHER INFORMATION: ZKA256 VH

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Thr Trp Val Arg Gln Ala Pro Gly Lys Gly Leu Glu Trp Val
        35                  40                  45
```

```
Ala Asn Ile Lys Gln Asp Gly Ser Glu Lys Tyr Tyr Val Asp Ser Val
        50                  55                  60

Lys Gly Arg Phe Thr Ile Ser Arg Asp Asn Lys Asn Ser Leu Tyr
 65                  70                  75                  80

Leu Gln Val Asn Ser Leu Arg Ala Glu Asp Thr Ala Ile Tyr Tyr Cys
                85                  90                  95

Ala Arg Asp Pro Gly Tyr Asp Asp Phe Trp Ser Gly Ser Tyr Ser Gly
            100                 105                 110

Ser Phe Asp Ile Trp Gly Gln Gly Thr Met Val Thr Val Ser Ser
            115                 120                 125
```

<210> SEQ ID NO 199
<211> LENGTH: 8
<212> TYPE: PRT
<213> ORGANISM: Artificial Sequence
<220> FEATURE:
<223> OTHER INFORMATION: ZKB42 CDRH1

<400> SEQUENCE: 199

```
Gly Phe Thr Phe Asn Asn Tyr Gly
 1               5
```

<210> SEQ ID NO 200
<211> LENGTH: 8
<212> TYPE: PRT
<213> ORGANISM: Artificial Sequence
<220> FEATURE:
<223> OTHER INFORMATION: ZKB42 CDRH2

<400> SEQUENCE: 200

```
Ile Ser Tyr Asp Gly Asn Lys Lys
 1               5
```

<210> SEQ ID NO 201
<211> LENGTH: 16
<212> TYPE: PRT
<213> ORGANISM: Artificial Sequence
<220> FEATURE:
<223> OTHER INFORMATION: ZKB42 CDRH3

<400> SEQUENCE: 201

```
Val Lys Tyr Gly Glu Arg Ile Asn Gly Tyr Ser Asp Pro Phe Asp His
 1               5                  10                  15
```

<210> SEQ ID NO 202
<211> LENGTH: 123
<212> TYPE: PRT
<213> ORGANISM: Artificial Sequence
<220> FEATURE:
<223> OTHER INFORMATION: ZKB42 VH

<400> SEQUENCE: 202

```
Gln Val Gln Val Val Glu Ser Gly Gly Gly Val Val Gln Pro Gly Arg
 1               5                  10                  15

Ser Leu Arg Leu Phe Cys Ala Ala Ser Gly Phe Thr Phe Asn Asn Tyr
            20                  25                  30

Gly Met His Trp Val Arg Gln Ala Pro Gly Lys Gly Leu Glu Trp Val
        35                  40                  45

Ala Leu Ile Ser Tyr Asp Gly Asn Lys Lys Tyr Tyr Ala Asp Ser Val
    50                  55                  60

Lys Gly Arg Phe Ser Ile Ser Arg Asp Asn Ser Lys Asn Thr Leu Tyr
 65                  70                  75                  80
```

-continued

Leu Gln Met Asn Arg Leu Arg Ser Gly Asp Thr Ala Val Tyr His Cys
                85                  90                  95

Val Lys Tyr Gly Glu Arg Ile Asn Gly Tyr Ser Asp Pro Phe Asp His
            100                 105                 110

Trp Gly Gln Gly Thr Leu Val Thr Val Ser Ser
        115                 120

<210> SEQ ID NO 203
<211> LENGTH: 8
<212> TYPE: PRT
<213> ORGANISM: Artificial Sequence
<220> FEATURE:
<223> OTHER INFORMATION: ZKB85 CDRH1

<400> SEQUENCE: 203

Gly Tyr Thr Phe Thr Thr Tyr Ala
1               5

<210> SEQ ID NO 204
<211> LENGTH: 8
<212> TYPE: PRT
<213> ORGANISM: Artificial Sequence
<220> FEATURE:
<223> OTHER INFORMATION: ZKB85 CDRH2

<400> SEQUENCE: 204

Ile Asn Thr Asn Thr Gly Asn Pro
1               5

<210> SEQ ID NO 205
<211> LENGTH: 11
<212> TYPE: PRT
<213> ORGANISM: Artificial Sequence
<220> FEATURE:
<223> OTHER INFORMATION: ZKB85 CDRH3

<400> SEQUENCE: 205

Ala Arg Val Ile Val Pro Tyr Ala Phe Asp Ile
1               5                   10

<210> SEQ ID NO 206
<211> LENGTH: 118
<212> TYPE: PRT
<213> ORGANISM: Artificial Sequence
<220> FEATURE:
<223> OTHER INFORMATION: ZKB85 VH

<400> SEQUENCE: 206

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ala Met Asn Trp Val Arg Gln Ala Pro Gly Gln Gly Pro Glu Trp Val
        35                  40                  45

Gly Trp Ile Asn Thr Asn Thr Gly Asn Pro Thr Tyr Ala Gln Gly Phe
    50                  55                  60

Thr Gly Arg Phe Val Leu Ser Leu Asp Thr Ser Val Ser Thr Ala Phe
65                  70                  75                  80

Leu Gln Ile Ser Ser Leu Lys Ala Glu Asp Thr Ala Val Tyr Tyr Cys
                85                  90                  95

Ala Arg Val Ile Val Pro Tyr Ala Phe Asp Ile Trp Gly Gln Gly Thr
            100                 105                 110

```
Met Val Thr Val Ser Ser
        115

<210> SEQ ID NO 207
<211> LENGTH: 8
<212> TYPE: PRT
<213> ORGANISM: Artificial Sequence
<220> FEATURE:
<223> OTHER INFORMATION: ZKB47 CDRH1

<400> SEQUENCE: 207

Gly Tyr Thr Phe Thr Asn Tyr Tyr
1               5

<210> SEQ ID NO 208
<211> LENGTH: 8
<212> TYPE: PRT
<213> ORGANISM: Artificial Sequence
<220> FEATURE:
<223> OTHER INFORMATION: ZKB47 CDRH2

<400> SEQUENCE: 208

Ile Asn Pro Ser Gly Gly Pro Thr
1               5

<210> SEQ ID NO 209
<211> LENGTH: 15
<212> TYPE: PRT
<213> ORGANISM: Artificial Sequence
<220> FEATURE:
<223> OTHER INFORMATION: ZKB47 CDRH3

<400> SEQUENCE: 209

Ala Arg Asp Gln Tyr Gly Gly Tyr Ala Arg Tyr Gly Met Asp Val
1               5                   10                  15

<210> SEQ ID NO 210
<211> LENGTH: 122
<212> TYPE: PRT
<213> ORGANISM: Artificial Sequence
<220> FEATURE:
<223> OTHER INFORMATION: ZKB47 VH

<400> SEQUENCE: 210

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Pro Thr Ser Tyr Ala Gln Lys Phe
    50                  55                  60

Gln Gly Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Tyr Gly Gly Tyr Ala Arg Tyr Gly Met Asp Val Trp
            100                 105                 110

Gly Gln Gly Thr Thr Val Thr Val Ser Ser
        115                 120

<210> SEQ ID NO 211
```

```
<211> LENGTH: 8
<212> TYPE: PRT
<213> ORGANISM: Artificial Sequence
<220> FEATURE:
<223> OTHER INFORMATION: ZKC6 CDRH1

<400> SEQUENCE: 211

Gly Tyr Thr Phe Thr Gly Tyr Tyr
1               5

<210> SEQ ID NO 212
<211> LENGTH: 8
<212> TYPE: PRT
<213> ORGANISM: Artificial Sequence
<220> FEATURE:
<223> OTHER INFORMATION: ZKC6 CDRH2

<400> SEQUENCE: 212

Ile Asn Pro Asn Ser Gly Gly Thr
1               5

<210> SEQ ID NO 213
<211> LENGTH: 12
<212> TYPE: PRT
<213> ORGANISM: Artificial Sequence
<220> FEATURE:
<223> OTHER INFORMATION: ZKC6 CDRH3

<400> SEQUENCE: 213

Ala Arg Val Ser Asp Trp Gly Phe Ala Phe Asp Ile
1               5                   10

<210> SEQ ID NO 214
<211> LENGTH: 119
<212> TYPE: PRT
<213> ORGANISM: Artificial Sequence
<220> FEATURE:
<223> OTHER INFORMATION: ZKC6 VH

<400> SEQUENCE: 214

Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95

Ala Arg Val Ser Asp Trp Gly Phe Ala Phe Asp Ile Trp Gly Gln Gly
            100                 105                 110

Thr Met Val Thr Val Ser Gln
        115

<210> SEQ ID NO 215
<211> LENGTH: 8
<212> TYPE: PRT
<213> ORGANISM: Artificial Sequence
<220> FEATURE:
<223> OTHER INFORMATION: ZKA160 CDRH1
```

```
<400> SEQUENCE: 215

Gly Gly Ser Ile Thr Ser Tyr Ser
1               5

<210> SEQ ID NO 216
<211> LENGTH: 7
<212> TYPE: PRT
<213> ORGANISM: Artificial Sequence
<220> FEATURE:
<223> OTHER INFORMATION: ZKA160 CDRH2

<400> SEQUENCE: 216

Ile Phe Tyr Ser Gly Ser Thr
1               5

<210> SEQ ID NO 217
<211> LENGTH: 15
<212> TYPE: PRT
<213> ORGANISM: Artificial Sequence
<220> FEATURE:
<223> OTHER INFORMATION: ZKA160 CDRH3

<400> SEQUENCE: 217

Ala Arg Asp Gln Thr Met Pro Val Trp Val Gly Gly Met Asp Val
1               5                   10                  15

<210> SEQ ID NO 218
<211> LENGTH: 121
<212> TYPE: PRT
<213> ORGANISM: Artificial Sequence
<220> FEATURE:
<223> OTHER INFORMATION: ZKA160 VH

<400> SEQUENCE: 218

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
            20                  25                  30

Ser Trp Ser Trp Ile Arg Gln Pro Pro Gly Lys Gly Leu Glu Trp Ile
        35                  40                  45

Gly Tyr Ile Phe Tyr Ser Gly Ser Thr Asp Tyr Asn Pro Ser Leu Lys
    50                  55                  60

Ser Arg Val Thr Ile Ser Val Asp Thr Ser Lys Asp Gln Phe Ser Leu
65                  70                  75                  80

Arg Leu Arg Ser Val Thr Ala Ala Asp Thr Ala Val Tyr Tyr Cys Ala
                85                  90                  95

Arg Asp Gln Thr Met Pro Val Trp Val Gly Gly Met Asp Val Trp Gly
            100                 105                 110

Gln Gly Thr Thr Val Thr Val Ser Ser
        115                 120

<210> SEQ ID NO 219
<211> LENGTH: 8
<212> TYPE: PRT
<213> ORGANISM: Artificial Sequence
<220> FEATURE:
<223> OTHER INFORMATION: ZKA172 CDRH1

<400> SEQUENCE: 219

Gly Tyr Ile Phe Thr Arg Tyr Trp
1               5
```

```
<210> SEQ ID NO 220
<211> LENGTH: 8
<212> TYPE: PRT
<213> ORGANISM: Artificial Sequence
<220> FEATURE:
<223> OTHER INFORMATION: ZKA172 CDRH2

<400> SEQUENCE: 220

Ile Asp Pro Ser Asp Ser Tyr Thr
1               5

<210> SEQ ID NO 221
<211> LENGTH: 13
<212> TYPE: PRT
<213> ORGANISM: Artificial Sequence
<220> FEATURE:
<223> OTHER INFORMATION: ZKA172 CDRH3

<400> SEQUENCE: 221

Ala Arg Gln Glu Thr Ala Arg Glu Asp Gly Met Ala Val
1               5                   10

<210> SEQ ID NO 222
<211> LENGTH: 120
<212> TYPE: PRT
<213> ORGANISM: Artificial Sequence
<220> FEATURE:
<223> OTHER INFORMATION: ZKA172 VH

<400> SEQUENCE: 222

Glu Val Gln Leu Val Gln Ser Gly Ala Glu Val Lys Lys Pro Gly Lys
1               5                   10                  15

Ser Leu Arg Ile Ser Cys Lys Gly Ser Gly Tyr Ile Phe Thr Arg Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Glu Thr Ala Arg Glu Asp Gly Met Ala Val Trp Gly Gln
            100                 105                 110

Gly Thr Thr Val Thr Val Ser Ser
        115                 120

<210> SEQ ID NO 223
<211> LENGTH: 10
<212> TYPE: PRT
<213> ORGANISM: Artificial Sequence
<220> FEATURE:
<223> OTHER INFORMATION: ZKA174 CDRH1

<400> SEQUENCE: 223

Gly Gly Ser Met Ser Asn Ser Tyr Tyr His
1               5                   10

<210> SEQ ID NO 224
<211> LENGTH: 7
<212> TYPE: PRT
<213> ORGANISM: Artificial Sequence
<220> FEATURE:
<223> OTHER INFORMATION: ZKA174 CDRH2
```

```
<400> SEQUENCE: 224

Ile Tyr Tyr Ser Gly Ser Thr
1               5

<210> SEQ ID NO 225
<211> LENGTH: 18
<212> TYPE: PRT
<213> ORGANISM: Artificial Sequence
<220> FEATURE:
<223> OTHER INFORMATION: ZKA174 CDRH3

<400> SEQUENCE: 225

Ala Arg Asn Pro Val Phe Asn Pro Leu Thr Leu Thr His Asp Ala Phe
1               5                   10                  15

Asp Ile

<210> SEQ ID NO 226
<211> LENGTH: 126
<212> TYPE: PRT
<213> ORGANISM: Artificial Sequence
<220> FEATURE:
<223> OTHER INFORMATION: ZKA174 VH

<400> SEQUENCE: 226

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Met Ser Asn Ser
                20                  25                  30

Tyr Tyr His Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Asn Pro Val Phe Asn Pro Leu Thr Leu Thr His Asp Ala
            100                 105                 110

Phe Asp Ile Trp Gly Gln Gly Thr Met Val Thr Val Ser Ser
        115                 120                 125

<210> SEQ ID NO 227
<211> LENGTH: 8
<212> TYPE: PRT
<213> ORGANISM: Artificial Sequence
<220> FEATURE:
<223> OTHER INFORMATION: ZKA189 CDRH1

<400> SEQUENCE: 227

Gly Phe Thr Phe Ser Ser Tyr Ala
1               5

<210> SEQ ID NO 228
<211> LENGTH: 8
<212> TYPE: PRT
<213> ORGANISM: Artificial Sequence
<220> FEATURE:
<223> OTHER INFORMATION: ZKA189 CDRH2

<400> SEQUENCE: 228

Ile Ser Gly Ser Gly Asp Asn Thr
```

<210> SEQ ID NO 229
<211> LENGTH: 18
<212> TYPE: PRT
<213> ORGANISM: Artificial Sequence
<220> FEATURE:
<223> OTHER INFORMATION: ZKA189 CDRH3

<400> SEQUENCE: 229

Ala Lys Trp Pro Tyr Tyr Asp Phe Trp Ser Gly Ser Glu Ser Tyr Phe
1               5                   10                  15

Asp Pro

<210> SEQ ID NO 230
<211> LENGTH: 125
<212> TYPE: PRT
<213> ORGANISM: Artificial Sequence
<220> FEATURE:
<223> OTHER INFORMATION: ZKA189 VH

<400> SEQUENCE: 230

Gly Val Gln Leu Leu Glu Ser Gly Gly Ala Leu Val Gln Pro Gly Lys
1               5                   10                  15

Ser Leu Arg Leu Ser Cys Ala Ala Ser Gly Phe Thr Phe Ser Ser Tyr
            20                  25                  30

Ala Leu Thr Trp Val Arg Gln Ala Pro Gly Lys Gly Leu Gln Trp Val
        35                  40                  45

Ser Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Pro Tyr Tyr Asp Phe Trp Ser Gly Ser Glu Ser Tyr Phe
            100                 105                 110

Asp Pro Trp Gly Gln Gly Thr Leu Val Thr Val Ser Ser
        115                 120                 125

<210> SEQ ID NO 231
<211> LENGTH: 8
<212> TYPE: PRT
<213> ORGANISM: Artificial Sequence
<220> FEATURE:
<223> OTHER INFORMATION: ZKA195 CDRH1

<400> SEQUENCE: 231

Gly Tyr Asn Phe Pro Ser Tyr Trp
1               5

<210> SEQ ID NO 232
<211> LENGTH: 8
<212> TYPE: PRT
<213> ORGANISM: Artificial Sequence
<220> FEATURE:
<223> OTHER INFORMATION: ZKA195 CDRH2

<400> SEQUENCE: 232

Ile Asp Pro Ser Asp Ser Tyr Thr
1               5

<210> SEQ ID NO 233

```
<211> LENGTH: 15
<212> TYPE: PRT
<213> ORGANISM: Artificial Sequence
<220> FEATURE:
<223> OTHER INFORMATION: ZKA195 CDRH3

<400> SEQUENCE: 233

Ala Arg Ala Asp Cys Arg Ser Thr Ser Cys Tyr Leu Val Phe Glu
1               5                   10                  15

<210> SEQ ID NO 234
<211> LENGTH: 121
<212> TYPE: PRT
<213> ORGANISM: Artificial Sequence
<220> FEATURE:
<223> OTHER INFORMATION: ZKA195 VH

<400> SEQUENCE: 234

Glu Val Gln Leu Val Gln Ser Gly Ala Glu Val Lys Lys Pro Gly Glu
1               5                   10                  15

Ser Leu Arg Ile Ser Cys Lys Asp Ser Gly Tyr Asn Phe Pro Ser Tyr
                20                  25                  30

Trp Ile His Trp Val Arg Gln Met Pro Gly Lys Gly Leu Glu Trp Met
            35                  40                  45

Gly Thr Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Asp Cys Arg Ser Thr Ser Cys Tyr Leu Val Phe Glu Gly
                100                 105                 110

Gln Gly Thr Leu Val Thr Val Ser Ser
            115                 120

<210> SEQ ID NO 235
<211> LENGTH: 8
<212> TYPE: PRT
<213> ORGANISM: Artificial Sequence
<220> FEATURE:
<223> OTHER INFORMATION: ZKA215 CDRH1

<400> SEQUENCE: 235

Gly Tyr Thr Phe Thr Ser Tyr Trp
1               5

<210> SEQ ID NO 236
<211> LENGTH: 8
<212> TYPE: PRT
<213> ORGANISM: Artificial Sequence
<220> FEATURE:
<223> OTHER INFORMATION: ZKA215 CDRH2

<400> SEQUENCE: 236

Ile Asp Pro Ser Asp Ser His Thr
1               5

<210> SEQ ID NO 237
<211> LENGTH: 11
<212> TYPE: PRT
<213> ORGANISM: Artificial Sequence
<220> FEATURE:
<223> OTHER INFORMATION: ZKA215 CDRH3
```

```
<400> SEQUENCE: 237

Ala Arg His Ala Leu Pro Asn Tyr Phe Asp Ser
1               5                  10

<210> SEQ ID NO 238
<211> LENGTH: 118
<212> TYPE: PRT
<213> ORGANISM: Artificial Sequence
<220> FEATURE:
<223> OTHER INFORMATION: ZKA215 VH

<400> SEQUENCE: 238

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser His Thr Asp Tyr Ser Pro Ser Phe
    50                  55                  60

Gln Gly His Val Thr Ile Ser Ala Asp Lys Ser Ile Ser Ala Ala Tyr
65                  70                  75                  80

Leu Gln Trp Ser Ser Leu Lys Ala Ser Asp Thr Ala Met Tyr Tyr Cys
                85                  90                  95

Ala Arg His Ala Leu Pro Asn Tyr Phe Asp Ser Trp Gly Gln Gly Thr
            100                 105                 110

Leu Val Thr Val Ser Ser
        115

<210> SEQ ID NO 239
<211> LENGTH: 8
<212> TYPE: PRT
<213> ORGANISM: Artificial Sequence
<220> FEATURE:
<223> OTHER INFORMATION: ZKA218 CDRH1

<400> SEQUENCE: 239

Gly Phe Pro Phe Ser Ser Tyr Trp
1               5

<210> SEQ ID NO 240
<211> LENGTH: 8
<212> TYPE: PRT
<213> ORGANISM: Artificial Sequence
<220> FEATURE:
<223> OTHER INFORMATION: ZKA218 CDRH2

<400> SEQUENCE: 240

Ile Asn Ser Asp Gly Arg Asn Thr
1               5

<210> SEQ ID NO 241
<211> LENGTH: 15
<212> TYPE: PRT
<213> ORGANISM: Artificial Sequence
<220> FEATURE:
<223> OTHER INFORMATION: ZKA218 CDRH3

<400> SEQUENCE: 241

Ala Arg Gly Gly Tyr Asp Tyr Asp Ser Ser Gly Cys Phe Asp Tyr
1               5                   10                  15
```

<210> SEQ ID NO 242
<211> LENGTH: 122
<212> TYPE: PRT
<213> ORGANISM: Artificial Sequence
<220> FEATURE:
<223> OTHER INFORMATION: ZKA218 VH

<400> SEQUENCE: 242

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Arg Asn Thr Asn Tyr Ala Asp Ser Val
50                  55                  60

Lys Gly Arg Phe Thr Ile Ser Arg Asp Asn Ala Glu Asn Thr Val Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Tyr Asp Ser Ser Gly Cys Phe Asp Tyr Trp
            100                 105                 110

Gly Gln Gly Thr Leu Val Thr Val Ser Ser
        115                 120

<210> SEQ ID NO 243
<211> LENGTH: 8
<212> TYPE: PRT
<213> ORGANISM: Artificial Sequence
<220> FEATURE:
<223> OTHER INFORMATION: ZKB75 CDRH1

<400> SEQUENCE: 243

Gly Phe Thr Phe Ser Asn Tyr Ala
1               5

<210> SEQ ID NO 244
<211> LENGTH: 8
<212> TYPE: PRT
<213> ORGANISM: Artificial Sequence
<220> FEATURE:
<223> OTHER INFORMATION: ZKB75 CDRH2

<400> SEQUENCE: 244

Ile Ser Gly Thr Gly Gly Ser Thr
1               5

<210> SEQ ID NO 245
<211> LENGTH: 25
<212> TYPE: PRT
<213> ORGANISM: Artificial Sequence
<220> FEATURE:
<223> OTHER INFORMATION: ZKB75 CDRH3

<400> SEQUENCE: 245

Ala Lys Asp Ser Ala Ser Arg Gly Gly Tyr Cys Ser Gly Gly Val Cys
1               5                   10                  15

Tyr Leu Asn Pro Gly His His Asp Tyr
            20                  25

<210> SEQ ID NO 246
<211> LENGTH: 132
<212> TYPE: PRT

```
<213> ORGANISM: Artificial Sequence
<220> FEATURE:
<223> OTHER INFORMATION: ZKB75 VH

<400> SEQUENCE: 246

Glu Val Gln Val Leu Glu Ser Gly Gly Gly Leu Leu Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Ala Ser Arg Gly Gly Tyr Cys Ser Gly Gly Val Cys
            100                 105                 110

Tyr Leu Asn Pro Gly His His Asp Tyr Trp Gly Gln Gly Thr Leu Val
        115                 120                 125

Thr Val Ser Ser
    130

<210> SEQ ID NO 247
<211> LENGTH: 8
<212> TYPE: PRT
<213> ORGANISM: Artificial Sequence
<220> FEATURE:
<223> OTHER INFORMATION: ZKB83 CDRH1

<400> SEQUENCE: 247

Gly Tyr Ser Phe Thr Asn Tyr Trp
1               5

<210> SEQ ID NO 248
<211> LENGTH: 8
<212> TYPE: PRT
<213> ORGANISM: Artificial Sequence
<220> FEATURE:
<223> OTHER INFORMATION: ZKB83 CDRH2

<400> SEQUENCE: 248

Ile Asp Pro Ser Asp Ser Tyr Thr
1               5

<210> SEQ ID NO 249
<211> LENGTH: 27
<212> TYPE: PRT
<213> ORGANISM: Artificial Sequence
<220> FEATURE:
<223> OTHER INFORMATION: ZKB83 CDRH3

<400> SEQUENCE: 249

Ala Arg Leu Arg Gly Ser Leu Tyr Cys Ser Gly Gly Arg Cys Tyr Ser
1               5                   10                  15

Val Pro Gly Glu Thr Pro Asn Trp Phe Asp Pro
            20                  25

<210> SEQ ID NO 250
<211> LENGTH: 134
<212> TYPE: PRT
```

```
<213> ORGANISM: Artificial Sequence
<220> FEATURE:
<223> OTHER INFORMATION: ZKB83 VH

<400> SEQUENCE: 250

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Asn Tyr
            20                  25                  30

Trp Ile Thr Trp Val Arg Gln Met Pro Gly Lys Gly Leu Glu Trp Met
        35                  40                  45

Gly Ser Ile Asp Pro Ser Asp Ser Tyr Thr Asn Tyr Ser Pro Ser Phe
    50                  55                  60

Gln Gly His Val Thr Ile Ser Ala Asp Trp Ser Ile Asn Thr Ala Tyr
65                  70                  75                  80

Leu Gln Trp Ser Ser Leu Lys Ala Ser Asp Thr Ala Lys Tyr Tyr Cys
                85                  90                  95

Ala Arg Leu Arg Gly Ser Leu Tyr Cys Ser Gly Arg Cys Tyr Ser
            100                 105                 110

Val Pro Gly Glu Thr Pro Asn Trp Phe Asp Pro Trp Gly Gln Gly Thr
        115                 120                 125

Leu Val Thr Val Ser Ser
    130

<210> SEQ ID NO 251
<211> LENGTH: 8
<212> TYPE: PRT
<213> ORGANISM: Artificial Sequence
<220> FEATURE:
<223> OTHER INFORMATION: ZKC3 CDRH1

<400> SEQUENCE: 251

Gly Gly Ser Ile Thr Ser Tyr Tyr
1               5

<210> SEQ ID NO 252
<211> LENGTH: 7
<212> TYPE: PRT
<213> ORGANISM: Artificial Sequence
<220> FEATURE:
<223> OTHER INFORMATION: ZKC3 CDRH2

<400> SEQUENCE: 252

Ile Tyr Tyr Ser Gly Ser Thr
1               5

<210> SEQ ID NO 253
<211> LENGTH: 15
<212> TYPE: PRT
<213> ORGANISM: Artificial Sequence
<220> FEATURE:
<223> OTHER INFORMATION: ZKC3 CDRH3

<400> SEQUENCE: 253

Ala Arg Val Gly Gly Ala Pro Tyr Tyr Tyr Tyr Gly Met Asp Val
1               5                   10                  15

<210> SEQ ID NO 254
<211> LENGTH: 121
<212> TYPE: PRT
<213> ORGANISM: Artificial Sequence
<220> FEATURE:
<223> OTHER INFORMATION: ZKC3 VH
```

<400> SEQUENCE: 254

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Gly Ala Pro Tyr Tyr Tyr Gly Met Asp Val Trp Gly
            100                 105                 110

Gln Gly Thr Thr Val Thr Val Ser Ser
        115                 120

<210> SEQ ID NO 255
<211> LENGTH: 8
<212> TYPE: PRT
<213> ORGANISM: Artificial Sequence
<220> FEATURE:
<223> OTHER INFORMATION: ZKC18 CDRH1

<400> SEQUENCE: 255

Gly Phe Thr Phe Gly Asp Tyr Ala
1               5

<210> SEQ ID NO 256
<211> LENGTH: 10
<212> TYPE: PRT
<213> ORGANISM: Artificial Sequence
<220> FEATURE:
<223> OTHER INFORMATION: ZKC18 CDRH2

<400> SEQUENCE: 256

Ile Arg Ser Lys Ala Tyr Gly Gly Thr Thr
1               5                   10

<210> SEQ ID NO 257
<211> LENGTH: 13
<212> TYPE: PRT
<213> ORGANISM: Artificial Sequence
<220> FEATURE:
<223> OTHER INFORMATION: ZKC18 CDRH3

<400> SEQUENCE: 257

Ser Arg Asp His Thr Gly Thr Thr Tyr Ala Phe Asp Ile
1               5                   10

<210> SEQ ID NO 258
<211> LENGTH: 122
<212> TYPE: PRT
<213> ORGANISM: Artificial Sequence
<220> FEATURE:
<223> OTHER INFORMATION: ZKC18 VH

<400> SEQUENCE: 258

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ser Arg Asp His Thr Gly Thr Thr Tyr Ala Phe Asp Ile Trp
            100                 105                 110

Gly Gln Gly Thr Met Val Thr Val Ser Gln
        115                 120

<210> SEQ ID NO 259
<211> LENGTH: 8
<212> TYPE: PRT
<213> ORGANISM: Artificial Sequence
<220> FEATURE:
<223> OTHER INFORMATION: ZKD1 CDRH1

<400> SEQUENCE: 259

Gly Phe Thr Phe Ser Ser Tyr Gly
1               5

<210> SEQ ID NO 260
<211> LENGTH: 8
<212> TYPE: PRT
<213> ORGANISM: Artificial Sequence
<220> FEATURE:
<223> OTHER INFORMATION: ZKD1 CDRH2

<400> SEQUENCE: 260

Ile Trp Tyr Asp Gly Ser Asn Lys
1               5

<210> SEQ ID NO 261
<211> LENGTH: 19
<212> TYPE: PRT
<213> ORGANISM: Artificial Sequence
<220> FEATURE:
<223> OTHER INFORMATION: ZKD1 CDRH3

<400> SEQUENCE: 261

Ala Arg Asp Arg Arg Gly Tyr Gly Asp Tyr Val Gly Tyr Tyr Tyr Gly
1               5                   10                  15

Met Asp Val

<210> SEQ ID NO 262
<211> LENGTH: 126
<212> TYPE: PRT
<213> ORGANISM: Artificial Sequence
<220> FEATURE:
<223> OTHER INFORMATION: ZKD1 VH

<400> SEQUENCE: 262

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val

```
                35                  40                  45
Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Gly Tyr Gly Asp Tyr Val Gly Tyr Tyr Tyr Gly
            100                 105                 110

Met Asp Val Trp Gly Gln Gly Thr Thr Val Thr Val Ser Ser
            115                 120                 125

<210> SEQ ID NO 263
<211> LENGTH: 95
<212> TYPE: PRT
<213> ORGANISM: Zika virus
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid

<400> SEQUENCE: 263

Thr Ala Ala Phe Thr Phe Thr Lys Xaa Pro Ala Glu Xaa Xaa His Gly
1               5                   10                  15

Thr Val Thr Val Glu Xaa Gln Tyr Xaa Gly Xaa Asp Gly Pro Cys Lys
                20                  25                  30

Xaa Pro Xaa Gln Met Ala Val Asp Xaa Gln Thr Leu Thr Pro Val Gly
            35                  40                  45

Arg Leu Ile Thr Ala Asn Pro Val Ile Thr Glu Xaa Thr Glu Asn Ser
```

```
                  50                  55                  60

Lys Met Met Leu Glu Leu Asp Pro Pro Phe Gly Asp Ser Tyr Ile Val
 65                  70                  75                  80

Ile Gly Xaa Gly Xaa Lys Lys Ile Thr His His Trp His Arg Ser
                  85                  90                  95

<210> SEQ ID NO 264
<211> LENGTH: 95
<212> TYPE: PRT
<213> ORGANISM: Zika virus

<400> SEQUENCE: 264

Thr Ala Ala Phe Thr Phe Thr Lys Ile Pro Ala Glu Thr Leu His G

```
<223> OTHER INFORMATION: X may be any (naturally occurring) amino acid,
      preferably A or G
<220> FEATURE:
<221> NAME/KEY: misc_feature
<222> LOCATION: (35)..(35)
<223> OTHER INFORMATION: X may be any (naturally occurring) amino acid
      except R, preferably T or A
<220> FEATURE:
<221> NAME/KEY: misc_feature
<222> LOCATION: (41)..(41)
<223> OTHER INFORMATION: X may be any (naturally occurring) amino acid,
      preferably V or I
<220> FEATURE:
<221> NAME/KEY: misc_feature
<222> LOCATION: (43)..(43)
<223> OTHER INFORMATION: X may be any (naturally occurring) amino acid,
      preferably A or V
<220> FEATURE:
<221> NAME/KEY: misc_feature
<222> LOCATION: (49)..(49)
<223> OTHER INFORMATION: X may be any (naturally occurring) amino acid,
      preferably M or T
<220> FEATURE:
<221> NAME/KEY: misc_feature
<222> LOCATION: (68)..(68)
<223> OTHER INFORMATION: X may be any (naturally occurring) amino acid,
      preferably S or G
<220> FEATURE:
<221> NAME/KEY: misc_feature
<222> LOCATION: (70)..(70)
<223> OTHER INFORMATION: X may be any (naturally occurring) amino acid,
      preferably E or K
<220> FEATURE:
<221> NAME/KEY: misc_feature
<222> LOCATION: (91)..(91)
<223> OTHER INFORMATION: X may be any (naturally occurring) amino acid,
      preferably V or I
<220> FEATURE:
<221> NAME/KEY: misc_feature
<222> LOCATION: (93)..(93)
<223> OTHER INFORMATION: X may be any (naturally occurring) amino acid,
      preferably E, A, K, or D
<220> FEATURE:
<221> NAME/KEY: misc_feature
<222> LOCATION: (94)..(94)
<223> OTHER INFORMATION: X may be any (naturally occurring) amino acid,
      preferably E, A, or K, more preferably K or A

<400> SEQUENCE: 265

Xaa Gly Xaa Xaa Tyr Ser Leu Cys Thr Ala Ala Phe Thr Phe Thr Lys
1               5                   10                  15

Xaa Pro Ala Glu Xaa Xaa His Gly Thr Val Thr Val Glu Xaa Gln Tyr
            20                  25                  30

Xaa Gly Xaa Asp Gly Pro Cys Lys Xaa Pro Xaa Gln Met Ala Val Asp
        35                  40                  45

Xaa Gln Thr Leu Thr Pro Val Gly Arg Leu Ile Thr Ala Asn Pro Val
    50                  55                  60

Ile Thr Glu Xaa Thr Xaa Asn Ser Lys Met Met Leu Glu Leu Asp Pro
65                  70                  75                  80

Pro Phe Gly Asp Ser Tyr Ile Val Ile Gly Xaa Gly Xaa Xaa Lys Ile
                85                  90                  95

Thr His His Trp His Arg Ser Gly
            100

<210> SEQ ID NO 266
<211> LENGTH: 26
<212> TYPE: DNA
<213> ORGANISM: Artificial Sequence
<220> FEATURE:
<223> OTHER INFORMATION: Zika-E-F1 primer
```

```
<400> SEQUENCE: 266
tgcaaacgcg gtcgcaaacc tggttg                                    26

<210> SEQ ID NO 267
<211> LENGTH: 25
<212> TYPE: DNA
<213> ORGANISM: Artificial Sequence
<220> FEATURE:
<223> OTHER INFORMATION: ZIKV-E-R1 primer

<400> SEQUENCE: 267
cgtgccaagg taatggaatg tcgtg                                     25

<210> SEQ ID NO 268
<211> LENGTH: 25
<212> TYPE: DNA
<213> ORGANISM: Artificial Sequence
<220> FEATURE:
<223> OTHER INFORMATION: ZIKV-Ef1530 primer

<400> SEQUENCE: 268
agcctaggac ttgattgtga accga                                     25

<210> SEQ ID NO 269
<211> LENGTH: 25
<212> TYPE: DNA
<213> ORGANISM: Artificial Sequence
<220> FEATURE:
<223> OTHER INFORMATION: ZIKV-E-R2769 primer

<400> SEQUENCE: 269
ttacagatcc cacaacgacc gtcag                                     25

<210> SEQ ID NO 270
<211> LENGTH: 25
<212> TYPE: DNA
<213> ORGANISM: Artificial Sequence
<220> FEATURE:
<223> OTHER INFORMATION: ZIKV-E-F2

<400> SEQUENCE: 270
acttggtcat gatactgctg attgc                                     25

<210> SEQ ID NO 271
<211> LENGTH: 25
<212> TYPE: DNA
<213> ORGANISM: Artificial Sequence
<220> FEATURE:
<223> OTHER INFORMATION: ZIKV-E-R2

<400> SEQUENCE: 271
tcggttcaca atcaagtcct aggct                                     25

<210> SEQ ID NO 272
<211> LENGTH: 25
<212> TYPE: DNA
<213> ORGANISM: Artificial Sequence
<220> FEATURE:
<223> OTHER INFORMATION: ZIKV-E-f2058

<400> SEQUENCE: 272
gctaaccccg taatcactga aagca                                     25

<210> SEQ ID NO 273
<211> LENGTH: 25
```

```
<212> TYPE: DNA
<213> ORGANISM: Artificial Sequence
<220> FEATURE:
<223> OTHER INFORMATION: ZIKV-E-r2248

<400> SEQUENCE: 273
aagactgcca ttctcttggc acctc                                          25
```